(12) United States Patent
Maekawa et al.

(10) Patent No.: US 10,175,228 B2
(45) Date of Patent: Jan. 8, 2019

(54) METHOD OF USING TRANSMEMBRANE CHANNEL-LIKE PROTEIN 6 (TMC6) PROTEIN TO IDENTIFY SUBSTANCES AFFECTING SALTY TASTE

(71) Applicant: Ajinomoto Co., Inc., Chuo-ku (JP)

(72) Inventors: Takami Maekawa, Kawasaki (JP); Takashi Kondoh, Kawasaki (JP); Yutaka Maruyama, Kawasaki (JP)

(73) Assignee: Ajinomoto Co., Inc., Chuo-ku (JP)

( * ) Notice: Subject to any disclaimer, the term of this patent is extended or adjusted under 35 U.S.C. 154(b) by 0 days.

(21) Appl. No.: 15/821,205

(22) Filed: Nov. 22, 2017

(65) Prior Publication Data

US 2018/0095071 A1    Apr. 5, 2018

Related U.S. Application Data

(63) Continuation of application No. 15/654,162, filed on Jul. 19, 2017.

(30) Foreign Application Priority Data

Jul. 19, 2016 (JP) ................................ 2016-141446

(51) Int. Cl.
*G01N 33/50* (2006.01)
*G01N 33/68* (2006.01)
*C07K 14/705* (2006.01)
*G01N 33/566* (2006.01)

(52) U.S. Cl.
CPC ....... *G01N 33/5008* (2013.01); *C07K 14/705* (2013.01); *G01N 33/566* (2013.01); *G01N 33/6872* (2013.01); *G01N 2333/705* (2013.01); *G01N 2500/04* (2013.01); *G01N 2500/10* (2013.01)

(58) Field of Classification Search
CPC ........... G01N 33/5008; G01N 33/6872; C07K 14/705
See application file for complete search history.

(56) References Cited

U.S. PATENT DOCUMENTS

2012/0028263 A1    2/2012  Ishiwatari et al.

FOREIGN PATENT DOCUMENTS

| EP | 1 279 733 | 1/2003 |
|---|---|---|
| WO | WO 03/048305 | 6/2003 |
| WO | WO 2005/019258 | 3/2005 |
| WO | WO 2009/008950 | 1/2009 |
| WO | WO 2010/065863 | 6/2010 |
| WO | 2011/040475 A1 | 4/2011 |

OTHER PUBLICATIONS

Chandrashekar et al., "The cells and peripheral representation of sodium taste in mice", Letters, Nature, vol. 464, Mar. 2010, pp. 297-302.
Roper, S., "The Taste of Table Salt", Pflügers Arch—Eur J Physiol, vol. 467, 2015, pp. 457-463.
Kurima et al., "Characterization of the transmembrane channel-like (TMC) gene family: functional clues from hearing loss and epidermodysplasia verruciformis", Genomics, vol. 82, 2003, pp. 300-308.
Keresztes et al., "TMC and EVER genes belong to a larger novel family, the TMC gene family encoding transmembrane proteins", BMC Genomics, vol. 4, No. 24, 2003, pp. 1-11.
Wang et al., "TMC-1 Mediates Alkaline Sensation in *C. elegans* through Nociceptive Neurons", Neuron, vol. 91, Jul. 2016, pp. 146-154 (w/ attached Supplemental Information).
Notice of Reason for Rejection, dated Sep. 12, 2017, in the corr. Japanese Patent Application No. 2017-139639 (w/ English translation).
Chatzigeorgiou et al., "tmc-1 encodes a sodium-sensitive channel required for salt chemosensation in C. elegans", Nature, vol. 494, Feb. 2013, pp. 95-99.
Sirianant et al., "TMC8 (EVER2) attenuates intracellular signaling by $Zn^{2+}$ and $Ca^{2+}$ and suppresses activation of $Cl^-$ currents", Cellular Signalling, vol. 26, Issue 12, Dec. 2014, pp. 2826-2833.

*Primary Examiner* — Robert S Landsman
(74) *Attorney, Agent, or Firm* — Oblon, McClelland, Maier & Neustadt, L.L.P.

(57) ABSTRACT

A method for screening an objective substance such as a salty-taste modifying substance is provided. It is identified by using a TMC6 protein whether a test substance is an objective substance such as a salty-taste modifying substance.

25 Claims, 23 Drawing Sheets

Specification includes a Sequence Listing.

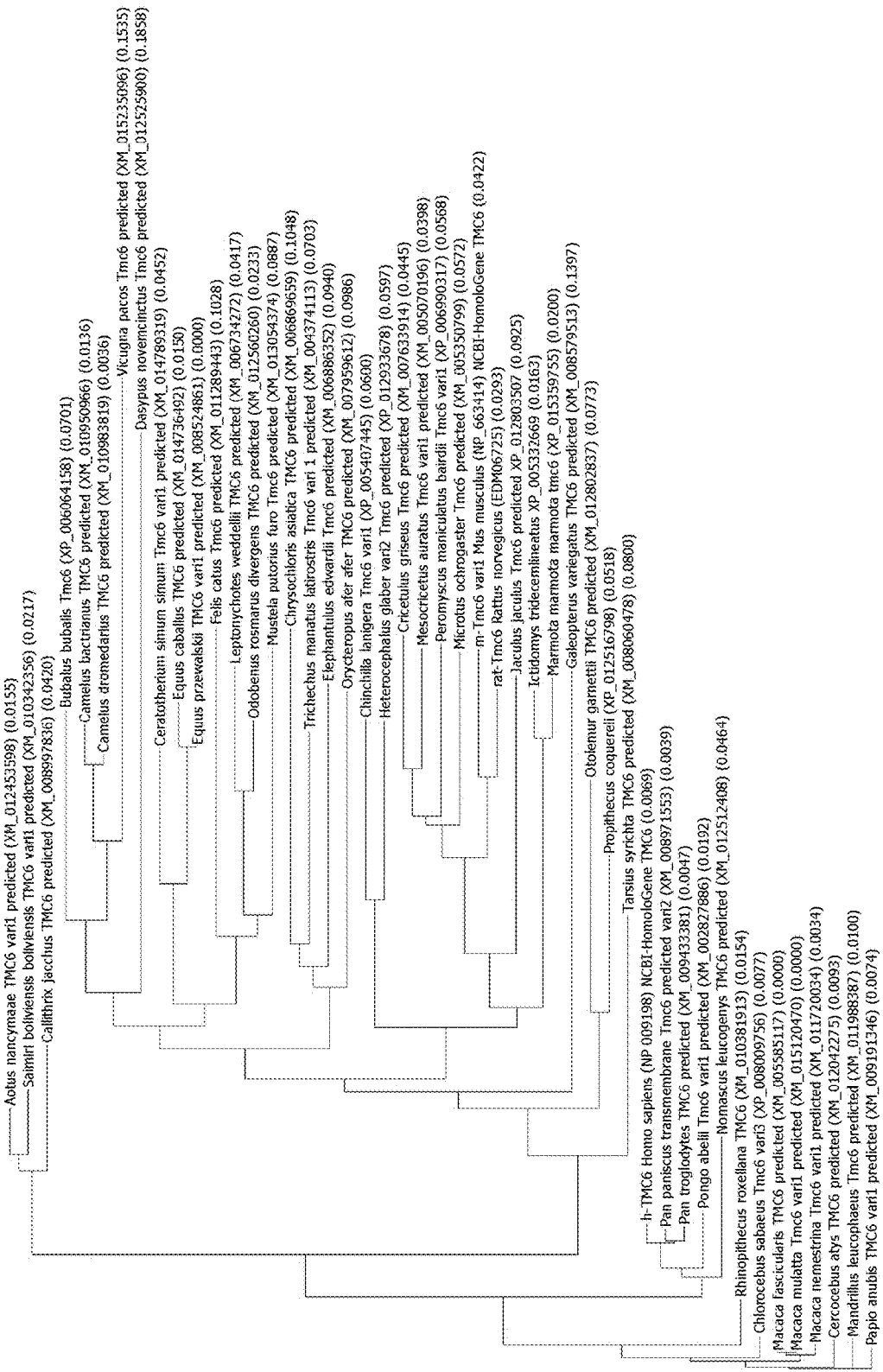
[Fig. 1]

```
                                                                                                          200
-------------------------------RGATGSGQHTLSGSE--GAHSTATLRILASMPSRTIGRSRGAIISQYYNRTVQLRRR-S-SRPLLGNLVR-S
-------------------------------RGAAGSGLHTLSGSE--GAHSTATLRVLASMPSRTIGRSRGAIISQYYNRTVQLRRR-S-SRPLLGNLVR-S
-------------------------------RGAAGSGQHTLLGSE--GTHSAATLRVLASMPSRTIGRSRGAIISQYYNRTVQLRRR-S-SRPLLGNLVR-S
-------------------------------TGALGASGSDHETMLGPEGAPVYSMATLRILASMPSRTIGRSRGAIISQYYNRTVKLRRRAG--RPQLRDMGR-S
-------------------------------ALGASGDDHQALLGPEGAPVHSMATLRILASMPSRTIASP---------------G-PSRG--------
-------------------------------ALGASGSDHETMLGPEGAPVHSMATLRILASMPSRTIGRSRGAILSQLYNRTVRLRRR-AARRPQLRDMGR-S
--------------------------------------------------------------------------------------------------
-------------------------------TAPPEASGGSPLGGPE----LGAATLRILACMPSRTIGRSRGAIISQYYNRTARLRRSG--RPLLRDAAR-S
-------------------------------GSHHQAFLGPEGVPDYSTATLRILASMPSRTIGRSRGAILSQYYNRTVRLRRRAG--RPQLRGVGR-S
-------------------------------LLDMSFCFVGSGHQALLGPEGVPDYSTATLRILASMPSRTIGRSRGAILSQYYNRTVRLRRRAG--RPPLGGVGR-S
-------------------------------LLDMSFCFVGSGHQALLGPEGVPDYSTATLRILASMPSRTIGRSRGAILSQYYNRTVBLRRRAG--RPPLGGVGR-S
-------------------------------SGRQALVGPEDAAAYSTATLRILASMPSRTIG--------EWDPGRPGLGVAL--RPQLGGVGR-S
-------------------------------CGQHALPGPEDALAHSAATLRMLASMPSRTIGRSRGAVICQYYNRSVRLRRRVS--RPELKGVGR-S
GAPDAVGRALSLPCPLQAWGGDWVGEIWPAVSPGRLDESFCFVGSGQQALPGPEDALVHSTATLRILASMPSRTIGRSRGAVICQYYNRSVRLRRRVS--RPELKGVGR-S
-------------------------------SGSRIPPGPEDAGAPSTATLRILASMPSRTIGRSRGAIISQYYNRTVQLRRRVS--RPELRGVGR-S
-------------------------------DGSHQDVLGQGHTPAYSAATLRILASMPSRTIGRSRGAIISQYYNRTVRLRRRGS--RSLHSWDH-A
-------------------------------PGAPGGGHGSDLGPGGAPAYSAATLRILASMPSRTIGRSRGAIISQYYNRTIRLRRRSS--RPLLSANGR-A
-------------------------------PGAPGRDHQAILEPGGGPSYSAATLRVLASMPSRTIGRSRGAIISQYYNRTVRLRRRG-----HRPPLH-G
-------------------------------VVDGDHQAGPGPEGAPAYSAATLRVLASMPSRTIGRSRGAIISQYYNRTMQLRRCGR--RPLLGAEGR-G
-------------------------------ALASGHQILLGAEGGPVYSTATLNILASMPSRTIGRSRGAIISQYYNRTVRMRRRSS--RPPLGPVMC-S
-------------------------------APASGHQTLLEPEGGPVYSTATLSILASMPSRTIGRSRGAIISKYYNHTVRMRRRHSGSRPILGPWC-S
-------------------------------RGRQTLPRPAGAPVHSSATLRMLASMPSRTIGRSRGAIISQYYNRTVRLRRRRN-SRPLLGNVVR-S
-------------------------------RGHQTLPRPEGAQVHSSATLRILASMPSRTIGRSRGAIISQYYNRTVRLRHR-S-SRPLLGSVAR-S
-------------------------------RGYQTLPRPEGAPAHSMATLRILASMPSRTIGRSRGAIISQYYNRTVRLRHR-S-SRPLLGNVAP-S
-------------------------------RGYQTLPRPEGAPTHSTATLRILASMPSRTIGRSRGAIISEYYNRTVRLRRR-S-SRPLLGNWR-C
-------------------------------RGDQTLPGLEGAPALSSATLRILASMPSRTIGRSRGAIISQYYNRTVRLRRR-S-SRPLLGNVVP-S
-------------------------------RGDQTLPRPEGAPVLSTATLRILASMPSRTIGRSRGAIISQYYNRTVRLRRR-S-SRPLLGNVVR-S
-------------------------------RGHPTLLEPGGVPAYSSATLRILASMPSRTIGRSRGAIISQYYNRTVRLRRR-S-SRPLLGNVVH-S
-------------------------------SGHQSLLGPEGAPVHSAATLRILASMPSRTIGRSRGAIISQYYNRTVKLRRR-G-SRPLLGDWH-S
-------------------------------SGHQTLLGPEGAPVHSAATLRILASMPSRTIGRSRGAIISQYYNRTVKLRRR-G-SRPLLGDLVR-S
-------------------------------WGAPDDSHQALLGPEVAPAHSTATLRILASMPSRTIGRSRGAVISQYYNRTVRLRRR-S-SRPLLGENSR-S
-------------------------------QETPGSSHETFLGPESAPVHSTATLRILASMPSRTIGRSRGAIISQYYNRTMRLRRR-S-GRPLLGDVWARS
-------------------------------PGDPGRGHETLLGPEGAPVHSMATLRILASMPSRTIGRSRGAIISQYYSRTMRLRRR-S-GRPLLGDVWTRS
-------------------------------PGASGSDHQTLRQPEGVPVHSMATLRILASMPSRTIGRSRGAIISQYYSRTMQLRRR-G-SRPLLGDVWR-S
-------------------------------PGASGSDHQTLRQPEGVPVHSTATLRILASMPSRTIGRSRGAIISQYYSRTMQLRRR-G-SRPLLGDVWR-S
-------------------------------REVTGSSQQTLWRPE--GTQSTATLRILASMPSRTIGRSRGAIISQYYSRTMQLRCR-S-SRPLLGNFVH-S
-------------------------------REVTGSSQQTLWRPE--GTQSTATLRILASMPSRTIGRSRGAIISQYYSRTMQLRCR-S-SRPLLGNFVH-S
-------------------------------REATGSGQQTLWRPE--GTQSTATLRILASMPSRTIGRSRGAIISQYYSRTMQLRCR-S-SRPLLGNFVR-S
-------------------------------REATGSGQQTLWRPE--GTQSAATLRILASMPSRTIGRSRGAIISQYYSRTMQLRCR-S-SRPLLGNFVR-S
-------------------------------QEATGSGQQTLRRPE--GTQSAATLRILASMPSRTIGRSRGAIISQYYSRTMQLRCR-S-SRPLLGNLVL-S
-------------------------------QEATGSGQQTLRRPE--GTQSAATLRILASMPSRTIGRSRGAIISQYYSRTMQLRCR-S-SRPLLGSFVL-S
-------------------------------QEATGSGQQTLRRPE--GTQSAATLRILASMPSRTIGRSRGAIISQYYSRTMQLRCR-S-SRPLLGNFVL-S
-------------------------------QEATGSGQQTLRRPE--GTQSAATLRILASMPSRTIGRSRGAIISQYYSRTMQLRCR-S-SRPLLGNFVL-S
-------------------------------QEATGSGQQTLRRPE--GTQSAATLRILASMPSRTIGRSRGAIISQYYSRTMQLRCR-S-SRPLLGDFVL-S
-------------------------------QEATGSGQQTLRRPE--GTQSAATLRILASMPSRTIGRSRGAIISQYYSRTMQLRCR-S-SRPLLGDFVL-S
-------------------------------QEATGSGQQTLRRPE--GTQSAATLRILASMPSRTIGRSRGAIISQYYSRTMQLRCR-S-SRPLLGDFVL-S
-------------------------------QEATGSGQQMLRRPE--GTQSAATLRILASMPSRTIGRSRGAIISQYYSRTMQLRCR-S-SRPLLGDFVL-S
```

FIG. 3A

```
                                       201
Aotus nancymaae                 (127) ARPSLRLYDLELDPRAQEEEEKQSLLVKELQSLAVAQRDHMLRGMPLSLAEKRSLREKSRTPRGKWRGQRGHG-GVCSCCGW
Saimiri boliviensis boliviensis (127) ARPSLRLYDLELDPRAQEEEEKQSLLVKELQSLAVAQRDHMLRGMPLSLAEKRSLREKSQTPRGKWRGQRGHG-GVCSCCGW
Callithrix jacchus              (124) ARPSLRLYDLELDPRAQEEEEKQSLLVRELQSLAVAQRDHMLRGMPLSLAEKRSLREKSRTPRGKWRGQRGHG-SIFSCCGW
Bubalus bubelis                 (133) ARPSLRLYDLELDSAVLEEEEKRGLLVKELQGLTAAQRDHMLRGMPLSLAEKRCLREEESRPPGKHRAQRHHG--LLSCCDQ
Camelus bactrianus              (109) ----------APTLVLEEEEKRVLLVKELQGLTVAQRDHVLRGMPLSLAEKRCLREESRTPRGKRRATQGGR-GLPSCCSQ
Camelus dromedaries             (133) ARPSLRLYDLELDPLVLEEEEKRVLLVKELQGLTVAQRDHVLRGMPLSLAEKRCLREESRTPRGKRRATQGGR-GLPSCCSQ
Vicugna pacos                   (21)  -----------------EEGKRVLLVKELQGLTVAQRDHVLRGMPLSLAEKRCLREESRTPRGKRRARQGGR-GLPSCCSQ
Dasypus novemcinctus            (128) ----SARRDLELDAAAAQEEEEKRGLLVKELQALPGAQRDHTLRGMPMSLAEKRCLREESPPATRRDQQGRG--GVSRGSR
Ceratotherium simum simum       (131) ARPSLRLYDLELDPMAFQEEEEKRILLVKELQGLTVAQRDHMLRGMPLSLAEKRSLREDSWIQKGKQRGPQQRR-GLFSCCSR
Equus caballus                  (144) ARPSLRLYDLELDPTAFQEEEKRTLCEGASG------------------CRLCPRDESWTQSQKQRGPQGRR-GLLPCCSR
Equus przewalskii               (144) ARPSLRLYDLELDPTAFQEEEKRTLLVKELQGLTVTQRDHMLRGMPLSLAEKRSLREESWTQSGKQRGPQQRR-GLFSCCSR
Felis catus                     (122) ARPSLRLYDLELDPAALEEEEKRSLLVKELQSLTVAQRGHMLKGMPLGLAEKRSLRSVPIGF-----GRPP---HPLPCWGL
Leptonychotes weddellii         (126) ARPSLRLYDLELDPAALQEEEKRFLLVKELEGLPVAQRNHMLRGMPLGLAEKRCLREETQTPKEKQRGRQGPH-GLFPCCGR
Odobenus rosmarus divergens     (182) ARPSLRLYDLELDPAALQEEEKRFLLVKELQGLPVAQRDHMLRGMPLGLAEKRCLREESQTPTGKQRGRQGPR-GLFPCCGR
Mustels putor furo              (131) ARPSLRLYDLELDPAALEEEEKRLLLVKELQGLPVAQRDHMLRGMPLGLAEKRCLREESRTPRGKRRGRPGR-GLLPCCGR
Chrysochloris asiatica          (123) ARPSLRSHDLELDPATREEEEKRGLLVRELQGLTVAQQDHMLREMPLSLAEKRCLRQESRTPRGKLRSQQDRH-GVCSFQCQ
Trichechus manatus latirostris  (136) ARPSLRSHDLELDPMAYQEEEEKRSLLVRELQGLTGAQRDHMLRRMPLSLAEKRCLREASETARETWRGQQGRR-GVWSCCSQ
Elephantulus edwardii           (131) ARPSLHGRDLELDPDIHQEEEEKRSLLVQELQGLSGTQQDHMLSAEKRCLREESQTPVGKRRGQQGPR-GVCSCCNR
Orycteropus afer afer           (129) ARPSLRSLDLELDPTAREEEEKRALLVTELQGLTGAQQDQLLRGMPLSLAEKRCLRQESRTPSGKQRGQQAQR-GVWSCCSR
Chinchilla lanigera             (133) ARPSLRLYDLELDPAALQEEEEKRSLLVKELQGLSAAQRDHMLRGMPLSLQEKRFLREKSRIPRGKQRGQQGCG--RVFYCSR
Heterocephalus glaber           (136) ARPSLRLYDLELDPADLEEEEKWSLLVKELQGLPVAQRDHMLRGMPLSLQEKRVLREKSRTPRGKQRGQHG--GVFSCSR
Cricetulus griseus              (125) ARPSLRLYDLELDHTVMEEDEKRSLLVKELQGLSMAQRDHMTRNMPLSLGEKRWLREKSWSPKGKQQGQKGRG--GTFSCSR
Mesocricetus auratus            (123) ARPSLRQYDLELDHTVLEEDEKRSLLVKELQGLPMAQRDHMVRNMPLSLGEKRWLREKSWSPKGNRRDQQGRG-RAISCCRR
Peromyscus maniculatus bairdii  (125) ARPSLRLYDLELDHTLLEDDEKRSLLVKELQGLSVAQRDHMVRNMPLNLGEKRWLREKSWSPKGKRRGQQGRG-GVFSCCTR
Microtus ochrogaster            (123) ARPSLRLYDLELDHTLLEEDEKRSLLVKELQGLSVAQRDHMVRNMPLSLGEKRWLREKSWSPKGKRRGQQDRG-GAFSCCSR
Mus musculus                    (123) ARPSLRLYDSELDSTLLEEDEKRSLLVKELQGLSAAQRDHMVRNMPLSLGEKRCLREKSWSPKGKRRHLQGRS-GAFSCCSR
Rattus norvegicus               (124) ARPSLRLYDSELDPTLLEEDEKRSLLVKELQGLSVAQRDHMVRNMPLSLGEKRWLREKSWSPKVKRRDQQGRRRGAFSCCSR
Jaculus jaculus                 (124) ARPSLRLYDSELDSTLLEEDEKRSLLVKELQGLSAAQRGHMLRGMPLSLAEKRWLREKSWGPSGKHKGHSGRG--GTFCCSR
Ictidomys tridecemlineatus      (129) ARPSLRLYDSELDPTLLEEDEKQGLLVKELQGLSVAQRDHMLRGMPLNLAEKRCLREKSQVQRGKRRARQDRG-GVTSCCSR
Marmota matmota marmot          (130) ARPSLRLYDLELGPRALEED-----------------------------------------------------
Galeopterus variegatus          (132) ARPSLRLYDSELDPAAGEEEEKLNLLVKELQGLSVAQRDHMLRGMPVNLAEKRLRDKSQTLRGMRRGQQHRG-GVCSCCGR
Otolemur garnettii              (127) ARPSLRLYDSELDPMAQEEEEKQNLLVKELQGLSAAQRDHMLRGMPLSLAEKRSLREKSQTSHRKWKGQSSRV-GVFSCCGR
Propithecus coquereli           (127) ARPSLRLYDSELDPMAQEEEEKRNLLVKELQGLSAAQRDHMLRGMPLSLGEKRGLREKSQTPHGKRRGQPGRV-GLFSCCGR
Tarsius syrichta                (126) ARPSLRLYDSELDPMARGEEEKQSLLVKELQGLSVAQRDHMLRGMPLSLAEKRCLREKSRTPRGERRGQQGHG-GGFSCCSR
Homo sapiens                    (124) AWPSLRLYDSELDPTALEEEEKQSLLVKELQGLAVAQRDHMLRGMPLSLAEKRSLREKSRTPRGKWRGQPGSG-GVCSCCGR
Pan paniscus                    (124) ARPSLRLYDSELDPTAREEEEKQSLLVKELQGLAVAQRDHMLRGMPLSLAEKRSLREKSRTPRGKWRGQPGSG-GVCSCCGR
Pan troglodytes                 (124) ARPSLRLYDSELDPMAREEEEKQSLLVKELQGLAVAQRDHMLRGMPLSLAEKRSLREKSRTPRGKWRGQPGSG-GVCSCCGR
Pongo abelii                    (124) ARPSLRLYDSELDPMAREEEEKQSLLVKELQGLAVAQRDHMLRGMPLSLAEKRSLREKSRTLRGKWRGQPGSG-GVCSCCGR
Nomascus leucogenys             (124) ARPSLRLYDSELDPVAREEEEKQSLLVKELQGLAVAQRDHMLRGMPLSLAEKRSLREKSRTLRGKWRGQPGSG-GVCSCCGR
Rhinopithecus roxellana         (124) ARPSLRLYDSELDPTAREEEEKQSLLVKELQGLAVAQRDHMLRGMPLSLAEKRSLREKSRTPTGKWRGQPGSG-GVCSCCGR
Chlorocebus sabaeus             (124) ARPSLRLYDSELDPTAREEEEKQSLLVKELQGLAVAQRDHMLRGMPLSLAEKRSLREKSRTPRGKWRGQPGSG-GVCSCCGR
Macaca fascicularis             (125) ARPSLRLYDSELDPTAREEEEKQSLLVKELQGLAVAQRDHMLRGMPLSLAEKRSLREKSRTPRGKWRGQPGSG-GVCSCCGR
Macaca mulatta                  (125) ARPSLRLYDSELDPTAREEEEKQSLLVKELQGLAVAQRDHMLRGMPLSLAEKRSLREKSRTPRGKWRGQPGSG-GVCSCCGR
Macaca nemestrina               (125) ARPSLRLYDSELDPTAREEEEKQSLLVKELQGLAVAQRDHMLRGMPLSLAEKRSLREKSRTPRGKWRGQPGSG-GVCSCCGR
Cercocebus atys                 (125) ARPSLRLYDSELDPTAREEEEKQSLLVKELQGLAVAQRDHMLRGMPLSLAEKRSLREKSRTPRGKWRGQPGSG-GVCSCCGR
Mandrillus leucophaeus          (125) ARPSLRLYDSELDPTAREEEEKQSLLVKELQGLAVAQRDHMLRGMPLSLAEKRSLREKSRTPRGKWRGQPGSG-GVCSCCGR
Papio Anubis                    (125) ARPSLRLYDSELDPTAREEEEKQSLLVKELQGLAVAQRDHMLRGMPLSLAEKRSLREKSRTPRGKWRGQPGSG-GVCSCCGR
```

FIG. 3B

```
                                                                                                                             400
----LRYACVLTLHSLGLALLSSLQALTPWRDALKRIGGQFGSSVLSYFLFLKTLLAFN------ALLLLLLL--AFIVGPQAAFPPAL--PGPVPVCTGLELLTGAG--CFTHTVMY
----LRYACVLTLHSLGLALLSSLQALTPWRYALKRIGGQFGSSVLSYFLFLKTLLAFN------ALLLLLLL--AFIVGPQAAFPPAL--PGPVPVCTGLELLTGAG--CFTHTVMY
----LRYACVLTLHSLGLALLSSLQALTPWRYALKRIGGQFGSSVLSYFLFLKTLLAFN------ALLLLLLL--AFMVGPQAAFPPAL--PGPVPVCTGLELLTGAG--CFTHTVMY
----LRDSCVLG---------------------------------------------------------------------------------------------------HFTHSVMY
----LQDSCVLALHNLGLVLLSGLQALKPWRYALKRIGGQFGSSVLSYFLFLKTLLAFN------ALLLLPLL--AFIVGVQAAFPPAP--PASVPAFTGLELLTGGG--RFAHTVLY
----LQDSCVLALHNLGLVLLSGLQALKPWRYALKRIGGQFGSSVLSYFLFLKTLLAFN------ALLLLPLL--AFIVGVQAAFPPAP--PASVPAFTGLELLTGGG--RFAHTVLY
----LQDSCVLALHNLGLVLLSGLQALKPWRYALKRIGGQFGSSVLSSSIFRSHDWVGGSWSCWWGLVPEPSSSHLWLVGTVLDRADLEWPVGTRRPPALGWRWGRG-------RVT
----LRYGCVLALHNLGLRLLSSLHALTPWRYALKPLWLLMPHAAGP-ATFLVSLPCFRGGGPGGSRMAWPST--ALPLGVPALCLLCPQDLGLVWAEALTRQACSPQG-SFSHTVMY
----LRYACVLALHNLGLVLLSGLQALTPWRYALKQIGGQFGSSVLSYFLFLKTLLAFN------ALLLLPLL--AFIVGVQAAFPPAPS--GSVPAFTGLELLTGGG--SPSHSAMY
----LRYACGLALHSLGLALLSALQALTPWRYALKQIGGQFGSSVLSYFLFLKTLLAFN------ALLLLPLL--AFIVGVQAAFPPAPS--GSVPTFTGLELLTGGG--RFSHSAMY
----LRYACGLALHSLGLALLSALQALTPWRYALKQIGGQFGSSVLSYFLFLKTLLAFN------ALLLLPLL--AFIVGVQAAFPPAPS--GSVPTFTGLELLTGGG--RFSHSAMY
TLLPFSPWCPQALHGLGLWLLAGLHGLKPWRYALKRIGGQFGSSVLSYFLFLKTLLAFN------ALLLLPLL--AFMVGVQAAFPPPAS-PGPVPAFTGLELLTGGG--RLTHTVMY
----LRDACVLALHNLGLGLLGGLHALRPWHYALKQIGGQFGSSVLSYFLFLKTLLAFN------ALLLLPLL--AFIVGVQAAFPPPAP-PGSVPSFTGLELLTGGG--RFTHTVLY
----LRDACVLALHSLGLGLLAGLHALRPWNRYALKQIGGQFGSSVLSYFLFLKTLLAFN------ALLLLPLL--AFIVGVQAAFPPPAP-PGSAPSFTGLELLTGGG--RFTHTVMY
----LRDACVLALHGLGLALLSGLLALVPWRYALKRIGGRFGSSALSYFLFLKTLLAFN------ALLLAAAA--ARLPGGRAGRLPAARLPGLCPQLHGPGAAHGRGQLQLHCPVLR
----LKYGCVLTLHNLGLGLLSSLHALVPWHYALKQIGGQFGSSVLSYFLFLKTLLAFN------ALLLLPLL--AFIVGVQAAFPPTS--PSPTPTFTGLELLIGGG--SFTHTVMY
----LKYGCVLALHNLGLGLLSGLHALTPWHYALKQIGGQFGSSVLSYFLFLKTLLAFN------ALLLLPLL--AFIVGVQAAFPPSP--PHPTPAFTGLELLTGGG--YFTHTVMY
----LKYSCVLALHSMGLVLLSGLNSLTPWHYALKQIGGQFGSSVLSYFLFLKTLLAFN------ALLLLPLL--AFIVGVQAAFPPTP--LHPTPTFTGLELLTGGG--YFTHTVMY
----LKYGCVLAFHNLGLGLLSGLSALTPWHYTLKRIGGQFGSSVLSYFLFLKTLLASN------ALLLLPLL--AFIVGVQAAFPPTP--RGPAPTFTGLELLTGAG--YFTHTVMY
----LRYTCALALHSLGLALLTRLHALKPWRYALKQIGGLFGSSVLSYFLFLKTLLAFN------ALLLLPLV--AFLMAVQAAFPP-E--AHPVPRCTGLELLTGGG--CFTHTVMY
----LRYTCALALHSLGLVLLTCLHALRPWNRYALKQIGGGFGSSVLSYFLFLKTLLAFN------MLLLLPLV--AFLMAVQAAFPP-E--AHPVPRCTGLELLTGGG--CFTHTVMY
----LRYSCILALHSLGLVLLSGLYAARPWRYALKQIGGGFGSSVLSYFLFLKTLLAFN------ALMLLPLL--AFLVGVQAAFPPDP--SGLVPTFSGLELLTGRG--CFTHTVMY
----LRYACILALHSLGLMLLSGLYAARPWRYALKQIGGGFGSSVLSYFLFLKTLLAFN------ALMLLPLL--AFLVGVQAAFPPDP--SGPVPAFSGLELLTGGG--SFTHTVMY
----LRYSCILALHSLGLVLLSGLYAARPWRYALKQIGGGFGSSVLSYFLFLKTLLAFN------TLMLLPLL--AFLVGVQAVFPPDP--AGPVPTFSGLELLTGGG--WETHTVMY
----LRYSCILALHSLGLVLMSGLYAARPWRYALKQIGGGFGSSVLSYFIFLKTLLAFN------VLMLLPLL--GFLVGVQAAFPPDP--PDPVPTCSGLELLTGRG--CETHTVMY
----LRYTCMLALHSLGLALASGLYAARPWRYALKQIGGGFGSSVLSYFLFLKTLLAFN------ALMLLPLL--AFLVGVQAAFPPDP--AGPVPTFSGLELLTGGG--RETHTVMY
----LRYTCMLALHSLGLALASGLYAARPWRYALKQIGGGFGSSVLSYFLFLKTLLAFN------TLMLLPLL--AFLVGVQAAFPPDP--AGPVPTFSGLELLTGGG--WETHTVMY
----LRYSCILALHSLGLALASGLHAARPWRYTLKQISGGFGSSVLSYFLFLKTLLAFN------ALLLLPLL--AFLAGVQAAFPPAP--RGPAPAFSGLELLTGGG--YFAHTVMY
----LRYACILALHSLGLALASGLHAVRPWHHTLKQIGGGFGSSVLSYFLFLKTLLAFN------ALLLLLPL--GFLVGVQAAFPPGP--PDPAPAFTGLELLTGGG--CFAHTVMY
-------------------------------------------------------------------------------------------------------------
----LGYACVLASHSLGLVLLSGLHALAPWRFALKQIGGGFGSSVLSYFLFLKTLLVFN------ALLLLLLL--AFIVGPQAAFPQGP---VPT-AFMGLELLTGGG--GFAHTVMY
----LGYACILTSRSLGLTLLSGLQATPWHYTLKRIGGQFGSSVLSYFLFLKTLVAFN------GLLLLPLL--AFMVGVQAAFPPDPG-PGSGPACTGLELLTGAG--CFTHTVMY
----LRYACVLALHSLGLALLSGLHALTPWRYALKRIGGQFGSSVLSYFLFLKTLMAFN------ALLLLPLL--AFMVGVQAAFPPDPG-PGPRPTCTGLELLTGAG--CFTHTVMY
----LRYACILALHSLGVALLSRLHALMPWNRYALKQIGGQFGSSVLSYFLFLKTLLAFN------ALLLLPLL--AFIVGAQAAFPAAP--SATASACTGLELLTGT---------MR
----LRYACVLALHSLGLALLSALQALTPWNRYALKRIGGQFGSSVLSYFLFLKTLVAFN------ALLLLLLV--AFIMGPQVAFPPAL--PGPAPVCTGLELLTGAG--CFTHTVMY
----LRYACVLALHSLGLALLSALQALMPWRYALKRIGGQFGSSVLSYFLFLKTLVAFN------ALLLLLLV--AFIMGPQVAFPPAL--PGPAPVCTGLELLTGAG--CFTHTVMY
----LRYACVLALHSLGLALLSALQALMPWRYALKRIGGQFGSSVLSYFLFLKTLVAFN------ALLLLLLV--AFIMGPQVAFPPAL--PGPAPVCTGLELLTGAG--CFTHTVMY
----LRYACVLALHSLGLALLSALQALTPWRYALKRIGGQFGSSVLSYFLFLKTLVAFN------ALLLLLLV--AFITGPQVAFPPA---LGPVPVCTGLELLTGAG--CFTHTVMY
----LRYACVLALHSLGLALLSALQALTPWRYALKRIGGQFGSSVLSYFLFLKTLVAFN------ALLLLLLV--AFIMGPQVAFPPTL--PGPAPVCTGLELLTGAG--CFTHTVMY
----LRYACVLALHSLGLALLSGLQALTPWRYALKRIGGQFGSSVLSYFLFLKTLVAFN------ALLLLLLV--AFIMGPQVAFLPTL--PGPAPVCTGLELLTGAG--CFTHTVMF
----LRYACVLALHSLGLALLSGLQALTPWRYALKRIGGQFGSSVLSYFLFLKTLVAFN------ALLLLLLV--AFIMGPQVAFPPAL--PGPAPICTGLELLTGAG--CFTHTVMF
----LRYACVLALHSLGLALLSGLQALTPWRYALKRIGGQFGSSVLSYFLFLKTLVAFN------ALLLLLLV--AFIVGPQVAFPPAL--PGPAPICTGLELLTGAG--CFTHTVMF
----LRYACVLALHSLGLALLSGLQALTPWRYALKRIGGQFGSSVLSYFLFLKTLVAFN------ALLLLLLV--ACIVGPQVAFPPAL--PGPAPICTGLELLTGAG--CFTHTVMF
----LRYACVLALHSLGLALLSGLQALTPWRYALKRIGGQFGSSVLSYFLFLKTLVAFN------ALLLLLLV--AFIVGPQVAFPPAL--PGPAPICTGLELLTGAG--CFTDTVMF
----LRYACVLALHSLGLALLSGLQALTPWRYALKRIGGQFGSSVLSYFLFLKTLVAFN------ALLLLLLV--AFIVGPQVAFLPAL--PGPAPICTGLELLTGAG--CFTHTVMF
```

FIG. 4A

```
                                           401
Aotus nancymaae                  (310) YGHYSNATLNQPCGGPLEGGRCSPRAGGLPYNMPLAYLFTVGVGFFITCISLVYSMAHSFGESYRVDSTSGIHAITVFCSW
Saimiri boliviensis boliviensis  (310) YGHYSNATLNQPCGGPLEGGRCSPRASGLPYNMPLAYLFTVGVGFFITCITLVYSMAHSFGESYRVGSTSGIHAITVFCSW
Callithrix jacchus               (307) YGHYSNATLNQPCAGPLEGGRCSPGAGSLPYNMPLAYLFTVGVGFFITCITLVYSMAHSFGESYRVGSTSGIHAITVFCSW
Bubalus bubelis                  (229) YGYYSNATLNQPCASPLDGSQCTPEAGSLPYSMPLAYLFTLGAAFFITCITLVYSMSHSFGESYRVGSTSGVHAITVFCSW
Camelus bactrianus               (281) Y-----------------DQCPPEAGGLPYNMPLAYLFTVGVAFFITCITLVYSMSRSFGESYRVGSTSGVHAISVFCSW
Camelus dromedaries              (316) YGYYSNATLNQPCASPPDGGQCPPEAGGLPYNMPLAYLFTVGVAFFITCITLVYSMSRSFGESYRVGSTSGVHAISVFCSW
Vicugna pacos                    (191) GGP-SSTGWAPPSGCWMLAAQSIRGVLSAPSAPTQSLLGSASP-----------SMSRSFGESYRVGSTSGVHAISVFCSW
Dasypus novemcinctus             (314) YGYYSNATLNQPCEPAQDGGQCAPGAGGLPYSMPLAYLFTLGVAFFITCITLVYSMSRSFGESYRVGSTLGAHAVAVFCSW
Ceratotherium simum simum        (314) YGYYSNATLNQPCSPRPDGGQCTPDAGGLPYNMPLAYLFTMGVAFFITCITLVYSMSHSFGESYRVGSTSGVHAITVFCSW
Equus caballus                   (308) YGYYSNTTLNQLCGPPLDGSQCTPEAGGLPYNMPLAYLFTMGMSFFITCITLVYSMSRSFGESYRVGSTSGVHAITVFCSW
Equus przewalskii                (327) YGYYSNTTLNQLCGPPLDGSQCTPEAGGLPYNMPLAYLFTMGMSFFITCITLVYSMSRSFGESYRVGSTSGVHAITVFCSW
Felis catus                      (303) YGYYSNSTLNPPCVPAPDGGQCGRETDGLPYNMPLAYLFTVGGAFFITCITLVYSMSHSFGESYRVGSTSGVHAITVFCSW
Leptonychotes weddellii          (310) YGYYSNSTVSQPCVPPSGGGQCSRETDSLPYSMPLAYLFTVGLAFFITCITLVYSMSHSFGESYRVGSTSGVHAMTVFCSW
Odobenus rosmarus divergens      (366) YGYYSNSTLNQPCAPPLAGGQCSREAAGLPYSMPLAYLFTVGLAFFITCITLVYSMSHSFGESYRVGSTSGVHAMTVFCSW
Mustels putor furo               (318) LGYYSNSSLTRPCALPP-GGPCGREAESLPYNMPLAYLFTVGVAFFITCITLVYSMSHSFGESYRVGSASGVHAMTVFCSW
Chrysochloris asiatica           (306) YGYYSNTTVNQQCALPGDGSHCISGAGGLPYNMPLAYLFTMGMAFFITCITLVYSMSHSFGESYRVGSTSGIHAITIFCSW
Trichechus manatus latirostris   (319) YGYYSNTTLNQQCAPPLDGNQCTRGEGGLPYSMPLAYLFTMGVAFFITCITLVYSMSHSFGESYRVGSTSGIHAITVFCSW
Elephantulus edwardii            (314) LGYYSNITLNQPCAPPLEGSQCTPGARGLPYNMPLAYLFTMGTAFFITCITLVYSMSRSFGDSYRVGSTLGVHAITVFCSW
Orycteropus afer afer            (312) YGYYSNFTLNQPCTHPPDGAQCTPGAGDLPYNMPLAYLFTMGAIFFTTGITLVYSMSRSFGESYRVGSTLGIHAITVFCSW
Chinchilla lanigera              (314) YGYYRNTMLNTPCSSPQ----CSPGAGSLPYNMPVAYLFTVGATFFITCITLVYSMSHSFGESYRVGSTKGVHAITVFCSW
Heterocephalus glaber            (317) YGYYSNTTLNTPCGPLQ----CGPRAGSLPYSMPLAYLFTVGAAFFITCITLVYSMSHSFGESYRVGSTKGIHAITVFCSW
Cricetulus griseus               (307) YGYYSNTTLSQSCASPRETG-----QDSLPYNMPLAYLFTVGAAFFITCITLVYSMSHSFGESYRVGSTKGIHALTVFCSW
Mesocricetus auratus             (306) YGYYSNTTLSQSCGSPRESGQCSPRLGSLPYDMPLAYLFTVGAAFFITCITLVYSMSHSFGESYRVGSTKGIHALTVFCTW
Peromyscus maniculatus bairdii   (308) YGYYSNTTLSQSCASPWESGQCSPRLGSLPYNMPLAYLFTVGAVFFMTCITLVYSMSHSFGESYRVGSTKGIHALMVFCTW
Microtus ochrogaster             (306) YGYYSNSTLSQSCDSSRDSGRCSPGSGSLPYNMPLAYLFTVGAAFFITCITLVYSMSHSFGESYRVGSTKGIHALTVFCTW
Mus musculus                     (306) YGYYSNSTLSPSCDAPREGGQCSPRLGSLPYNMPLAYLFTMGATFFLTCIILVYSMSHSFGESYRVGSTKGIHALTVFCTW
Rattus norvegicus                (308) YGYYSNTTLRQSCASAREGGLCSPRLGSLPYNMPLAYLFTVGAAFFITCIVLVYSMSHSFGESYRVGSTKGIHALTVFCTW
Jaculus jaculus                  (306) YGYYSNATLSQPCAAPQDSGHCSSRAGSLPYSMPLAYLLTVGAVFFTTCITLVYSMSHSFGESYRVGSTKGVHALTVFCTW
Ictidomys tridecemlineatus       (312) YGYYSNATLSQSCVPPRDGHQCSPGASSLPYNMPLAYLFTMGAAFFITCISLVYSMAHAFGESYRVGSTKGVHALTVFCTW
Marmota matmota marmot           (150) --------------------------------------------------------------------------------
Galeopterus variegatus           (313) YGYYSNATLNQPCAPQPNGSQCTPRAGSLPYNMPLAYLFTVGAAAFITCITLVYSMSHSFGESYRVGSTSGVHAITAFCSW
Otolemur garnettii               (311) YGYYSNATMGWPCDHPLEGGPCRPRAGGLSYHMPLAYLFTLGVAFFMTCITLVYSMAAFGESYRVGSTSGVHALTVFCSW
Propithecus coquereli            (311) YGYYSNATLNQPCGQPLEGGGCRPRAGGLPYNMPLAYLFTVGVAFFITCITLVYSMAHAFGESYRVGSTSGVHAITVFCSW
Tarsius syrichta                 (302) --------S-----CPLTGDQCTPRVGGLPYNMPLAYLFTMGVAFFITCIALVYSMAHSFGESYRVGSTSGVHAITAFCSW
Homo sapiens                     (307) YGHYSNATLNQPCGSPLDGSQCTPRVGGLPYNMPLAYLSTVGVSFFITCITLVYSMAHSFGESYRVGSTSGIHAITVFCSW
Pan paniscus                     (307) YGHYSNATLNQPCGSPLDGSQCTPRVGGLPYNMPLAYLSTVGVSFFITCITLVYSMAHSFGESYRVGSTSGIHAITVFCSW
Pan troglodytes                  (307) YGHYSNATLNQPCGSPLDGSQCTPRVGGLPYNMPLAYLSTVGVSFFITCITLVYSMAHSFGESYRVGSTSGIHAITVFCSW
Pongo abelii                     (307) YGHYSNATLNQPCGSPLDGSQCTPRVGGLPYNMPLAYLSTVGVSFFMTCITLVYSMAHSFGESYRVGSTSGIHAITVFCSW
Nomascus leucogenys              (307) YGHYSNATLNQPCGSPLDGSQCTPRVGGLPYNMPLAYLSTVGMSFFITCITLVYSMAHSFGESYRVGSTSGIHALTVFCSW
Rhinopithecus roxellana          (307) YGHYSNATLNQPCGSPLDGSQCTPRVGGLPYNMPLAYLVTVGAGFFITCITLVYSMAHSFGESYRVGSTSGIHAITVFCSW
Chlorocebus sabaeus              (307) YGHYSNATLNQPCGSPLDGSQCTPRVGGLPYNMPLAYLYTVGAGFFISCITLVYSMAHSFGESYRVGSTSGIHAITVFCSW
Macaca fascicularis              (308) YGHYSNATLNQPCGSPLDGSQCTPRVGGLPYNMPLAYLYTVGAGFFITCITLVYSMAHSFGESYRVGSTSGIHAITVFCSW
Macaca mulatta                   (308) YGHYSNATLNQPCGSPLDGSQCTPRVGGLPYNMPLAYLYTVGAGFFITCITLVYSMAHSFGESYRVGSTSGIHAITVFCSW
Macaca nemestrina                (307) YGHYSNATLNQPCGSPLDGSQCTPRVGGLPYNMPLAYLYTVGAGFFITCITLVYSMAHSFGESYRVGSTSGVHAITVFCSW
Cercocebus atys                  (308) YGHYSNATLNQPCGSPLDGSQCTPRVGGLPYNMPLAYLYTVGAGFFITCITLVYSMAHSFGESYRVGSTSGIHAITVFCSW
Mandrillus leucophaeus           (307) YGHYSNATLNQPCGSPLDGSQCTPRVGGLPYNMPLAYLVTVGAGFFITCITLVYSMAHSFGESYRVGSTSGIHAITVFCSW
Papio Anubis                     (308) YGHYSNATLNQPCGSPLDGSQCTPRVGGLPYNMPLAYLYTVGAGFFITCITLVYSMAHSFGESYRVGSTSGIHAITVFCSW
```

FIG. 4B

```
                                                                                                              600
DCKVTQKRASRLQQDNIRTRLKELLAEWQLRQGP--RSVCRRLRQAAALG---------LVWLLCLGTALGCAVAVHVFSEFMIQS--------------------------
DYKVTQKWASRLQQDNIRTRLKELLAEWQLRQSP--RSVCRRLRQVATLG---------LVWLLCLGTALGCAVAVHVFSEFMIQS--------------------------
DYKVTQKRASRLQQDNIRTRLKELLAEWQLRQSP--RSVCRRLRQAAALG---------LTWLLCLGTALGCAVAVHVFSEFMIQS--------------------------
DYKVTQRWATRLQHDNIRTQLKELLAEWQSRQHR--RSVCGQLRRVAVLG---------LVWLLCLGTTLGCTLAVYTFSELMIKVQRGRGRPPRRPGPPALLAGTLGLPHPPPRPPP
DYKVTQKWASRLQHDNIRTQLKELLAVWQLRQGP--RSMCWRLRRVAVLG---------LVWLLCLGITLGCTLAVYTFSELMIKS--------------------------
DYKVTQKWASRLQQDNIRTQLKELLAVWQLRRGP--RSMCWRLRRVAVLG---------LVWLLCLGTTLGCTLAVYTFSELMIKS--------------------------
DYKVTQKWASRLQHDNIRTQLKVSCRGWGLRPPPPPRSRGHQCASAPVGDGSPPLLPPWDPALRLPPQWTRPCPLGPCGDTAPPLLX--------------------------
DYKVTQKWASRLQHDNIRTQLKELLAEWQVRRDP--RSVQALRRAALLG---------LGWLLCLGTVLGCAVAVYAFSES-------------------------------
DYKVTQKWASRLQQDNIRTQLKELLAEWQLQQGP--QSMCWRLRRVAVLG---------LVWLLCLGTTLGCTMAVYTFSELMIKS--------------------------
DYKVTQKWPSRLQQDNIRTQLKELLAEWQLQQGP--RSMCWRLRRVATLG---------FVWLLCLGTTLGCTLAVYTFSELMIKN--------------------------
DYKVTQKWPSRLQQDNIRTQLKELLAEWQLQQGP--RSMCWRLRRVATLG---------FVWLLCLGTTLGCTLAVYTFSELMIKN--------------------------
DHKVTQRRASRLGHDNIRTHLKELLAEGQLRRGP--RSMCCRLRRVAVLG---------LVWLLCLAITLGCTVAVYTFSELMIQS--------------------------
DHKVTQRRASRLQHDNIRTHLKELLAEWQRRQGS--QSACGRLRRVAVRG---------LVWLLSLAITLGCTVAVYTFSELMIKS--------------------------
DHKVTQRRASRLQHDNIRTHLKELLAEWQRRRGS--RSACGRLRWVAVRG---------LVWLLSLAITLGCTVAVYAFSELMIKS--------------------------
DHKVTQRRASRLQCDNIRTHLKELLAERQRRQGP--RSACGRLRHVAVLG---------LVWLLCLAITVGCTMAVYAFSELMIKS--------------------------
DYKVTQKWASRLGQDNLRTQLKELLAEWQLRQGP--WNLCGRLRRVAVLG---------LVWLLCLAITLGCTVAVYTFSEFLIQS--------------------------
DHKVTQRWASRLGQNNLRTHLKELLAEWQLRLVP--RSMWGGLKRVAVRG---------LVWLLSLVTTMGCAMAVYTFSELMIQS--------------------------
DHKVTQDWATILGQNNLHTHLKEMLAEWQLQRVP--RSVCGRLRRVAVLG---------LVWLLCLGTTMGCAVAVYTFSEHMIQS--------------------------
DYKVTQKWASRLQQDNLRTQLKELLAEWQLRQRP--RSVCGRLRRAAVLL---------LVWFLCLATVLGCAVGMYTFSELMIQS--------------------------
DYKVTQKWASRLQRDNIRTQLKELLAEWRLRRSP--QSVCGRLRQVTVLA---------LVWLLCLGVALGCAVAVLTFSEVTIQS--------------------------
DYKVTQNWASRLQRDNICTQLKELLAEWRLCKGS--QSTCGRLRRAAVLA---------LVWLLSLAAVLGCAVAVLTFSELRIQS--------------------------
DYKVTQKRASRVGRDSICTQLKELLAEWQRERP--QSACGRLWQAAMLG---------LGWLLCLGTTMGCAAAVLTFSEVMIQR--------------------------
DYKVTQKRASRVQQDSICTQLKELLAEWQRERP--QSACGRLWQVAMLG---------LGWLLCLGATVGCAVAVLTFSEVMIQR--------------------------
DYKVTQKRASRVQQDSICTQLKELLAEWQRKRP--RSACGRLWQVVVLG---------LGWLLCLGTTMGCAVAVLTFSEVMVQR--------------------------
DYKVTQKRASRVQQDSICTKVLLAVWQLQKHP--RSACGRLWQAAMLA---------LGGLLCLGTTVGCAAAVFTFSEVMMQR--------------------------
DYKVTQKRASRVQQDSICTQLKELLAEWHLRKRP--QSVCGQLRQVVVLG---------LGWLLCLGSTMGCTVAVLTFSEVMIQR--------------------------
DYKVTQKRASRVQQDSIRTQLKELLAEWQLRKRP--RSVCGQLRQVVVLG---------LGWLLCLGSTVGCTVAVLTFSETMIQR--------------------------
DYKVTQKRASRVQQDNICTQLKELLSEWQLRKCP--QSTCGRLRQVVVLG---------LVWLLCGSTTMGCAVAVLTFSEVMIQR--------------------------
DYKVTEKRASRLQQDNIRTQLKELLAEWQLHRSP--QSLRGRLRQAVLLG---------LAWLLCLGSMLGCSVAVLVFSEVMIQR--------------------------
------------------------G--DALQ---------------------------------------------------------------------------------S
DYKVTQKWASRLQHDNIRTRLKELLAAWQLQQEP--RSMCGRLRQVAVLV---------LVWLLCLGTTLGCAAAVFNFSEVMLES--------------------------
DYKVTQKRAVRLQHGNIRTRLKS------------CGLCWRLQQAAVLG---------LVWLLCLGVVLGCAVAVYTFSELVIQG--------------------------
DYKVTQKRASRLQHDNIRTRLKELLAEWQLRQST--RSLCGRLQQAAVLG---------LVWLLCLGTVSGCAAAVHAFSEFMIQG--------------------------
DYKVTQKRASRLQHDSVRTRLKELLAEWRLRQEP--RSVCGKMRQAAVLG---------IVWLLCLGTVLGCAVAVHAFSELMLQG--------------------------
DYKVTQKRASRLQQDNIRTRLKELLAEWQLRHSP--RSVCGRLRQAAVLG---------LVWLLCLGTALGCAVAVHVFSEFMIQG--------------------------
DYKVTQKRASRLQQDNIRTRLKELLAEWQLRHSP--RSVCGRLRQAAVLG---------LVWLLCLGTALACAVAVHVFSEFMIQG--------------------------
DYKVTQKRASRLQQDNIRTRLKELLAEWQLRHSP--RSVCGRLRQAAVLG---------LVWLLCLGTALACAVAVHVFSEFMIQG--------------------------
DYKVTQKRASRLQQDNIRTRLKELLAEWQLRHSP--RSVCGLLRQAAVLG---------LVWLLCLGTALACAVAVHVFSEFMIQG--------------------------
DYKVTQKRASRLQQDNIRTRLKELLAEWQLRHSP--RSVCGLLRQAAVLG---------LVWLLCLGTALACAVAIHVFSEFMIQG--------------------------
DYKVTQKRASRLQQDNIRTRLKELLAEWQLRHSP--RSVCGLLRQAAVLG---------LVWLLCLGTALACAVAHVFSEFLIQG--------------------------
DYKVTQKRASRLQQDNIRTRLKELLAEWQLRHSP--RSVCGRLRQAAVLG---------LVWLLCLGTALACAVAIHVFSEFLIQG--------------------------
DYKVTQKRASRLQQDNIRTRLKELLAEWQLRHSP--RSVCGRLRQAAVLG---------LVWLLCLGTALACAVAIHVFSEFLIQG--------------------------
DYKVTQKRASRLQQDNIRTRLKELLAEWQLRHSP--RSVCGRLRQAAVLG---------LVWLLCLGTALACAVAIHVFSEFLIQG--------------------------
DYKVNQKRASRLQQDNIRTRLKELLAEWQLRHSP--RSVCGRLRQVAALG---------LVWLLCLGTALACAVAIHVFSEFLIQG--------------------------
DYKVNQKRASRLQQDNIRTRLKELLAEWQLRHSP--RSVCGRLRQAAALG---------LVWLLCLGTALACAVAIHVFSEFLIQG--------------------------
DYKVNQKRASRLQQDNIRTRLKELLAEWQLRHSP--RSVCGRLRQAVALG---------LVWLLCLGTALACAVAIHVFSEFLIQG--------------------------
```

FIG. 5A

```
                                            601
Aotus nancymaae                    (466) ----------------------------------------------------------------
Saimiri boliviensis boliviensis    (466) ----------------------------------------------------------------
Callithrix jacchus                 (463) ----------------------------------------------------------------
Bubalus bubelis                    (417) EDTFLPVLVLILVLSNAINTSFCFLVFWFLFSLFFRHLCSILPSPPPAPLPVRFEHRAWGGGGVPAICTCSVPPRPLPAAPS
Camelus bactrianus                 (419) ----------------------------------------------------------------
Camelus dromedaries                (472) ----------------------------------------------------------------
Vicugna pacos                      (347) ----------------------------------------------------------------
Dasypus novemcinctus               (466) ----------------------------------------------------------------
Ceratotherium simum simum          (470) ----------------------------------------------------------------
Equus caballus                     (464) ----------------------------------------------------------------
Equus przewalskii                  (482) ----------------------------------------------------------------
Felis catus                        (459) ----------------------------------------------------------------
Leptonychotes weddellii            (466) ----------------------------------------------------------------
Odobenus rosmarus divergens        (522) ----------------------------------------------------------------
Mustels putor furo                 (473) ----------------------------------------------------------------
Chrysochloris asiatica             (462) ----------------------------------------------------------------
Trichechus manatus latirostris     (475) ----------------------------------------------------------------
Elephantulus edwardii              (470) ----------------------------------------------------------------
Orycteropus afer afer              (468) ----------------------------------------------------------------
Chinchilla lanigera                (466) ----------------------------------------------------------------
Heterocephalus glaber              (469) ----------------------------------------------------------------
Cricetulus griseus                 (458) ----------------------------------------------------------------
Mesocricetus auratus               (462) ----------------------------------------------------------------
Peromyscus maniculatus bairdii     (464) ----------------------------------------------------------------
Microtus ochrogaster               (462) ----------------------------------------------------------------
Mus musculus                       (462) ----------------------------------------------------------------
Rattus norvegicus                  (464) ----------------------------------------------------------------
Jaculus jaculus                    (462) ----------------------------------------------------------------
Ictidomys tridecemlineatus         (468) ----------------------------------------------------------------
Marmota matmota marmot             (156) ----------------------------------------------------------------
Galeopterus variegatus             (469) ----------------------------------------------------------------
Otolemur garnettii                 (456) ----------------------------------------------------------------
Propithecus coquereli              (467) ----------------------------------------------------------------
Tarsius syrichta                   (445) ----------------------------------------------------------------
Homo sapiens                       (463) ----------------------------------------------------------------
Pan paniscus                       (463) ----------------------------------------------------------------
Pan troglodytes                    (463) ----------------------------------------------------------------
Pongo abelii                       (463) ----------------------------------------------------------------
Nomascus leucogenys                (463) ----------------------------------------------------------------
Rhinopithecus roxellana            (463) ----------------------------------------------------------------
Chlorocebus sabaeus                (463) ----------------------------------------------------------------
Macaca fascicularis                (464) ----------------------------------------------------------------
Macaca mulatta                     (464) ----------------------------------------------------------------
Macaca nemestrina                  (464) ----------------------------------------------------------------
Cercocebus atys                    (464) ----------------------------------------------------------------
Mandrillus leucophaeus             (463) ----------------------------------------------------------------
Papio Anubis                       (464) ----------------------------------------------------------------
```

FIG. 5B

```
                                                                                                                    800
-----------------------PETAGQEAALLVLPLVVGLLNLGAPYLCRILAALERHDSPVLEVYMAICR--------------------------NLILKL
-----------------------LEAAGQEAALLVLPLVVGLLNLGSPYLCRILAALERHDSPVLEVYVAICR--------------------------NLILKL
-----------------------LEAAGKEAALLVLPLVVGLLNLGAPYLCRILAALERHDSPVLEVYVAICR--------------------------NLILKM
PPRSGPAVDLTLSLGPLRGRPLPRPAPPQQSPVSAKREAVLLLLPLVVCLLNLGGPYLFRILAALERHDSPVLEVYVAICR--------------------------NLILKM
-----------------------PGSTEREGALLALPLVVCLLNLGAPYLYRGLAALERHDSPVLEVYVAICR--------------------------NLILKM
-----------------------PGSTEREGALLALPLVVCLLNLGAPYLYRGLAALERHDSPVLEVYVAICR--------------------------NLILKM
-----------------GSPGSTEREGALLALPLVVCLLNLGAPYLYRGLAALERHDSPVLEVYVAICR--------------------------NLILKM
----------------------------------------MIQCR--------------------------NLILKM
-----------------------PVSAEREWELLALPLVVCLLNLGAPYLYRGLAALERHDSPMLEVYVAICR--------------------------NLILKM
-----------------------PVSAEREWELLALPLVVCLLNLGAPYLYRGLAALERHDSPILEVYVAICR--------------------------NLILKM
-----------------------PVSAEREWELLALPLVVCLLNLGAPYLYRGLAALERHDSPILEVYVAICRCVTRWGRWAFLGQGLCLPGAPPSASTPLVLCRNLILKM
-----------------------PVSAEQGGALLALPMVVCLLNLGAPYLYRGLAALERHDSPVLXXXXXXXRP--------------------------NLILKM
-----------------------PVSVEQEGALLALPMVVCLLNLGAPYLFRCLAALERHDSPVLEVYVAVCR--------------------------NLILKM
-----------------------PVSAEQEGALLALPMVVCLLNLGAPYLFRCLAALERHDSPVLEVYVAVCR--------------------------NLILKM
-----------------------PVSADQEGALLALPMVVCLLNLGAPYLFRCLAALERHDSPVLEVYLAICR--------------------------NLIFKM
-----------------------PVATGQVG-LLVLPLMVSVTNLVAPYLYRMLAALEQHESPVLEVYVAICR--------------------------NLILKV
-----------------------PVATSQEAALLTLPLVVSLINLVAPYLYRGLAALEQHESPVLEVYVAICR--------------------------NLILKM
-----------------------PLAAGQEAALLSLPLVVSLINLVAPYLFRGLASLEQHESPVQEVYVAICR--------------------------NLILKM
-----------------------PVATGQEVGLLVLPLVVSLANLLVPYLYRLLATLERHESPVLEVYVAVCR--------------------------NLLLKA
-----------------------PAAAGREAGLLVLPMVVCLLNLAAPYLFRGLATLEQHDSPVLEVYLAVCR--------------------------NLILKM
-----------------------PVVADQEAGLLVLPLVICLLNLGAPYLFRGLATLERHDSPVLEVYVAIGR--------------------------NLMLKT
-----------------------PDADGQGVELLALPLVVSLLNLGASYLFRGLATLERHDSPVLEVYMAICR--------------------------SLILKM
-----------------------PTAGGQGVELLALPLVVSLLNLGASYLFRGLATLERHESPVLEVYMAICR--------------------------SLILKM
-----------------------SAAGGQGLELLALPLVVSVLNLGASYLFRGLATLERHDSPVLEVYMAICR--------------------------SLILKM
--------------------------GQGVELLALPLVVSALNLGASYLFCGLATLERHDSPVLEVYMAICR--------------------------SLILKT
-----------------------PASGGQGVEALALPLVVSVLNLGASYLFRGLATLERHDSPVLEVYMAICR--------------------------NLILKM
-----------------------PASGGQGLEMLALPLVVSVLNLVASYLFRGLAALERHDSPVLEVYMAICR--------------------------NLILKM
-----------------------SPAGQEVGLLALPLVVSVLNLGASYLFRGLAALERHESPVLEVYVAICR--------------------------NLILKM
-----------------------PVSAGQEARLLALPLVVSLLNLGASYLFRGLAALERHESPGLEVYVAICR--------------------------NLILKM
-----------------------PVSAGQEARLLALPLVVSLLNLGASYLFRGLAALERHESPGLEVYVSICR--------------------------NLILKM
-----------------------PVAAGQEAALLALPLVVCLLHLAAPYLYRGLAALERHGSPVLEVYMAIFR--------------------------NLMLKM
-----------------------PVAAGQEVTLLALPLVVCLLNLMAPYLYRGLATLEPHDSPVLEVYVAICR--------------------------NLILKT
-----------------------PVAAGQEVALLALPMVVCLLNLGAPYLYRGLAALEPQDSPVLEVYVAICR--------------------------NLMLKM
-----------------------PVVAGREVALLALPLVVSLLNLGAPYLCRGLAALEQHDSPVLEVYVAVCR--------------------------NLILKM
-----------------------PEAAGQEAVLLVLPLVVGLLNLGAPYLCRVLAALEPHDSPVLEVYVAICR--------------------------NLILKL
-----------------------PEAVGQEAVLLVLPLVVGLLNLGAPYLCRVLAALEPHDSPVLEVYVAICR--------------------------NLILKL
-----------------------PEAVGQEAALLVLPLVVGLLNLGAPYLCRVLAALEPHDSPVLEVYVAICR--------------------------NLILKL
-----------------------PEAAGQEAALLVLPLVVGLLNLGAPYLCRVLAALEPHDSPVMEVYVAICR--------------------------NLILKL
-----------------------PEAAGQEAALLVLPLVVGLLNLGAPYLCRVLAALEPHDSPVLEVYVAICR--------------------------NLILKL
-----------------------PEAAGQEAALLVLPLVVGLLNLGAPYLCRVLAALEPHDSPVLEVYVAICR--------------------------NLILKL
-----------------------PEAAGQEASLLVLPLVVGLLNLGAPYLCRVLAALEPHDSPVLEVYVAICR--------------------------NLILKL
-----------------------PEAAGQEAALLVLPLVVGLLNLGAPYLCRVLAALEPHDSPVLEVYVAICR--------------------------NLILKL
-----------------------PEAAGQEAALLVLPLVVGLLNLGAPYLCRVLAALEPHDSPVLEVYVAICR--------------------------NLILKL
-----------------------PEAAGQEAALLVLPLVVGLLNLGAPYLCRVLAALEPHDSPVLEVYVAICR--------------------------NLILKL
-----------------------PEAAGQEAALLVLPLVVGLLNLGAPYLCRVLAALEPHDSPVLEVYVAICR--------------------------XXXXXX
-----------------------PEAAGQEAALLVLPLVVGLLNLGAPYLCRVLAALEPHDSPVLEVYVAICR--------------------------NLILKL
```

FIG. 6A

```
                                         801
Aotus nancymaae                   (522) AVLGTLCYHYLGRRVGVLGGQCWEDFVGQELYRFLVMDFVLTLLDTLFGELVWRIISEKKLKRRRKPEFDIARMVLELIYGQTL
Saimiri boliviensis boliviensis   (522) AILGTLCYRYLGRRVGVLRGGCWEDSVGQELYRFLVMDFVLTLLDTLFGELVWRIISEKKLKRRRKPEFDIARMVLELIYGQTL
Callithrix jacchus                (519) AILGTLCYHYLGRRVGVLRGGQCWEDFVGQELYRFLVMDFILMLLDTLFGELVWRIISEKKLKRRRKPEFDIARMVLELIYGQTL
Bubalus bubelis                   (585) VTLGILCYHYLGRRVGTLKDQCWENFVGQELYRLMVMDFIFTLLLDTLFGELVWRLFSEKQLKRKGKPEFDIAGMVLELIYGQTL
Camelus bactrianus                (475) VTLGILCYHYLGRRVGTLRDQCWENFVGQELYRLMVMDFLFTLLDTLFGELVWRLISERTLKRRGKPEFDIAGMVLELIYGQTL
Camelus dromedaries               (528) VTLGILCYHYLGRRVGTLRDQCWENFVGQELYRLMVMDFLFTLLDTLFGELVWRLISERTLKRRGKPEFDIAGMVLELIYGQTL
Vicugna pacos                     (405) VTLGILCYHYLGRRVGTLRDQCWENFVGQELYRLMVMDFLFTLLDTLFGELVWRLISERTLKRRGKPEFDIAGMVLELIYGQTL
Dasypus novemcinctus              (477) VTLGVLCYHYLGRRLGTLRGGCWENFVGQELYRFVMDFLFVLLDTLFGELVWRLVAEKKLKRRKPEFDIAGMVLELIYGQTL
Ceratotherium simum simum         (526) VILAILCYHYLGRRVGALKDQCWENFVGQELYRLMVMDFIFMLLDTLFGELVWRLISERKLKPKGKPEFDIARMVLELIYGQTL
Equus caballus                    (520) VILAILCYHYLGRRVGALKGGCWENFVGQELYRLMVMDFIFMLLDTLFGELVWRFISEKQRKKRGKPEFDIARMVLELIYGQTL
Equus przewalskii                 (571) VILGILCYHYLGRRVGALKGGCWENFVGQELYRLMVMDFIFMLLDTLFGELVWRFISEKQRKKRGKPEFDIARMVLELIYGQTL
Felis catus                       (516) VILGILCYHYLGRRVGALRDQCWENFVGQELYRLMLDFIFILLDTLFGELVWRLISERKLKRKEKPEFDIAGMVLELIYGQTL
Leptonychotes weddellii           (522) VILGILCYHYLGRRVGTLKDQCWENFVGQELYRLMLDFIFVLLDTLFGELVWRLISEKQLKRREKPEFDIAGMVLELIYGQTL
Odobenus rosmarus divergens       (578) VILGILCYHYLGRRVGALDGQCWENFVGQELYRLVVLDFIFVLLDTLFGELVWRLISEKQLKRREKPEFDIAGMVLELIYGQTL
Mustels putor furo                (529) AILGILCYHYLGRRVGTLKDQCWENFVGQELYRLTMLDFIFVLLDTLFGELVWRLISEKKLKRREKPEFDIAGMVLELIYGQTL
Chrysochloris asiatica            (517) ITLGILCYHYLGRRVDILKDQCWEDFVGQELYRFMVDFFFTLVDTLFGELVWRLITERLKRQRKPEFDIARMVLELIYGQTL
Trichechus manatus latirostris    (531) VILGILCYHYLGRRVALKGGCWENFVGQELYRFNVMDFIFMLVDTLFGELVWRLISEKKLKRRQKPEFDIARMVLDLIYGQTL
Elephantulus edwardii             (526) VILGILCYHYLGRRVGLSGGCWENFVGQELYRFMVMDFLLLDTLIGELAWRLVSEKKSRSRRAKPEFDIAGMLGLIYGQTL
Orycteropus afer afer             (524) ILLGILCYHYLGRRVGLNGGCWEDFVGQELYRFMVMDFIFTLLDTLFGELMWRLVSEKKSRSRRAKPEFDIAGNLLGLIYGQTL
Chinchilla lanigera               (522) AILGVLCYHYLGRRVATLQDQCWEDFVGQELYRFMVMDFIFALLDSLFGELVWRLISERRLRRR-KPEFDIARMVLDLIYGQTL
Heterocephalus glaber             (525) AILGVLCYHYLGRRVATLQGRCWEDFVGQELYRFMVMDFIFALLDSLFGELVWRLISERRLRG--KPEFDIARMVLDLIYGQTL
Cricetulus griseus                (514) AVLGVLCYHYLGRRVAKLQAPCWEDFVGQELYRFLVVDFIFTLLDSLFGELVWRLISEKKLKR-QKPEFDIARMVLDLIYGQTL
Mesocricetus auratus              (518) AVLGVLCYHYLARRVAKLQAPCWEDFVGQELYRFLVVDFIFMLLDSLFGELVWRLISEKKLKRRQKPEFDIARMVLDLIYGQTL
Peromyscus maniculatus bairdii    (520) AVLGVLCYHYLGRHRVATLGGGCWEDFVGQELYRFLVVDFIFTLLDSLFGELVWRLISEKKLKRRQKPEFDIARMVLDLIYGQTL
Microtus ochrogaster              (514) AVLGVLCYHYLGRRVATLGDGCWENFVGQELYRFLVVDFIFTLLDSLFGELVWRLISEKKLKRRQKPEFDIARMVLDLIYGQTL
Mus musculus                      (518) AVLGVLCYHYLGRRVATLGGGCWEDFVGQELYRFMVVDFIFMLLDSLFGELVWRLISEKKLKRGQKPEFDIARMVLDLIYGQTL
Rattus norvegicus                 (520) AVLGVLCYHYLGRRVAALQDQCWEDFVGQELYRFMVMDFIFVLLDSLFGELVWRLISEKKLKTGQKPEFDIARMVLDLIYGQTL
Jaculus jaculus                   (517) VILGVLCYHYLGRHVAALPSRCWEDFVGQELYRFLVMDFLFALLDLLFGELVWRLISEKKLKRQRKPEFDIARMVLDLIYGQTL
Ictidomys tridecemlineatus        (524) AILGILCYHYLGRRVAALQGGCWEDFVGQELYRFMVMDFVFALLDTLFGELVWRLISERKLKRRRKPEFDIARMVLDLIYGQTL
Marmota matmota marmot            (212) AILGILCYHYLGRRVAALQGGCWEDFVGQELYRFMVMDFLFALLDTLFGELVWRLISERKLKRRRKPEFDIARMVLDLIYGQTL
Galeopterus variegatus            (525) AILGVLCYHYLGRRVAALRDQCWEDFVGQELYRFVVMDFIFALLDTLFGELVWRFISEKKLKRRRKPEFDIARMVLDLIYGQTL
Otolemur garnettii                (512) VILGVLCYHYLGRRVGALQDRCWEDFVGQELYRFMVVDFLFALLDTLFGELVWRVISEKKMRKRKPEFDIARMVLELIYGQTL
Propithecus coquereli             (523) VILGVLCYHYLGRRVGALQDQCWEDFVGQELYRFVVLDFLFTLLDTLFGELVWRVISEKKTKTRRAKPEFDIARMVLELIYGQTL
Tarsius syrichta                  (501) VVMGTLCYHYLGRRVGALQGGCWEDFVGQELYRFMVMDFVFALLDTLFGELVWRAISEKKRRRKPEFDIARMVLELIYGQTL
Homo sapiens                      (519) AILGTLCYHYLGRRVGVLQGGCWEDFVGQELYRFLVMDFVLMLLDTLFGELVWRIISEKKLKRRRKPEFDIARMVLELIYGQTL
Pan paniscus                      (519) AILGTLCYHYLGRRVGVLQGGCWEDFVGQELYRFLVMDFVLMLLDTLFGELVWRIISEKKLKRRRKPEFDIARMVLELIYGQTL
Pan troglodytes                   (519) AILGTLCYHYLGRRVGVLQGGCWEDFVGQELYRFLVMDFVLMLLDTLFGELVWRIISEKKLKRRRKPEFDIARMVLELIYGQTL
Pongo abelii                      (519) AILGTLCYHYLDHRVGVLQGGCWEDFVGQELYRFLVMDFVLMLLDTLFGELVWRIISEKKLKRRRKPEFDIARMVLELIYGQTL
Nomascus leucogenys               (519) AILGTLCYHYLGRRVGVLQGGCWEDFIGQELYRFLVMDFVLMLLDTLFGELVWRIISEKKLKRRRKPEFDIARMVLELIYGQTL
Rhinopithecus roxellana           (519) AILGTLCYHYLGRRVAVLQGGCWEDFVGQELYRFLVMDFVLMLLDTLFGELVWRIISEKKLKRRRKPEFDIARMVLELIYGQTL
Chlorocebus sabaeus               (519) AILGTLCYHYLGRRVAVLQSGCWEDFVGQELYRFLVMDFVLMLDTLFGELVWRIISEKKLKRRRKPEFDIARMVLELIYGQTL
Macaca fascicularis               (520) AILGTLCYHYLGRRVAVLQDQCWEDFVGQELYRFLVMDFVLMLLDTLFGELVWRIISEKKLKRRRKPEFDIARMVLELIYGQTL
Macaca mulatta                    (520) AILGTLCYHYLGRRVAVLQGGCWEDFVGQELYRFLVMDFVLMLLDTLFGELVWRIISEKKLKRRRKPEFDIARMVLELIYGQTL
Macaca nemestrina                 (520) AILGTLCYHYLGRRVAVLQGGCWEDFVGQELYRFLVMDFVLMLLDTLFGELVWRIISEKKLKRRRKPEFDIARMVLELIYGQTL
Cercocebus atys                   (520) AILGTLCYHYLGRRVAVLQGGCWENFVGQELYRFLVMDFVLMLLDTLFGELVWRIISEKKLKRRRKPEFDIARMVLELIYGQTL
Mandrillus leucophaeus            (520) AILGTLCYHYLGRRVAVLQGGCWEDFVGQELYRFLVMDFVLMLLDTLFGELVWRIISEKKLKRRRKPEFDIARMVLELIYGQTL
Papio Anubis                      (512) AILGTLCYHYLGRRVAVLQGGCWEDFVGQELYRFLVMDFVLMLLDTLFGELVWRIISEKKLKRR-KPEFDIARMALELIYGQTL
```

```
                                          1001
Aotus nancymaae                    (714) LPWVHRYLVENTFFVFLVSALLLAVIYLNIQVVRGQRKVICLLKEQISNEGEDKIFLINKLHSIYERKERE
Saimiri boliviensis boliviensis    (714) LPWVHQYLVENTFFVFLVSALLLAVIYLNIQVVRGQRKVICLLKEQISNEGEDKIFLINKLHSIYEKKERE
Callithrix jacchus                 (711) LPWVHRYLVENTFFVFLVSAXXXXXXXXXXXXVRGQRKVICLLKEQISNEGEDKIFLINKLHSIYERKERE
Bubalus bubelis                    (777) LPWIHRYLVEDTFPIYLVSALLLAVIYLNIQVVKGQRKVICLLKEQISNEGEDKIFLINKLQRVYERKERS
Camelus bactrianus                 (667) LPWIHRYLLENTFPIYLVSALLLAVIYLNIQVVKGQRKVICLLKEQISNEGEDKIFLINKLQSVYERKERS
Camelus dromedaries                (720) LPWIHRYLLENTFPIYLVSALLLAVIYLNIQVVKGQRKVICLLKEQISNEGEDKIFLINKLQSVYERKERS
Vicugna pacos                      (597) LPWIHRYLLENTFPIYLVSALLLAVIYLNIQVVKGQRKVICLLKEQISNEGEDKIFLINKLQSVYERKERS
Dasypus novemcinctus               (669) LPWVHRYLVEKPVLAFLLSALLLAVIYLNTQVVKGQRQVICLLKEQISNEGEDKIFLINKLHSVYERKERS
Ceratotherium simum simum          (718) LPWIHRYLVENTFPIYLVSAVLLAVIYLNIQVVKGQRKVICLLREQISNEGEDKIFLINKLHSVYERKERS
Equus caballus                     (712) LPWIHRYLVENTFPIYLVSALLLAVIYLNIQVVKGQRKVICLLKEQISNEGEDKIFLINKLHSVYEGKERS
Equus przewalskii                  (763) LPWIHRYLVENTFPIYLVSALLLAVIYLNIQVVKGQRKVICLLKEQISNEGEDKIFLINKLHSVYEGKERS
Felis catus                        (708) LPWVHRYLVENTFPVYLVSALLLAVIYLNIQVVKGQRKVICLLREQISNEGEDKIFLINKLHSVYEKKERS
Leptonychotes weddellii            (714) LPWVHRYLVENTFPVYLVSALLLAVIYLHIQVVKGQRRVICLLKEQISNEGEDKVFLINKLHSVYERKERS
Odobenus rosmarus divergens        (770) LPWVHRYLVENTFPVYLVSALLLAVIYLHIQVVKGQRRVICLLKEQISNEGEDKVFLINKLHSVYERKERS
Mustels putor furo                 (721) LPWVHRYLVENTFPIYLVSALLLAVIYLNIQVVKGQRRVICLLKEQISNEGEDKVFLINRLHSVYERKERS
Chrysochloris asiatica             (709) VPWVYHYLLENTFFIFLVSTLLLAVIYLNIQVVKGQRKIICLLKEQISNEGEDKIFLNEIHSVYERKERR
Trichechus manatus latirostris     (723) LSWVHHYLLENTFFIFLVSALLL------------------------------------
Elephantulus edwardii              (718) LPWVVHYLLENTFFIFLVSAILLAVIYLNIQVVKGQRKVICLLKEQISNEGEDKIFLINKLHSVYERKERS
Orycteropus afer afer              (716) LPWVVHYLLENTFLIFLVSALLLAVIYLNIQVVKGQRKVICLLKEQISNEGEDKMFLINKLHSVYEKKERS
Chinchilla lanigera                (713) LSWLHWYLVENTFFLFLVSALLLAVIYLNIQVVKGQRKVICLLKEQIRNEGEDKIFLINRLHSVYERKERS
Heterocephalus glaber              (715) LSWLHRYLVENTFFLFLASALLLAVIYLNIQVVKGQRKVICLLKEQIRNEGEDKIFLINRLHSVYERKERR
Cricetulus griseus                 (705) LPWLHHFLVENTFFLFLVSALLLAVIYLNIQVVKAQRKVICLLKEQIRNEGEDKVFLINKLHSVYEAGERR
Mesocricetus auratus               (710) LPWLHHVLVENTFFLFLVSALLLAVIYLNIQVVKGQRKVIRLLKEQIRNEGEDKVFLINRLHSVYEEGERS
Peromyscus maniculatus bairdii     (712) LPWLYHFLVENTFFLFLMSALLLSVIYLNIQAVKGQRKVIRLLKEQIRNEGEDKIFLINKLHSVYEDGERS
Microtus ochrogaster               (706) LPWLHHLLVENTFFLFLVSALLLAVIYLNIQVVKGQRKVICLLKEQIRNEGEDKIFLINKLHSVYEG-EQN
Mus musculus                       (710) LPWLHHFLVENTFFLFLASALLLAVIYFNIQVVKGQRKVICLLKEQIRNEGEDKIFLINKLHSVYEEEGRS
Rattus norvegicus                  (712) LPWLHHFLVENTFFLFLVSALLLAVIYLNIQVVKGQRKVICLLKEQIRNEGEDKIFLINKLHSVYEEEGMS
Jaculus jaculus                    (709) LPWLYGYLVENTFFLFLVSALLLAVIYLNIQVVKGQRKVICLLKEQIRNEGEDKIFLINKLHSVYERKQRS
Ictidomys tridecemlineatus         (716) VPWLHRYLVDSTFFLFLASALLLAIIYFNIQVVKGQRKVISLLKEQIRNEGEDKIFLINRLHSVYERKERS
Marmota matmota marmot             (404) VPWLHRYLVESTFFLFLASALLLAIIYFNIQVVKGQRKVISLLKEQIRNEGEDKIFLINRLHSVYERKERS
Galeopterus variegatus             (717) LSWLYQHLVEDTVFIFLASALLLAVIYLNIQVVKGQRKVICLLKEQISNVTRIMRGIWIRWHRHATAGLA
Otolemur garnettii                 (704) LPWVHRHLLENTFFIFLLSALLLAVIYFNIQVVRGQQKVIGLLKEQISHEGEDKIFLINKLHSVYERKERS
Propithecus coquereli              (715) LPWVHRHLVENTFFIFLLSALLLAVIYFNIQVVRGQRKVICLLKEQISHEGEDKIFLINKLHSIYEKKERK
Tarsius syrichta                   (693) LPWVHRNLVENTFFIFLVSALLLAVIYFNIQVVRGQRKVICLLKEQISNEGEDKIFLINKLHSVYERKERK
Homo sapiens                       (711) LPWVHRYLMENTFFVFLVSALLLAVIYLNIQVVRGQRKVICLLKEQISNEGEDKIFLINKLHSIYERKERE
Pan paniscus                       (711) LPWVHRYLVENTFFVFLVSALLLAVIYLNIQVVRGQRKVICLLKEQISNEGEDKIFLINKLHSIYERKERE
Pan troglodytes                    (711) LPWVHRYLGENTFFVFLVSALLLAVIYLNIQVVRGQRKVICLLKEQISNEGEDKIFLINKLHSIYERKERE
Pongo abelii                       (711) LPWVHRYLGENTFFVFLVSALLLAVIYLNIQVVRGQRKVICLLKEQISNEGEDKIFLINKLHSIYERKERE
Nomascus leucogenys                (714) VPVCPKHSNDGSHIAWWV----------N---------------TE--EGEDKIFLINKLHSIYERKERE
Rhinopithecus roxellana            (711) LPWVHRYLVENTFFVFLVSALLLAVIYLNIQVVRGQRRVICLLKEQISNEGEDKIFLINKLHSIYERKERE
Chlorocebus sabaeus                (711) LPWVHRYLVENTFFVFLVSALLLAVIYLNIQVVRGQRRVICLLKEQISNEGEDKIFLINKLHSIYERKERE
Macaca fascicularis                (712) LPWVHRYLVENTFFVFLVSALLLAVIYLNIQVVRGQRRVICLLKEQISNEGEDKIFLINKLHSIYERKERE
Macaca mulatta                     (712) LPWVHRYLVENTFFVFLVSALLLAVIYLNIQVVRGQRRVICLLKEQISNEGEDKIFLINKLHSIYERKERE
Macaca nemestrina                  (676) ----------------------------------------------------------
Cercocebus atys                    (711) LPWVHRYLVENTFFVFLVSALLLAVIYLNIQVVRGQRRVICLLKEQISNEGEDKIFLINKLHSIYERKERE
Mandrillus leucophaeus             (712) LPWVHRYLVENTFFVFLVSALLLAVIYLNIQVVRGQRRVICLLKEQISNEGEDKIFLINKLHSIYERKERE
Papio Anubis                       (712) LPWVHRYLVENTFFVFLVSALLLAVIYLNIQVVRGQRRVICLLKEQISNEGEDKIFLINKLHSIYERKERE
```

FIG. 7B

```
                                                                                                    1164
E--------------------RS-RFRTSQAAVPPTLFTDERDA-----------------------------------
E--------------------RS-RVRTSQAAVPPTLFTDERDA-----------------------------------
E--------------------RS-RVRTSQAAIPPTLFTDERDA-----------------------------------
R-------------------AGRTEEAVTPPALFADGWDAQ-------------------------------------
R-------------------VGRTEAAVMPPALFTDDGDTW-------------------------------------
R-------------------VGRTEAAAMPPALFTDDGDTW-------------------------------------
R-------------------AGRTEEAAMPPALFTDDGDAW-------------------------------------
SFQKLS--------------QSKHLSWARCTHGLAGPHDATESRLQANCRGHFD-------------------------
R-------------------VGRAHEAETPPTLLADEQDAR-------------------------------------
R-------------------VGRAQEAEVPPTLPADERDAR-------------------------------------
R-------------------VGRAQEAEVPPTLPADERDAR-------------------------------------
R-------------------GGRTQEAER----LEEDPDAR-------------------------------------
RHI-----------------GGLPSRFEAVQR----FLHPPEA-----------------------------------
--------------------R--AGRTQEAER----LTDDPDAW----------------------------------
R-------------------AGRSQETER----LVDHPDAW-------------------------------------
SFLMP---------------TLGLGENAHLSSRVTLAETVMVT-----------------------------------
------------------------------------------------------------------------------
R-----------------------------------------------------------------------------
R-----------------------------------------------------------------------------
R-------------------AGRAAEVATPALVPDAGDK---------------------------------------
R-------------------AGRSAETATPALLTDAGDK---------------------------------------
RR-------------PGRTQEEPCNP---SHHDPARRDLDLRSPQDTAVE-----------------------------
RR-------------PGRTQEEPCNP---SHHDPARRDLDLRSPQDPAVE-----------------------------
RTQ---EATAATALLVDGGDRKEPCTP---SHRDPSGRDLNLRSPRDTTVE----------------------------
RPE---EATTSSAQFVDGGD----------SHHDPAGRDLDTALE---------------------------------
R--------------PGRTQDTTEPP---AWHEDGGDQKEPCNPRSP-------------------------------
R--------------PGRTQEATIPP---AAPED--------------------------------------------
S--------------AVLSLQLS---LPVQGSGRDELLLRDSDTL---------------------------------
RAHRNEEAVTPSALLADGGDSWWDSEGPGRLPQHPQLRSVTTSWQAETRI-----------------------------
RAHRNEEAVTPSALLADGGDSWWDSEGPGRLPQHPQLRSVTTSWQAETRI-----------------------------
ICR-----------------ALPAGTGSPRGGDSSPRQDTWRVLGRAAPCGYRQSLRIFAILEVAFGLPPAGGTHVGTRTLLSALIL
R-----------------------------------------------------------------------------
E------------------GEERSRCAGRSGKEES--------------------------------------------
EKA----------------RSRAGGTEEAATPPALLTEGRDARWDGNGPRRLTLQPELLA-------------------
E------------------RSRVGTTEEAAAPPALLTDEQDA-------------------------------------
E------------------RSRVGTTEEAAAPPALLTDEQDA-------------------------------------
E------------------RSRVGTTEEAAAPPALLTDEQDA-------------------------------------
E------------------RSRVGTTEEAAAPPALLTDEQDA-------------------------------------
E------------------RSRVGTTEEAAHR------------------------------------------------
E------------------RSRVGTTEETAAPPALLTEERGD-------------------------------------
E------------------RSRVGTTEETAAPPALLTDERDD-------------------------------------
E------------------RSRVGTTEETAAPPTLLTDERDD-------------------------------------
E------------------RSRVGTTEETAAPPTLLTDERDD-------------------------------------
------------------------------------------------------------------------------
E------------------RSRVGTTEETAAPPAVLTDERDD-------------------------------------
E------------------RSRVGTTEETAAPPTLLTDERDD-------------------------------------
E------------------RSRVGTTEETAAPPTLLTDERDD-------------------------------------
```

[Fig. 8]
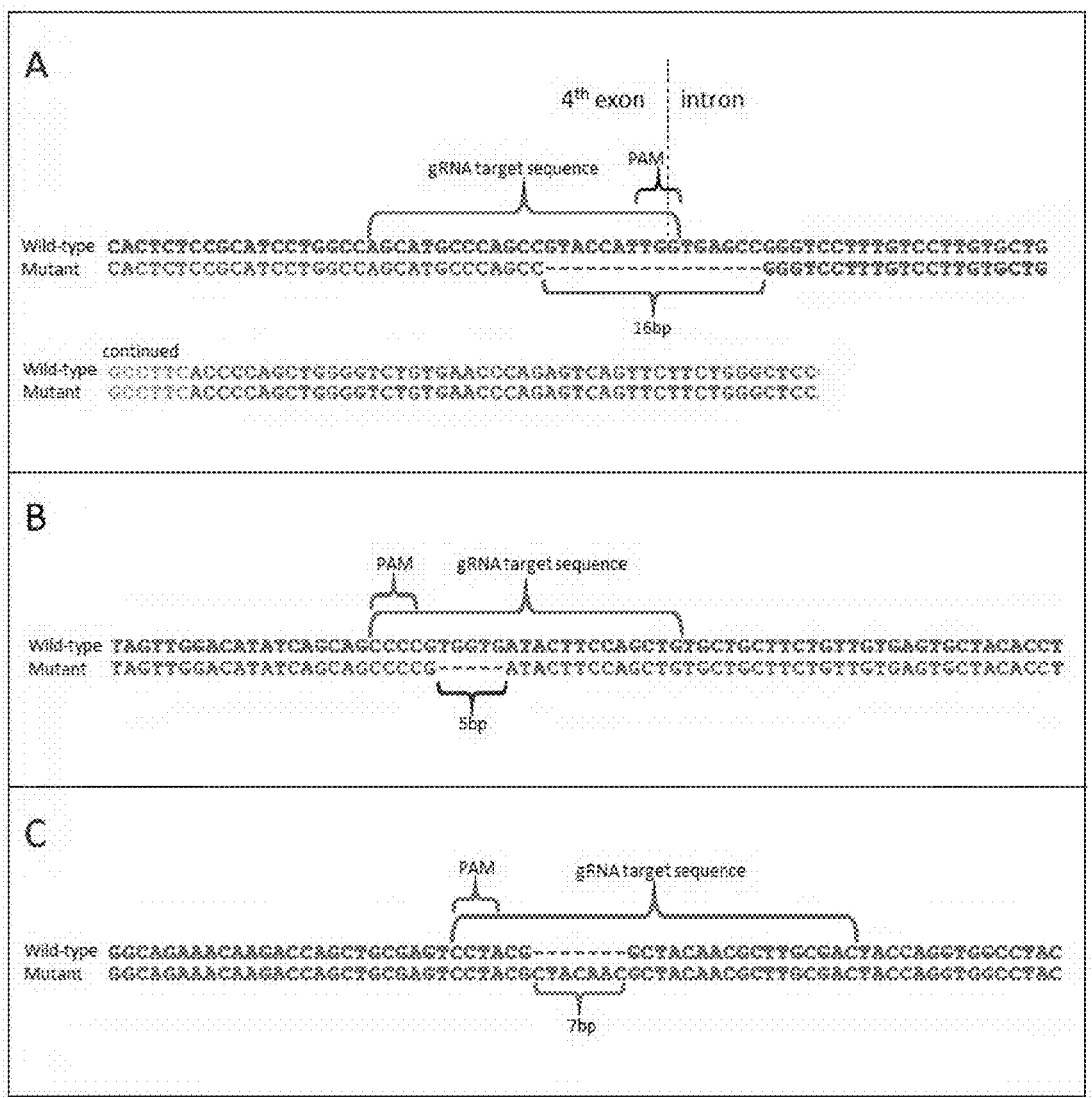

[Fig. 9]
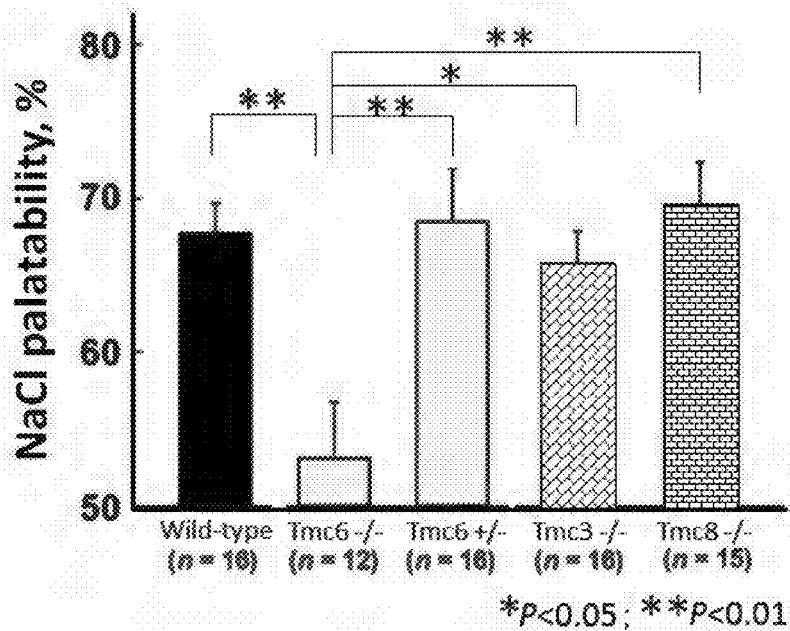
[Fig. 10]
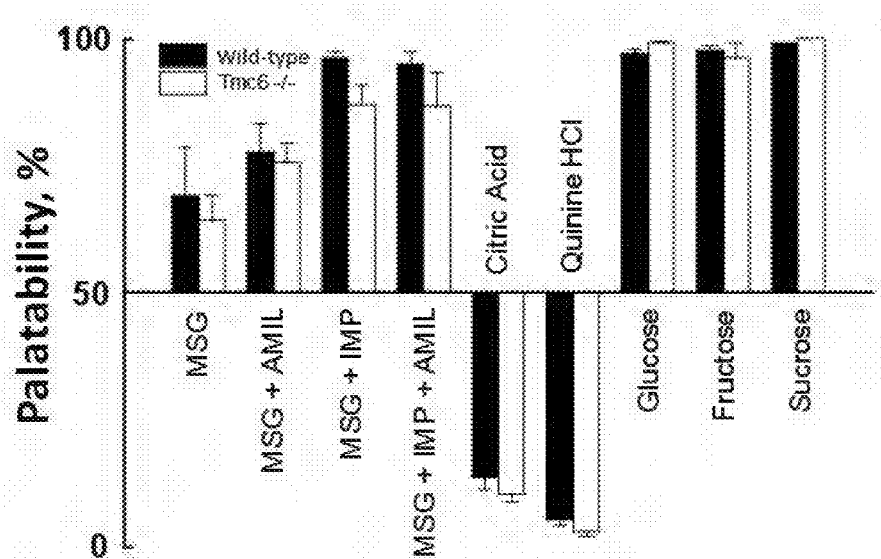

[Fig. 11]
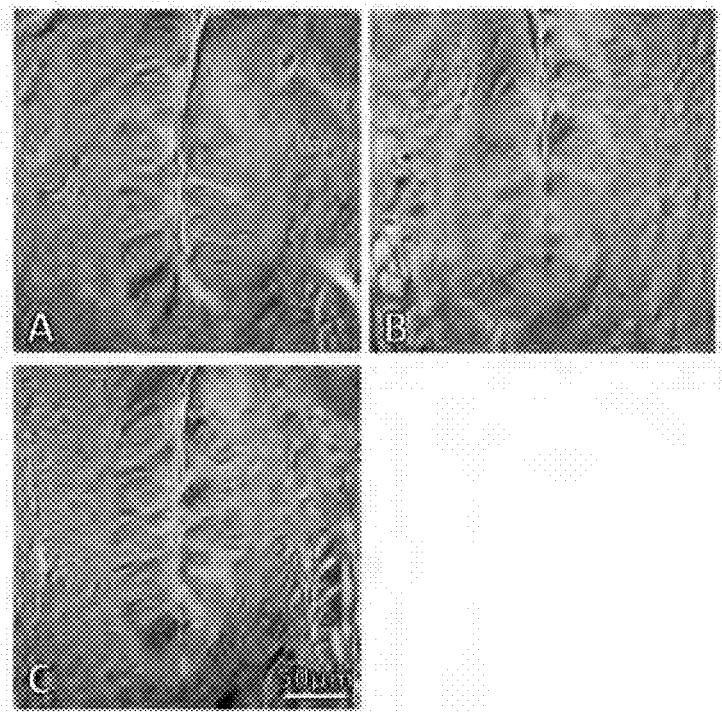
[Fig. 12]
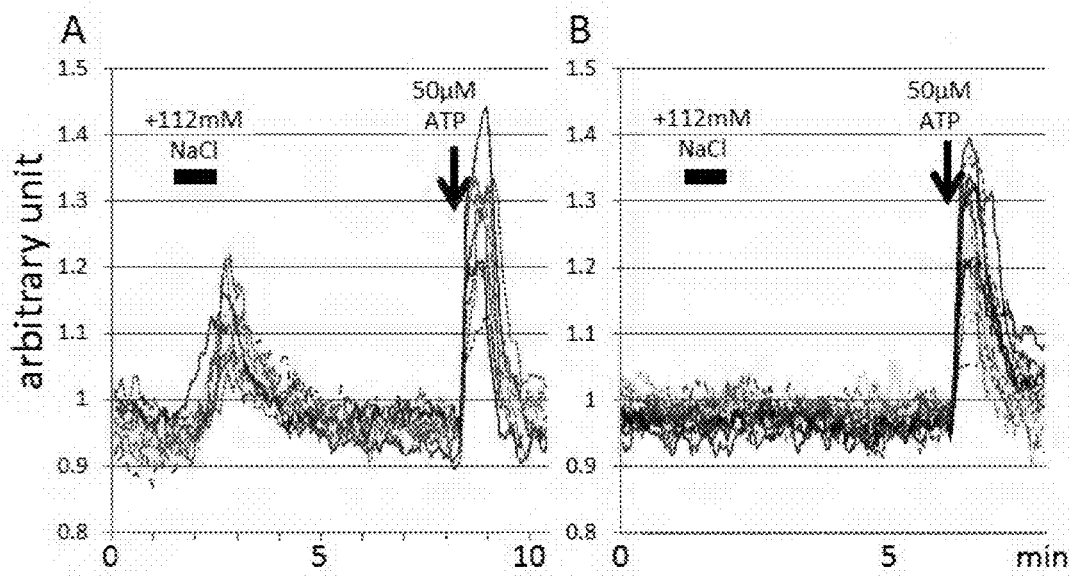

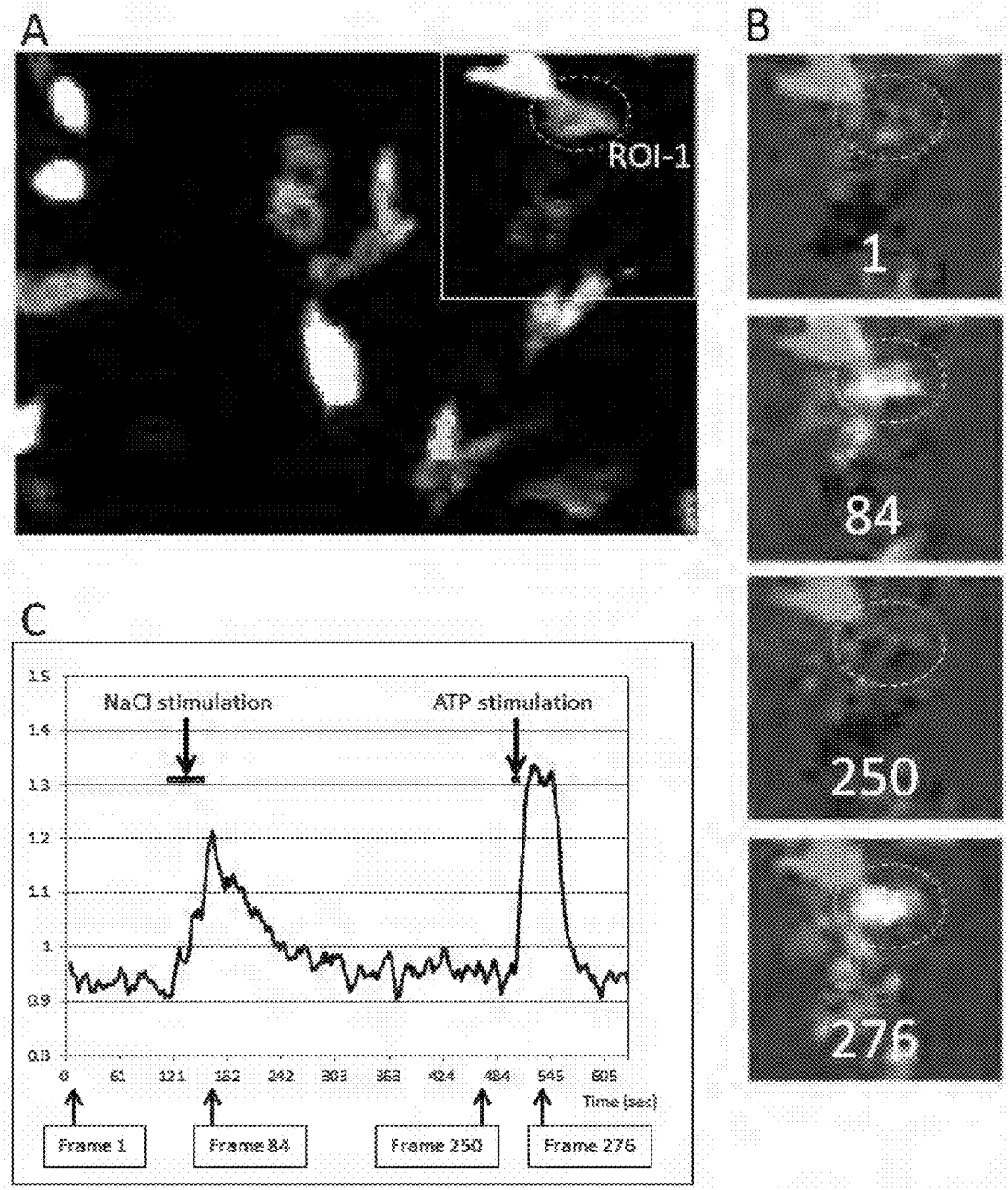
[Fig. 13]

[Fig. 14]
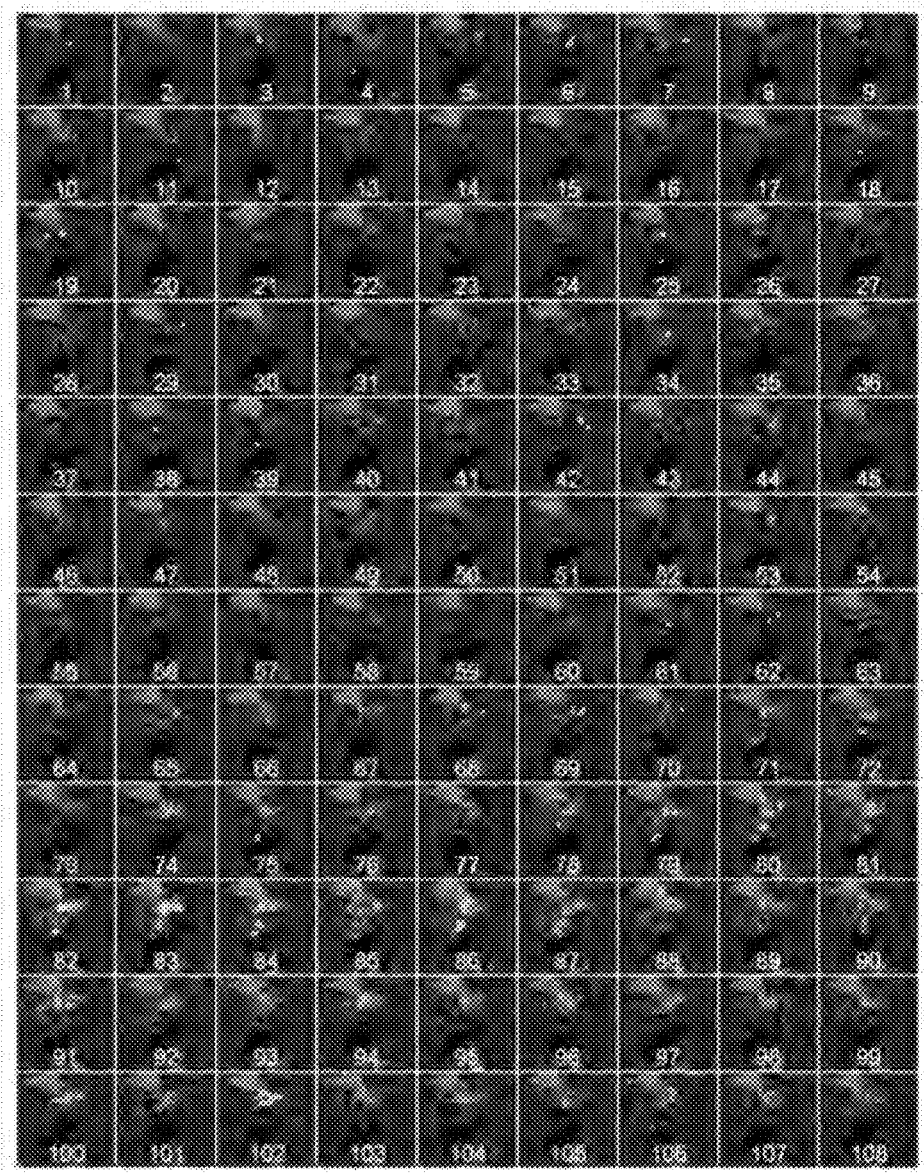

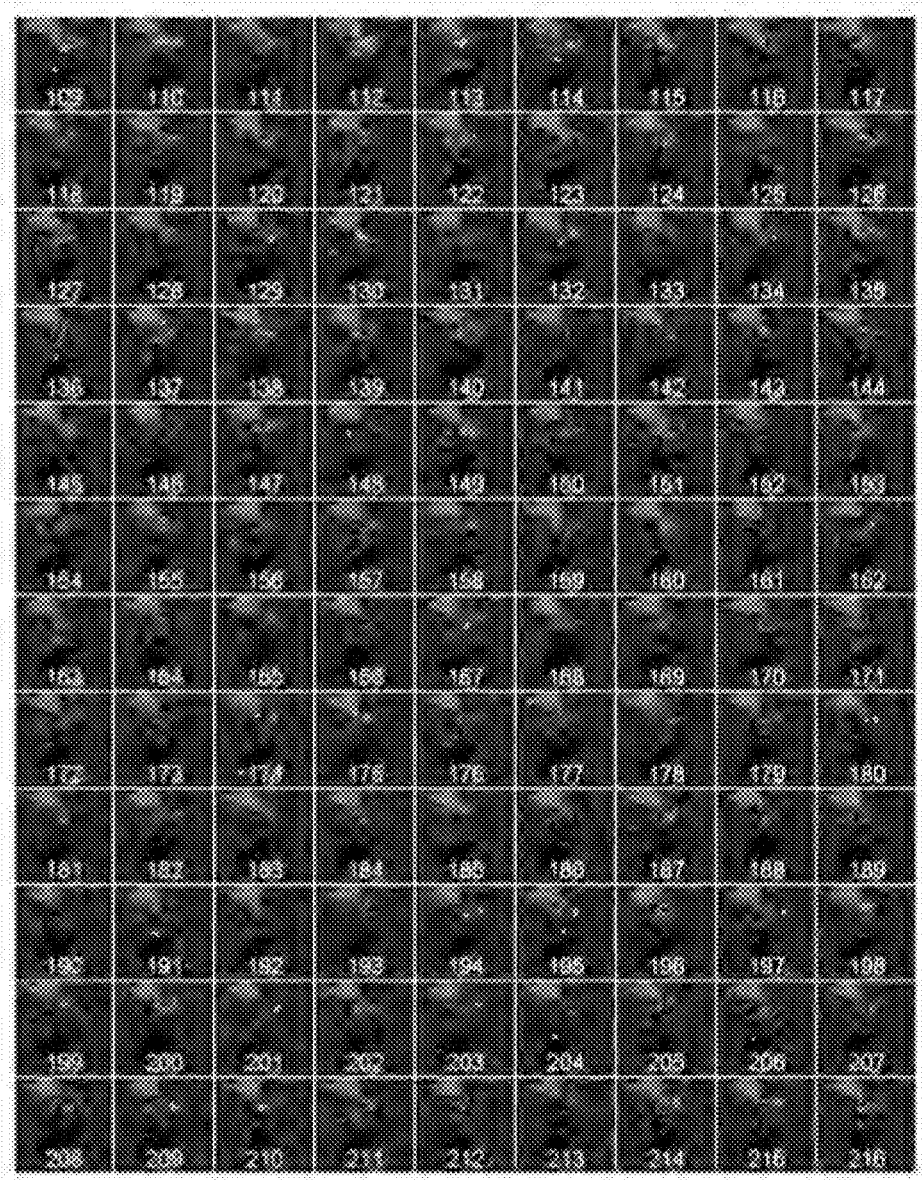
[Fig. 15]

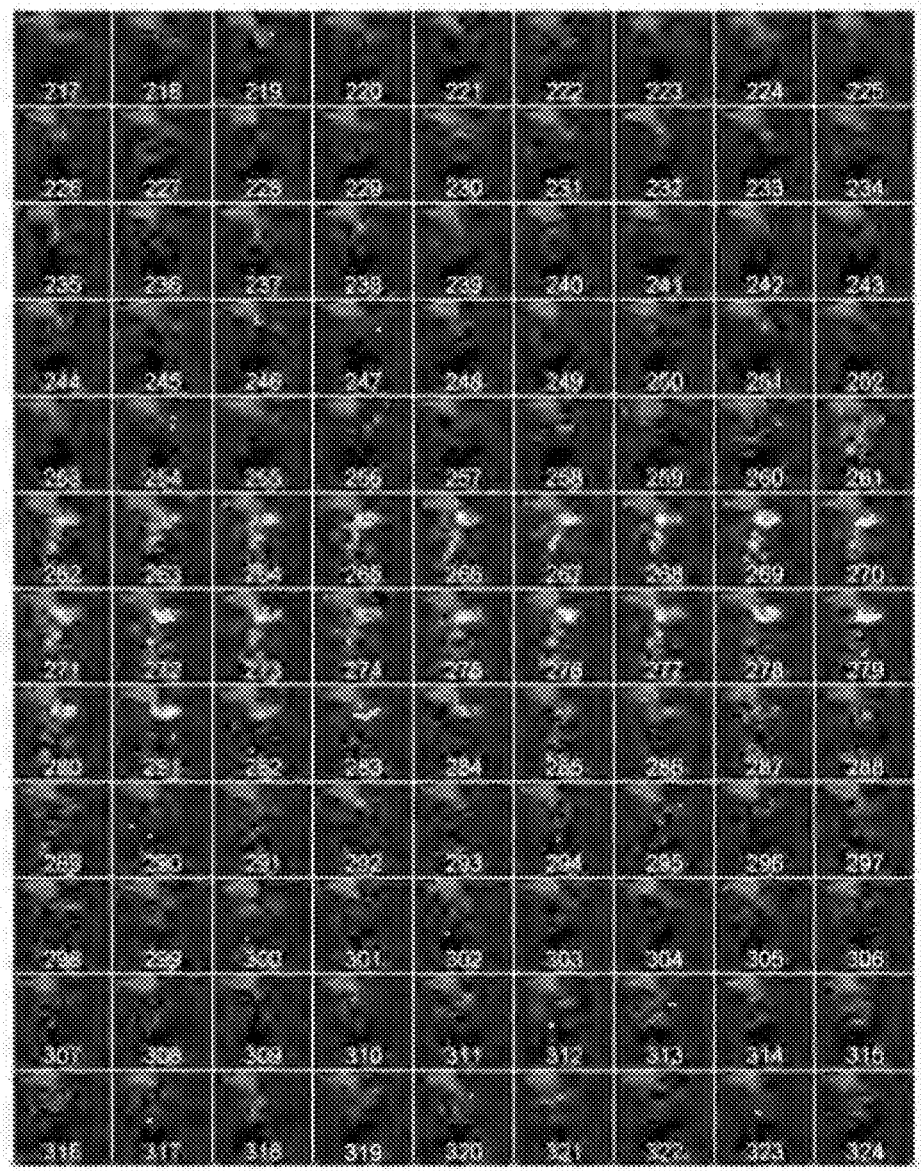
[Fig. 16]

[Fig. 17]
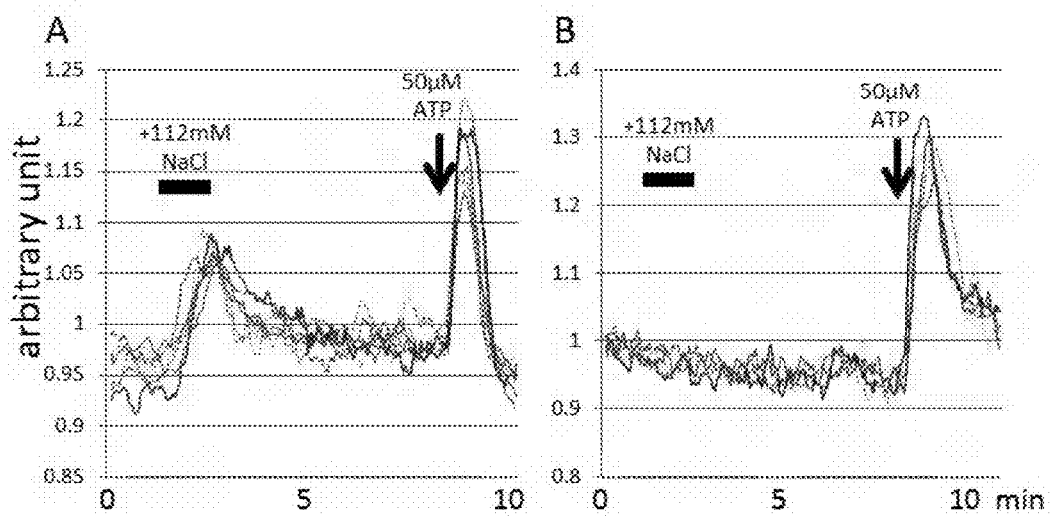

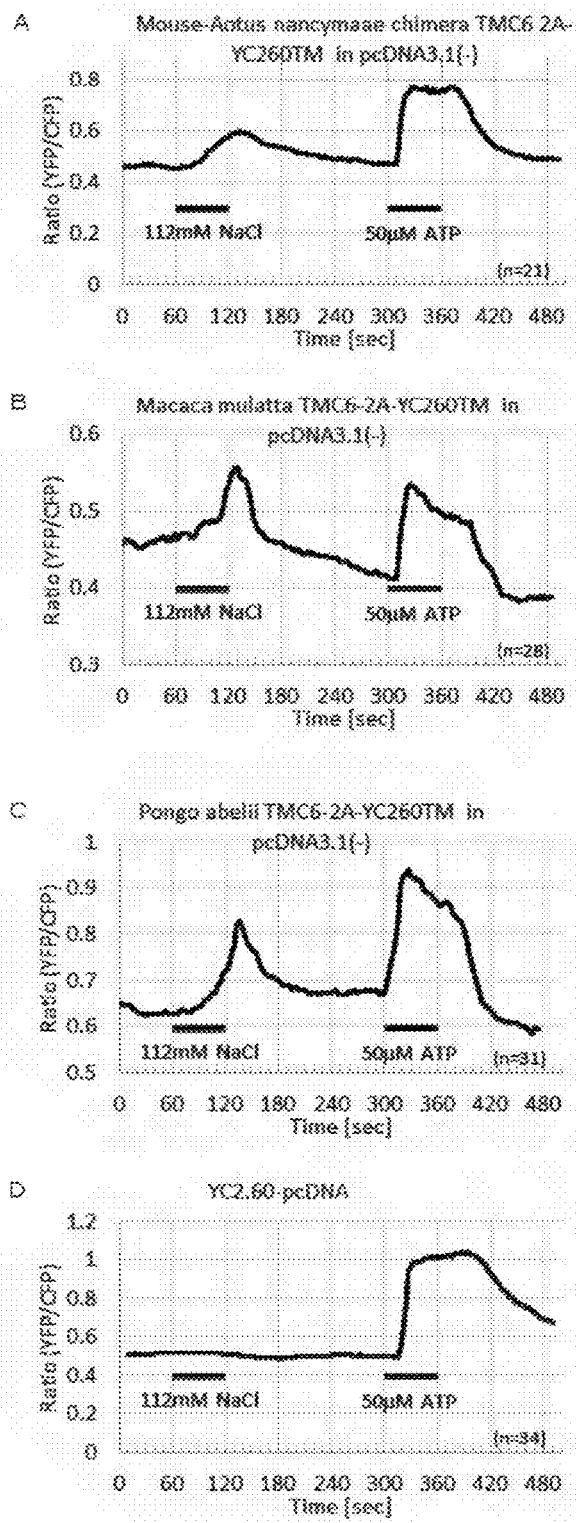

[Fig. 19]
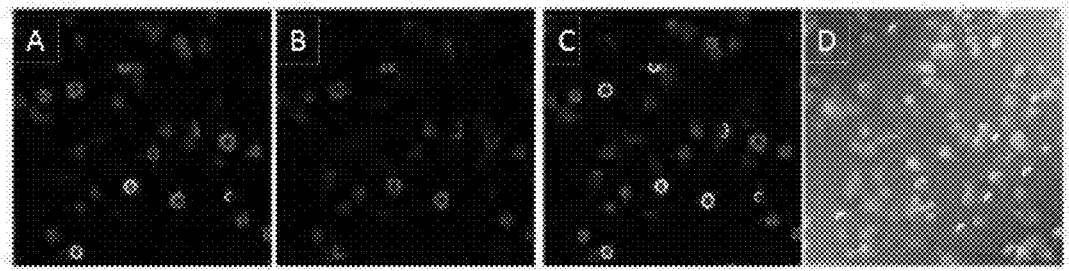
[Fig. 20]
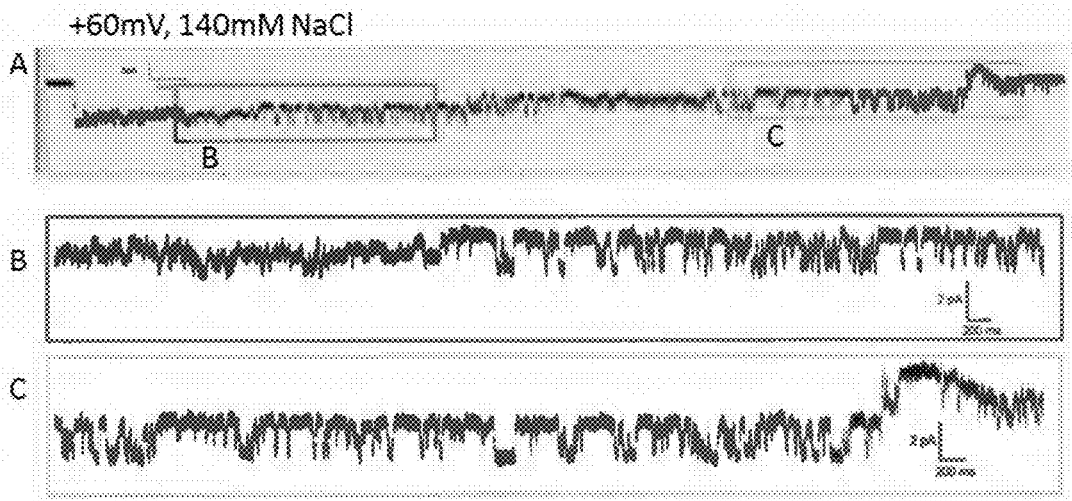
[Fig. 21]
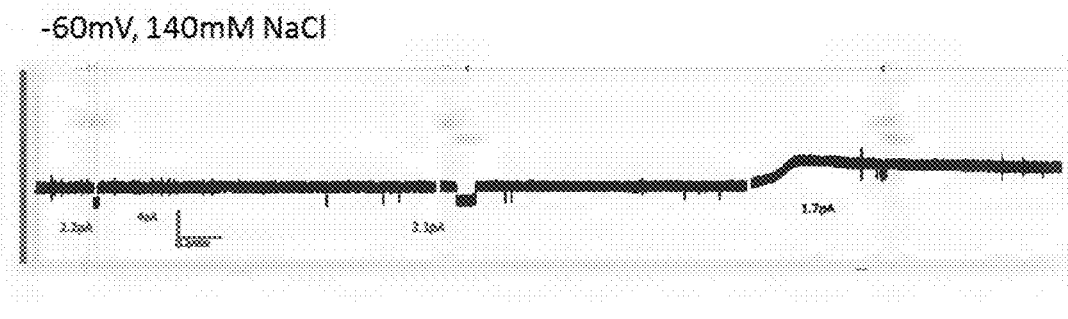

SEQUENCE LISTING

```
<160> NUMBER OF SEQ ID NOS: 72

<210> SEQ ID NO 1
<211> LENGTH: 807
<212> TYPE: PRT
<213> ORGANISM: Aotus nancymaae

<400> SEQUENCE: 1

Met Asp Met Ala Gln Pro Leu Pro Phe Val Leu Asp Val Pro Glu Thr
1               5                   10                  15

Pro Glu Asp Gln Gly Ser Gln Glu Pro Ser Pro Tyr Asp Glu Ser Glu
                20                  25                  30

Val His Asp Ser Phe His Gln Leu Ile Gln Glu Gln Ser Arg Trp Ala
            35                  40                  45

Ala Gln Glu Gly Leu Glu Leu Gln Arg Ala Arg Gly Ala Thr Gly
    50                  55                  60

Ser Gly Gln His Thr Leu Ser Gly Ser Glu Gly Ala His Ser Thr Ala
65                  70                  75                  80

Thr Leu Arg Ile Leu Ala Ser Met Pro Ser Arg Thr Ile Gly Arg Ser
                85                  90                  95

Arg Gly Ala Ile Ile Ser Gln Tyr Tyr Asn Arg Thr Val Gln Leu Arg
            100                 105                 110

Arg Arg Ser Ser Arg Pro Leu Leu Gly Asn Leu Val Arg Ser Ala Arg
        115                 120                 125

Pro Ser Leu Arg Met Tyr Asp Leu Glu Leu Asp Pro Arg Ala Gln Glu
    130                 135                 140

Glu Glu Glu Lys Gln Ser Leu Leu Val Lys Glu Leu Gln Ser Leu Ala
145                 150                 155                 160

Val Ala Gln Arg Asp His Met Leu Arg Gly Met Pro Leu Ser Leu Ala
                165                 170                 175

Glu Lys Arg Ser Leu Arg Glu Lys Ser Arg Thr Pro Arg Gly Lys Trp
            180                 185                 190

Arg Gly Gln Arg Gly His Gly Gly Val Cys Ser Cys Cys Gly Trp Leu
        195                 200                 205

Arg Tyr Ala Cys Val Leu Thr Leu His Ser Leu Gly Leu Ala Leu Leu
    210                 215                 220

Ser Ser Leu Gln Ala Leu Thr Pro Trp Arg Asp Ala Leu Lys Arg Ile
225                 230                 235                 240

Gly Gly Gln Phe Gly Ser Ser Val Leu Ser Tyr Phe Leu Phe Leu Lys
                245                 250                 255

Thr Leu Leu Ala Phe Asn Ala Leu Leu Leu Leu Leu Leu Ala Phe
            260                 265                 270

Ile Val Gly Pro Gln Ala Ala Phe Pro Pro Ala Leu Pro Gly Pro Val
        275                 280                 285

Pro Val Cys Thr Gly Leu Glu Leu Leu Thr Gly Ala Gly Cys Phe Thr
    290                 295                 300

His Thr Val Met Tyr Tyr Gly His Tyr Ser Asn Ala Thr Leu Asn Gln
305                 310                 315                 320

Pro Cys Gly Gly Pro Leu Glu Gly Gly Arg Cys Ser Pro Arg Ala Gly
```

-continued

```
                325                 330                 335
Gly Leu Pro Tyr Asn Met Pro Leu Ala Tyr Leu Phe Thr Val Gly Val
                340                 345                 350
Gly Phe Phe Ile Thr Cys Ile Ser Leu Val Tyr Ser Met Ala His Ser
                355                 360                 365
Phe Gly Glu Ser Tyr Arg Val Asp Ser Thr Ser Gly Ile His Ala Ile
            370                 375                 380
Thr Val Phe Cys Ser Trp Asp Cys Lys Val Thr Gln Lys Arg Ala Ser
385                 390                 395                 400
Arg Leu Gln Gln Asp Asn Ile Arg Thr Arg Leu Lys Glu Leu Leu Ala
                405                 410                 415
Glu Trp Gln Leu Arg Gln Gly Pro Arg Ser Val Cys Arg Arg Leu Arg
                420                 425                 430
Gln Ala Ala Leu Gly Leu Val Trp Leu Leu Cys Leu Gly Thr Ala
                435                 440                 445
Leu Gly Cys Ala Val Ala Val His Val Phe Ser Glu Phe Met Ile Gln
            450                 455                 460
Ser Pro Glu Thr Ala Gly Gln Glu Ala Ala Leu Leu Val Leu Pro Leu
465                 470                 475                 480
Val Val Gly Leu Leu Asn Leu Gly Ala Pro Tyr Leu Cys Arg Ile Leu
                485                 490                 495
Ala Ala Leu Glu Pro His Asp Ser Pro Val Leu Glu Val Tyr Met Ala
                500                 505                 510
Ile Cys Arg Asn Leu Ile Leu Lys Leu Ala Val Leu Gly Thr Leu Cys
                515                 520                 525
Tyr His Trp Leu Gly Arg Arg Val Gly Val Leu Gln Gly Gln Cys Trp
            530                 535                 540
Glu Asp Phe Val Gly Gln Glu Leu Tyr Arg Phe Leu Val Met Asp Phe
545                 550                 555                 560
Val Leu Thr Leu Leu Asp Thr Leu Phe Gly Glu Leu Val Trp Arg Ile
                565                 570                 575
Ile Ser Glu Lys Lys Leu Lys Arg Arg Arg Lys Pro Glu Phe Asp Ile
                580                 585                 590
Ala Arg Asn Val Leu Glu Leu Ile Tyr Gly Gln Thr Leu Ala Trp Leu
            595                 600                 605
Gly Val Leu Phe Ser Pro Leu Leu Pro Ala Val Gln Ile Ile Lys Leu
                610                 615                 620
Leu Leu Val Phe Tyr Ile Lys Lys Thr Ser Leu Leu Ala Asn Cys Gln
625                 630                 635                 640
Ala Pro Arg Arg Pro Trp Leu Ala Ser His Met Ser Thr Val Phe Leu
                645                 650                 655
Thr Leu Leu Cys Phe Pro Ala Phe Leu Gly Ala Ala Val Phe Leu Cys
            660                 665                 670
Tyr Ala Val Trp Gln Val Lys Pro Ser Gly Ile Cys Gly Pro Phe Arg
                675                 680                 685
Thr Leu Asp Thr Met Tyr Glu Ala Gly Arg Val Trp Val Arg His Leu
                690                 695                 700
Glu Ala Ala Gly Pro Arg Val Ser Trp Leu Pro Trp Val His Arg Tyr
705                 710                 715                 720
Leu Val Glu Asn Thr Phe Phe Val Phe Leu Val Ser Ala Leu Leu Leu
                725                 730                 735
Ala Val Ile Tyr Leu Asn Ile Gln Val Val Arg Gly Gln Arg Lys Val
            740                 745                 750
```

```
Ile Cys Leu Leu Lys Glu Gln Ile Ser Asn Glu Gly Glu Asp Lys Ile
            755                 760                 765

Phe Leu Ile Asn Lys Leu His Ser Ile Tyr Glu Arg Lys Glu Arg Glu
            770                 775                 780

Glu Arg Ser Arg Phe Arg Thr Ser Gln Ala Ala Val Pro Pro Thr Leu
785                 790                 795                 800

Phe Thr Asp Glu Arg Asp Ala
                805

<210> SEQ ID NO 2
<211> LENGTH: 807
<212> TYPE: PRT
<213> ORGANISM: Saimiri boliviensis boliviensis

<400> SEQUENCE: 2

Met Asp Thr Ala Gln Pro Pro Phe Val Leu Asp Val Pro Glu Thr
1               5                   10                  15

Pro Gly Asp Gln Gly Ser Arg Glu Pro Ser Pro Tyr Asp Glu Ser Glu
            20                  25                  30

Val His Asp Ser Phe His Gln Leu Ile Gln Glu Gln Ser Arg Trp Ala
        35                  40                  45

Ala Gln Glu Gly Leu Glu Leu Gln Gln Arg Ala Arg Gly Ala Ala Gly
    50                  55                  60

Ser Gly Leu His Thr Leu Ser Gly Ser Glu Gly Ala His Ser Thr Ala
65                  70                  75                  80

Thr Leu Arg Ile Leu Ala Ser Met Pro Ser Arg Thr Ile Gly Arg Ser
                85                  90                  95

Arg Gly Ala Ile Ile Ser Gln Tyr Tyr Asn Arg Thr Val Gln Leu Arg
            100                 105                 110

Arg Arg Ser Ser Arg Pro Leu Leu Gly Asn Leu Val Arg Ser Ala Arg
        115                 120                 125

Pro Ser Leu Arg Met Tyr Asp Leu Glu Leu Asp Pro Arg Ala Gln Glu
    130                 135                 140

Glu Glu Glu Lys Gln Ser Leu Leu Val Lys Glu Leu Gln Ser Leu Ala
145                 150                 155                 160

Val Ala Gln Arg Asp His Met Leu Arg Gly Met Pro Leu Ser Leu Ala
                165                 170                 175

Glu Lys Arg Ser Leu Arg Glu Lys Ser Gln Thr Pro Arg Gly Lys Trp
            180                 185                 190

Arg Gly Gln Arg Gly His Gly Gly Val Cys Ser Cys Cys Gly Trp Leu
        195                 200                 205

Arg Tyr Ala Cys Val Leu Thr Leu His Ser Leu Gly Leu Ala Leu Leu
    210                 215                 220

Ser Ser Leu Gln Ala Leu Thr Pro Trp Arg Tyr Ala Leu Lys Arg Ile
225                 230                 235                 240

Gly Gly Gln Phe Gly Ser Ser Val Leu Ser Tyr Phe Leu Phe Leu Lys
                245                 250                 255

Thr Leu Leu Ala Phe Asn Ala Leu Leu Leu Leu Leu Leu Ala Phe
            260                 265                 270

Ile Val Gly Pro Gln Ala Ala Phe Pro Ala Leu Pro Gly Pro Val
        275                 280                 285

Pro Val Cys Thr Gly Leu Glu Leu Leu Thr Gly Ala Gly Cys Phe Thr
    290                 295                 300

His Thr Val Met Tyr Tyr Gly His Tyr Ser Asn Ala Thr Leu Asn Gln
```

-continued

```
            305                 310                 315                 320
        Pro Cys Gly Gly Pro Leu Glu Gly Gly Arg Cys Ser Pro Arg Ala Ser
                        325                 330                 335
        Gly Leu Pro Tyr Asn Met Pro Leu Ala Tyr Leu Phe Thr Val Gly Val
                        340                 345                 350
        Gly Phe Phe Ile Thr Cys Ile Thr Leu Val Tyr Ser Met Ala His Ser
                        355                 360                 365
        Phe Gly Glu Ser Tyr Arg Val Gly Ser Thr Ser Gly Ile His Ala Ile
                370                 375                 380
        Thr Val Phe Cys Ser Trp Asp Tyr Lys Val Thr Gln Lys Trp Ala Ser
        385                 390                 395                 400
        Arg Leu Gln Gln Asp Asn Ile Arg Thr Arg Leu Lys Glu Leu Leu Ala
                        405                 410                 415
        Glu Trp Gln Leu Arg Gln Ser Pro Arg Ser Val Cys Arg Arg Leu Arg
                        420                 425                 430
        Gln Val Ala Thr Leu Gly Leu Val Trp Leu Leu Cys Leu Gly Thr Ala
                        435                 440                 445
        Leu Gly Cys Ala Val Ala Val His Val Phe Ser Glu Phe Met Ile Gln
                450                 455                 460
        Ser Leu Glu Ala Ala Gly Gln Glu Ala Ala Leu Leu Val Leu Pro Leu
        465                 470                 475                 480
        Val Val Gly Leu Leu Asn Leu Gly Ser Pro Tyr Leu Cys Arg Ile Leu
                        485                 490                 495
        Ala Ala Leu Glu Pro His Asp Ser Pro Val Leu Glu Val Tyr Val Ala
                        500                 505                 510
        Ile Cys Arg Asn Leu Ile Leu Lys Leu Ala Ile Leu Gly Thr Leu Cys
                        515                 520                 525
        Tyr Arg Trp Leu Gly Arg Arg Val Gly Val Leu Arg Gly Gln Cys Trp
                        530                 535                 540
        Glu Asp Ser Val Gly Gln Glu Leu Tyr Arg Phe Leu Val Met Asp Phe
        545                 550                 555                 560
        Val Leu Thr Leu Leu Asp Thr Leu Phe Gly Glu Leu Val Trp Arg Ile
                        565                 570                 575
        Ile Ser Glu Lys Lys Leu Lys Arg Arg Arg Lys Pro Glu Phe Asp Ile
                        580                 585                 590
        Ala Arg Asn Val Leu Glu Leu Ile Tyr Gly Gln Thr Leu Thr Trp Leu
                        595                 600                 605
        Gly Val Leu Phe Ser Pro Leu Leu Pro Ala Val Gln Ile Ile Lys Leu
                        610                 615                 620
        Leu Leu Val Phe Tyr Ile Lys Lys Thr Ser Leu Leu Ala Asn Cys Gln
        625                 630                 635                 640
        Ala Pro Arg Arg Pro Trp Leu Ala Ser His Met Ser Thr Val Phe Leu
                        645                 650                 655
        Thr Leu Leu Cys Phe Pro Ala Phe Leu Gly Ala Ala Val Phe Leu Cys
                        660                 665                 670
        Tyr Ala Val Trp Gln Val Lys Pro Ser Asp Ile Cys Gly Pro Phe Arg
                        675                 680                 685
        Thr Leu Asp Thr Met Tyr Glu Ala Gly Arg Val Trp Val Arg His Leu
                        690                 695                 700
        Glu Ala Ala Gly Pro Arg Val Ser Trp Leu Pro Trp Val His Arg Tyr
        705                 710                 715                 720
        Leu Val Glu Asn Thr Phe Phe Val Phe Leu Val Ser Ala Leu Leu Leu
                        725                 730                 735
```

```
Ala Val Ile Tyr Leu Asn Ile Gln Val Val Arg Gly Gln Arg Lys Val
                740                 745                 750

Ile Cys Leu Leu Lys Glu Gln Ile Ser Asn Glu Gly Glu Asp Lys Ile
                755                 760                 765

Phe Leu Ile Asn Lys Leu His Ser Ile Tyr Glu Lys Lys Glu Arg Glu
                770                 775                 780

Glu Arg Ser Arg Val Arg Thr Ser Gln Ala Val Val Pro Pro Thr Leu
785                 790                 795                 800

Leu Thr Asp Glu Arg Asp Ala
                805

<210> SEQ ID NO 3
<211> LENGTH: 804
<212> TYPE: PRT
<213> ORGANISM: Callithrix jacchus
<220> FEATURE:
<221> NAME/KEY: misc_feature
<222> LOCATION: (731)..(742)
<223> OTHER INFORMATION: Xaa can be any naturally occurring amino acid

<400> SEQUENCE: 3

Met Ala Gln Pro Leu Pro Phe Val Leu Asp Val Pro Glu Thr Pro Gly
1               5                   10                  15

Asp Gln Gly Gln Glu Pro Ser Pro Tyr Asp Glu Ser Glu Val His Asp
                20                  25                  30

Ser Phe Gln Gln Leu Ile Gln Glu Gln Ser Trp Arg Ala Ala Gln Glu
            35                  40                  45

Gly Leu Glu Leu Gln Gln Arg Ala Arg Gln Ala Ala Gly Ser Gly Gln
    50                  55                  60

His Thr Leu Leu Gly Ser Glu Gly Thr His Ser Ala Ala Thr Leu Arg
65                  70                  75                  80

Ile Leu Ala Ser Met Pro Ser Arg Thr Ile Gly Arg Ser Arg Gly Ala
                85                  90                  95

Ile Ile Ser Gln Tyr Tyr Asn Arg Thr Val Gln Leu Arg Arg Arg Ser
            100                 105                 110

Ser Arg Pro Leu Leu Gly Asn Leu Val Arg Ser Ala Arg Pro Ser Leu
        115                 120                 125

Arg Met Tyr Asp Leu Glu Leu Asp Pro Arg Ala Gln Glu Glu Glu Glu
130                 135                 140

Lys Gln Ser Leu Leu Val Arg Glu Leu Gln Ser Leu Ala Val Ala Gln
145                 150                 155                 160

Arg Asp His Met Leu Arg Gly Met Pro Leu Ser Leu Ala Glu Lys Arg
                165                 170                 175

Ser Leu Arg Glu Lys Ser Arg Thr Pro Arg Gly Lys Trp Arg Gly Gln
            180                 185                 190

Arg Gly His Gly Ser Ile Phe Ser Cys Cys Gly Trp Leu Arg Tyr Ala
        195                 200                 205

Cys Val Leu Thr Leu His Ser Leu Gly Leu Ala Leu Leu Ser Ser Leu
    210                 215                 220

Gln Ala Leu Thr Pro Trp Arg Tyr Ala Leu Lys Arg Ile Gly Gly Gln
225                 230                 235                 240

Phe Gly Ser Ser Val Leu Ser Tyr Phe Leu Phe Leu Lys Thr Leu Leu
                245                 250                 255

Ala Phe Asn Ala Leu Leu Leu Leu Leu Leu Ala Phe Met Val Gly
            260                 265                 270
```

```
Pro Gln Ala Ala Phe Pro Pro Ala Leu Pro Gly Val Pro Val Cys
            275                 280                 285

Thr Gly Leu Glu Leu Leu Thr Gly Ala Gly Cys Phe Thr His Thr Val
290                 295                 300

Met Tyr Tyr Gly His Tyr Ser Asn Ala Thr Leu Asn Gln Pro Cys Ala
305                 310                 315                 320

Gly Pro Leu Glu Gly Gly Arg Cys Ser Pro Gly Ala Gly Ser Leu Pro
                325                 330                 335

Tyr Asn Met Pro Leu Ala Tyr Leu Phe Thr Val Gly Val Gly Phe Phe
            340                 345                 350

Ile Thr Cys Ile Thr Leu Val Tyr Ser Met Ala His Ser Phe Gly Glu
            355                 360                 365

Ser Tyr Arg Val Gly Ser Thr Ser Gly Ile His Ala Ile Thr Val Phe
370                 375                 380

Cys Ser Trp Asp Tyr Lys Val Thr Gln Lys Arg Ala Ser Arg Leu Gln
385                 390                 395                 400

Gln Asp Asn Ile Arg Thr Arg Leu Lys Glu Leu Leu Ala Glu Trp Gln
                405                 410                 415

Leu Arg Gln Ser Pro Arg Ser Val Cys Arg Arg Leu Arg Gln Ala Ala
            420                 425                 430

Ala Leu Gly Leu Thr Trp Leu Leu Cys Leu Gly Thr Ala Leu Gly Cys
            435                 440                 445

Ala Val Ala Val His Val Phe Ser Glu Phe Met Ile Gln Ser Leu Glu
            450                 455                 460

Ala Ala Gly Lys Glu Ala Ala Leu Leu Val Leu Pro Leu Val Val Gly
465                 470                 475                 480

Leu Leu Asn Leu Gly Ala Pro Tyr Leu Cys Arg Ile Leu Ala Ala Leu
                485                 490                 495

Glu Pro His Asp Ser Pro Val Leu Glu Val Tyr Val Ala Ile Cys Arg
            500                 505                 510

Asn Leu Ile Leu Lys Leu Ala Ile Leu Gly Thr Leu Cys Tyr His Trp
            515                 520                 525

Leu Gly Arg Arg Val Gly Val Leu Arg Gly Gln Cys Trp Glu Asp Phe
530                 535                 540

Val Gly Gln Glu Leu Tyr Arg Phe Leu Val Met Asp Phe Ile Leu Met
545                 550                 555                 560

Leu Leu Asp Thr Leu Phe Gly Glu Leu Val Trp Arg Ile Ile Ser Glu
                565                 570                 575

Lys Lys Leu Lys Arg Arg Arg Lys Pro Glu Phe Asp Ile Ala Arg Asn
            580                 585                 590

Val Leu Glu Leu Ile Tyr Gly Gln Thr Leu Thr Trp Leu Gly Val Leu
            595                 600                 605

Phe Ser Pro Leu Leu Pro Ala Val Gln Ile Ile Lys Leu Leu Leu Val
610                 615                 620

Phe Tyr Ile Lys Lys Ala Ser Leu Leu Ala Asn Cys Gln Ala Pro Arg
625                 630                 635                 640

Arg Pro Trp Leu Ala Ser His Met Ser Thr Val Phe Leu Thr Leu Leu
                645                 650                 655

Cys Phe Pro Ala Phe Leu Gly Thr Ala Val Phe Leu Cys Tyr Ala Val
            660                 665                 670

Trp His Val Lys Pro Ser Gly Ile Cys Gly Pro Phe Arg Thr Leu Asp
            675                 680                 685

Thr Met Tyr Glu Ala Gly Arg Val Trp Val Arg His Leu Glu Ala Gly
```

```
            690                 695                 700
Gly Pro Arg Val Ser Trp Leu Pro Trp Val His Gln Tyr Leu Val Glu
705                 710                 715                 720

Asn Thr Phe Phe Val Phe Leu Val Ser Ala Xaa Xaa Xaa Xaa Xaa
                725                 730                 735

Xaa Xaa Xaa Xaa Xaa Val Arg Gly Gln Arg Lys Val Ile Cys Leu
            740                 745                 750

Leu Lys Glu Gln Ile Ser Asn Glu Gly Glu Asp Lys Ile Phe Leu Ile
            755                 760                 765

Asn Lys Leu His Ser Ile Tyr Glu Arg Lys Glu Arg Glu Arg Ser
            770                 775                 780

Arg Val Arg Thr Gly Gln Ala Ala Ile Pro Pro Thr Leu Leu Thr Asp
785                 790                 795                 800

Glu Arg Asp Ala

<210> SEQ ID NO 4
<211> LENGTH: 869
<212> TYPE: PRT
<213> ORGANISM: Bubalus bubalis

<400> SEQUENCE: 4

Met Ser Gln Ser Pro Ala Phe Val Leu Asn Val Leu Glu Thr Pro Glu
1               5                   10                  15

Asp Pro Glu Gly Ser Gln Glu Pro Ser Pro Tyr Asp Glu Ser Glu Val
                20                  25                  30

His Asp Ser Phe His Gln Leu Ile Gln Glu Gln Ser Arg Trp Val Ala
            35                  40                  45

Glu Glu Gly Leu Glu Leu Gln Gln Arg Gln Pro Gly Thr Gly Ala Leu
        50                  55                  60

Gly Ala Ser Gly Ser Asp His Glu Thr Met Leu Gly Pro Glu Gly Ala
65                  70                  75                  80

Pro Val Tyr Ser Met Ala Thr Leu Arg Ile Leu Ala Ser Met Pro Ser
                85                  90                  95

Arg Thr Ile Gly Arg Ser Arg Gly Ala Ile Ile Ser Gln Tyr Tyr Ser
            100                 105                 110

Arg Thr Val Lys Leu Arg Arg Arg Ala Gly Arg Pro Gln Leu Arg Asp
        115                 120                 125

Met Gly Arg Ser Ala Arg Pro Ser Leu Arg Leu Tyr Asp Leu Glu Leu
130                 135                 140

Asp Ser Ala Val Leu Glu Glu Glu Lys Arg Gly Leu Leu Val Lys
145                 150                 155                 160

Glu Leu Gln Gly Leu Thr Ala Ala Gln Arg Asp His Met Leu Arg Gly
                165                 170                 175

Met Pro Leu Ser Leu Ala Glu Lys Arg Cys Leu Arg Glu Glu Ser Arg
            180                 185                 190

Pro Pro Arg Gly Lys His Arg Ala Gln Arg His His Gly Leu Leu Ser
        195                 200                 205

Cys Cys Asp Gln Leu Arg Asp Ser Cys Val Leu Gly His Phe Thr His
210                 215                 220

Ser Val Met Tyr Tyr Gly Tyr Tyr Ser Asn Ala Thr Leu Asn Gln Pro
225                 230                 235                 240

Cys Ala Ser Pro Leu Asp Gly Ser Gln Cys Thr Pro Glu Ala Gly Ser
                245                 250                 255

Leu Pro Tyr Ser Met Pro Leu Ala Tyr Leu Phe Thr Leu Gly Ala Ala
```

```
                260                 265                 270
Phe Phe Ile Thr Cys Ile Thr Leu Val Tyr Ser Met Ser His Ser Phe
            275                 280                 285
Gly Glu Ser Tyr Arg Val Gly Ser Thr Ser Gly Val His Ala Ile Thr
        290                 295                 300
Val Phe Cys Ser Trp Asp Tyr Lys Val Thr Gln Arg Trp Ala Thr Arg
305                 310                 315                 320
Leu Gln His Asp Asn Ile Arg Thr Gln Leu Lys Glu Leu Leu Ala Glu
                325                 330                 335
Trp Gln Ser Arg Gln His Arg Arg Ser Ala Cys Gly Gln Leu Arg Arg
            340                 345                 350
Val Ala Val Leu Gly Leu Val Trp Leu Leu Cys Leu Gly Thr Thr Leu
        355                 360                 365
Gly Cys Thr Leu Ala Val Tyr Thr Phe Ser Glu Leu Met Ile Lys Val
    370                 375                 380
Gln Arg Gly Arg Gly Arg Pro Pro Arg Pro Gly Pro Pro Ala Leu
385                 390                 395                 400
Leu Ala Gly Thr Leu Gly Leu Pro His Pro Pro Arg Pro Pro
                405                 410                 415
Glu Asp Thr Phe Leu Pro Val Leu Val Leu Ile Leu Val Leu Ser Asn
            420                 425                 430
Ala Ile Met Thr Ser Phe Cys Phe Leu Val Phe Trp Phe Leu Phe Ser
        435                 440                 445
Leu Phe Phe Arg His Leu Cys Ser Ile Leu Pro Ser Pro Pro Ala
    450                 455                 460
Pro Leu Pro Val Arg Phe Glu His Arg Ala Trp Gly Gly Gly Val
465                 470                 475                 480
Pro Ala Ile Cys Thr Cys Ser Val Pro Pro Arg Pro Leu Pro Ala Ala
                485                 490                 495
Pro Ser Pro Pro Arg Ser Gly Pro Ala Val Asp Leu Thr Leu Ser Leu
            500                 505                 510
Gly Pro Leu Arg Gly Pro Leu Arg Pro Ala Pro Gln Gln Ser
        515                 520                 525
Pro Val Ser Ala Lys Arg Glu Ala Val Leu Leu Leu Pro Leu Val
    530                 535                 540
Val Cys Leu Leu Asn Leu Gly Gly Pro Tyr Leu Phe Arg Ile Leu Ala
545                 550                 555                 560
Ala Leu Glu Arg His Asp Ser Pro Val Leu Glu Val Tyr Val Ala Ile
                565                 570                 575
Cys Arg Asn Leu Ile Leu Lys Met Val Thr Leu Gly Ile Leu Cys Tyr
            580                 585                 590
His Trp Leu Gly Arg Arg Val Gly Thr Leu Lys Asp Gln Cys Trp Glu
        595                 600                 605
Asn Phe Val Gly Gln Glu Leu Tyr Arg Leu Met Val Met Asp Phe Ile
    610                 615                 620
Phe Thr Leu Leu Asp Thr Leu Leu Gly Glu Leu Val Trp Arg Leu Phe
625                 630                 635                 640
Ser Glu Lys Gln Leu Lys Arg Lys Gly Lys Pro Glu Phe Asp Ile Ala
                645                 650                 655
Gly Asn Val Leu Glu Leu Ile Tyr Gly Gln Thr Leu Thr Trp Leu Gly
            660                 665                 670
Val Leu Phe Ser Pro Leu Leu Pro Ala Met Gln Ile Ile Lys Leu Leu
        675                 680                 685
```

Leu Leu Phe Tyr Ile Lys Lys Ala Ser Leu Met Ala Asn Cys Gln Ala
            690                 695                 700

Pro Arg Arg Pro Trp Lys Ala Ser His Met Ser Thr Val Phe Ile Ser
705                 710                 715                 720

Leu Leu Cys Phe Pro Ser Phe Leu Gly Ala Ala Val Phe Leu Cys Tyr
                725                 730                 735

Ala Val Trp Gln Val Lys Pro Ser Ser Thr Cys Gly Pro Phe Arg Thr
            740                 745                 750

Leu Asp Thr Met Tyr Glu Ala Gly Lys Val Trp Val Arg Arg Leu Glu
            755                 760                 765

Lys Ala Gly Pro Arg Val Ser Trp Leu Pro Trp Ile His Arg Tyr Leu
770                 775                 780

Val Glu Asp Thr Phe Pro Ile Tyr Leu Val Ser Ala Leu Leu Leu Ala
785                 790                 795                 800

Val Ile Tyr Leu Asn Ile Gln Val Val Lys Gly Gln Arg Lys Val Ile
            805                 810                 815

Cys Leu Leu Lys Glu Gln Ile Ser Asn Glu Gly Glu Asp Lys Ile Phe
            820                 825                 830

Leu Ile Asn Lys Leu Gln Arg Val Tyr Glu Arg Lys Glu Arg Ser Arg
            835                 840                 845

Ala Gly Arg Thr Glu Glu Ala Val Thr Pro Ala Leu Phe Ala Asp
            850                 855                 860

Gly Trp Asp Ala Gln
865

<210> SEQ ID NO 5
<211> LENGTH: 759
<212> TYPE: PRT
<213> ORGANISM: Camelus bactrianus

<400> SEQUENCE: 5

Met Ala Gln Pro Pro Val Phe Val Leu Ser Val Pro Glu Thr Pro Asp
1               5                   10                  15

Asp Pro Glu Gly Ser Gln Glu Pro Ser Pro Tyr Asp Glu Ser Glu Val
            20                  25                  30

His Asp Ser Phe Tyr Gln Leu Ile Gln Glu Gln Ser Arg Trp Ala Ala
        35                  40                  45

Glu Glu Gly Leu Glu Leu Gln Gln Arg Glu Pro Gly Pro Gly Ala Leu
    50                  55                  60

Gly Ala Leu Gly Asp Asp His Gln Ala Leu Leu Gly Pro Glu Gly Val
65                  70                  75                  80

Pro Val His Ser Met Ala Thr Leu Arg Ile Leu Ala Ser Met Pro Ser
                85                  90                  95

Arg Thr Ile Ala Ala Ser Pro Gly Pro Ser Arg Gly Ala Pro Thr Leu
            100                 105                 110

Val Leu Glu Glu Glu Lys Arg Val Leu Leu Val Lys Glu Leu Gln
        115                 120                 125

Gly Leu Thr Val Ala Gln Arg Asp His Val Leu Arg Gly Met Pro Leu
    130                 135                 140

Ser Leu Ala Glu Lys Arg Cys Leu Arg Glu Ser Arg Thr Pro Arg
145                 150                 155                 160

Gly Lys Arg Arg Ala Arg Gln Gly Gly Arg Gly Leu Pro Ser Cys Cys
                165                 170                 175

Ser Gln Leu Gln Asp Ser Cys Val Leu Ala Leu His Asn Leu Gly Leu

-continued

```
            180                 185                 190
Val Leu Leu Ser Gly Leu Gln Ala Leu Lys Pro Trp Arg Tyr Ala Leu
            195                 200                 205
Lys Arg Ile Gly Gly Gln Phe Gly Ser Ser Val Leu Ser Tyr Phe Leu
            210                 215                 220
Phe Leu Lys Thr Leu Leu Ala Phe Asn Ala Leu Leu Leu Pro Leu
225             230                 235                 240
Leu Ala Phe Ile Val Gly Val Gln Ala Ala Phe Pro Pro Ala Pro Pro
                245                 250                 255
Ala Ser Val Pro Ala Phe Thr Gly Leu Glu Leu Leu Thr Gly Gly Gly
            260                 265                 270
Arg Phe Ala His Thr Val Leu Tyr Tyr Asp Gln Cys Pro Pro Glu Ala
            275                 280                 285
Gly Gly Leu Pro Tyr Asn Met Pro Leu Ala Tyr Leu Phe Thr Val Gly
            290                 295                 300
Val Ala Phe Phe Ile Thr Cys Ile Thr Leu Val Tyr Ser Met Ser Arg
305             310                 315                 320
Ser Phe Gly Glu Ser Tyr Arg Val Gly Ser Thr Ser Gly Val His Ala
                325                 330                 335
Ile Ser Val Phe Cys Ser Trp Asp Tyr Lys Val Thr Gln Lys Trp Ala
            340                 345                 350
Ser Arg Leu Gln His Asp Asn Ile Arg Thr Gln Leu Lys Glu Leu Leu
            355                 360                 365
Ala Val Trp Gln Leu Arg Arg Gly Pro Arg Ser Met Cys Trp Arg Leu
            370                 375                 380
Arg Arg Val Ala Val Leu Gly Leu Val Trp Leu Leu Cys Leu Gly Ile
385             390                 395                 400
Thr Leu Gly Cys Thr Val Ala Val Tyr Ser Phe Ser Glu Leu Met Ile
                405                 410                 415
Lys Ser Pro Gly Ser Thr Glu Arg Glu Gly Ala Leu Leu Ala Leu Pro
            420                 425                 430
Leu Val Val Cys Leu Leu Asn Leu Gly Ala Pro Tyr Leu Tyr Arg Gly
            435                 440                 445
Leu Ala Ala Leu Glu Arg His Asp Ser Pro Val Leu Glu Val Tyr Val
            450                 455                 460
Ala Ile Cys Arg Asn Leu Ile Leu Lys Met Val Thr Leu Gly Ile Leu
465             470                 475                 480
Cys Tyr His Trp Leu Gly Arg Arg Val Gly Thr Leu Arg Asp Gln Cys
                485                 490                 495
Trp Glu Asn Phe Val Gly Gln Glu Leu Tyr Arg Leu Met Val Met Asp
                500                 505                 510
Phe Leu Phe Thr Leu Leu Asp Thr Leu Phe Gly Glu Leu Val Trp Arg
            515                 520                 525
Leu Ile Ser Glu Arg Thr Leu Lys Arg Arg Gly Lys Pro Glu Phe Asp
            530                 535                 540
Ile Ala Gly Asn Val Leu Glu Leu Ile Tyr Gly Gln Thr Leu Thr Trp
545             550                 555                 560
Leu Gly Val Leu Phe Ser Pro Leu Leu Pro Ala Met Gln Ile Ile Lys
                565                 570                 575
Leu Leu Leu Leu Phe Tyr Val Lys Lys Thr Ser Leu Met Ala Asn Cys
            580                 585                 590
Gln Ala Pro Arg Arg Pro Trp Lys Ala Ser His Met Ser Thr Val Phe
            595                 600                 605
```

```
Ile Ser Leu Leu Cys Phe Pro Ser Phe Leu Gly Ala Ala Ile Phe Leu
        610                 615                 620

Cys Tyr Ala Val Trp Gln Val Lys Pro Ser Ser Ile Cys Gly Pro Phe
625                 630                 635                 640

Arg Thr Leu Asp Thr Met Tyr Glu Ala Gly Lys Val Trp Val Arg His
                645                 650                 655

Leu Glu Arg Ala Gly Pro Arg Val Ser Trp Leu Pro Trp Ile His Arg
                660                 665                 670

Tyr Leu Leu Glu Asn Thr Phe Pro Ile Tyr Leu Val Ser Ala Leu Leu
            675                 680                 685

Leu Ala Val Ile Tyr Leu Asn Ile Gln Val Val Lys Gly Gln Arg Lys
690                 695                 700

Val Ile Cys Leu Leu Lys Glu Gln Ile Ser Asn Glu Gly Glu Asp Lys
705                 710                 715                 720

Ile Phe Leu Ile Asn Lys Leu Gln Ser Val Tyr Glu Arg Lys Glu Arg
                725                 730                 735

Ser Arg Val Gly Arg Thr Glu Ala Ala Val Met Pro Pro Ala Leu Phe
                740                 745                 750

Thr Asp Asp Gly Asp Thr Trp
            755

<210> SEQ ID NO 6
<211> LENGTH: 812
<212> TYPE: PRT
<213> ORGANISM: Camelus dromedaries

<400> SEQUENCE: 6

Met Ala Gln Pro Pro Val Phe Val Leu Ser Val Pro Glu Thr Pro Asp
1               5                   10                  15

Asp Pro Glu Gly Gln Glu Pro Ser Pro Tyr Asp Glu Ser Glu Val His
                20                  25                  30

Asp Ser Phe Tyr Gln Leu Ile Gln Glu Gln Ser Arg Trp Ala Ala Glu
            35                  40                  45

Glu Gly Leu Glu Leu Gln Gln Arg Glu Pro Gly Pro Gly Ala Leu Gly
        50                  55                  60

Ala Leu Gly Asp Asp His Gln Ala Leu Leu Gly Pro Glu Gly Val Pro
65                  70                  75                  80

Val His Ser Met Ala Thr Leu Arg Ile Leu Ala Ser Met Pro Ser Arg
                85                  90                  95

Thr Ile Gly Arg Ser Arg Gly Ala Ile Leu Ser Gln Leu Tyr Asn Arg
                100                 105                 110

Thr Val Arg Leu Arg Arg Arg Ala Ala Arg Pro Gln Leu Arg Asp
                115                 120                 125

Val Gly Arg Ser Ala Arg Pro Ser Leu Arg Leu Tyr Asp Leu Glu Leu
        130                 135                 140

Asp Pro Leu Val Leu Glu Glu Glu Lys Arg Val Leu Leu Val Lys
145                 150                 155                 160

Glu Leu Gln Gly Leu Thr Val Ala Gln Arg Asp His Val Leu Arg Gly
                165                 170                 175

Met Pro Leu Ser Leu Ala Glu Lys Arg Cys Leu Arg Glu Glu Ser Arg
                180                 185                 190

Thr Pro Arg Gly Lys Arg Arg Ala Arg Gln Gly Gly Arg Gly Leu Pro
                195                 200                 205

Ser Cys Cys Ser Gln Leu Gln Asp Ser Cys Val Leu Ala Leu His Asn
```

-continued

```
              210                 215                 220
Leu Gly Leu Val Leu Leu Ser Gly Leu Gln Ala Leu Lys Pro Trp Arg
225                 230                 235                 240

Tyr Ala Leu Lys Arg Ile Gly Gly Gln Phe Gly Ser Ser Val Leu Ser
                245                 250                 255

Tyr Phe Leu Phe Leu Lys Thr Leu Leu Ala Phe Asn Ala Leu Leu Leu
                260                 265                 270

Leu Pro Leu Leu Ala Phe Ile Val Gly Val Gln Ala Ala Phe Pro Pro
            275                 280                 285

Ala Pro Pro Ala Ser Val Pro Ala Phe Thr Gly Leu Glu Leu Leu Thr
        290                 295                 300

Gly Gly Gly Arg Phe Ala His Thr Val Leu Tyr Tyr Gly Tyr Tyr Ser
305                 310                 315                 320

Asn Ala Thr Leu Ser Gln Pro Cys Ala Ser Pro Pro Asp Gly Gly Gln
                325                 330                 335

Cys Pro Pro Glu Ala Gly Gly Leu Pro Tyr Asn Met Pro Leu Ala Tyr
                340                 345                 350

Leu Phe Thr Val Gly Val Ala Phe Phe Ile Thr Cys Ile Thr Leu Val
            355                 360                 365

Tyr Ser Met Ser Arg Ser Phe Gly Glu Ser Tyr Arg Val Gly Ser Thr
        370                 375                 380

Ser Gly Val His Ala Ile Ser Val Phe Cys Ser Trp Asp Tyr Lys Val
385                 390                 395                 400

Thr Gln Lys Trp Ala Ser Arg Leu Gln His Asp Asn Ile Arg Thr Gln
                405                 410                 415

Leu Lys Glu Leu Leu Ala Val Trp Gln Leu Arg Arg Gly Pro Arg Ser
            420                 425                 430

Met Cys Trp Arg Leu Arg Arg Val Ala Val Leu Gly Leu Val Trp Leu
        435                 440                 445

Leu Cys Leu Gly Thr Thr Leu Gly Cys Thr Val Ala Val Tyr Ser Phe
    450                 455                 460

Ser Glu Leu Met Ile Lys Ser Pro Gly Ser Thr Glu Arg Glu Gly Ala
465                 470                 475                 480

Leu Leu Ala Leu Pro Leu Val Val Cys Leu Leu Asn Leu Gly Ala Pro
                485                 490                 495

Tyr Leu Tyr Arg Gly Leu Ala Ala Leu Glu Arg His Asp Ser Pro Val
            500                 505                 510

Leu Glu Val Tyr Val Ala Ile Cys Arg Asn Leu Ile Leu Lys Met Val
        515                 520                 525

Thr Leu Gly Ile Leu Cys Tyr His Trp Leu Gly Arg Arg Val Gly Thr
    530                 535                 540

Leu Arg Asp Gln Cys Trp Glu Asn Phe Val Gly Gln Glu Leu Tyr Arg
545                 550                 555                 560

Leu Met Val Met Asp Phe Leu Phe Thr Leu Asp Thr Leu Phe Gly
                565                 570                 575

Glu Leu Val Trp Arg Leu Ile Ser Glu Arg Thr Leu Lys Arg Arg Gly
            580                 585                 590

Lys Pro Glu Phe Asp Ile Ala Gly Asn Val Leu Glu Leu Ile Tyr Gly
        595                 600                 605

Gln Thr Leu Thr Trp Leu Gly Val Leu Phe Ser Pro Leu Leu Pro Ala
    610                 615                 620

Met Gln Ile Ile Lys Leu Leu Leu Leu Phe Tyr Val Lys Lys Thr Ser
625                 630                 635                 640
```

```
Leu Met Ala Asn Cys Gln Ala Pro Arg Arg Pro Trp Lys Ala Ser His
                645                 650                 655

Met Ser Thr Val Phe Ile Ser Leu Leu Cys Phe Pro Ser Phe Leu Gly
            660                 665                 670

Ala Ala Ile Phe Leu Cys Tyr Ala Val Trp Gln Val Lys Pro Ser Ser
                675                 680                 685

Ile Cys Gly Pro Phe Arg Thr Leu Asp Thr Met Tyr Glu Ala Gly Lys
            690                 695                 700

Val Trp Val Arg His Leu Glu Arg Ala Gly Pro Arg Val Ser Trp Leu
705                 710                 715                 720

Pro Trp Ile His Arg Tyr Leu Leu Glu Asn Thr Phe Pro Ile Tyr Leu
                725                 730                 735

Val Ser Ala Leu Leu Leu Ala Val Ile Tyr Leu Asn Ile Gln Val Val
            740                 745                 750

Lys Gly Gln Arg Lys Val Ile Cys Leu Leu Lys Glu Gln Ile Ser Asn
        755                 760                 765

Glu Gly Glu Asp Lys Ile Phe Leu Ile Asn Lys Leu Gln Ser Val Tyr
    770                 775                 780

Glu Arg Lys Glu Arg Ser Arg Val Gly Arg Thr Glu Ala Ala Ala Met
785                 790                 795                 800

Pro Pro Ala Leu Phe Thr Asp Asp Gly Asp Thr Trp
                805                 810

<210> SEQ ID NO 7
<211> LENGTH: 689
<212> TYPE: PRT
<213> ORGANISM: Vicugna pacos
<220> FEATURE:
<221> NAME/KEY: misc_feature
<222> LOCATION: (346)..(346)
<223> OTHER INFORMATION: Xaa can be any naturally occurring amino acid

<400> SEQUENCE: 7

Met Ala Gln Pro Pro Val Phe Val Leu Ser Val Pro Glu Thr Pro Asp
1               5                   10                  15

Asp Pro Glu Gly Glu Gly Lys Arg Val Leu Leu Val Lys Glu Leu
            20                  25                  30

Gln Gly Leu Thr Val Ala Gln Arg Asp His Val Leu Arg Gly Met Pro
        35                  40                  45

Leu Ser Leu Ala Glu Lys Arg Cys Leu Arg Glu Glu Ser Arg Thr Pro
    50                  55                  60

Arg Gly Lys Arg Arg Ala Arg Gln Gly Gly Arg Gly Leu Pro Ser Cys
65                  70                  75                  80

Cys Ser Gln Leu Gln Asp Ser Cys Val Leu Ala Leu His Asn Leu Gly
                85                  90                  95

Leu Val Leu Leu Ser Gly Leu Gln Ala Leu Lys Pro Trp Arg Tyr Ala
            100                 105                 110

Leu Lys Arg Ile Gly Gly Gln Phe Gly Ser Ser Val Leu Ser Ser Ser
        115                 120                 125

Ile Phe Arg Ser His Asp Trp Val Gly Ser Trp Ser Cys Trp Trp
    130                 135                 140

Gly Leu Val Pro Glu Pro Ser Ser His Leu Trp Leu Val Gly Thr
145                 150                 155                 160

Val Leu Asp Arg Ala Asp Leu Glu Trp Pro Val Gly Pro Thr Arg Arg
                165                 170                 175
```

```
Pro Arg Ala Leu Gly Trp Arg Trp Gly Arg Gly Arg Val Thr Gly Gly
            180                 185                 190

Pro Ser Ser Thr Gly Trp Ala Pro Pro Ser Gly Cys Trp Val Leu Ala
        195                 200                 205

Ala Arg Ser Ile Arg Gly Val Leu Ser Ala Pro Ser Ala Pro Thr Gln
    210                 215                 220

Ser Leu Leu Gly Ser Ala Ser Pro Ser Met Ser Arg Ser Phe Gly Glu
225                 230                 235                 240

Ser Tyr Arg Val Gly Ser Thr Ser Gly Val His Ala Ile Ser Val Phe
                245                 250                 255

Cys Ser Trp Asp Tyr Lys Val Thr Gln Lys Trp Ala Ser Arg Leu Gln
            260                 265                 270

His Asp Asn Ile Arg Thr Gln Leu Lys Val Ser Cys Arg Gly Trp Gly
        275                 280                 285

Leu Arg Pro Pro Pro Pro Arg Ser Arg Gly His Gln Cys Ala Ser
    290                 295                 300

Ala Pro Val Gly Asp Gly Ser Pro Leu Leu Pro Pro Trp Asp Pro
305                 310                 315                 320

Ala Leu Arg Leu Pro Pro Gln Trp Thr Arg Pro Cys Pro Leu Gly Pro
                325                 330                 335

Cys Gly Asp Thr Ala Pro Pro Leu Leu Xaa Gln Ser Pro Gly Ser Thr
            340                 345                 350

Glu Arg Glu Gly Ala Leu Leu Ala Leu Pro Leu Val Val Cys Leu Leu
        355                 360                 365

Asn Leu Gly Ala Pro Tyr Leu Tyr Arg Gly Leu Ala Ala Leu Glu Arg
370                 375                 380

His Asp Ser Pro Val Leu Glu Val Tyr Val Ala Ile Cys Arg Asn Leu
385                 390                 395                 400

Ile Leu Lys Met Val Thr Leu Gly Ile Leu Cys Tyr His Trp Leu Gly
                405                 410                 415

Arg Arg Val Gly Thr Leu Arg Asp Gln Cys Trp Glu Asn Phe Val Gly
            420                 425                 430

Gln Glu Leu Tyr Arg Leu Met Val Met Asp Phe Leu Phe Thr Leu Leu
        435                 440                 445

Asp Thr Leu Phe Gly Glu Leu Val Trp Arg Leu Ile Ser Glu Arg Thr
450                 455                 460

Leu Lys Arg Arg Gly Lys Pro Glu Phe Asp Ile Ala Gly Asn Val Leu
465                 470                 475                 480

Glu Leu Ile Tyr Gly Gln Thr Leu Thr Trp Leu Gly Val Leu Phe Ser
                485                 490                 495

Pro Leu Leu Pro Ala Met Gln Ile Ile Lys Leu Leu Leu Leu Phe Tyr
            500                 505                 510

Val Lys Lys Thr Ser Leu Met Ala Asn Cys Gln Ala Pro Arg Arg Pro
        515                 520                 525

Trp Lys Ala Ser His Met Ser Thr Val Phe Ile Ser Leu Leu Cys Phe
530                 535                 540

Pro Ser Phe Leu Gly Ala Ala Ile Phe Leu Cys Tyr Ala Val Trp Gln
545                 550                 555                 560

Val Lys Pro Ser Ser Ile Cys Gly Pro Phe Arg Thr Leu Asp Thr Met
                565                 570                 575

Tyr Glu Ala Gly Lys Val Trp Val Arg His Leu Glu Arg Ala Gly Pro
            580                 585                 590

Arg Val Ser Trp Leu Pro Trp Ile His Arg Tyr Leu Leu Glu Asn Thr
```

```
                595                 600                 605
Phe Pro Ile Tyr Leu Val Ser Ala Leu Leu Ala Val Ile Tyr Leu
    610                 615                 620
Asn Ile Gln Val Val Lys Gly Gln Arg Lys Val Ile Cys Leu Leu Lys
625                 630                 635                 640
Glu Gln Ile Ser Asn Glu Gly Glu Asp Lys Ile Phe Leu Ile Asn Lys
                645                 650                 655
Leu Gln Ser Val Tyr Glu Arg Lys Glu Arg Ser Arg Ala Gly Arg Thr
            660                 665                 670
Glu Glu Ala Ala Met Pro Pro Ala Leu Phe Thr Asp Asp Gly Asp Ala
        675                 680                 685
Trp

<210> SEQ ID NO 8
<211> LENGTH: 780
<212> TYPE: PRT
<213> ORGANISM: Dasypus novemcinctus

<400> SEQUENCE: 8

Met Ala Arg Pro Leu Ala Phe Val Leu Asp Val Arg Glu Ser Pro Glu
1               5                   10                  15
Asp Gln Gly Leu Asp Pro Ser Pro Tyr Asp Glu Ser Glu Val His Asp
                20                  25                  30
Ser Phe His Gln Leu Ile Glu Gln Ser Gln Trp Val Ala Ala
            35                  40                  45
Gly Ala Glu Glu Gly Leu Glu Leu Gln Glu Met Gly Pro Gly Thr Ala
        50                  55                  60
Pro Pro Glu Ala Ser Gly Ser Pro Leu Gly Gly Pro Glu Leu Gly
65                  70                  75                  80
Ala Ala Thr Leu Arg Ile Leu Ala Cys Met Pro Ser Arg Thr Ile Gly
                85                  90                  95
Arg Ser Arg Gly Ala Ile Ile Ser Gln Tyr Tyr Asn Arg Thr Ala Arg
                100                 105                 110
Leu Arg Arg Arg Ser Gly Arg Pro Leu Leu Arg Asp Ala Ala Arg Ser
            115                 120                 125
Ala Arg Arg Asp Leu Glu Leu Asp Ala Ala Ala Gln Glu Glu Glu
        130                 135                 140
Lys Arg Gly Leu Leu Val Lys Glu Leu Gln Ala Leu Pro Gly Ala Gln
145                 150                 155                 160
Arg Asp His Thr Leu Arg Gly Met Pro Met Ser Leu Ala Glu Lys Arg
                165                 170                 175
Cys Leu Arg Glu Glu Ser Arg Ser Pro Arg Ala Thr Arg Arg Asp Gln
                180                 185                 190
Gln Gly Arg Gly Gly Val Ser Arg Gly Ser Arg Leu Arg Tyr Gly Cys
            195                 200                 205
Val Leu Ala Leu His Asn Leu Gly Leu Arg Leu Ser Ser Leu His
        210                 215                 220
Ala Leu Thr Pro Trp Arg Tyr Ala Leu Lys Pro Leu Trp Leu Leu Trp
225                 230                 235                 240
Pro His Ala Ala Gly Pro Ala Thr Phe Leu Val Ser Leu Pro Cys Phe
                245                 250                 255
Arg Gly Gly Gly Pro Gly Gly Ser Arg Met Ala Trp Pro Ser Thr Ala
                260                 265                 270
Leu Pro Leu Gly Val Pro Ala Leu Cys Leu Leu Cys Pro Gln Asp Leu
```

-continued

```
                275                 280                 285
Gly Leu Val Trp Ala Glu Ala Leu Thr Arg Gln Ala Cys Ser Pro Gln
290                 295                 300
Gly Ser Phe Ser His Thr Val Met Tyr Tyr Gly Tyr Tyr Ser Asn Ala
305                 310                 315                 320
Thr Leu Asn Gln Pro Cys Glu Pro Ala Gln Asp Gly Gly Gln Cys Ala
                325                 330                 335
Pro Gly Ala Gly Gly Leu Pro Tyr Ser Met Pro Leu Ala Tyr Leu Phe
            340                 345                 350
Thr Leu Gly Val Ala Phe Phe Ile Thr Cys Ile Thr Leu Val Tyr Ser
        355                 360                 365
Met Ser Arg Ser Phe Gly Glu Ser Tyr Arg Val Gly Ser Thr Leu Gly
    370                 375                 380
Ala His Ala Val Ala Val Phe Cys Ser Trp Asp Tyr Lys Val Thr Gln
385                 390                 395                 400
Lys Trp Ala Ser Arg Leu Gln His Asp Asn Ile Arg Thr Gln Leu Lys
                405                 410                 415
Glu Leu Leu Ala Glu Trp Gln Val Arg Arg Asp Pro Arg Ser Val Cys
            420                 425                 430
Ala Ala Leu Arg Arg Ala Ala Leu Gly Leu Gly Trp Leu Leu Cys
        435                 440                 445
Leu Gly Thr Val Leu Gly Cys Ala Val Ala Val Tyr Ala Phe Ser Glu
    450                 455                 460
Ser Met Ile Gln Cys Arg Asn Leu Leu Leu Lys Met Val Thr Leu Gly
465                 470                 475                 480
Val Leu Cys Tyr His Trp Leu Gly Arg Arg Leu Gly Thr Leu Arg Gly
                485                 490                 495
Gln Cys Trp Glu Asn Phe Val Gly Gln Glu Leu Tyr Arg Phe Val Val
            500                 505                 510
Met Asp Phe Leu Phe Val Leu Leu Asp Thr Leu Leu Gly Glu Leu Val
        515                 520                 525
Trp Arg Leu Val Ala Glu Lys Lys Leu Lys Lys Arg Arg Lys Pro Glu
    530                 535                 540
Phe Asp Ile Ala Gly Asn Val Leu Glu Leu Ile Tyr Gly Gln Thr Leu
545                 550                 555                 560
Thr Trp Leu Gly Val Leu Phe Ser Pro Leu Pro Ala Val Gln Thr
                565                 570                 575
Val Lys Leu Leu Leu Leu Phe Tyr Val Lys Lys Ala Ser Leu Met Ala
            580                 585                 590
Asn Cys Gln Ala Pro Arg Arg Pro Trp Leu Ala Ser His Met Ser Thr
        595                 600                 605
Val Phe Val Thr Leu Leu Cys Phe Pro Ser Phe Leu Gly Ala Ala Val
    610                 615                 620
Phe Leu Cys Phe Val Ile Trp Gln Val Lys Pro Ser Asp Thr Cys Gly
625                 630                 635                 640
Pro Phe Arg Gly Leu Asp Thr Met Tyr Glu Ala Gly Lys Ala Trp Val
                645                 650                 655
Arg Gln Leu Glu Lys Gly Gly His Gly Val Ser Trp Leu Pro Trp Val
            660                 665                 670
His Arg Tyr Leu Val Glu Lys Pro Val Leu Ala Phe Leu Leu Ser Ala
        675                 680                 685
Leu Leu Leu Ala Val Ile Tyr Leu Asn Thr Gln Val Val Lys Gly Gln
    690                 695                 700
```

```
Arg Gln Val Ile Cys Leu Leu Lys Glu Gln Ile Ser Asn Glu Gly Glu
705                 710                 715                 720

Asp Lys Ile Phe Leu Ile Asn Lys Leu His Ser Val Tyr Glu Arg Lys
            725                 730                 735

Glu Arg Ser Ser Phe Gln Lys Leu Ser Gln Ser Lys His Leu Ser Trp
        740                 745                 750

Ala Arg Cys Thr Thr His Gly Leu Ala Gly Pro His Asp Ala Thr Glu
    755                 760                 765

Ser Arg Leu Gln Ala Asn Cys Arg Gly His Phe Asp
770                 775                 780

<210> SEQ ID NO 9
<211> LENGTH: 810
<212> TYPE: PRT
<213> ORGANISM: Ceratotherium simum simum

<400> SEQUENCE: 9

Met Ala Gln Thr Pro Ala Phe Ile Phe Asn Val Pro Glu Thr Pro Glu
1               5                   10                  15

Asp Gln Gly Gln Glu Pro Ser Pro Tyr Asp Glu Ser Glu Val His His
            20                  25                  30

Ser Phe His Gln Leu Ile Gln Glu Gln Ser Gln Trp Ala Ala Glu Glu
        35                  40                  45

Gly Leu Glu Leu Gln Gln Arg Val Pro Glu Ala Asp Thr Leu Gly Ala
    50                  55                  60

Ser Gly Ser Gly His Gln Ala Phe Leu Gly Pro Glu Gly Val Pro Asp
65                  70                  75                  80

Tyr Ser Thr Ala Thr Leu Arg Ile Leu Ala Ser Met Pro Ser Arg Thr
                85                  90                  95

Ile Gly Arg Ser Arg Gly Ala Ile Leu Ser Gln Tyr Tyr Asn Arg Thr
            100                 105                 110

Val Arg Leu Arg Arg Arg Ser Ser Arg Pro Gln Leu Arg Gly Val Gly
        115                 120                 125

Arg Ser Ala Arg Pro Ser Leu Arg Leu Tyr Asp Leu Glu Leu Asp Pro
130                 135                 140

Met Ala Phe Gln Glu Glu Lys Arg Ile Leu Leu Val Lys Glu Leu
145                 150                 155                 160

Gln Gly Leu Thr Val Ala Gln Arg Asp His Met Leu Arg Gly Met Pro
                165                 170                 175

Leu Ser Leu Ala Glu Lys Arg Ser Leu Arg Glu Asp Ser Trp Ile Gln
            180                 185                 190

Lys Gly Lys Gln Arg Gly Pro Gln Gly Arg Arg Gly Leu Phe Ser Cys
        195                 200                 205

Cys Ser Arg Leu Arg Tyr Ala Cys Val Leu Ala Leu His Asn Leu Gly
210                 215                 220

Leu Val Leu Leu Ser Gly Leu Gln Ala Leu Thr Pro Trp Arg Tyr Ala
225                 230                 235                 240

Leu Lys Gln Ile Gly Gly Gln Phe Gly Ser Ser Val Leu Ser Tyr Phe
                245                 250                 255

Leu Phe Leu Lys Thr Leu Leu Ala Phe Asn Ala Leu Leu Leu Leu Pro
            260                 265                 270

Leu Leu Ala Phe Ile Val Gly Val Gln Ala Ala Phe Pro Pro Ala Pro
        275                 280                 285

Ser Gly Ser Val Pro Ala Phe Thr Gly Leu Glu Leu Leu Thr Gly Gly
```

```
            290                 295                 300
Gly Ser Phe Ser His Ser Ala Met Tyr Tyr Gly Tyr Tyr Ser Asn Ala
305                 310                 315                 320

Thr Leu Asn Gln Pro Cys Ser Pro Arg Asp Gly Gln Cys Thr
                325                 330                 335

Pro Asp Ala Gly Gly Leu Pro Tyr Asn Met Pro Leu Ala Tyr Leu Phe
                340                 345                 350

Thr Met Gly Val Ala Phe Phe Ile Thr Cys Ile Thr Leu Val Tyr Ser
            355                 360                 365

Met Ser His Ser Phe Gly Glu Ser Tyr Arg Val Gly Ser Thr Ser Gly
            370                 375                 380

Val His Ala Ile Thr Val Phe Cys Ser Trp Asp Tyr Lys Val Thr Gln
385                 390                 395                 400

Lys Trp Pro Ser Arg Leu Gln Gln Asp Asn Ile Arg Thr Gln Leu Lys
                405                 410                 415

Glu Leu Leu Ala Glu Trp Gln Leu Gln Gln Gly Pro Gln Ser Val Trp
                420                 425                 430

Gly Arg Leu Arg Gln Val Ala Val Leu Gly Leu Val Trp Leu Leu Cys
            435                 440                 445

Leu Gly Thr Thr Leu Gly Cys Thr Met Ala Val Tyr Ala Phe Ser Glu
            450                 455                 460

Leu Met Ile Lys Ser Pro Val Ser Ala Glu Arg Glu Trp Glu Leu Leu
465                 470                 475                 480

Ala Leu Pro Leu Val Cys Leu Leu Asn Leu Gly Ala Pro Tyr Leu
                485                 490                 495

Tyr Arg Cys Leu Ala Ala Leu Glu Arg His Asp Ser Pro Met Leu Glu
                500                 505                 510

Val Tyr Val Ala Ile Cys Arg Asn Leu Ile Leu Lys Met Val Ile Leu
            515                 520                 525

Ala Ile Leu Cys Tyr His Trp Leu Gly Arg Arg Val Gly Ala Leu Lys
            530                 535                 540

Asp Gln Cys Trp Glu Asn Phe Val Gly Gln Glu Leu Tyr Arg Leu Met
545                 550                 555                 560

Val Met Asp Phe Ile Phe Met Leu Leu Asp Thr Leu Phe Gly Glu Leu
                565                 570                 575

Val Trp Arg Leu Ile Ser Glu Arg Lys Leu Lys Arg Lys Gly Lys Pro
                580                 585                 590

Glu Phe Asp Ile Ala Arg Asn Val Leu Glu Leu Ile Tyr Gly Gln Thr
            595                 600                 605

Leu Thr Trp Leu Gly Val Leu Phe Ala Pro Leu Leu Pro Ala Met Gln
            610                 615                 620

Ile Val Lys Leu Leu Phe Leu Phe Tyr Val Lys Lys Thr Ser Leu Val
625                 630                 635                 640

Ala Asn Cys Arg Ala Pro Arg Arg Pro Trp Leu Ala Ser His Met Ser
                645                 650                 655

Thr Val Phe Ile Ser Leu Leu Cys Phe Pro Ser Phe Leu Gly Ala Ala
                660                 665                 670

Ile Phe Leu Cys Tyr Ala Ile Trp Gln Val Lys Pro Ser Ser Ile Cys
            675                 680                 685

Gly Pro Phe Arg Thr Leu Asn Thr Met Tyr Glu Ala Gly Lys Val Trp
            690                 695                 700

Val Arg His Leu Glu Lys Ala Gly Pro Lys Val Ser Trp Leu Pro Trp
705                 710                 715                 720
```

Ile His Arg Tyr Leu Val Glu Asn Thr Phe Pro Ile Tyr Leu Val Ser
                725                 730                 735

Ala Val Leu Leu Ala Val Ile Tyr Leu Asn Ile Gln Val Val Lys Gly
                740                 745                 750

Gln Arg Lys Val Ile Cys Leu Leu Arg Glu Gln Ile Ser Asn Glu Gly
            755                 760                 765

Glu Asp Lys Ile Phe Leu Ile Asn Lys Leu His Ser Val Tyr Glu Arg
        770                 775                 780

Lys Glu Arg Ser Arg Val Gly Arg Ala His Glu Ala Glu Thr Pro Pro
785                 790                 795                 800

Thr Leu Leu Ala Asp Glu Gln Asp Ala Arg
                805                 810

<210> SEQ ID NO 10
<211> LENGTH: 804
<212> TYPE: PRT
<213> ORGANISM: Equus caballus

<400> SEQUENCE: 10

Met Ala Gln Pro Pro Ala Phe Val Phe Asn Val Pro Glu Thr Pro Glu
1               5                   10                  15

Asp Gln Gly Gln Asp Pro Ser Pro Tyr Asp Glu Ser Glu Val His Asp
            20                  25                  30

Ser Phe His Gln Leu Ile Glu Gln Ser Leu Arg Ala Ala Glu Glu
        35                  40                  45

Gly Leu Glu Leu Arg Val Leu Pro Gln Arg Glu Pro Gly Pro Glu Thr
50                  55                  60

Leu Gly Ala Ser Glu Leu Leu Asp Met Ser Phe Cys Phe Val Gly Ser
65                  70                  75                  80

Gly His Gln Ala Leu Leu Gly Pro Glu Gly Val Pro Asp Tyr Ser Thr
                85                  90                  95

Ala Thr Leu Arg Ile Leu Ala Ser Met Pro Ser Arg Thr Ile Gly Arg
            100                 105                 110

Ser Arg Gly Ala Ile Leu Ser Gln Tyr Tyr Asn Arg Thr Val Arg Leu
        115                 120                 125

Arg Arg Arg Gly Ser Arg Pro Pro Leu Gly Gly Val Gly Arg Ser Ala
    130                 135                 140

Arg Pro Ser Leu Arg Leu Tyr Asp Leu Glu Leu Asp Pro Thr Ala Phe
145                 150                 155                 160

Gln Glu Glu Glu Lys Arg Thr Leu Cys Glu Gly Ala Ser Gly Cys Arg
                165                 170                 175

Leu Cys Pro Arg Asp Glu Ser Trp Thr Gln Ser Gly Lys Gln Arg Gly
            180                 185                 190

Pro Gln Gly Arg Arg Gly Leu Leu Pro Cys Cys Ser Arg Leu Arg Tyr
        195                 200                 205

Ala Cys Gly Leu Ala Leu His Ser Leu Gly Leu Ala Leu Leu Ser Ala
    210                 215                 220

Leu Gln Ala Leu Thr Pro Trp Arg Tyr Ala Leu Lys Gln Ile Gly Gly
225                 230                 235                 240

Gln Phe Gly Ser Ser Val Leu Ser Tyr Phe Leu Phe Leu Lys Thr Leu
                245                 250                 255

Leu Ala Phe Asn Ala Leu Leu Leu Pro Leu Leu Ala Phe Ile Val
            260                 265                 270

Gly Val Gln Ala Ala Phe Pro Pro Ala Pro Ala Gly Ser Val Pro Thr

```
             275                 280                 285
Phe Thr Gly Leu Glu Leu Leu Thr Gly Gly Arg Phe Ser His Ser
290                 295                 300
Val Met Tyr Tyr Gly Tyr Tyr Ser Asn Thr Thr Leu Asn Gln Leu Cys
305                 310                 315                 320
Gly Pro Pro Leu Asp Gly Ser Gln Cys Thr Pro Glu Ala Gly Gly Leu
                    325                 330                 335
Pro Tyr Asn Met Pro Leu Ala Tyr Leu Phe Thr Met Gly Met Ser Phe
                340                 345                 350
Phe Ile Thr Cys Ile Thr Leu Val Tyr Ser Met Ser Arg Ser Phe Gly
            355                 360                 365
Glu Ser Tyr Arg Val Gly Ser Thr Ser Gly Val His Ala Ile Thr Val
370                 375                 380
Phe Cys Ser Trp Asp Tyr Lys Val Thr Gln Lys Trp Pro Ser Arg Leu
385                 390                 395                 400
Gln Gln Asp Asn Ile Arg Thr Gln Leu Lys Glu Leu Leu Ala Glu Trp
                    405                 410                 415
Gln Leu Gln Gln Gly Pro Arg Ser Val Trp Gly Arg Leu Arg Gln Val
                420                 425                 430
Ala Ile Leu Gly Phe Val Trp Leu Leu Cys Leu Gly Thr Thr Leu Gly
            435                 440                 445
Cys Thr Leu Ala Val Tyr Ala Phe Ser Glu Leu Met Ile Lys Asn Pro
450                 455                 460
Val Ser Ala Glu Arg Glu Trp Glu Leu Leu Ala Leu Pro Leu Val Val
465                 470                 475                 480
Cys Leu Leu Asn Leu Gly Ala Pro Tyr Leu Tyr Arg Gly Leu Ala Ala
                    485                 490                 495
Leu Glu Arg His Asp Ser Pro Ile Leu Glu Val Tyr Val Ala Ile Cys
                500                 505                 510
Arg Asn Leu Ile Leu Lys Met Val Ile Leu Gly Ile Leu Cys Tyr His
            515                 520                 525
Trp Leu Gly Arg Arg Val Gly Ala Leu Lys Gly Gln Cys Trp Glu Asn
530                 535                 540
Phe Val Gly Gln Glu Leu Tyr Arg Leu Met Val Met Asp Phe Val Phe
545                 550                 555                 560
Thr Leu Leu Asp Thr Leu Phe Gly Glu Leu Val Trp Arg Phe Ile Ser
                    565                 570                 575
Glu Lys Gln Arg Lys Lys Arg Gly Lys Pro Glu Phe Asp Ile Ala Arg
                580                 585                 590
Asn Val Leu Glu Leu Ile Tyr Gly Gln Thr Leu Thr Trp Leu Gly Val
            595                 600                 605
Leu Phe Ser Pro Leu Leu Pro Ala Met Gln Ile Met Lys Leu Leu Val
610                 615                 620
Leu Phe Tyr Val Lys Lys Thr Ser Leu Met Ala Asn Cys Arg Ala Pro
625                 630                 635                 640
Arg Arg Pro Trp Leu Ala Ser His Met Ser Thr Val Phe Val Ser Leu
                    645                 650                 655
Leu Cys Phe Pro Ser Phe Leu Gly Ala Ala Val Phe Leu Cys Tyr Ala
                660                 665                 670
Ile Trp Gln Val Arg Pro Ser Ser Ile Cys Gly Pro Phe Arg Thr Leu
            675                 680                 685
Asp Thr Met Tyr Glu Ala Gly Lys Val Trp Val Arg His Leu Glu Lys
690                 695                 700
```

```
Ala Gly Pro Arg Val Ser Trp Leu Pro Trp Ile His Arg Tyr Leu Val
705                 710                 715                 720

Glu Asn Thr Phe Pro Ile Tyr Leu Val Ser Ala Leu Leu Leu Ala Val
            725                 730                 735

Ile Tyr Leu Asn Ile Gln Val Val Lys Gly Gln Arg Lys Val Ile Cys
        740                 745                 750

Leu Leu Lys Glu Gln Ile Ser Asn Glu Gly Glu Asp Lys Ile Phe Leu
            755                 760                 765

Ile Asn Lys Leu His Ser Val Tyr Glu Gly Lys Glu Arg Ser Arg Val
770                 775                 780

Gly Arg Ala Gln Glu Ala Glu Val Pro Pro Thr Leu Pro Ala Asp Glu
785                 790                 795                 800

Arg Asp Ala Arg

<210> SEQ ID NO 11
<211> LENGTH: 855
<212> TYPE: PRT
<213> ORGANISM: Equus przewalskii

<400> SEQUENCE: 11

Met Ala Gln Pro Pro Ala Phe Val Phe Asn Val Pro Glu Thr Pro Glu
1               5                   10                  15

Asp Gln Gly Gln Asp Pro Ser Pro Tyr Asp Glu Ser Glu Val His Asp
            20                  25                  30

Ser Phe His Gln Leu Ile Gln Glu Gln Ser Leu Arg Ala Ala Glu Glu
        35                  40                  45

Gly Leu Glu Leu Arg Val Leu Pro Gln Arg Glu Pro Gly Pro Glu Thr
    50                  55                  60

Leu Gly Ala Ser Glu Leu Leu Asp Met Ser Phe Cys Phe Val Gly Ser
65                  70                  75                  80

Gly His Gln Ala Leu Leu Gly Pro Glu Gly Val Pro Asp Tyr Ser Thr
                85                  90                  95

Ala Thr Leu Arg Ile Leu Ala Ser Met Pro Ser Arg Thr Ile Gly Arg
            100                 105                 110

Ser Arg Gly Ala Ile Leu Ser Gln Tyr Tyr Asn Arg Thr Val Arg Leu
        115                 120                 125

Arg Arg Arg Gly Ser Arg Pro Pro Leu Gly Gly Val Gly Arg Ser Ala
    130                 135                 140

Arg Pro Ser Leu Arg Leu Tyr Asp Leu Glu Leu Asp Pro Thr Ala Phe
145                 150                 155                 160

Gln Glu Glu Glu Lys Arg Thr Leu Leu Val Lys Glu Leu Gln Gly Leu
                165                 170                 175

Thr Val Thr Gln Arg Asp His Met Leu Arg Gly Met Pro Leu Ser Leu
            180                 185                 190

Ala Glu Lys Arg Ser Leu Arg Glu Glu Ser Trp Thr Gln Ser Gly Lys
        195                 200                 205

Gln Arg Gly Pro Gln Gly Arg Arg Gly Leu Leu Pro Cys Cys Ser Arg
    210                 215                 220

Leu Arg Tyr Ala Cys Gly Leu Ala Leu His Ser Leu Gly Leu Ala Leu
225                 230                 235                 240

Leu Ser Ala Leu Gln Ala Leu Thr Pro Trp Arg Tyr Ala Leu Lys Gln
                245                 250                 255

Ile Gly Gly Gln Phe Gly Ser Ser Val Leu Ser Tyr Phe Leu Phe Leu
            260                 265                 270
```

```
Lys Thr Leu Leu Ala Phe Asn Ala Leu Leu Leu Pro Leu Leu Ala
            275                 280                 285

Phe Ile Val Gly Val Gln Ala Ala Phe Pro Pro Ala Pro Gly Ser
        290                 295                 300

Val Pro Thr Phe Thr Gly Leu Glu Leu Leu Thr Gly Gly Arg Phe
305                 310                 315                 320

Ser His Ser Val Met Tyr Tyr Gly Tyr Tyr Ser Asn Thr Thr Leu Asn
                325                 330                 335

Gln Leu Cys Gly Pro Pro Leu Asp Gly Ser Gln Cys Thr Pro Glu Ala
            340                 345                 350

Gly Gly Leu Pro Tyr Asn Met Pro Leu Ala Tyr Leu Phe Thr Met Gly
            355                 360                 365

Met Ser Phe Phe Ile Thr Cys Ile Thr Leu Val Tyr Ser Met Ser Arg
370                 375                 380

Ser Phe Gly Glu Ser Tyr Arg Val Gly Ser Thr Ser Gly Val His Ala
385                 390                 395                 400

Ile Thr Val Phe Cys Ser Trp Asp Tyr Lys Val Thr Gln Lys Trp Pro
                405                 410                 415

Ser Arg Leu Gln Gln Asp Asn Ile Arg Thr Gln Leu Lys Glu Leu Leu
            420                 425                 430

Ala Glu Trp Gln Leu Gln Gln Gly Pro Arg Ser Val Trp Gly Arg Leu
            435                 440                 445

Arg Gln Val Ala Ile Leu Gly Phe Val Trp Leu Leu Cys Leu Gly Thr
            450                 455                 460

Thr Leu Gly Cys Thr Leu Ala Val Tyr Ala Phe Ser Glu Leu Met Ile
465                 470                 475                 480

Lys Asn Pro Val Ser Ala Glu Arg Glu Trp Glu Leu Leu Ala Leu Pro
                485                 490                 495

Leu Val Val Cys Leu Leu Asn Leu Gly Ala Pro Tyr Leu Tyr Arg Gly
            500                 505                 510

Leu Ala Ala Leu Glu Arg His Asp Ser Pro Ile Leu Glu Val Tyr Val
            515                 520                 525

Ala Ile Cys Arg Cys Val Thr Arg Trp Gly Arg Trp Ala Phe Leu Gly
            530                 535                 540

Gln Gly Leu Cys Leu Pro Gly Ala Pro Pro Ser Ala Ser Thr Pro Leu
545                 550                 555                 560

Val Leu Cys Arg Asn Leu Ile Leu Lys Met Val Ile Leu Gly Ile Leu
                565                 570                 575

Cys Tyr His Trp Leu Gly Arg Arg Val Gly Ala Leu Lys Gly Gln Cys
            580                 585                 590

Trp Glu Asn Phe Val Gly Gln Glu Leu Tyr Arg Leu Met Val Met Asp
            595                 600                 605

Phe Val Phe Thr Leu Leu Asp Thr Leu Phe Gly Glu Leu Val Trp Arg
610                 615                 620

Phe Ile Ser Glu Lys Gln Arg Lys Lys Arg Gly Lys Pro Glu Phe Asp
625                 630                 635                 640

Ile Ala Arg Asn Val Leu Glu Leu Ile Tyr Gly Gln Thr Leu Thr Trp
                645                 650                 655

Leu Gly Val Leu Phe Ser Pro Leu Leu Pro Ala Met Gln Ile Met Lys
            660                 665                 670

Leu Leu Val Leu Phe Tyr Val Lys Lys Thr Ser Leu Met Ala Asn Cys
            675                 680                 685
```

Arg Ala Pro Arg Arg Pro Trp Leu Ala Ser His Met Ser Thr Val Phe
690                 695                 700

Val Ser Leu Leu Cys Phe Pro Ser Phe Leu Gly Ala Ala Val Phe Leu
705                 710                 715                 720

Cys Tyr Ala Ile Trp Gln Val Arg Pro Ser Ser Ile Cys Gly Pro Phe
            725                 730                 735

Arg Thr Leu Asp Thr Met Tyr Glu Ala Gly Lys Val Trp Val Arg His
            740                 745                 750

Leu Glu Lys Ala Gly Pro Arg Val Ser Trp Leu Pro Trp Ile His Arg
            755                 760                 765

Tyr Leu Val Glu Asn Thr Phe Pro Ile Tyr Leu Val Ser Ala Leu Leu
770                 775                 780

Leu Ala Val Ile Tyr Leu Asn Ile Gln Val Val Lys Gly Gln Arg Lys
785                 790                 795                 800

Val Ile Cys Leu Leu Lys Glu Gln Ile Ser Asn Glu Gly Glu Asp Lys
            805                 810                 815

Ile Phe Leu Ile Asn Lys Leu His Ser Val Tyr Glu Gly Lys Glu Arg
            820                 825                 830

Ser Arg Val Gly Arg Ala Gln Glu Ala Glu Val Pro Pro Thr Leu Pro
            835                 840                 845

Ala Asp Glu Arg Asp Ala Arg
850                 855

<210> SEQ ID NO 12
<211> LENGTH: 796
<212> TYPE: PRT
<213> ORGANISM: Felis catus
<220> FEATURE:
<221> NAME/KEY: misc_feature
<222> LOCATION: (501)..(506)
<223> OTHER INFORMATION: Xaa can be any naturally occurring amino acid

<400> SEQUENCE: 12

Met Ala Gln Pro Leu Pro Phe Val Leu Asn Val Pro Glu Ile Pro Glu
1               5                   10                  15

Asp His Asp Arg Glu Pro Ser Pro Tyr Asp Glu Ser Gly Val His Asp
            20                  25                  30

Ser Phe Tyr Gln Leu Ile Gln Glu Gln Ser Gln Cys Val Ala Glu Glu
        35                  40                  45

Gly Leu Glu Leu Arg Gln Arg Gly Leu Gly Ala Ala Ala Pro Gly Thr
    50                  55                  60

Ser Gly Ser Gly Arg Gln Ala Leu Val Gly Pro Glu Asp Ala Ala Ala
65                  70                  75                  80

Tyr Ser Thr Ala Thr Leu Arg Ile Leu Ala Ser Met Pro Ser Arg Thr
                85                  90                  95

Ile Gly Glu Trp Asp Pro Gly Arg Pro Gly Leu Gly Val Ala Leu Arg
            100                 105                 110

Pro Gln Leu Gly Gly Val Gly Arg Ser Ala Arg Pro Ser Leu Arg Leu
        115                 120                 125

Tyr Asp Leu Glu Leu Asp Pro Ala Ala Leu Glu Glu Glu Lys Arg
    130                 135                 140

Ser Leu Leu Val Lys Glu Leu Gln Ser Leu Thr Val Ala Gln Arg Gly
145                 150                 155                 160

His Met Leu Lys Gly Met Pro Leu Gly Leu Ala Glu Lys Arg Ser Leu
                165                 170                 175

Arg Ser Val Pro Ile Gly Pro Gly Arg Pro Pro His Pro Leu Pro Cys

-continued

```
                180                 185                 190
Trp Gly Leu Thr Leu Leu Pro Phe Ser Pro Trp Cys Pro Gln Ala Leu
            195                 200                 205
His Gly Leu Gly Leu Trp Leu Ala Gly Leu His Gly Leu Lys Pro
        210                 215                 220
Trp Arg Tyr Ala Leu Lys Arg Ile Gly Gly Gln Phe Gly Ser Ser Val
225                 230                 235                 240
Leu Ser Tyr Phe Leu Phe Leu Lys Thr Leu Leu Ala Phe Asn Ala Leu
                245                 250                 255
Leu Leu Leu Pro Leu Leu Ala Phe Val Val Gly Val Gln Ala Ala Phe
            260                 265                 270
Pro Pro Pro Ala Ser Pro Gly Pro Val Pro Ala Phe Thr Gly Leu Glu
        275                 280                 285
Leu Leu Thr Gly Gly Gly Arg Leu Thr His Thr Val Met Tyr Tyr Gly
        290                 295                 300
Tyr Tyr Ser Asn Ser Thr Leu Asn Pro Pro Cys Val Pro Ala Pro Asp
305                 310                 315                 320
Gly Gly Gln Cys Gly Arg Glu Thr Asp Gly Leu Pro Tyr Asn Met Pro
                325                 330                 335
Leu Ala Tyr Leu Phe Thr Val Gly Gly Ala Phe Ile Thr Cys Ile
            340                 345                 350
Thr Leu Val Tyr Ser Met Ser His Ser Phe Gly Glu Ser Tyr Arg Val
                355                 360                 365
Gly Ser Thr Ser Gly Val His Ala Ile Thr Val Phe Cys Ser Trp Asp
        370                 375                 380
His Lys Val Thr Gln Arg Ala Ser Arg Leu Gln His Asp Asn Ile
385                 390                 395                 400
Arg Thr His Leu Lys Glu Leu Leu Ala Glu Gly Gln Leu Arg Gln Gly
                405                 410                 415
Pro Arg Ser Val Cys Gly Arg Leu Arg Gln Val Ala Val Leu Gly Leu
            420                 425                 430
Val Trp Leu Leu Cys Leu Ala Ile Thr Leu Gly Cys Thr Val Ala Val
        435                 440                 445
Tyr Ala Phe Ser Glu Leu Met Ile Gln Ser Pro Val Ser Ala Glu Gln
        450                 455                 460
Gly Gly Ala Leu Leu Ala Leu Pro Val Val Cys Leu Leu Asn Leu
465                 470                 475                 480
Gly Ala Pro Tyr Leu Tyr Arg Gly Leu Ala Ala Leu Glu Arg His Asp
                485                 490                 495
Ser Pro Val Leu Xaa Xaa Xaa Xaa Xaa Xaa Thr Arg Pro Asn Leu Ile
            500                 505                 510
Leu Lys Met Val Ile Leu Gly Ile Leu Cys Tyr His Trp Leu Gly Arg
        515                 520                 525
Arg Val Gly Ala Leu Arg Asp Gln Cys Trp Glu Asn Phe Val Gly Gln
        530                 535                 540
Glu Leu Tyr Arg Leu Met Val Leu Asp Phe Ile Phe Ile Leu Leu Asp
545                 550                 555                 560
Thr Leu Phe Gly Glu Leu Val Trp Arg Leu Ile Ser Glu Arg Lys Leu
                565                 570                 575
Lys Arg Lys Glu Lys Pro Glu Phe Asp Ile Ala Gly Asn Val Leu Glu
            580                 585                 590
Leu Ile Tyr Gly Gln Thr Leu Thr Trp Leu Gly Val Leu Phe Ala Pro
        595                 600                 605
```

```
Leu Leu Pro Ala Val Gln Ile Ile Lys Leu Val Phe Leu Phe Tyr Ile
            610                 615                 620

Lys Lys Thr Ser Leu Met Ala Asn Cys Gln Ala Pro Arg Arg Pro Trp
625                 630                 635                 640

Leu Ala Ser His Met Ser Thr Val Phe Ile Ser Leu Leu Cys Phe Pro
            645                 650                 655

Ser Phe Leu Gly Ala Ala Val Phe Leu Cys Tyr Ala Val Trp Gln Val
            660                 665                 670

Lys Pro Ser Ser Thr Cys Gly Pro Phe Arg Thr Leu Asp Thr Met Tyr
            675                 680                 685

Glu Ala Gly Lys Val Trp Val Arg Arg Leu Glu Lys Ala Gly Pro Arg
            690                 695                 700

Val Ser Trp Leu Pro Trp Val His Arg Tyr Leu Val Glu Asn Thr Phe
705                 710                 715                 720

Pro Val Tyr Leu Val Ser Ala Leu Leu Leu Ala Val Ile Tyr Leu Asn
            725                 730                 735

Ile Gln Val Val Lys Gly Gln Arg Lys Val Ile Cys Leu Leu Arg Glu
            740                 745                 750

Gln Ile Ser Asn Glu Gly Glu Asp Lys Ile Phe Leu Ile Asn Lys Leu
            755                 760                 765

His Ser Val Tyr Glu Lys Lys Glu Arg Ser Arg Gly Gly Arg Thr Gln
            770                 775                 780

Glu Ala Glu Arg Leu Glu Glu Asp Pro Asp Ala Arg
785                 790                 795

<210> SEQ ID NO 13
<211> LENGTH: 806
<212> TYPE: PRT
<213> ORGANISM: Leptonychotes weddellii

<400> SEQUENCE: 13

Met Ala Gln Pro Leu Asn Phe Val Leu Asn Val Pro Glu Thr Pro Glu
1               5                   10                  15

Glu His Ser Gln Glu Pro Ser Pro Tyr Asp Glu Asn Glu Val His Asp
            20                  25                  30

Ser Phe His Gln Leu Ile Gln Glu Gln Ser Gln Trp Val Ala Glu Glu
            35                  40                  45

Gly Leu Glu Leu Gln Gln Arg Glu Pro Gly Ala Gly Gly Cys Gly Gln
        50                  55                  60

His Ala Leu Pro Gly Pro Glu Asp Ala Leu Ala His Ser Ala Ala Thr
65                  70                  75                  80

Leu Arg Val Leu Ala Ser Met Pro Ser Arg Thr Ile Gly Arg Ser Arg
                85                  90                  95

Gly Ala Val Ile Cys Gln Tyr Tyr Asn Arg Ser Val Arg Leu Arg Arg
            100                 105                 110

Arg Val Ser Arg Pro Glu Leu Lys Gly Val Gly Arg Ser Ala Arg Pro
            115                 120                 125

Ser Leu Arg Leu Tyr Asp Leu Glu Leu Asp Pro Ala Ala Leu Gln Glu
        130                 135                 140

Glu Glu Lys Arg Phe Leu Leu Val Lys Glu Leu Glu Gly Leu Pro Val
145                 150                 155                 160

Ala Gln Arg Asn His Met Leu Arg Gly Met Pro Leu Gly Leu Ala Glu
                165                 170                 175

Lys Arg Cys Leu Arg Glu Glu Thr Gln Thr Pro Lys Glu Lys Gln Arg
```

```
               180                 185                 190
Gly Arg Gln Gly Pro His Gly Leu Phe Pro Cys Cys Gly Arg Leu Arg
            195                 200                 205

Asp Ala Cys Val Leu Ala Leu His Asn Leu Gly Leu Gly Leu Leu Gly
210                 215                 220

Gly Leu His Ala Leu Arg Pro Trp His Tyr Ala Leu Lys Gln Ile Gly
225                 230                 235                 240

Gly Gln Phe Gly Ser Ser Val Leu Ser Tyr Phe Leu Phe Leu Lys Thr
            245                 250                 255

Leu Leu Ala Phe Asn Ala Leu Leu Leu Pro Leu Leu Ala Phe Ile
        260                 265                 270

Val Gly Val Gln Ala Ala Phe Pro Pro Ala Pro Pro Gly Ser Val
    275                 280                 285

Pro Ser Phe Thr Gly Leu Glu Leu Leu Thr Gly Gly Arg Phe Thr
    290                 295                 300

His Thr Val Leu Tyr Tyr Gly Tyr Tyr Ser Asn Ser Thr Val Ser Gln
305                 310                 315                 320

Pro Cys Val Pro Pro Ser Gly Gly Gln Cys Ser Arg Glu Ala Asp
            325                 330                 335

Ser Leu Pro Tyr Ser Met Pro Leu Ala Tyr Leu Phe Thr Val Gly Leu
            340                 345                 350

Ala Phe Phe Ile Thr Cys Ile Thr Leu Val Tyr Ser Met Ser His Ser
        355                 360                 365

Phe Gly Glu Ser Tyr Arg Val Gly Ser Thr Ser Gly Val His Ala Val
    370                 375                 380

Thr Val Phe Cys Ser Trp Asp His Lys Val Thr Gln Arg Arg Ala Ser
385                 390                 395                 400

Arg Leu Gln His Asp Asn Ile Arg Thr His Leu Lys Glu Leu Leu Ala
            405                 410                 415

Glu Trp Gln Arg Arg Gly Ser Gln Ser Ala Cys Gly Arg Leu Arg
        420                 425                 430

Arg Val Ala Val Arg Gly Leu Val Trp Leu Leu Ser Leu Gly Thr Thr
        435                 440                 445

Leu Gly Cys Thr Val Ala Val Tyr Ala Phe Ser Glu Leu Met Ile Lys
    450                 455                 460

Ser Pro Val Ser Val Glu Gln Glu Gly Ala Leu Leu Ala Leu Pro Val
465                 470                 475                 480

Val Val Cys Leu Leu Asn Leu Gly Ala Pro Tyr Leu Phe Arg Cys Leu
            485                 490                 495

Ala Ala Leu Glu Arg His Asp Ser Pro Val Leu Glu Val Tyr Val Ala
            500                 505                 510

Val Cys Arg Asn Leu Ile Leu Lys Met Val Ile Leu Gly Ile Leu Cys
        515                 520                 525

Tyr His Trp Leu Gly Arg Arg Val Gly Thr Leu Lys Asp Gln Cys Trp
    530                 535                 540

Glu Asn Phe Val Gly Gln Glu Leu Tyr Arg Leu Met Val Leu Asp Phe
545                 550                 555                 560

Ile Phe Val Leu Leu Asp Thr Leu Phe Gly Glu Leu Val Trp Arg Leu
            565                 570                 575

Ile Ser Glu Lys Gln Leu Lys Arg Arg Glu Lys Pro Glu Phe Asp Ile
            580                 585                 590

Ala Gly Asn Val Leu Glu Leu Ile Tyr Gly Gln Thr Leu Thr Trp Leu
        595                 600                 605
```

Gly Val Leu Phe Ser Pro Leu Leu Pro Ala Ile Gln Ile Val Lys Leu
610                 615                 620

Leu Leu Ile Phe Tyr Val Lys Lys Thr Ser Leu Arg Ala Asn Cys Gln
625                 630                 635                 640

Ala Pro Arg Arg Pro Trp Leu Ala Ser His Met Ser Thr Val Phe Ile
            645                 650                 655

Ser Leu Leu Cys Phe Pro Ser Phe Leu Gly Ala Ala Val Phe Leu Cys
            660                 665                 670

Phe Ala Val Trp Arg Val Lys Pro Ser Ser Thr Cys Gly Pro Phe Arg
            675                 680                 685

Ser Leu Asn Ser Met Tyr Glu Ala Gly Lys Val Trp Val Arg His Leu
690                 695                 700

Glu Glu Ala Gly Pro Arg Val Ser Trp Leu Pro Trp Val His Arg Tyr
705                 710                 715                 720

Leu Val Glu Asn Thr Phe Pro Val Tyr Leu Val Ser Ala Leu Leu Leu
                725                 730                 735

Ala Val Ile Tyr Leu His Ile Gln Val Val Lys Gly Gln Arg Arg Val
                740                 745                 750

Ile Cys Leu Leu Lys Glu Gln Ile Ser Asn Glu Gly Glu Asp Lys Val
            755                 760                 765

Phe Leu Ile Asn Lys Leu His Ser Val Tyr Glu Arg Lys Glu Arg Ser
770                 775                 780

Arg His Ile Gly Gly Leu Pro Ser Pro Phe Glu Ala Val Gln Arg Phe
785                 790                 795                 800

Leu His Pro Pro Glu Ala
            805

<210> SEQ ID NO 14
<211> LENGTH: 858
<212> TYPE: PRT
<213> ORGANISM: Odobenus rosmarus divergens

<400> SEQUENCE: 14

Met Ala Gln Pro Leu Asn Phe Val Leu Asn Val Ala Glu Thr Pro Glu
1               5                   10                  15

Asp His Gly Gln Glu Pro Ser Pro Tyr Asp Glu Ser Glu Val His Asp
                20                  25                  30

Ser Phe His Gln Leu Ile Gln Glu Gln Ser Gln Trp Val Ala Glu Glu
            35                  40                  45

Gly Leu Glu Leu Gln Gln Arg Glu Pro Gly Ala Gly Pro Glu Thr
50                  55                  60

Ser Gly Glu Pro Ser Ala Gln Gly Pro Gly Ala Pro Asp Ala Val Gly
65                  70                  75                  80

Arg Ala Leu Ser Leu Pro Cys Pro Leu Gln Ala Trp Gly Gly Asp Trp
                85                  90                  95

Val Gly Glu Ile Trp Pro Ala Val Ser Pro Gly Arg Leu Asp Glu Ser
                100                 105                 110

Phe Cys Phe Val Gly Ser Gly Gln Gln Ala Leu Pro Gly Pro Glu Asp
            115                 120                 125

Ala Leu Val His Ser Thr Ala Thr Leu Arg Ile Leu Ala Ser Met Pro
130                 135                 140

Ser Arg Thr Ile Gly Arg Ser Arg Gly Ala Val Ile Cys Gln Tyr Tyr
145                 150                 155                 160

Asn Arg Ser Val Arg Leu Arg Arg Arg Val Ser Arg Pro Glu Leu Lys

-continued

```
                165                 170                 175
Gly Val Gly Arg Ser Ala Arg Pro Ser Leu Arg Leu Tyr Asp Leu Glu
            180                 185                 190
Leu Asp Pro Ala Ala Leu Gln Glu Glu Lys Arg Phe Leu Leu Val
        195                 200                 205
Lys Glu Leu Gln Gly Leu Pro Val Ala Gln Arg Asp His Met Leu Arg
    210                 215                 220
Gly Met Pro Leu Gly Leu Ala Glu Lys Arg Cys Leu Arg Glu Ser
225                 230                 235                 240
Gln Thr Pro Thr Gly Lys Gln Arg Gly Arg Gln Gly Pro Arg Gly Leu
                245                 250                 255
Phe Pro Cys Cys Gly Arg Leu Arg Asp Ala Cys Val Leu Ala Leu His
            260                 265                 270
Ser Leu Gly Leu Gly Leu Leu Ala Gly Leu His Ala Leu Arg Pro Trp
        275                 280                 285
Arg Tyr Ala Leu Lys Gln Ile Gly Gly Gln Phe Gly Ser Ser Val Leu
    290                 295                 300
Ser Tyr Phe Leu Phe Leu Lys Thr Leu Leu Ala Phe Asn Ala Leu Leu
305                 310                 315                 320
Leu Leu Pro Leu Leu Ala Phe Ile Val Gly Val Gln Ala Ala Phe Pro
                325                 330                 335
Pro Pro Ala Pro Pro Gly Ser Ala Pro Ser Phe Thr Gly Leu Glu Leu
            340                 345                 350
Leu Thr Gly Gly Gly Arg Phe Thr His Thr Val Met Tyr Tyr Gly Tyr
        355                 360                 365
Tyr Ser Asn Ser Thr Leu Asn Gln Pro Cys Ala Pro Pro Leu Ala Gly
    370                 375                 380
Gly Gln Cys Ser Arg Glu Ala Ala Gly Leu Pro Tyr Ser Met Pro Leu
385                 390                 395                 400
Ala Tyr Leu Phe Thr Val Gly Leu Ala Phe Phe Ile Thr Cys Ile Thr
                405                 410                 415
Leu Val Tyr Ser Met Ser His Ser Phe Gly Glu Ser Tyr Arg Val Gly
            420                 425                 430
Ser Thr Ser Gly Val His Ala Val Thr Val Phe Cys Ser Trp Asp His
        435                 440                 445
Lys Val Thr Gln Arg Arg Ala Ser Arg Leu Gln His Asp Asn Ile Arg
    450                 455                 460
Thr His Leu Lys Glu Leu Leu Ala Glu Trp Gln Arg Arg Gly Ser
465                 470                 475                 480
Arg Ser Ala Cys Gly Arg Leu Arg Trp Val Ala Val Arg Gly Leu Val
                485                 490                 495
Trp Leu Leu Ser Leu Gly Thr Thr Leu Gly Cys Thr Val Ala Val Tyr
            500                 505                 510
Ala Phe Ser Glu Leu Met Ile Lys Ser Pro Val Ser Ala Glu Gln Glu
        515                 520                 525
Gly Ala Leu Leu Ala Leu Pro Val Val Cys Leu Leu Asn Leu Gly
    530                 535                 540
Ala Pro Tyr Leu Phe Arg Cys Leu Ala Ala Leu Glu Arg His Asp Ser
545                 550                 555                 560
Pro Val Leu Glu Val Tyr Val Ala Val Cys Arg Asn Leu Ile Leu Lys
                565                 570                 575
Met Val Ile Leu Gly Ile Leu Cys Tyr His Trp Leu Gly Arg Arg Val
            580                 585                 590
```

```
Gly Ala Leu Lys Asp Gln Cys Trp Glu Asn Phe Val Gly Gln Glu Leu
            595                 600                 605

Tyr Arg Leu Val Val Leu Asp Phe Ile Phe Val Leu Leu Asp Thr Leu
610                 615                 620

Phe Gly Glu Leu Val Trp Arg Leu Ile Ser Glu Lys Gln Leu Lys Arg
625                 630                 635                 640

Arg Glu Lys Pro Glu Phe Asp Ile Ala Gly Asn Val Leu Glu Leu Ile
            645                 650                 655

Tyr Gly Gln Thr Leu Thr Trp Leu Gly Val Leu Phe Ser Pro Leu Leu
            660                 665                 670

Pro Ala Ile Gln Ile Val Lys Leu Leu Leu Val Phe Tyr Val Lys Lys
            675                 680                 685

Thr Ser Leu Met Ala Asn Cys Gln Ala Pro Arg Arg Pro Trp Leu Ala
            690                 695                 700

Ser His Met Ser Thr Val Phe Ile Thr Leu Leu Cys Phe Pro Ser Phe
705                 710                 715                 720

Leu Gly Ala Ala Ile Phe Leu Cys Phe Ala Val Trp Arg Val Lys Pro
                725                 730                 735

Ser Ser Thr Cys Gly Pro Phe Arg Asn Leu Asp Ser Met Tyr Glu Ala
                740                 745                 750

Gly Lys Val Trp Val Arg His Leu Glu Glu Ala Gly Pro Arg Val Ser
            755                 760                 765

Trp Leu Pro Trp Val His Arg Tyr Leu Val Glu Asn Thr Phe Pro Val
770                 775                 780

Tyr Leu Val Ser Ala Leu Leu Ala Val Ile Tyr Leu His Ile Gln
785                 790                 795                 800

Val Val Lys Gly Gln Arg Arg Val Ile Cys Leu Leu Lys Glu Gln Ile
                805                 810                 815

Ser Asn Glu Gly Glu Asp Lys Val Phe Leu Ile Asn Lys Leu His Ser
            820                 825                 830

Val Tyr Glu Arg Lys Glu Arg Ser Arg Ala Gly Arg Thr Gln Glu Ala
            835                 840                 845

Glu Arg Leu Thr Asp Asp Pro Asp Ala Trp
            850                 855

<210> SEQ ID NO 15
<211> LENGTH: 809
<212> TYPE: PRT
<213> ORGANISM: Mustela putorius furo

<400> SEQUENCE: 15

Met Ala Gln Pro Leu Asn Phe Val Leu His Val Pro Glu Thr Pro Glu
1               5                   10                  15

Asp His Gly Gln Glu Pro Ser Pro Tyr Asp Glu Ser Asp Val His Asp
            20                  25                  30

Ser Phe His Gln Leu Ile Gln Glu Gln Ser Arg Trp Val Ala Glu Glu
        35                  40                  45

Gly Leu Glu Leu Gln Glu Arg Glu Arg Gly Ala Gly Ala Pro Gln Thr
    50                  55                  60

Thr Gly Ser Gly Ser Arg Ile Pro Pro Gly Pro Glu Asp Ala Gly Ala
65                  70                  75                  80

Pro Ser Thr Ala Thr Leu Arg Ile Leu Ala Ser Met Pro Ser Arg Thr
                85                  90                  95

Ile Gly Arg Ser Arg Gly Ala Ile Ile Ser Gln Tyr Tyr Asn Arg Thr
```

-continued

```
                100                 105                 110
Val Gln Leu Arg Arg Val Ser Arg Pro Glu Leu Arg Gly Val Gly
            115                 120                 125
Arg Ser Ala Arg Pro Ser Leu Arg Leu Tyr Asp Leu Glu Leu Asp Pro
130             135                 140
Ala Ala Leu Glu Glu Glu Lys Arg Leu Leu Val Lys Glu Leu
145                 150                 155             160
Gln Gly Leu Thr Val Ala Gln Arg Asp His Met Leu Arg Gly Met Pro
                165                 170                 175
Leu Gly Leu Ala Glu Lys Arg Cys Leu Arg Glu Glu Ser Arg Thr Pro
            180                 185                 190
Arg Gly Lys Arg Arg Gly Arg Pro Gly Arg Gly Leu Leu Pro Cys
        195                 200                 205
Cys Gly Arg Leu Arg Asp Ala Cys Val Leu Ala Leu His Gly Leu Gly
        210                 215                 220
Leu Ala Leu Leu Ser Gly Leu Ala Leu Val Pro Trp Arg Tyr Ala
225                 230                 235             240
Leu Lys Arg Ile Gly Gly Arg Phe Gly Ser Ser Ala Leu Ser Tyr Phe
                245                 250                 255
Leu Phe Leu Lys Thr Leu Leu Ala Phe Asn Ala Leu Leu Ala Ala
                260                 265                 270
Ala Ala Ala Arg Leu Pro Gly Gly Arg Ala Gly Arg Leu Pro Ala Ala
            275                 280                 285
Arg Leu Pro Gly Leu Cys Pro Gln Leu His Gly Pro Gly Ala Ala His
        290                 295                 300
Gly Arg Gly Gln Leu Gln Leu His Cys Pro Val Leu Arg Leu Gly Tyr
305                 310                 315                 320
Tyr Ser Asn Ser Ser Leu Thr Arg Pro Cys Ala Leu Pro Pro Gly Gly
                325                 330                 335
Pro Cys Gly Arg Glu Ala Glu Ser Leu Pro Tyr Asn Met Pro Leu Ala
            340                 345                 350
Tyr Leu Phe Thr Val Gly Val Ala Phe Phe Ile Thr Cys Ile Thr Leu
            355                 360                 365
Val Tyr Ser Met Ser Arg Ser Phe Gly Glu Ser Tyr Arg Val Gly Ser
        370                 375                 380
Ala Ser Gly Val His Ala Val Thr Val Phe Cys Ser Trp Asp His Lys
385                 390                 395                 400
Val Thr Gln Arg Arg Ala Ser Arg Leu Gln Cys Asp Asn Ile Arg Thr
                405                 410                 415
His Leu Lys Glu Leu Leu Ala Glu Arg Gln Arg Gln Gly Pro Arg
            420                 425                 430
Ser Ala Cys Gly Arg Leu Arg His Val Ala Val Leu Gly Leu Val Trp
        435                 440                 445
Leu Leu Cys Leu Gly Thr Thr Val Gly Cys Thr Met Ala Val Tyr Ala
        450                 455                 460
Phe Ser Glu Leu Met Ile Lys Ser Pro Val Ser Ala Asp Gln Glu Gly
465                 470                 475             480
Ala Leu Leu Ala Leu Pro Val Val Cys Leu Leu Asn Leu Gly Ala
                485                 490                 495
Pro Tyr Leu Phe Arg Cys Leu Ala Ala Leu Glu Arg Gln Asp Ser Pro
            500                 505                 510
Val Leu Glu Val Tyr Leu Ala Ile Cys Arg Asn Leu Ile Phe Lys Met
        515                 520                 525
```

```
Ala Ile Leu Gly Ile Leu Cys Tyr His Trp Leu Gly Arg Arg Val Gly
            530                 535                 540

Thr Leu Lys Asp Gln Cys Trp Glu Asn Phe Val Gly Gln Glu Leu Tyr
545                 550                 555                 560

Arg Leu Thr Val Leu Asp Phe Ile Phe Val Leu Leu Asp Thr Leu Phe
                565                 570                 575

Gly Glu Leu Val Trp Arg Leu Ile Ser Glu Lys Lys Leu Lys Arg Arg
            580                 585                 590

Glu Lys Pro Glu Phe Asp Ile Ala Gly Asn Val Leu Glu Leu Ile Tyr
            595                 600                 605

Gly Gln Thr Leu Thr Trp Leu Gly Val Leu Phe Cys Pro Leu Leu Pro
            610                 615                 620

Ala Val Gln Ile Ile Lys Leu Leu Leu Ile Phe Tyr Val Lys Lys Thr
625                 630                 635                 640

Ser Leu Met Ala Asn Cys Gln Ala Pro Arg Arg Pro Trp Leu Ala Ser
                645                 650                 655

His Met Ser Thr Val Phe Val Ser Leu Leu Cys Phe Pro Ser Phe Leu
            660                 665                 670

Gly Ala Ala Val Phe Leu Cys Tyr Ala Val Trp Gln Val Lys Pro Ser
            675                 680                 685

Ser Thr Cys Gly Pro Phe Arg Thr Leu Asp Thr Met Tyr Glu Ala Gly
690                 695                 700

Lys Val Trp Val Arg Arg Leu Glu Ala Ala Gly Pro Arg Val Ser Trp
705                 710                 715                 720

Leu Pro Trp Val His Arg Tyr Leu Val Glu Asn Thr Phe Pro Ile Tyr
                725                 730                 735

Leu Val Ser Ala Leu Leu Leu Ala Val Ile Tyr Leu Asn Ile Gln Val
            740                 745                 750

Val Lys Gly Gln Arg Arg Val Ile Cys Leu Leu Lys Glu Gln Ile Ser
            755                 760                 765

Asn Glu Gly Glu Asp Lys Val Phe Leu Ile Asn Arg Leu His Ser Val
770                 775                 780

Tyr Glu Arg Lys Glu Arg Ser Arg Ala Gly Arg Ser Gly Glu Thr Glu
785                 790                 795                 800

Arg Leu Val Asp His Pro Asp Ala Trp
                805

<210> SEQ ID NO 16
<211> LENGTH: 807
<212> TYPE: PRT
<213> ORGANISM: Chrysochloris asiatica

<400> SEQUENCE: 16

Met Ala Phe Thr Leu His Val Pro Glu Thr Pro Glu Asp Trp Gly Arg
1               5                   10                  15

Glu Pro Ser Pro Tyr Asp Glu Asp Val His His Ser Phe His Glu
                20                  25                  30

Leu Ile Gln Glu Gln Ser Gln Arg Val Ala Ala Ser Glu Pro Gln Val
            35                  40                  45

Glu Leu Glu Leu Gln Asp Ile Glu Pro Asp Gly Ser His Gln Asp Val
            50                  55                  60

Leu Gly Gln Gly His Thr Pro Ala Tyr Ser Ala Ala Thr Leu Arg Ile
65                  70                  75                  80

Leu Ala Ser Met Pro Ser Arg Thr Ile Gly Arg Ser Arg Gly Ala Ile
```

```
                     85                  90                  95
Ile Ser Gln Tyr Tyr Asn Arg Thr Val Arg Leu Arg Arg Gly Ser
            100                 105                 110

Arg Ser Leu His Ser Val Val Asp His Ala Ala Arg Pro Ser Leu Arg
            115                 120                 125

Ser His Asp Leu Glu Leu Asp Pro Ala Thr Arg Glu Glu Glu Lys
        130                 135                 140

Arg Gly Leu Leu Val Arg Glu Leu Gln Gly Leu Thr Val Ala Gln Gln
145                 150                 155                 160

Asp His Met Leu Arg Glu Met Pro Leu Ser Leu Ala Glu Lys Arg Cys
                165                 170                 175

Leu Arg Gln Glu Ser Arg Thr Pro Arg Gly Lys Leu Arg Ser Gln Gln
                180                 185                 190

Asp Arg His Gly Val Cys Ser Phe Cys Lys Gln Leu Lys Tyr Gly Cys
            195                 200                 205

Val Leu Thr Leu His Asn Leu Gly Leu Gly Leu Leu Ser Ser Leu His
        210                 215                 220

Ala Leu Thr Pro Trp His Tyr Ala Leu Lys Arg Ile Gly Gly Gln Phe
225                 230                 235                 240

Gly Ser Ser Val Leu Ser Tyr Phe Leu Phe Leu Lys Thr Leu Leu Ala
                245                 250                 255

Phe Asn Ala Leu Leu Leu Pro Leu Leu Ala Phe Ile Val Gly Val
            260                 265                 270

Gln Ala Ala Phe Pro Pro Thr Ser Pro Ser Pro Thr Pro Thr Phe Thr
            275                 280                 285

Gly Leu Glu Leu Leu Ile Gly Gly Ser Phe Thr His Thr Val Met
        290                 295                 300

Tyr Tyr Gly Tyr Tyr Ser Asn Thr Thr Val Asn Gln Gln Cys Ala Leu
305                 310                 315                 320

Pro Gly Asp Gly Ser His Cys Ile Ser Gly Ala Gly Gly Leu Pro Tyr
                325                 330                 335

Asn Met Pro Leu Ala Tyr Leu Phe Thr Met Gly Met Ala Phe Phe Ile
            340                 345                 350

Thr Cys Ile Thr Leu Val Tyr Ser Met Ser His Ser Phe Gly Glu Ser
            355                 360                 365

Tyr Arg Val Gly Ser Thr Ser Gly Ile His Ala Ile Thr Ile Phe Cys
            370                 375                 380

Ser Trp Asp Tyr Lys Val Thr Gln Lys Trp Ala Ser Arg Leu Gln Gln
385                 390                 395                 400

Asp Asn Leu Arg Thr Gln Leu Lys Glu Leu Leu Ala Glu Trp Gln Leu
                405                 410                 415

Arg Gln Gly Pro Trp Asn Leu Cys Gly Arg Leu Arg Val Ala Val
            420                 425                 430

Leu Gly Leu Val Trp Leu Leu Cys Leu Gly Ile Thr Leu Gly Cys Ala
            435                 440                 445

Val Ala Val Tyr Thr Phe Ser Glu Phe Leu Ile Gln Ser Pro Val Ala
            450                 455                 460

Thr Gly Gln Val Gly Leu Leu Val Leu Pro Leu Met Val Ser Val Thr
465                 470                 475                 480

Asn Leu Val Ala Pro Tyr Leu Tyr Arg Met Leu Ala Ala Leu Glu Gln
                485                 490                 495

His Glu Ser Pro Val Leu Glu Val Tyr Val Ala Ile Cys Arg Asn Leu
            500                 505                 510
```

```
Ile Leu Lys Val Ile Thr Leu Gly Ile Leu Cys Tyr His Trp Leu Gly
            515                 520                 525

Arg Arg Val Asp Ile Leu Lys Asp Gln Cys Trp Glu Asp Phe Val Gly
        530                 535                 540

Gln Glu Leu Tyr Arg Phe Met Val Met Asp Phe Phe Thr Leu Val
545                 550                 555                 560

Asp Thr Leu Phe Gly Glu Leu Val Trp Arg Leu Ile Thr Glu Arg Lys
                565                 570                 575

Leu Lys Arg Gln Arg Lys Pro Glu Phe Asp Ile Ala Arg Asn Val Leu
            580                 585                 590

Glu Leu Ile Tyr Gly Gln Thr Leu Thr Trp Leu Gly Val Leu Phe Ser
        595                 600                 605

Pro Leu Leu Pro Ala Val Gln Ile Leu Lys Leu Leu Leu Phe Tyr
610                 615                 620

Ile Lys Lys Thr Ser Leu Met Ala Asn Cys Gln Ala Pro His Arg Pro
625                 630                 635                 640

Trp Leu Ala Ser His Met Ser Thr Val Phe Ile Thr Leu Leu Cys Phe
                645                 650                 655

Pro Ser Phe Leu Gly Ala Ala Ile Phe Leu Cys Tyr Ala Ile Trp Gln
            660                 665                 670

Val Lys Pro Ser Ser Met Cys Gly Pro Phe Arg Ser Leu Gly Thr Met
        675                 680                 685

Tyr Glu Ala Gly Lys Val Trp Val His His Leu Glu Gln Ala Gly Pro
690                 695                 700

Arg Val Ser Trp Val Pro Trp Val Tyr His Tyr Leu Leu Glu Asn Thr
705                 710                 715                 720

Phe Phe Ile Phe Leu Val Ser Thr Leu Leu Ala Val Ile Tyr Leu
                725                 730                 735

Asn Ile Gln Val Val Lys Gly Gln Arg Lys Ile Ile Cys Leu Leu Lys
            740                 745                 750

Glu Gln Ile Ser Asn Glu Gly Glu Asp Lys Ile Phe Leu Ile Asn Glu
        755                 760                 765

Ile His Ser Val Tyr Lys Arg Lys Glu Arg Ser Phe Leu Met Pro
770                 775                 780

Thr Leu Gly Leu Gly Glu Asn Ala His Leu Ser Ser Arg Val Thr Leu
785                 790                 795                 800

Ala Glu Thr Val Met Val Thr
                805

<210> SEQ ID NO 17
<211> LENGTH: 745
<212> TYPE: PRT
<213> ORGANISM: Trichechus manatus latirostris

<400> SEQUENCE: 17

Met Ala Phe Val Leu Asn Val Pro Glu Ile Pro Glu Asp Ser Ser Gln
1               5                   10                  15

Glu Pro Ser Pro Tyr Asp Glu Asp Val His Asp Ser Phe His Gln
            20                  25                  30

Leu Ile Arg Glu Gln Ser Gln Trp Val Ala Ala Gly Pro Glu Thr
        35                  40                  45

Ala Gly Pro Glu Ala Gly Leu Glu Leu Met Glu Arg Glu Pro Gly Ala
50                  55                  60

Gly Thr Pro Gly Ala Pro Gly Gly Gly His Gln Ser Asp Leu Gly Pro
```

```
                65                  70                  75                  80
Gly Gly Ala Pro Ala Tyr Ser Ala Ala Thr Leu Arg Ile Leu Ala Asn
                    85                  90                  95
Met Pro Ser Arg Thr Ile Gly Arg Ser Arg Gly Ala Ile Ile Ser Gln
                    100                 105                 110
Tyr Tyr Asn Arg Thr Ile Arg Leu Arg Arg Arg Ser Arg Pro Leu
                    115                 120                 125
Leu Ser Ala Met Gly Arg Ser Ala Arg Pro Ser Leu Arg Ser His Asp
                    130                 135                 140
Leu Glu Leu Asp Pro Met Ala Tyr Gln Glu Glu Lys Arg Ser Leu
145                 150                 155                 160
Leu Val Arg Glu Leu Gln Gly Leu Thr Gly Ala Gln Arg Asp His Met
                    165                 170                 175
Leu Arg Arg Met Pro Leu Ser Leu Ala Glu Lys Arg Cys Leu Arg Glu
                    180                 185                 190
Ala Ser Glu Thr Ala Arg Glu Thr Trp Arg Gly Gln Gln Gly Arg Arg
                    195                 200                 205
Gly Val Trp Ser Cys Cys Ser Gln Phe Lys Tyr Gly Cys Val Leu Ala
                    210                 215                 220
Leu His Asn Leu Gly Leu Gly Leu Leu Ser Gly Leu His Ala Leu Thr
225                 230                 235                 240
Pro Trp Arg Tyr Ala Leu Lys Arg Ile Gly Gly Gln Phe Gly Ser Ser
                    245                 250                 255
Val Leu Ser Tyr Phe Leu Phe Leu Lys Thr Leu Leu Ala Phe Asn Ala
                    260                 265                 270
Leu Leu Leu Leu Pro Leu Leu Ala Phe Ile Val Gly Val Gln Ala Ala
                    275                 280                 285
Phe Pro Pro Ser Pro Pro His Pro Thr Pro Ala Phe Thr Gly Leu Glu
                    290                 295                 300
Leu Leu Thr Gly Gly Gly Tyr Phe Thr His Thr Val Met Tyr Tyr Gly
305                 310                 315                 320
Tyr Tyr Ser Asn Thr Thr Leu Asn Gln Gln Cys Ala Pro Pro Leu Asp
                    325                 330                 335
Gly Asn Gln Cys Thr Arg Gly Glu Gly Gly Leu Pro Tyr Asn Met Pro
                    340                 345                 350
Leu Ala Tyr Leu Phe Thr Met Gly Val Ala Phe Phe Ile Thr Cys Ile
                    355                 360                 365
Thr Leu Val Tyr Ser Met Ser His Ser Phe Gly Glu Ser Tyr Arg Val
                    370                 375                 380
Gly Ser Thr Ser Gly Ile His Ala Ile Thr Val Phe Cys Ser Trp Asp
385                 390                 395                 400
Tyr Lys Val Thr Gln Arg Trp Ala Ser Arg Leu Gln Gln Asn Asn Leu
                    405                 410                 415
Arg Thr Gln Leu Lys Glu Leu Leu Ala Glu Trp Gln Leu Arg Leu Val
                    420                 425                 430
Pro Arg Ser Met Trp Gly Gln Leu Lys Arg Val Ala Val Leu Gly Leu
                    435                 440                 445
Val Trp Leu Leu Cys Leu Val Thr Thr Met Gly Cys Ala Met Ala Val
                    450                 455                 460
Tyr Thr Phe Ser Glu Leu Met Ile Gln Ser Pro Val Ala Thr Ser Gln
465                 470                 475                 480
Glu Ala Ala Leu Leu Thr Leu Pro Leu Val Val Ser Leu Ile Asn Leu
                    485                 490                 495
```

-continued

Val Ala Pro Tyr Leu Tyr Arg Gly Leu Ala Ala Leu Glu Gln His Glu
            500                 505                 510

Ser Pro Val Leu Glu Val Tyr Val Ala Ile Cys Arg Asn Leu Ile Leu
        515                 520                 525

Lys Met Val Ile Leu Gly Ile Leu Cys Tyr His Trp Leu Gly Arg Arg
    530                 535                 540

Val Arg Ala Leu Lys Gly Gln Cys Trp Glu Asp Phe Val Gly Gln Glu
545                 550                 555                 560

Leu Tyr Arg Phe Met Val Met Asp Phe Ile Phe Met Leu Val Asp Thr
                565                 570                 575

Leu Phe Gly Glu Leu Val Trp Arg Leu Ile Ser Glu Lys Lys Leu Lys
            580                 585                 590

Arg Arg Gln Lys Pro Glu Phe Asp Ile Ala Arg Asn Val Leu Asp Leu
        595                 600                 605

Ile Tyr Gly Gln Thr Leu Thr Trp Leu Gly Val Leu Phe Ser Pro Leu
    610                 615                 620

Leu Pro Ala Met Gln Ile Leu Lys Leu Leu Leu Phe Tyr Ile Lys
625                 630                 635                 640

Lys Thr Ser Leu Met Ala Asn Cys Gln Ala Pro Arg Arg Pro Trp Leu
                645                 650                 655

Ala Ser His Met Ser Thr Val Phe Met Thr Leu Leu Cys Phe Pro Ser
            660                 665                 670

Phe Leu Gly Ala Ala Val Phe Leu Cys Tyr Ala Val Trp Gln Val Lys
        675                 680                 685

Pro Ser Ser Met Cys Gly Pro Phe Gln Thr Leu Asp Thr Met Tyr Glu
    690                 695                 700

Ala Gly Lys Val Trp Val Arg Arg Leu Glu Arg Ala Gly Pro Arg Val
705                 710                 715                 720

Ser Trp Leu Ser Trp Val His His Tyr Leu Leu Glu Asn Thr Phe Phe
                725                 730                 735

Ile Phe Leu Val Ser Ala Leu Leu Leu
            740                 745

<210> SEQ ID NO 18
<211> LENGTH: 789
<212> TYPE: PRT
<213> ORGANISM: Elephantulus edwardii

<400> SEQUENCE: 18

Met Ala Phe Val Leu Asn Val Pro Glu Thr Pro Gly Asp Trp Gly Ser
1               5                   10                  15

Gln Glu Pro Ser Pro Tyr Asp Glu Asp Glu Val His Asn Ser Phe His
            20                  25                  30

Gln Leu Ile Gln Glu Gln Ser Gln Trp Val Glu Ala Ser Gly Pro Glu
        35                  40                  45

Glu Gly Leu Glu Leu Pro Ala Trp Glu Pro Arg Ser Gly Ala Ala Glu
    50                  55                  60

Thr Pro Gly Ala Pro Gly Arg Asp His Gln Ala Ile Leu Glu Pro Gly
65                  70                  75                  80

Gly Gly Pro Ser Tyr Ser Ala Ala Thr Leu Arg Val Leu Ala Ser Met
                85                  90                  95

Pro Ser Arg Thr Ile Gly Arg Ser Arg Gly Ala Ile Ile Ser Gln Tyr
            100                 105                 110

Tyr Asn Arg Thr Val Arg Leu Arg Arg Arg Gly His Arg Pro Pro Leu

```
            115                 120                 125
His Gly Ala Arg Pro Ser Leu His Gly Arg Asp Leu Glu Leu Asp Pro
130                 135                 140

Asp Ile His Gln Glu Glu Lys Arg Ser Leu Leu Val Gln Glu Leu
145                 150                 155                 160

Gln Gly Leu Ser Gly Thr Gln Asp His Met Leu Arg Gly Met Pro
                165                 170                 175

Leu Ser Leu Ala Glu Lys Arg Gly Leu Arg Glu Glu Ser Gln Thr Pro
            180                 185                 190

Val Gly Lys Arg Arg Gly Gln Gln Gly Pro Arg Gly Val Cys Ser Cys
            195                 200                 205

Cys Asn Arg Leu Lys Tyr Ser Cys Val Leu Ala Leu His Ser Met Gly
            210                 215                 220

Leu Val Leu Leu Ser Gly Leu Asn Ser Leu Thr Pro Trp His Tyr Ala
225                 230                 235                 240

Leu Lys Arg Ile Gly Gly Gln Phe Gly Ser Ser Val Leu Ser Tyr Phe
                245                 250                 255

Leu Phe Leu Lys Thr Leu Leu Ala Phe Asn Ala Leu Leu Leu Pro
            260                 265                 270

Leu Leu Ala Phe Ile Val Gly Val Gln Ala Ala Phe Pro Pro Thr Pro
            275                 280                 285

Leu His Pro Ala Pro Thr Phe Thr Gly Leu Glu Leu Leu Thr Gly Gly
290                 295                 300

Gly Tyr Phe Thr His Thr Val Met Tyr Gly Tyr Tyr Ser Asn Ile
305                 310                 315                 320

Thr Leu Asn Gln Pro Cys Ala Pro Pro Leu Glu Gly Ser Gln Cys Thr
                325                 330                 335

Pro Gly Ala Arg Gly Leu Pro Tyr Asn Met Pro Leu Ala Tyr Leu Phe
            340                 345                 350

Thr Met Gly Thr Ala Phe Phe Ile Thr Cys Ile Thr Leu Val Tyr Ser
            355                 360                 365

Met Ser Arg Ser Phe Gly Asp Ser Tyr Arg Val Gly Ser Thr Leu Gly
            370                 375                 380

Val His Ala Ile Thr Val Phe Cys Ser Trp Asp Tyr Lys Val Thr Gln
385                 390                 395                 400

Asp Trp Ala Thr Ile Leu Gln Gln Asn Leu His Thr Gln Leu Lys
                405                 410                 415

Glu Met Leu Ala Glu Trp Gln Leu Gln Arg Val Pro Arg Ser Val Cys
            420                 425                 430

Gly Arg Leu Arg Arg Val Ala Val Leu Gly Leu Val Trp Leu Leu Cys
            435                 440                 445

Leu Gly Thr Thr Met Gly Cys Ala Val Ala Val Tyr Ala Phe Ser Glu
            450                 455                 460

His Met Met Gln Ser Pro Leu Ala Ala Gly Gln Glu Ala Ala Leu Leu
465                 470                 475                 480

Ser Leu Pro Leu Val Val Ser Leu Ile Asn Leu Val Ala Pro Tyr Leu
                485                 490                 495

Phe Arg Gly Leu Ala Ser Leu Glu Gln His Glu Ser Pro Val Gln Glu
            500                 505                 510

Val Tyr Val Ala Ile Cys Arg Asn Leu Ile Leu Lys Met Val Ile Leu
            515                 520                 525

Gly Ile Leu Ser Tyr His Trp Leu Gly Arg Arg Val Gly Val Leu Ser
            530                 535                 540
```

Gly Gln Cys Trp Glu Asp Phe Val Gly Gln Glu Leu Tyr Arg Phe Met
545                 550                 555                 560

Val Met Asp Phe Ile Phe Leu Leu Leu Asp Thr Leu Ile Gly Glu Leu
                565                 570                 575

Ala Trp Arg Leu Val Ser Glu Lys Lys Leu Lys Arg Pro Arg Lys Pro
            580                 585                 590

Glu Phe Asp Ile Ala Arg Asn Val Leu Asp Leu Ile Tyr Gly Gln Thr
        595                 600                 605

Leu Thr Trp Leu Gly Val Leu Phe Ser Pro Leu Leu Pro Ala Met Gln
    610                 615                 620

Ile Leu Lys Leu Leu Leu Phe Tyr Ile Lys Lys Thr Ser Leu Met
625                 630                 635                 640

Ala Asn Cys Gln Ala Pro Arg Arg Pro Trp Leu Ala Ser Arg Met Ser
                645                 650                 655

Met Val Phe Ala Thr Leu Leu Cys Phe Pro Ser Phe Leu Gly Ala Ala
                660                 665                 670

Val Phe Val Cys Cys Ala Val Trp Arg Val Lys Pro Ser Ser Met Cys
            675                 680                 685

Gly Pro Phe Gln Thr Leu Asp Thr Met Tyr Glu Ala Gly Lys Val Trp
        690                 695                 700

Val Arg His Leu Glu Gln Gly Gly His Gln Val Ser Trp Leu Pro Trp
705                 710                 715                 720

Val Tyr His Tyr Leu Leu Glu Asn Thr Phe Phe Ile Phe Leu Val Ser
                725                 730                 735

Ala Ile Leu Leu Ala Val Ile Tyr Leu Asn Ile Gln Val Val Lys Gly
                740                 745                 750

Gln Arg Lys Val Ile Cys Leu Leu Lys Glu Gln Ile Ser Asn Glu Gly
            755                 760                 765

Glu Asp Lys Ile Phe Leu Ile Asn Lys Leu His Ser Val Tyr Glu Arg
        770                 775                 780

Lys Glu Arg Ser Arg
785

<210> SEQ ID NO 19
<211> LENGTH: 787
<212> TYPE: PRT
<213> ORGANISM: Orycteropus afer afer

<400> SEQUENCE: 19

Met Ala Phe Val Leu Asn Val Pro Glu Thr Pro Asp Asp Trp Ser Gln
1               5                   10                  15

Glu Pro Ser Pro Tyr Asp Glu Asp Val His His Ser Phe His Gln
            20                  25                  30

Leu Ile Gln Glu Gln Ser Gln Trp Val Gly Ala Ser Gly Ser Glu Ala
        35                  40                  45

Gly Leu Gln Leu Thr Pro Gly Pro Ala Ala Leu Leu Thr Val Val Asp
    50                  55                  60

Gly Asp His Gln Ala Gly Pro Gly Pro Glu Gly Ala Pro Ala Tyr Ser
65                  70                  75                  80

Ala Ala Thr Leu Arg Ile Leu Ala Ser Met Pro Ser Arg Thr Ile Gly
                85                  90                  95

Arg Ser Arg Gly Ala Ile Ile Ser Gln Tyr Tyr Asn Arg Thr Met Gln
            100                 105                 110

Leu Arg Arg Cys Gly Arg Arg Pro Leu Leu Gly Ala Glu Gly Arg Gly

-continued

```
                115                 120                 125
Ala Arg Pro Ser Leu Arg Ser Leu Asp Leu Glu Leu Asp Pro Thr Ala
            130                 135                 140
Arg Glu Glu Glu Lys Arg Ala Leu Leu Val Thr Glu Leu Gln Gly
145                 150                 155                 160
Leu Thr Gly Ala Gln Gln Asp Gln Leu Leu Arg Gly Met Pro Leu Ser
                165                 170                 175
Leu Ala Glu Lys Arg Cys Leu Arg Gln Glu Ser Arg Thr Pro Ser Gly
                180                 185                 190
Lys Gln Arg Gly Trp Gln Ala Gln Arg Gly Val Trp Ser Cys Cys Ser
                195                 200                 205
Arg Leu Lys Tyr Gly Cys Val Leu Ala Phe His Asn Leu Gly Leu Gly
                210                 215                 220
Leu Leu Ser Gly Leu Ser Ala Leu Thr Pro Trp Arg Tyr Thr Leu Lys
225                 230                 235                 240
Arg Ile Gly Gly Gln Phe Gly Ser Ser Val Leu Ser Tyr Phe Leu Phe
                245                 250                 255
Leu Lys Thr Leu Leu Val Ser Asn Ala Leu Leu Leu Pro Leu Leu
                260                 265                 270
Ala Phe Ile Val Gly Val Gln Ala Ala Phe Pro Pro Asp Pro Arg Gly
                275                 280                 285
Pro Ala Pro Thr Phe Thr Gly Leu Glu Leu Leu Thr Gly Ala Gly Tyr
                290                 295                 300
Phe Thr His Thr Val Met Tyr Gly Tyr Tyr Ser Asn Phe Thr Leu
305                 310                 315                 320
Asn Gln Pro Cys Thr His Pro Pro Asp Gly Ala Gln Cys Thr Pro Gly
                325                 330                 335
Ala Gly Asp Leu Pro Tyr Asn Met Pro Leu Ala Tyr Leu Phe Thr Met
                340                 345                 350
Gly Ala Ile Phe Phe Thr Thr Gly Ile Thr Leu Val Tyr Ser Met Ser
                355                 360                 365
Arg Ser Phe Gly Glu Ser Tyr Arg Val Gly Ser Thr Leu Gly Ile His
                370                 375                 380
Ala Ile Thr Val Phe Cys Ser Trp Asp Tyr Lys Val Thr Gln Lys Trp
385                 390                 395                 400
Ala Ser Arg Leu Gln Gln Asp Asn Leu Arg Thr Gln Leu Lys Glu Leu
                405                 410                 415
Leu Ala Glu Trp Gln Leu Arg Gln Arg Pro Arg Ser Val Cys Gly Arg
                420                 425                 430
Leu Arg Arg Ala Ala Val Leu Leu Val Trp Phe Leu Cys Leu Ala
                435                 440                 445
Thr Val Leu Gly Cys Ala Val Gly Val Tyr Thr Phe Ser Glu Leu Met
450                 455                 460
Ile Gln Ser Pro Val Ala Thr Gly Gln Glu Val Gly Leu Leu Val Leu
465                 470                 475                 480
Pro Leu Val Val Ser Leu Ala Asn Leu Leu Val Pro Tyr Leu Tyr Arg
                485                 490                 495
Leu Leu Ala Thr Leu Glu Arg His Glu Ser Pro Val Leu Glu Val Tyr
                500                 505                 510
Val Ala Val Cys Arg Asn Leu Leu Lys Ala Ile Leu Leu Gly Ile
                515                 520                 525
Leu Cys Tyr His Trp Leu Gly Arg Val Gly Ala Leu Lys Gly Gln
                530                 535                 540
```

Cys Trp Glu Asp Phe Val Gly Gln Glu Leu Tyr Arg Phe Val Val Met
545                 550                 555                 560

Asp Phe Ile Phe Thr Leu Leu Asp Thr Leu Phe Gly Glu Leu Val Trp
            565                 570                 575

Arg Leu Val Ser Glu Lys Lys Ser Arg Ser Arg Arg Lys Pro Glu Phe
        580                 585                 590

Asp Ile Ala Gly Asn Leu Leu Gln Leu Ile Tyr Gly Gln Thr Leu Thr
    595                 600                 605

Trp Leu Gly Val Leu Phe Cys Pro Leu Leu Pro Ala Val Gln Val Leu
610                 615                 620

Lys Leu Leu Leu Leu Phe Tyr Val Lys Lys Thr Ser Leu Met Ala Asn
625                 630                 635                 640

Cys Gln Ala Pro Arg Arg Pro Trp Leu Ala Ser His Met Ser Thr Val
                645                 650                 655

Phe Leu Thr Leu Leu Cys Phe Pro Ser Phe Leu Gly Ala Ala Val Phe
            660                 665                 670

Leu Cys Ser Ala Ile Trp Gln Val Lys Pro Ser Ser Thr Cys Gly Pro
        675                 680                 685

Phe Gln Thr Leu Asp Thr Met Tyr Glu Ala Gly Lys Val Trp Val Arg
    690                 695                 700

His Leu Gln Arg Ala Gly Pro Arg Val Ser Trp Leu Pro Trp Val Tyr
705                 710                 715                 720

His Tyr Leu Leu Glu Asn Thr Phe Leu Ile Phe Leu Val Ser Ala Leu
                725                 730                 735

Leu Leu Ala Val Ile Tyr Leu Asn Ile Gln Val Val Lys Gly Gln Arg
            740                 745                 750

Lys Val Ile Cys Leu Leu Lys Glu Gln Ile Ser Asn Glu Gly Glu Asp
        755                 760                 765

Lys Met Phe Leu Ile Asn Lys Leu His Ser Val Tyr Glu Lys Lys Glu
    770                 775                 780

Arg Ser Arg
785

<210> SEQ ID NO 20
<211> LENGTH: 803
<212> TYPE: PRT
<213> ORGANISM: Chinchilla lanigera

<400> SEQUENCE: 20

Met Trp Thr Val Val Met Ala Gln Pro Leu Thr Leu Val Leu Asp Val
1               5                   10                  15

Pro Glu Thr Pro Gly Asp Gln Asp Pro Glu Leu Ser Pro Tyr Glu Glu
            20                  25                  30

Ser Glu Val His Asp Ser Phe His Gln Leu Ile Gln Glu Gln Ser Arg
        35                  40                  45

Trp Val Ala Glu Glu Gly Leu Glu Leu Gln Gln Val Ala Gly Asn Leu
    50                  55                  60

Gly Ala Leu Ala Ser Gly His Gln Ile Leu Leu Gly Ala Glu Gly Gly
65                  70                  75                  80

Pro Val Tyr Ser Thr Ala Thr Leu Asn Ile Leu Ala Ser Met Pro Ser
                85                  90                  95

Arg Thr Ile Gly Arg Ser Arg Gly Ala Ile Ile Ser Gln Tyr Tyr Asn
            100                 105                 110

Arg Thr Val Arg Met Arg Arg Arg Ser Ser Arg Pro Pro Leu Gly Pro

```
            115                 120                 125
Val Met Cys Ser Ala Arg Pro Ser Leu Arg Leu Tyr Asp Leu Glu Leu
130                 135                 140

Asp Pro Ala Ala Leu Gln Glu Glu Lys Arg Ser Leu Leu Val Lys
145                 150                 155                 160

Glu Leu Gln Gly Leu Ser Ala Ala Gln Arg Asp His Met Leu Arg Gly
                165                 170                 175

Met Pro Leu Ser Leu Gln Glu Lys Arg Phe Leu Arg Glu Lys Ser Arg
                180                 185                 190

Ile Pro Arg Gly Lys Gln Arg Gly Gln Gly Cys Gly Arg Val Phe
        195                 200                 205

Tyr Cys Ser Arg Leu Arg Tyr Thr Cys Ala Leu Ala Leu His Ser Leu
        210                 215                 220

Gly Leu Ala Leu Leu Thr Arg Leu His Ala Leu Lys Pro Trp Arg Tyr
225                 230                 235                 240

Ala Leu Lys Gln Ile Gly Gly Leu Phe Gly Ser Ser Val Leu Ser Tyr
                245                 250                 255

Phe Leu Phe Leu Lys Thr Leu Leu Ala Phe Asn Ala Leu Leu Leu Leu
                260                 265                 270

Pro Leu Val Ala Phe Leu Val Ala Val Gln Ala Ala Phe Pro Pro Glu
        275                 280                 285

Ala His Pro Val Pro Arg Cys Thr Gly Leu Glu Leu Leu Thr Gly Gly
        290                 295                 300

Gly Cys Phe Thr His Thr Val Met Tyr Tyr Gly Tyr Tyr Arg Asn Thr
305                 310                 315                 320

Met Leu Asn Thr Pro Cys Ser Ser Pro Gln Cys Ser Pro Gly Ala Gly
                325                 330                 335

Ser Leu Pro Tyr Asn Met Pro Val Ala Tyr Leu Phe Thr Val Gly Ala
                340                 345                 350

Thr Phe Phe Ile Thr Cys Ile Thr Leu Val Tyr Ser Met Ser His Ser
                355                 360                 365

Phe Gly Glu Ser Tyr Arg Val Gly Ser Thr Lys Gly Val His Ala Ile
        370                 375                 380

Thr Val Phe Cys Ser Trp Asp Tyr Lys Val Thr Gln Lys Trp Ala Ser
385                 390                 395                 400

Arg Leu Gln Arg Asp Asn Ile Arg Thr Gln Leu Lys Glu Leu Leu Ala
                405                 410                 415

Glu Trp Arg Leu Arg Arg Ser Pro Gln Ser Val Cys Gly Arg Leu Arg
                420                 425                 430

Gln Val Thr Val Leu Ala Leu Val Trp Leu Leu Cys Leu Gly Val Ala
        435                 440                 445

Leu Gly Cys Ala Val Ala Val Leu Thr Phe Ser Glu Val Thr Ile Gln
        450                 455                 460

Ser Pro Ala Ala Gly Arg Glu Ala Gly Leu Leu Val Leu Pro Val
465                 470                 475                 480

Val Val Cys Leu Leu Asn Leu Ala Ala Pro Tyr Leu Phe Arg Gly Leu
                485                 490                 495

Ala Thr Leu Glu Gln His Asp Ser Pro Val Leu Glu Val Tyr Leu Ala
                500                 505                 510

Val Cys Arg Asn Leu Ile Leu Lys Met Ala Ile Leu Gly Val Leu Cys
        515                 520                 525

Tyr His Trp Leu Gly Arg Arg Val Ala Thr Leu Gln Asp Gln Cys Trp
        530                 535                 540
```

```
Glu Asp Phe Val Gly Gln Glu Leu Tyr Arg Phe Leu Val Met Asp Phe
545                 550                 555                 560

Ile Phe Ala Leu Leu Asp Ser Leu Phe Gly Glu Val Trp Arg Leu
                565                 570                 575

Ile Ser Glu Arg Arg Leu Arg Arg Arg Lys Pro Glu Phe Asp Ile Ala
                580                 585                 590

Arg Asn Val Leu Asp Leu Ile Tyr Gly Gln Thr Leu Thr Trp Leu Gly
                595                 600                 605

Val Leu Phe Ser Pro Leu Leu Pro Ala Val Gln Ile Leu Arg Leu Leu
610                 615                 620

Ile Leu Phe Gln Val Lys Lys Ala Ser Leu Met Ala Asn Cys Gln Ala
625                 630                 635                 640

Pro Arg Arg Pro Trp Leu Ala Ser His Met Ser Thr Val Phe Leu Thr
                645                 650                 655

Leu Leu Cys Phe Pro Ala Phe Leu Gly Ala Ala Ile Phe Leu Cys Tyr
                660                 665                 670

Ala Val Trp Gln Val Lys Pro Ser Asp Thr Cys Gly Pro Phe Arg Ser
                675                 680                 685

Leu Asp Arg Met Tyr Glu Ala Gly Thr Val Trp Lys Arg His Leu Glu
                690                 695                 700

Gln Gly Ser Pro Gly Ala Pro Trp Leu Ser Trp Leu His Trp Tyr Leu
705                 710                 715                 720

Val Glu Asn Thr Phe Phe Leu Phe Leu Val Ser Ala Leu Leu Leu Ala
                725                 730                 735

Val Ile Tyr Leu Asn Ile Gln Val Val Lys Gly Gln Arg Lys Val Ile
                740                 745                 750

Cys Leu Leu Lys Glu Gln Ile Arg Asn Glu Gly Glu Asp Lys Ile Phe
                755                 760                 765

Leu Ile Asn Arg Leu His Ser Val Tyr Glu Arg Lys Glu Arg Ser Arg
                770                 775                 780

Ala Gly Arg Ala Ala Glu Val Ala Thr Pro Ala Leu Val Pro Asp Ala
785                 790                 795                 800

Gly Asp Lys

<210> SEQ ID NO 21
<211> LENGTH: 805
<212> TYPE: PRT
<213> ORGANISM: Heterocephalus glaber

<400> SEQUENCE: 21

Met Trp Thr Ala Val Met Ala Gln Gln Leu Ala Leu Val Leu Asp Val
1               5                   10                  15

Pro Glu Thr Pro Gly Asp Gln Asp Ser Leu Glu Leu Ser Pro Tyr Glu
                20                  25                  30

Glu Ser Glu Val His Asp Ser Phe His Gln Leu Ile Gln Glu Gln Ser
                35                  40                  45

Arg Trp Val Ala Glu Glu Gly Leu Glu Leu Gln Gln Val Ala Gly Asp
                50                  55                  60

Leu Gly Ala Pro Ala Ser Gly His Gln Thr Leu Leu Glu Pro Glu Gly
65                  70                  75                  80

Gly Pro Val Tyr Ser Thr Ala Thr Leu Ser Ile Leu Ala Ser Met Pro
                85                  90                  95

Ser Arg Thr Ile Gly Arg Ser Arg Gly Ala Ile Ile Ser Lys Tyr Tyr
                100                 105                 110
```

-continued

```
Asn His Thr Val Arg Leu Arg Arg Arg His Ser Gly Ser Arg Pro Ile
    115                 120                 125

Leu Gly Pro Val Val Cys Ser Ala Arg Pro Ser Leu Arg Leu Tyr Asp
    130                 135                 140

Leu Glu Leu Asp Pro Ala Asp Leu Glu Glu Glu Lys Trp Ser Leu
145                 150                 155                 160

Leu Val Lys Glu Leu Gln Gly Leu Pro Val Ala Gln Arg Asp His Met
                165                 170                 175

Leu Arg Gly Met Pro Leu Ser Leu Gln Glu Lys Arg Val Leu Arg Glu
                180                 185                 190

Lys Ser Arg Thr Pro Arg Gly Lys Gln Arg Gly Arg Gln Gly His Gly
                195                 200                 205

Gly Val Phe Cys Cys Ser Gln Leu Arg Tyr Thr Cys Val Leu Ala Leu
                210                 215                 220

His Ser Leu Gly Leu Val Leu Leu Thr Cys Leu His Ala Leu Arg Pro
225                 230                 235                 240

Trp Arg Tyr Ala Leu Lys Gln Ile Gly Gly Gln Phe Gly Ser Ser Val
                245                 250                 255

Leu Ser Tyr Phe Leu Phe Leu Lys Thr Leu Leu Ala Phe Asn Met Leu
                260                 265                 270

Leu Leu Leu Pro Leu Val Ala Phe Leu Val Ala Val Gln Ala Ala Phe
                275                 280                 285

Thr Pro Glu Ala His Pro Ala Pro Thr Cys Thr Gly Leu Glu Leu Leu
                290                 295                 300

Thr Gly Gly Gly Cys Phe Thr His Thr Val Met Tyr Tyr Gly Tyr Tyr
305                 310                 315                 320

Ser Asn Thr Thr Leu Asn Thr Pro Cys Gly Pro Leu Gln Cys Gly Pro
                325                 330                 335

Arg Ala Gly Ser Leu Pro Tyr Ser Met Pro Leu Ala Tyr Leu Phe Thr
                340                 345                 350

Val Gly Ala Ala Phe Phe Ile Thr Cys Ile Thr Leu Val Tyr Ser Met
                355                 360                 365

Ser His Ser Phe Gly Glu Ser Tyr Arg Val Gly Ser Thr Lys Gly Ile
                370                 375                 380

His Ala Ile Thr Val Phe Cys Ser Trp Asp Tyr Lys Val Thr Gln Asn
385                 390                 395                 400

Trp Ala Ser Arg Leu Gln Arg Asp Asn Ile Cys Thr Gln Leu Lys Glu
                405                 410                 415

Leu Leu Ala Glu Trp Arg Leu Cys Lys Gly Ser Gln Ser Thr Cys Gly
                420                 425                 430

Arg Leu Arg Arg Ala Ala Val Leu Ala Leu Val Trp Leu Leu Ser Leu
                435                 440                 445

Ala Ala Val Leu Gly Cys Ala Val Ala Val Leu Thr Phe Ser Glu Leu
                450                 455                 460

Arg Ile Gln Ser Pro Val Val Ala Asp Gln Glu Ala Gly Leu Leu Val
465                 470                 475                 480

Leu Pro Leu Val Ile Cys Leu Leu Asn Leu Gly Ala Pro Tyr Leu Phe
                485                 490                 495

Arg Gly Leu Ala Thr Leu Glu Arg His Asp Ser Pro Val Leu Glu Val
                500                 505                 510

Tyr Val Ala Ile Gly Arg Asn Leu Val Leu Lys Thr Ala Ile Leu Gly
                515                 520                 525
```

```
Val Leu Cys Tyr His Trp Leu Gly Arg Arg Val Ala Thr Leu Gln Gly
            530                 535                 540

Arg Cys Trp Glu Asp Phe Val Gly Gln Glu Leu Tyr Arg Phe Met Val
545                 550                 555                 560

Met Asp Phe Ile Phe Ala Leu Leu Asp Ser Leu Phe Gly Glu Leu Val
                565                 570                 575

Trp Arg Leu Ile Ser Glu Arg Leu Arg Gly Lys Pro Glu Phe Asp
            580                 585                 590

Ile Ala Arg Asn Val Leu Asp Leu Ile Tyr Gly Gln Thr Leu Thr Trp
            595                 600                 605

Leu Gly Val Leu Phe Ser Pro Leu Leu Pro Ala Val Gln Ile Leu Arg
610                 615                 620

Leu Leu Ile Leu Phe Gln Val Lys Lys Ala Ser Leu Met Ala Asn Cys
625                 630                 635                 640

Gln Ala Pro Arg Arg Pro Trp Leu Ala Ser His Met Ser Thr Val Phe
                645                 650                 655

Leu Thr Leu Leu Cys Phe Pro Ser Phe Leu Gly Ala Ala Val Phe Leu
            660                 665                 670

Cys Tyr Ala Val Trp Gln Val Lys Pro Ser Asp Thr Cys Gly Pro Phe
            675                 680                 685

Arg Ser Leu Asp Thr Met Tyr Glu Ala Gly Thr Val Trp Val Arg His
            690                 695                 700

Leu Glu Gln Val Gly Pro Gly Gly Ser Trp Leu Ser Trp Leu His Arg
705                 710                 715                 720

Tyr Leu Val Glu Asn Thr Phe Phe Leu Phe Leu Ala Ser Ala Leu Leu
                725                 730                 735

Leu Ala Val Ile Tyr Leu Asn Ile Gln Val Val Lys Gly Gln Arg Lys
            740                 745                 750

Val Ile Cys Leu Leu Lys Glu Gln Ile Arg Asn Glu Gly Glu Asp Lys
            755                 760                 765

Ile Phe Leu Ile Asn Arg Leu His Ser Val Tyr Glu Arg Lys Glu Arg
            770                 775                 780

Arg Arg Ala Gly Arg Ser Ala Glu Thr Ala Thr Pro Ala Leu Leu Thr
785                 790                 795                 800

Asp Ala Gly Asp Lys
            805

<210> SEQ ID NO 22
<211> LENGTH: 809
<212> TYPE: PRT
<213> ORGANISM: Cricetulus griseus

<400> SEQUENCE: 22

Met Ala Gln Pro Ala Ala Leu Val Leu Glu Val Pro Glu Ala Ala Gly
1               5                   10                  15

Asp Ala Asp Leu Glu Leu Ser Pro Cys Glu Glu Ser Asp Val His Asp
            20                  25                  30

Ser Phe His Arg Leu Ile Gln Glu Gln Ser Leu Arg Val Ala Glu Glu
        35                  40                  45

Gly Leu Glu Leu Pro Arg Gly Ala Ala Gly Arg Gly Arg Gln Thr
    50                  55                  60

Leu Pro Arg Pro Ala Gly Ala Pro Val His Ser Ser Ala Thr Leu Arg
65                  70                  75                  80

Val Leu Ala Ser Met Pro Ser Arg Thr Ile Gly Arg Ser Arg Gly Ala
                85                  90                  95
```

```
Ile Ile Ser Gln Tyr Tyr Asn Arg Thr Val Arg Leu Arg Arg Arg
            100                 105                 110

Asn Ser Arg Pro Leu Leu Gly Asn Val Val Arg Ser Ala Arg Pro Ser
        115                 120                 125

Leu Arg Leu Tyr Asp Leu Glu Leu Asp His Thr Val Met Glu Glu Asp
    130                 135                 140

Glu Lys Arg Ser Leu Leu Val Lys Glu Leu Gln Gly Leu Ser Met Ala
145                 150                 155                 160

Gln Arg Asp His Met Ile Arg Asn Met Pro Leu Ser Leu Gly Glu Lys
                165                 170                 175

Arg Trp Leu Arg Glu Lys Ser Trp Ser Pro Lys Gly Lys Gln Gln Gly
            180                 185                 190

Gln Lys Gly Arg Gly Gly Thr Phe Ser Cys Ser Arg Leu Arg Tyr Ser
            195                 200                 205

Cys Ile Leu Ala Leu His Ser Leu Gly Leu Val Leu Leu Ser Gly Leu
            210                 215                 220

Tyr Ala Ala Arg Pro Trp Arg Tyr Ala Leu Lys Gln Ile Gly Gly Gln
225                 230                 235                 240

Phe Gly Ser Ser Val Leu Ser Tyr Phe Leu Phe Leu Lys Thr Leu Leu
                245                 250                 255

Ala Phe Asn Ala Leu Met Leu Leu Pro Leu Leu Ala Phe Leu Val Gly
            260                 265                 270

Val Gln Ala Ala Phe Pro Pro Asp Pro Ser Gly Leu Val Pro Thr Phe
            275                 280                 285

Ser Gly Leu Glu Leu Leu Thr Gly Arg Gly Cys Phe Thr His Thr Val
            290                 295                 300

Met Tyr Gly Tyr Tyr Ser Asn Thr Thr Leu Ser Gln Ser Cys Ala
305                 310                 315                 320

Ser Pro Arg Glu Thr Gly Gln Asp Ser Leu Pro Tyr Asn Met Pro Leu
            325                 330                 335

Ala Tyr Leu Phe Thr Val Gly Ala Ala Phe Phe Ile Thr Cys Ile Thr
            340                 345                 350

Leu Val Tyr Ser Met Ser His Ser Phe Gly Ser Tyr Arg Val Gly
            355                 360                 365

Ser Thr Lys Gly Ile His Ala Leu Thr Val Phe Cys Ser Trp Asp Tyr
    370                 375                 380

Lys Val Thr Gln Lys Arg Ala Ser Arg Val Gln Gln Asp Ser Ile Cys
385                 390                 395                 400

Thr Gln Leu Lys Glu Leu Leu Ala Glu Trp Gln Leu Arg Glu Arg Pro
                405                 410                 415

Gln Ser Ala Cys Gly Gln Leu Trp Gln Ala Ala Met Leu Gly Leu Gly
            420                 425                 430

Trp Leu Leu Cys Leu Gly Thr Thr Met Gly Cys Ala Ala Ala Val Leu
            435                 440                 445

Thr Phe Ser Glu Val Met Ile Gln Arg Pro Asp Ala Asp Gly Gln Gly
        450                 455                 460

Val Glu Leu Leu Ala Leu Pro Leu Val Val Ser Val Leu Asn Leu Gly
465                 470                 475                 480

Ala Ser Tyr Leu Phe Arg Gly Leu Ala Thr Leu Glu Arg His Asp Ser
                485                 490                 495

Pro Val Leu Glu Val Tyr Met Ala Ile Cys Arg Ser Leu Ile Leu Lys
            500                 505                 510
```

Met Ala Val Leu Gly Val Leu Cys Tyr His Trp Leu Gly Arg Arg Val
            515                 520                 525

Ala Lys Leu Gln Ala Pro Cys Trp Glu Asp Phe Val Gly Gln Glu Leu
    530                 535                 540

Tyr Arg Phe Leu Val Val Asp Phe Ile Phe Thr Leu Leu Asp Ser Leu
545                 550                 555                 560

Phe Gly Glu Leu Val Trp Arg Leu Ile Ser Glu Lys Leu Lys Arg
                565                 570                 575

Gln Lys Pro Glu Phe Asp Ile Ala Arg Asn Val Leu Asp Leu Ile Tyr
                580                 585                 590

Gly Gln Thr Leu Thr Trp Leu Gly Val Leu Phe Ser Pro Leu Leu Pro
                595                 600                 605

Ala Val Gln Met Leu Arg Leu Leu Leu Phe Tyr Val Lys Lys Ala
    610                 615                 620

Ser Leu Met Ala Asn Cys Gln Ala Pro Arg Arg Pro Trp Leu Ala Ser
625                 630                 635                 640

His Met Ser Thr Val Phe Leu Thr Leu Leu Cys Phe Pro Ser Phe Leu
                645                 650                 655

Gly Ala Ala Val Phe Leu Cys Tyr Ala Val Trp Gln Val Lys Pro Ser
                660                 665                 670

Ser Thr Cys Gly Pro Phe Arg Thr Leu Asn Thr Met Tyr Glu Ala Gly
            675                 680                 685

Thr Val Trp Val His Arg Leu Glu Arg Ala Gly Ser Gly Ala Ser Trp
                690                 695                 700

Leu Pro Trp Leu His His Phe Leu Val Glu Asn Thr Phe Phe Leu Phe
705                 710                 715                 720

Leu Val Ser Ala Leu Leu Leu Ala Val Ile Tyr Leu Asn Ile Gln Val
                725                 730                 735

Val Lys Ala Gln Arg Lys Val Ile Cys Leu Leu Lys Glu Gln Ile Arg
                740                 745                 750

Asn Glu Gly Glu Asp Lys Val Phe Leu Ile Asn Lys Leu His Ser Val
                755                 760                 765

Tyr Glu Ala Gly Glu Arg Arg Arg Pro Gly Arg Thr Gln Glu Glu
770                 775                 780

Pro Cys Asn Pro Ser His His Asp Pro Ala Arg Arg Asp Leu Asp Leu
785                 790                 795                 800

Arg Ser Pro Gln Asp Thr Ala Val Glu
                805

<210> SEQ ID NO 23
<211> LENGTH: 813
<212> TYPE: PRT
<213> ORGANISM: Mesocricetus auratus

<400> SEQUENCE: 23

Met Ala Gln Pro Leu Ala Leu Val Leu Asp Val Pro Glu Pro Thr Gly
1               5                   10                  15

Asp Gly Asp Leu Glu Pro Ser Pro Tyr Glu Glu Ser Glu Val His Asp
                20                  25                  30

Ser Phe His Gln Leu Ile Gln Glu Gln Ser Leu Arg Val Ala Glu Glu
            35                  40                  45

Gly Leu Glu Leu Leu Pro Leu Val Pro Gly Arg Gly His Gln Thr Leu
    50                  55                  60

Pro Arg Pro Glu Gly Ala Gln Val His Ser Ser Ala Thr Leu Arg Ile
65                  70                  75                  80

-continued

```
Leu Ala Ser Met Pro Ser Arg Thr Ile Gly Arg Ser Arg Gly Ala Ile
            85                  90                  95
Ile Ser Gln Tyr Tyr Asn Arg Thr Val Arg Leu Arg His Arg Ser Ser
            100                 105                 110
Arg Pro Leu Leu Gly Ser Val Ala Arg Ser Ala Arg Pro Ser Leu Arg
            115                 120                 125
Gln Tyr Asp Leu Glu Leu Asp His Thr Val Leu Glu Glu Asp Glu Lys
130                 135                 140
Arg Ser Leu Leu Val Lys Glu Leu Gln Gly Leu Pro Met Ala Gln Arg
145                 150                 155                 160
Asp His Met Val Arg Asn Met Pro Leu Ser Leu Gly Glu Lys Arg Trp
                165                 170                 175
Leu Arg Glu Lys Ser Trp Ser Pro Lys Gly Asn Arg Arg Asp Gln Gln
            180                 185                 190
Gly Arg Gly Arg Ala Ile Ser Cys Cys Arg Arg Leu Arg Tyr Ala Cys
            195                 200                 205
Ile Leu Ala Leu His Ser Leu Gly Leu Met Leu Leu Ser Gly Leu Tyr
            210                 215                 220
Ala Ala Arg Pro Trp Arg Tyr Ala Leu Lys Gln Ile Gly Gly Gln Phe
225                 230                 235                 240
Gly Ser Ser Val Leu Ser Tyr Phe Leu Phe Leu Lys Thr Leu Leu Ala
                245                 250                 255
Phe Asn Ala Leu Met Leu Leu Pro Leu Leu Ala Phe Leu Val Gly Val
                260                 265                 270
Gln Ala Ala Phe Pro Pro Asp Pro Ser Gly Pro Val Pro Ala Phe Ser
                275                 280                 285
Gly Leu Glu Leu Leu Thr Gly Gly Ser Phe Thr His Thr Val Met
            290                 295                 300
Tyr Tyr Gly Tyr Tyr Ser Asn Thr Thr Leu Ser Gln Pro Cys Gly Ser
305                 310                 315                 320
Pro Arg Glu Ser Gly Gln Cys Ser Pro Arg Leu Gly Ser Leu Pro Tyr
                325                 330                 335
Asp Met Pro Leu Ala Tyr Leu Phe Thr Val Gly Ala Ala Phe Phe Ile
                340                 345                 350
Thr Cys Ile Thr Leu Val Tyr Ser Met Ser His Ser Phe Gly Glu Ser
                355                 360                 365
Tyr Arg Val Gly Ser Thr Lys Gly Ile His Ala Leu Thr Val Phe Cys
                370                 375                 380
Thr Trp Asp Tyr Lys Val Thr Gln Lys Arg Ala Ser Arg Val Gln Gln
385                 390                 395                 400
Asp Ser Ile Cys Thr Gln Leu Lys Glu Leu Leu Ala Glu Trp Gln Leu
                405                 410                 415
Arg Glu Arg Pro Gln Ser Ala Cys Gly Gln Leu Trp Gln Val Ala Met
                420                 425                 430
Leu Gly Leu Gly Trp Leu Leu Cys Leu Gly Ala Thr Val Gly Cys Ala
            435                 440                 445
Val Ala Val Leu Thr Phe Ser Glu Val Met Ile Gln Arg Pro Thr Ala
450                 455                 460
Gly Gly Gln Gly Val Glu Leu Leu Ala Leu Pro Leu Val Val Ser Val
465                 470                 475                 480
Leu Asn Leu Gly Ala Ser Tyr Leu Phe Arg Gly Leu Ala Thr Leu Glu
                485                 490                 495
```

Arg His Glu Ser Pro Val Leu Glu Val Tyr Met Ala Ile Cys Arg Ser
            500                 505                 510

Leu Ile Leu Lys Met Ala Val Leu Gly Val Leu Gly Tyr His Trp Leu
        515                 520                 525

Ala Arg Arg Val Ala Lys Leu Gln Ala Pro Cys Trp Glu Asp Phe Val
    530                 535                 540

Gly Gln Glu Leu Tyr Arg Phe Leu Val Val Asp Phe Ile Phe Met Leu
545                 550                 555                 560

Leu Asp Ser Leu Phe Gly Glu Leu Val Trp Arg Leu Ile Ser Glu Lys
                565                 570                 575

Lys Leu Lys Arg Arg Gln Lys Pro Glu Phe Asp Ile Ala Arg Asn Val
            580                 585                 590

Leu Asp Leu Ile Tyr Gly Gln Thr Leu Thr Trp Leu Gly Val Leu Phe
        595                 600                 605

Ser Pro Leu Leu Pro Ala Val Gln Ile Leu Arg Leu Leu Met Phe
    610                 615                 620

Tyr Val Lys Lys Ala Ser Leu Met Ala Asn Cys Gln Ala Pro Arg Arg
625                 630                 635                 640

Pro Trp Leu Ala Ser His Met Ser Thr Val Phe Leu Thr Leu Leu Cys
                645                 650                 655

Phe Pro Ser Phe Leu Gly Ala Ala Val Phe Leu Cys Tyr Ala Val Trp
            660                 665                 670

Gln Val Lys Pro Ser Ser Thr Cys Gly Pro Phe Arg Thr Leu Asn Thr
        675                 680                 685

Met Tyr Glu Ala Gly Thr Val Trp Val His Arg Leu Glu Arg Ala Gly
690                 695                 700

Ser Gly Ala Ser Trp Leu Pro Trp Leu His Val Leu Val Glu Asn
705                 710                 715                 720

Thr Phe Phe Leu Phe Leu Val Ser Ala Leu Leu Leu Ala Val Ile Tyr
                725                 730                 735

Leu Asn Ile Gln Val Val Lys Gly Gln Arg Lys Val Ile Arg Leu Leu
            740                 745                 750

Lys Glu Gln Ile Arg Asn Glu Gly Glu Asp Lys Val Phe Leu Ile Asn
        755                 760                 765

Arg Leu His Ser Val Tyr Glu Glu Gly Glu Arg Ser Arg Pro Gly Arg
    770                 775                 780

Thr Gln Glu Glu Pro Cys Asn Pro Ser His His Asp Pro Thr Arg Arg
785                 790                 795                 800

Asp Leu Asp Leu Arg Ser Pro Gln Asp Pro Ala Val Glu
                805                 810

<210> SEQ ID NO 24
<211> LENGTH: 827
<212> TYPE: PRT
<213> ORGANISM: Peromyscus maniculatus bairdii

<400> SEQUENCE: 24

Met Ala Gln Pro Leu Thr Leu Val Leu Asp Val Pro Glu Thr Thr Gly
1               5                   10                  15

Asp Glu Asp Ser Arg Glu Pro Ser Pro Tyr Glu Glu Ser Glu Val His
            20                  25                  30

Asp Ser Phe His Gln Leu Ile Gln Glu Gln Ser Leu Arg Val Ala Ala
        35                  40                  45

Glu Glu Gly Leu Glu Leu Leu Pro Leu Ala Pro Gly Arg Gly Tyr Gln
    50                  55                  60

-continued

| | | | | | | | | | | | | | | | |
|---|---|---|---|---|---|---|---|---|---|---|---|---|---|---|---|

Thr Leu Pro Arg Pro Glu Gly Ala Pro Ala His Ser Met Ala Thr Leu
65                  70                  75                  80

Arg Ile Leu Ala Ser Met Pro Ser Arg Thr Ile Gly Arg Ser Arg Gly
            85                  90                  95

Ala Ile Ile Ser Gln Tyr Tyr Asn Arg Thr Val Arg Leu Arg His Arg
            100                 105                 110

Ser Ser Arg Pro Leu Leu Gly Asn Val Ala Pro Ser Ala Arg Pro Ser
        115                 120                 125

Leu Arg Leu Tyr Asp Leu Glu Leu Asp His Thr Leu Leu Glu Asp Asp
        130                 135                 140

Glu Lys Arg Ser Leu Leu Val Lys Glu Leu Gln Gly Leu Ser Val Ala
145                 150                 155                 160

Gln Arg Asp His Met Val Arg Asn Met Pro Leu Asn Leu Gly Glu Lys
                165                 170                 175

Arg Trp Leu Arg Glu Lys Ser Trp Ser Pro Lys Gly Lys Arg Arg Gly
            180                 185                 190

Gln Gln Gly Arg Gly Gly Val Phe Ser Cys Cys Thr Arg Leu Arg Tyr
        195                 200                 205

Ser Cys Ile Leu Ala Leu His Ser Leu Gly Leu Val Leu Leu Ser Gly
        210                 215                 220

Leu Tyr Ala Ala Arg Pro Trp Arg Tyr Ala Leu Lys Gln Ile Gly Gly
225                 230                 235                 240

Gln Phe Gly Ser Ser Val Leu Ser Tyr Phe Leu Phe Lys Thr Leu
                245                 250                 255

Leu Ala Phe Asn Thr Leu Met Leu Leu Pro Leu Leu Ala Phe Leu Val
                260                 265                 270

Gly Val Gln Ala Val Phe Pro Pro Asp Pro Ala Gly Pro Val Pro Thr
        275                 280                 285

Phe Ser Gly Leu Glu Leu Leu Thr Gly Gly Gly Trp Phe Thr His Thr
    290                 295                 300

Val Met Tyr Tyr Gly Tyr Tyr Ser Asn Thr Thr Leu Ser Gln Ser Cys
305                 310                 315                 320

Ala Ser Pro Trp Glu Ser Gly Gln Cys Ser Pro Arg Leu Gly Ser Leu
                325                 330                 335

Pro Tyr Asn Met Pro Leu Ala Tyr Leu Phe Thr Val Gly Ala Val Phe
                340                 345                 350

Phe Met Thr Cys Ile Thr Leu Val Tyr Ser Met Ser His Ser Phe Gly
                355                 360                 365

Glu Ser Tyr Arg Val Gly Ser Thr Lys Gly Ile His Ala Leu Met Val
        370                 375                 380

Phe Cys Ser Trp Asp Tyr Lys Val Thr Gln Lys Arg Ala Ser Arg Val
385                 390                 395                 400

Gln Gln Asp Ser Ile Cys Thr Gln Leu Lys Glu Leu Leu Ala Glu Trp
                405                 410                 415

Gln Leu Arg Lys Arg Pro Arg Ser Ala Cys Gly Gln Leu Trp Gln Val
                420                 425                 430

Val Val Leu Gly Leu Gly Trp Leu Leu Cys Leu Gly Thr Thr Met Gly
        435                 440                 445

Cys Ala Val Ala Val Leu Thr Phe Ser Glu Val Met Val Gln Arg Ser
        450                 455                 460

Ala Ala Gly Gly Gln Gly Leu Glu Leu Leu Ala Leu Pro Leu Val Val
465                 470                 475                 480

```
Ser Val Leu Asn Leu Gly Ala Ser Tyr Leu Phe Arg Gly Leu Ala Thr
            485                 490                 495

Leu Glu Arg His Asp Ser Pro Val Leu Glu Val Tyr Met Ala Ile Cys
        500                 505                 510

Arg Ser Leu Ile Leu Lys Met Ala Val Leu Gly Val Leu Cys Tyr His
        515                 520                 525

Trp Leu Gly His Arg Val Ala Thr Leu Gln Gly Gln Cys Trp Glu Asp
    530                 535                 540

Phe Val Gly Gln Glu Leu Tyr Arg Phe Leu Val Asp Phe Ile Phe
545                 550                 555                 560

Thr Leu Leu Asp Ser Leu Phe Gly Glu Leu Val Trp Arg Leu Ile Ser
                565                 570                 575

Glu Lys Lys Leu Lys Arg Arg Gln Lys Pro Glu Phe Asp Ile Ala Arg
            580                 585                 590

Asn Val Leu Asp Leu Ile Tyr Gly Gln Thr Leu Thr Trp Leu Gly Val
        595                 600                 605

Leu Phe Ser Pro Leu Leu Pro Ala Val Gln Ile Leu Arg Leu Leu Phe
    610                 615                 620

Phe Phe Tyr Val Lys Lys Ala Ser Leu Met Ala Asn Cys Gln Ala Pro
625                 630                 635                 640

Arg Arg Pro Trp Leu Ala Ser His Met Ser Thr Val Phe Leu Thr Leu
                645                 650                 655

Leu Cys Phe Pro Ser Phe Leu Gly Ala Ala Val Phe Leu Cys Tyr Ala
            660                 665                 670

Val Trp Gln Val Lys Pro Ser Ser Ile Cys Gly Pro Phe Arg Thr Leu
        675                 680                 685

Asn Thr Met Tyr Glu Ala Gly Thr Val Trp Val Arg Arg Leu Glu His
    690                 695                 700

Ala Gly Ser Gly Ala Ser Trp Leu Pro Trp Leu Tyr His Phe Leu Val
705                 710                 715                 720

Glu Asn Thr Phe Phe Leu Phe Leu Met Ser Ala Leu Leu Leu Ser Val
                725                 730                 735

Ile Tyr Leu Asn Ile Gln Ala Val Lys Gly Gln Arg Lys Val Ile Arg
            740                 745                 750

Leu Leu Lys Glu Gln Ile Arg Asn Glu Gly Glu Asp Lys Ile Phe Leu
        755                 760                 765

Ile Asn Lys Leu His Ser Val Tyr Glu Asp Gly Glu Arg Ser Arg Thr
    770                 775                 780

Gln Glu Ala Thr Ala Ala Thr Ala Leu Leu Val Asp Gly Gly Asp Arg
785                 790                 795                 800

Lys Glu Pro Cys Thr Pro Ser His Arg Asp Pro Ser Gly Arg Asp Leu
                805                 810                 815

Asn Leu Arg Ser Pro Arg Asp Thr Thr Val Glu
            820                 825

<210> SEQ ID NO 25
<211> LENGTH: 807
<212> TYPE: PRT
<213> ORGANISM: Microtus ochrogaster

<400> SEQUENCE: 25

Met Ala Gln Pro Leu Thr Leu Val Leu Asn Val Pro Glu Thr Thr Gly
1               5                   10                  15

Asp Glu Asp Leu Glu Pro Ser Pro Tyr Glu Glu Ser Glu Val His Asp
            20                  25                  30
```

```
Ser Phe His Arg Leu Ile Gln Glu Gln Ser Leu Leu Val Ala Glu Glu
        35                  40                  45

Gly Leu Glu Leu Leu Pro Leu Ala Pro Asp Arg Gly Tyr Gln Thr Leu
 50                  55                  60

Pro Arg Pro Glu Gly Ala Pro Thr His Ser Thr Ala Thr Leu Arg Ile
 65                  70                  75                  80

Leu Ala Ser Met Pro Ser Arg Thr Ile Gly Arg Ser Arg Gly Ala Ile
                 85                  90                  95

Ile Ser Glu Tyr Tyr Asn Arg Thr Val Lys Leu Arg Arg Arg Ser Ser
                100                 105                 110

Arg Pro Leu Leu Gly Asn Met Val Arg Cys Ala Arg Pro Ser Leu Arg
                115                 120                 125

Leu Tyr Asp Leu Glu Leu Asp His Thr Ile Leu Glu Glu Asp Glu Lys
        130                 135                 140

Arg Ser Leu Leu Val Lys Glu Leu Gln Gly Leu Ser Val Ala Gln Arg
145                 150                 155                 160

Asp His Met Val Arg Asn Met Pro Leu Ser Leu Gly Glu Lys Arg Trp
                165                 170                 175

Leu Arg Glu Asn Ser Trp Ser Pro Lys Gly Lys Arg Arg Gly Gln Gln
                180                 185                 190

Asp Arg Gly Gly Ala Phe Ser Cys Ser Ser Arg Leu Arg Tyr Ser Cys
                195                 200                 205

Ile Leu Ala Leu His Ser Leu Gly Leu Val Leu Val Ser Gly Leu Tyr
        210                 215                 220

Ala Ala Arg Pro Trp Arg Tyr Ala Leu Lys Gln Ile Gly Gly Gln Phe
225                 230                 235                 240

Gly Ser Ser Val Leu Ser Tyr Phe Ile Phe Leu Lys Thr Leu Leu Ala
                245                 250                 255

Phe Asn Val Leu Met Leu Leu Pro Leu Leu Gly Phe Leu Val Gly Val
                260                 265                 270

Gln Ala Ala Phe Pro Pro Asp Pro Asp Pro Val Pro Thr Cys Ser
        275                 280                 285

Gly Leu Glu Leu Leu Thr Gly Arg Gly Cys Phe Thr His Thr Val Met
        290                 295                 300

Tyr Tyr Gly Tyr Tyr Ser Asn Ser Thr Leu Ser Gln Ser Cys Asp Ser
305                 310                 315                 320

Ser Arg Asp Ser Gly Arg Cys Ser Pro Gly Ser Gly Ser Leu Pro Tyr
                325                 330                 335

Asn Met Pro Leu Ala Tyr Leu Phe Thr Val Gly Ala Ala Phe Phe Ile
                340                 345                 350

Thr Cys Ile Thr Leu Val Tyr Ser Met Ser His Ser Phe Gly Glu Ser
        355                 360                 365

Tyr Arg Val Gly Ser Thr Lys Gly Ile His Ala Leu Thr Val Phe Cys
        370                 375                 380

Ser Trp Asp Tyr Lys Val Thr Gln Lys Arg Ala Ser Arg Val Gln Gln
385                 390                 395                 400

Asp Ser Ile Cys Thr Gln Leu Lys Glu Leu Leu Ala Val Trp Gln Leu
                405                 410                 415

Gln Lys His Pro Arg Ser Ala Cys Gly Gln Leu Trp Gln Ala Ala Met
                420                 425                 430

Leu Ala Leu Gly Gly Leu Leu Cys Leu Gly Thr Thr Val Gly Cys Ala
                435                 440                 445
```

-continued

```
Ala Ala Val Phe Thr Phe Ser Glu Val Met Met Gln Arg Gly Gln Gly
        450             455                 460

Val Glu Leu Leu Ala Leu Pro Leu Val Val Ser Ala Leu Asn Leu Gly
465             470                 475                 480

Ala Ser Tyr Leu Phe Cys Gly Leu Ala Thr Leu Glu Arg His Asp Ser
                485                 490                 495

Pro Val Leu Glu Val Tyr Met Ala Ile Cys Arg Ser Leu Ile Leu Lys
            500                 505                 510

Thr Ala Val Leu Gly Val Leu Cys Tyr His Trp Leu Gly Arg Arg Val
        515                 520                 525

Ala Thr Leu Gln Asp Gly Cys Trp Glu Asn Phe Val Gly Gln Glu Leu
530             535                 540

Tyr Arg Phe Leu Val Val Asp Phe Ile Phe Thr Leu Leu Asp Ser Leu
545                 550                 555                 560

Phe Gly Glu Leu Val Trp Arg Leu Ile Ser Glu Lys Lys Leu Lys Arg
                565                 570                 575

Arg Gln Lys Pro Glu Phe Asp Ile Ala Arg Asn Val Leu Asp Leu Ile
            580                 585                 590

Tyr Gly Gln Thr Leu Thr Trp Leu Gly Val Leu Phe Ser Pro Leu Leu
        595                 600                 605

Pro Ala Val Gln Ile Leu Arg Leu Leu Phe Leu Phe Tyr Val Lys Lys
610             615                 620

Ala Ser Leu Met Ala Asn Cys Gln Ala Pro Arg Pro Trp Leu Ala
625                 630                 635                 640

Ser His Met Ser Thr Val Phe Leu Thr Leu Leu Cys Phe Pro Ser Phe
                645                 650                 655

Leu Gly Ala Ala Val Phe Leu Cys Tyr Ala Val Trp Gln Val Lys Pro
            660                 665                 670

Ser Ser Thr Cys Gly Pro Phe Arg Thr Leu Asn Thr Met Tyr Glu Ala
        675                 680                 685

Gly Thr Val Trp Val Arg Arg Leu Glu His Ala Gly Ser Arg Gly Ser
690             695                 700

Trp Leu Pro Trp Leu His His Leu Leu Val Glu Asn Thr Phe Phe Leu
705                 710                 715                 720

Phe Leu Val Ser Ala Leu Leu Ala Val Ile Tyr Leu Asn Ile Gln
                725                 730                 735

Val Val Lys Gly Gln Arg Lys Val Ile Cys Leu Leu Lys Glu Gln Ile
            740                 745                 750

Arg Asn Glu Gly Glu Asp Lys Ile Phe Leu Ile Asn Lys Leu His Ser
        755                 760                 765

Val Tyr Glu Gly Glu Gln Asn Arg Pro Glu Glu Ala Thr Thr Ser Ser
770             775                 780

Ala Gln Phe Val Asp Gly Gly Asp Ser His His Asp Pro Ala Gly Arg
785                 790                 795                 800

Asp Leu Asp Thr Ala Leu Glu
                805
```

<210> SEQ ID NO 26
<211> LENGTH: 810
<212> TYPE: PRT
<213> ORGANISM: Mus musculus

<400> SEQUENCE: 26

```
Met Ala Gln Ser Leu Ala Leu Ala Leu Asp Val Pro Glu Thr Thr Gly
1               5                   10                  15
```

```
Asp Glu Gly Leu Glu Pro Ser Pro Tyr Glu Ser Glu Val His Asp
         20                  25                  30

Ser Phe His Gln Leu Ile Gln Glu Gln Ser Leu Arg Val Ala Glu Glu
         35                  40                  45

Gly Leu Glu Leu Pro Leu Gly Leu Gly Arg Gly Asp Gln Thr Leu
 50                  55                  60

Pro Gly Leu Glu Gly Ala Pro Ala Leu Ser Ser Ala Thr Leu Arg Ile
 65                  70                  75                  80

Leu Ala Ser Met Pro Ser Arg Thr Ile Gly Arg Ser Arg Gly Ala Ile
                 85                  90                  95

Ile Ser Gln Tyr Tyr Asn Arg Thr Val Arg Leu Arg Arg Ser Ser
        100                 105                 110

Arg Pro Leu Leu Gly Asn Val Val Pro Ser Ala Arg Pro Ser Leu Arg
            115                 120                 125

Leu Tyr Asp Leu Glu Leu Asp Ser Thr Ile Leu Glu Glu Asp Glu Lys
        130                 135                 140

Arg Ser Leu Leu Val Lys Glu Leu Gln Gly Leu Ser Ala Ala Gln Arg
145                 150                 155                 160

Asp His Met Val Arg Asn Met Pro Leu Ser Leu Gly Glu Lys Arg Cys
                165                 170                 175

Leu Arg Glu Lys Ser Trp Ser Pro Lys Gly Lys Arg His Leu Gln
            180                 185                 190

Gly Arg Ser Gly Ala Phe Ser Cys Cys Ser Arg Leu Arg Tyr Thr Cys
        195                 200                 205

Met Leu Ala Leu His Ser Leu Gly Leu Ala Leu Leu Ser Gly Leu Tyr
        210                 215                 220

Ala Ala Arg Pro Trp Arg Tyr Ala Leu Lys Gln Ile Gly Gly Gln Phe
225                 230                 235                 240

Gly Ser Ser Val Leu Ser Tyr Phe Leu Phe Leu Lys Thr Leu Leu Ala
                245                 250                 255

Phe Asn Ala Leu Met Leu Leu Pro Leu Leu Ala Phe Leu Val Gly Val
            260                 265                 270

Gln Ala Ala Phe Pro Pro Asp Pro Ala Gly Pro Val Pro Thr Phe Ser
        275                 280                 285

Gly Leu Glu Leu Leu Thr Gly Gly Arg Phe Thr His Thr Val Met
        290                 295                 300

Tyr Tyr Gly Tyr Tyr Ser Asn Ser Thr Leu Ser Pro Ser Cys Asp Ala
305                 310                 315                 320

Pro Arg Glu Gly Gly Gln Cys Ser Pro Arg Leu Gly Ser Leu Pro Tyr
                325                 330                 335

Asn Met Pro Leu Ala Tyr Leu Phe Thr Met Gly Ala Thr Phe Phe Leu
            340                 345                 350

Thr Cys Ile Ile Leu Val Tyr Ser Met Ser His Ser Phe Gly Glu Ser
        355                 360                 365

Tyr Arg Val Gly Ser Thr Lys Gly Ile His Ala Leu Thr Val Phe Cys
        370                 375                 380

Ser Trp Asp Tyr Lys Val Thr Gln Lys Arg Ala Ser Arg Val Gln Gln
385                 390                 395                 400

Asp Ser Ile Cys Thr Gln Leu Lys Glu Leu Leu Ala Glu Trp His Leu
                405                 410                 415

Arg Lys Arg Pro Arg Ser Val Cys Gly Gln Leu Arg Gln Val Val Val
            420                 425                 430
```

```
Leu Gly Leu Gly Trp Leu Leu Cys Leu Gly Ser Thr Met Gly Cys Thr
            435                 440                 445

Val Ala Val Leu Thr Phe Ser Glu Val Met Ile Gln Arg Pro Ala Ser
450                 455                 460

Gly Gly Gln Gly Val Glu Ala Leu Ala Leu Pro Leu Val Val Ser Val
465                 470                 475                 480

Leu Asn Leu Gly Ala Ser Tyr Leu Phe Arg Gly Leu Ala Thr Leu Glu
                485                 490                 495

Arg His Asp Ser Pro Val Leu Glu Val Tyr Met Ala Ile Cys Arg Asn
            500                 505                 510

Leu Ile Leu Lys Met Ala Val Leu Gly Val Leu Cys Tyr His Trp Leu
        515                 520                 525

Gly Arg Arg Val Ala Thr Leu Gln Gly Gln Cys Trp Glu Asp Phe Val
530                 535                 540

Gly Gln Glu Leu Tyr Arg Phe Met Val Val Asp Phe Ile Phe Met Leu
545                 550                 555                 560

Leu Asp Ser Leu Phe Gly Glu Leu Val Trp Arg Leu Ile Ser Glu Lys
                565                 570                 575

Lys Leu Lys Arg Gly Gln Lys Pro Glu Phe Asp Ile Ala Arg Asn Val
            580                 585                 590

Leu Asp Leu Ile Tyr Gly Gln Thr Leu Thr Trp Leu Gly Val Leu Phe
        595                 600                 605

Ser Pro Leu Leu Pro Ala Val Gln Ile Leu Arg Leu Leu Phe Leu Phe
610                 615                 620

His Ile Lys Lys Ala Ser Leu Met Ala Asn Cys Gln Ala Pro Arg Arg
625                 630                 635                 640

Pro Trp Leu Ala Ser His Met Ser Thr Val Phe Leu Thr Leu Leu Cys
                645                 650                 655

Phe Pro Ser Phe Leu Gly Ala Ala Val Phe Leu Cys Tyr Ala Val Trp
            660                 665                 670

Gln Val Arg Pro Ser Ser Thr Cys Gly Pro Phe Arg Thr Leu Asn Thr
        675                 680                 685

Met Tyr Glu Ala Gly Thr Val Trp Val Arg Arg Leu Glu His Ala Gly
690                 695                 700

Ser Gly Ala Ser Trp Leu Pro Trp Leu His His Phe Leu Val Glu Asn
705                 710                 715                 720

Thr Phe Phe Leu Phe Leu Ala Ser Ala Leu Leu Ala Val Ile Tyr
                725                 730                 735

Phe Asn Ile Gln Val Val Lys Gly Gln Arg Lys Val Ile Cys Leu Leu
            740                 745                 750

Lys Glu Gln Ile Arg Asn Glu Gly Asp Lys Ile Phe Leu Ile Asn
        755                 760                 765

Lys Leu His Ser Val Tyr Glu Glu Gly Arg Ser Arg Pro Gly Arg
770                 775                 780

Thr Gln Asp Thr Thr Glu Pro Pro Ala Trp His Glu Asp Gly Gly Asp
785                 790                 795                 800

Gln Lys Glu Pro Cys Asn Pro Arg Ser Pro
                805                 810

<210> SEQ ID NO 27
<211> LENGTH: 799
<212> TYPE: PRT
<213> ORGANISM: Rattus norvegicus

<400> SEQUENCE: 27
```

```
Met Ala Lys Pro Leu Ala Leu Ala Phe Asp Val Pro Glu Thr Thr Gly
  1               5                  10                 15

Gly Asp Glu Asp Leu Glu Pro Ser Pro Tyr Glu Glu Ser Glu Val His
             20                  25                  30

Asp Ser Phe His Gln Leu Ile Gln Glu Gln Ser Leu Arg Val Ala Glu
             35                  40                  45

Glu Gly Leu Glu Leu Leu Ser Leu Gly Pro Gly Arg Gly Asp Gln Thr
 50                  55                  60

Leu Pro Arg Pro Glu Gly Ala Pro Val Leu Ser Thr Ala Thr Leu Arg
 65                  70                  75                  80

Ile Leu Ala Ser Met Pro Ser Arg Thr Ile Gly Arg Ser Arg Gly Ala
                 85                  90                  95

Ile Ile Ser Gln Tyr Tyr Asn Arg Thr Val Arg Leu Arg Arg Ser
                100                 105                 110

Ser Arg Pro Leu Leu Gly Asn Val Val Arg Ser Ala Arg Pro Ser Leu
            115                 120                 125

Arg Leu Tyr Asp Leu Glu Leu Asp Pro Thr Ile Leu Glu Glu Asp Glu
            130                 135                 140

Lys Arg Ser Leu Leu Val Lys Glu Leu Gln Gly Leu Ser Val Ala Gln
145                 150                 155                 160

Arg Asp His Met Val Arg Asn Met Pro Leu Ser Leu Gly Glu Lys Arg
                165                 170                 175

Trp Leu Arg Glu Lys Ser Trp Ser Pro Lys Val Lys Arg Arg Asp Gln
                180                 185                 190

Gln Gly Arg Arg Gly Ala Phe Ser Cys Cys Ser Arg Leu Arg Tyr
                195                 200                 205

Thr Cys Met Leu Ala Leu His Ser Leu Gly Leu Ala Leu Leu Ser Gly
    210                 215                 220

Leu Tyr Ala Ala Arg Pro Trp Arg Tyr Ala Leu Lys Gln Ile Gly Gly
225                 230                 235                 240

Gln Phe Gly Ser Ser Val Leu Ser Tyr Phe Leu Phe Leu Lys Thr Leu
                245                 250                 255

Leu Ala Phe Asn Thr Leu Met Leu Leu Pro Leu Leu Ala Phe Leu Val
                260                 265                 270

Gly Val Gln Ala Ala Phe Pro Pro Asp Pro Ala Gly Pro Val Pro Thr
                275                 280                 285

Phe Ser Gly Leu Glu Leu Leu Thr Gly Gly Gly Trp Phe Thr His Thr
    290                 295                 300

Val Met Tyr Tyr Gly Tyr Tyr Ser Asn Thr Thr Leu Arg Gln Ser Cys
305                 310                 315                 320

Ala Ser Ala Arg Glu Gly Gly Leu Cys Ser Pro Arg Leu Gly Ser Leu
                325                 330                 335

Pro Tyr Asn Met Pro Leu Ala Tyr Leu Phe Thr Val Gly Ala Ala Phe
                340                 345                 350

Phe Ile Thr Cys Ile Val Leu Val Tyr Ser Met Ser His Ser Phe Gly
                355                 360                 365

Glu Ser Tyr Arg Val Gly Ser Thr Lys Gly Ile His Ala Leu Thr Val
    370                 375                 380

Phe Cys Ser Trp Asp Tyr Lys Val Thr Gln Lys Arg Ala Ser Arg Val
385                 390                 395                 400

Gln Gln Asp Ser Ile Arg Thr Gln Leu Lys Glu Leu Leu Ala Glu Trp
                405                 410                 415
```

Gln Leu Arg Lys Arg Pro Arg Ser Val Cys Gln Leu Arg Gln Val
            420                 425                 430

Val Val Leu Gly Leu Gly Trp Leu Cys Leu Gly Ser Thr Val Gly
            435                 440                 445

Cys Thr Val Ala Val Leu Thr Phe Ser Glu Thr Met Ile Gln Arg Pro
450                 455                 460

Ala Ser Gly Gly Gln Gly Leu Glu Met Leu Ala Leu Pro Leu Val Val
465                 470                 475                 480

Ser Val Leu Asn Leu Val Ala Ser Tyr Leu Phe Arg Gly Leu Ala Ala
            485                 490                 495

Leu Glu Arg His Asp Ser Pro Val Leu Glu Val Tyr Met Ala Ile Cys
            500                 505                 510

Arg Asn Leu Ile Leu Lys Met Ala Val Leu Gly Val Leu Cys Tyr His
            515                 520                 525

Trp Leu Gly Arg Arg Val Ala Ala Leu Gln Asp Gln Cys Trp Glu Asp
            530                 535                 540

Phe Val Gly Gln Glu Leu Tyr Arg Phe Met Val Val Asp Phe Ile Phe
545                 550                 555                 560

Val Leu Leu Asp Ser Leu Phe Gly Glu Leu Val Trp Arg Leu Ile Ser
            565                 570                 575

Glu Lys Lys Leu Lys Thr Gly Gln Lys Pro Glu Phe Asp Ile Ala Arg
            580                 585                 590

Asn Val Leu Asp Leu Ile Tyr Gly Gln Thr Leu Thr Trp Leu Gly Val
            595                 600                 605

Leu Phe Ser Pro Leu Leu Pro Ala Val Gln Ile Leu Arg Leu Leu
610                 615                 620

Leu Phe Tyr Ile Lys Lys Thr Ser Leu Ile Ala Asn Cys Gln Ala Pro
625                 630                 635                 640

Gly Arg Pro Trp Leu Ala Ser His Met Thr Thr Val Phe Leu Thr Leu
            645                 650                 655

Leu Cys Phe Pro Ser Phe Leu Gly Ala Ala Val Phe Leu Cys Tyr Ala
            660                 665                 670

Val Trp Gln Val Arg Pro Ser Ser Thr Cys Gly Pro Phe Arg Thr Leu
            675                 680                 685

Asn Thr Met Tyr Glu Ala Gly Thr Val Trp Val Arg Arg Leu Glu His
            690                 695                 700

Ala Gly Ser Gly Ala Ser Trp Leu Pro Trp Leu His His Phe Leu Val
705                 710                 715                 720

Glu Asn Thr Phe Phe Leu Phe Leu Val Ser Ala Leu Leu Leu Ala Val
            725                 730                 735

Ile Tyr Leu Asn Ile Gln Val Val Lys Gly Gln Arg Lys Val Ile Cys
            740                 745                 750

Leu Leu Lys Glu Gln Ile Arg Asn Glu Gly Glu Asp Lys Ile Phe Leu
            755                 760                 765

Ile Asn Lys Leu His Ser Val Tyr Glu Glu Gly Met Ser Arg Pro
            770                 775                 780

Gly Arg Thr Gln Glu Ala Thr Ile Pro Pro Ala Ala Pro Glu Asp
785                 790                 795

<210> SEQ ID NO 28
<211> LENGTH: 807
<212> TYPE: PRT
<213> ORGANISM: Jaculus jaculus

<400> SEQUENCE: 28

```
Met Ala Gln Ser Leu Thr Leu Val Leu Asp Val Pro Glu Thr Thr Gly
1               5                   10                  15

Asp Gln Asp Leu Glu Pro Ser Pro Tyr Glu Arg Glu Val His Asp
            20                  25                  30

Ser Phe His Arg Leu Ile Gln Glu Gln Ser Leu Leu Ala Ala Gln Glu
            35                  40                  45

Gly Leu Glu Leu Leu Pro Val Gly Arg Thr Ala Arg Gly His Pro Thr
50                  55                  60

Leu Leu Glu Pro Gly Gly Val Pro Ala Tyr Ser Ser Ala Thr Leu Arg
65                  70                  75                  80

Ile Leu Ala Ser Met Pro Ser Arg Thr Ile Gly Arg Ser Arg Gly Ala
                85                  90                  95

Ile Ile Ser Gln Tyr Tyr Asn Arg Thr Val Arg Leu Arg Arg Ser
                100                 105                 110

Ser Arg Pro Leu Leu Gly Asn Val Val His Ser Ala Arg Pro Ser Leu
            115                 120                 125

Arg Leu Tyr Asp Leu Glu Leu Asp Ser Thr Ala Leu Glu Glu Asp Glu
            130                 135                 140

Lys Arg Ser Leu Leu Val Lys Glu Leu Gln Gly Leu Ser Ala Ala Gln
145                 150                 155                 160

Arg Gly His Met Leu Arg Gly Met Pro Leu Ser Leu Ala Glu Lys Arg
                165                 170                 175

Trp Leu Arg Glu Lys Ser Trp Gly Pro Ser Gly Lys His Lys Gly His
            180                 185                 190

Ser Gly Arg Gly Gly Thr Phe Cys Cys Ser Arg Leu Arg Tyr Ser Cys
            195                 200                 205

Ile Leu Ala Leu His Ser Leu Gly Leu Ala Leu Leu Ser Gly Leu His
            210                 215                 220

Ala Ala Arg Pro Trp Arg Tyr Thr Leu Lys Gln Ile Ser Gly Gln Phe
225                 230                 235                 240

Gly Ser Ser Val Leu Ser Tyr Phe Leu Phe Leu Lys Thr Leu Leu Ala
                245                 250                 255

Phe Asn Ala Leu Leu Leu Leu Pro Leu Leu Ala Phe Leu Ala Gly Val
            260                 265                 270

Gln Ala Ala Phe Pro Pro Ala Pro Arg Gly Pro Ala Pro Ala Phe Ser
            275                 280                 285

Gly Leu Glu Leu Leu Thr Gly Gly Tyr Phe Ala His Thr Val Met
290                 295                 300

Tyr Tyr Gly Tyr Tyr Ser Asn Ala Thr Leu Ser Gln Pro Cys Ala Ala
305                 310                 315                 320

Pro Gln Asp Ser Gly His Cys Ser Ser Arg Ala Gly Ser Leu Pro Tyr
            325                 330                 335

Ser Met Pro Leu Ala Tyr Leu Leu Thr Val Gly Ala Val Phe Phe Thr
            340                 345                 350

Thr Cys Ile Thr Leu Val Tyr Ser Met Ser His Ser Phe Gly Glu Ser
            355                 360                 365

Tyr Arg Val Gly Ser Thr Lys Gly Val His Ala Leu Thr Val Phe Cys
            370                 375                 380

Ser Trp Asp Tyr Lys Val Thr Gln Lys Arg Ala Ser Arg Val Gln Gln
385                 390                 395                 400

Asp Asn Ile Cys Thr Gln Leu Lys Glu Leu Leu Ser Glu Trp Gln Leu
                405                 410                 415
```

-continued

Arg Lys Cys Pro Gln Ser Thr Cys Gly Arg Leu Arg Gln Val Val
                420                 425                 430

Leu Gly Leu Val Trp Leu Leu Cys Leu Gly Thr Thr Met Gly Cys Ala
435                 440                 445

Val Ala Val Leu Thr Phe Ser Glu Val Met Val Gln Pro Ser Pro Ala
        450                 455                 460

Gly Gln Glu Val Gly Leu Leu Ala Leu Pro Leu Val Val Ser Val Leu
465                 470                 475                 480

Asn Leu Gly Ala Ser Tyr Leu Phe Arg Gly Leu Ala Ala Leu Glu Arg
                485                 490                 495

His Glu Ser Pro Val Leu Glu Val Tyr Val Ala Ile Ser Arg Asn Leu
            500                 505                 510

Ile Leu Lys Met Val Ile Leu Gly Val Leu Cys Tyr His Trp Leu Gly
        515                 520                 525

Arg His Val Ala Ala Leu Pro Ser Arg Cys Trp Glu Asp Phe Val Gly
    530                 535                 540

Gln Glu Leu Tyr Arg Phe Leu Val Met Asp Phe Leu Phe Ala Leu Leu
545                 550                 555                 560

Asp Thr Leu Phe Gly Glu Leu Val Trp Arg Leu Ile Ser Glu Lys Lys
                565                 570                 575

Leu Lys Arg Gln Arg Lys Pro Glu Phe Asp Ile Ala Arg Asn Val Leu
            580                 585                 590

Asp Leu Ile Tyr Gly Gln Thr Leu Thr Trp Leu Gly Val Leu Phe Ser
        595                 600                 605

Pro Leu Leu Pro Ala Val Gln Ile Leu Arg Leu Leu Leu Phe Gln
    610                 615                 620

Val Lys Lys Ala Ser Leu Met Ala Asn Cys Gln Ala Pro Arg Arg Pro
625                 630                 635                 640

Trp Leu Ala Leu His Met Ser Thr Val Phe Leu Thr Leu Cys Phe
                645                 650                 655

Pro Ala Phe Leu Gly Ala Ala Val Phe Leu Cys Tyr Ala Ile Trp Gln
            660                 665                 670

Val Lys Pro Ser Ser Thr Cys Gly Pro Phe Arg Thr Leu Asp Thr Met
        675                 680                 685

Tyr Met Ala Gly Thr Val Trp Val Arg Arg Leu Glu Ser Ala Ser Ala
    690                 695                 700

Gly Ala Ser Trp Leu Pro Trp Leu Tyr Gly Tyr Leu Val Glu Asn Thr
705                 710                 715                 720

Phe Phe Leu Phe Leu Val Ser Ala Leu Leu Ala Val Ile Tyr Leu
                725                 730                 735

Asn Ile Gln Val Val Lys Gly Gln Arg Lys Val Ile Cys Leu Leu Lys
            740                 745                 750

Glu Gln Ile Arg Asn Glu Gly Glu Asp Lys Ile Phe Leu Ile Asn Lys
        755                 760                 765

Leu His Ser Val Tyr Glu Arg Lys Gln Arg Ser Ala Val Leu Ser
    770                 775                 780

Leu Gln Leu Ser Leu Pro Val Gln Gly Ser Gly Arg Asp Glu Leu Leu
785                 790                 795                 800

Leu Arg Asp Ser Asp Thr Leu
                805

<210> SEQ ID NO 29
<211> LENGTH: 836
<212> TYPE: PRT

<213> ORGANISM: Ictidomys tridecemlineatus

<400> SEQUENCE: 29

```
Met Ala Gln Pro Leu Ala Leu Val Leu Asn Val Pro Glu Ala Leu Gly
1               5                   10                  15
Asp Gln Asp Gln Glu Pro Ser Pro Tyr Glu Glu Ser Glu Val His Asp
            20                  25                  30
Ser Phe His Gln Leu Ile Gln Glu Gln Ser Gln Leu Ala Glu Glu Leu
        35                  40                  45
Glu Leu Gln Gln Arg Gln Leu Val Ala Gly Thr Leu Gly Val Pro Gly
    50                  55                  60
Ser Gly His Gln Ser Leu Leu Gly Pro Glu Gly Ala Pro Val His Ser
65                  70                  75                  80
Ala Ala Thr Leu Arg Ile Leu Ala Ser Met Pro Ser Arg Thr Ile Gly
                85                  90                  95
Arg Ser Arg Gly Ala Ile Ile Ser Gln Tyr Tyr Asn Arg Thr Val Lys
            100                 105                 110
Leu Arg Arg Arg Gly Ser Arg Pro Leu Leu Gly Asp Met Val His Ser
        115                 120                 125
Ala Arg Pro Ser Leu Arg Leu Tyr Asp Leu Glu Leu Asp Pro Thr Ala
    130                 135                 140
Leu Glu Glu Asp Glu Lys Gln Gly Leu Leu Val Lys Glu Leu Gln Gly
145                 150                 155                 160
Leu Ser Val Ala Gln Arg Asp His Met Leu Arg Gly Met Pro Leu Asn
                165                 170                 175
Leu Ala Glu Lys Arg Cys Leu Arg Glu Lys Ser Gln Val Gln Arg Gly
            180                 185                 190
Lys Arg Arg Ala Arg Gln Asp Arg Gly Gly Val Phe Ser Cys Cys Ser
        195                 200                 205
Arg Leu Arg Tyr Ala Cys Ile Leu Ala Leu His Ser Leu Gly Leu Ala
    210                 215                 220
Leu Leu Ser Gly Leu His Ala Val Arg Pro Trp Arg His Thr Leu Lys
225                 230                 235                 240
Gln Ile Gly Gly Gln Phe Gly Ser Ser Val Leu Ser Tyr Phe Leu Phe
                245                 250                 255
Leu Lys Thr Leu Leu Ala Phe Asn Ala Leu Leu Leu Leu Pro Leu
            260                 265                 270
Gly Leu Leu Val Gly Val Gln Ala Ala Leu Pro Pro Gly Pro Pro Asp
        275                 280                 285
Pro Ala Pro Ala Phe Thr Gly Leu Glu Leu Leu Thr Gly Gly Gly Cys
    290                 295                 300
Phe Thr His Thr Val Met Tyr Tyr Gly Tyr Tyr Ser Asn Ala Thr Leu
305                 310                 315                 320
Ser Gln Ser Cys Val Pro Pro Arg Asp Gly His Gln Cys Ser Pro Gly
                325                 330                 335
Ala Ser Ser Leu Pro Tyr Asn Met Pro Leu Ala Tyr Leu Phe Thr Met
            340                 345                 350
Gly Ala Ala Phe Phe Ile Thr Cys Ile Ser Leu Val Tyr Ser Met Ser
        355                 360                 365
His Ala Phe Gly Glu Ser Tyr Arg Val Gly Ser Thr Lys Gly Val His
    370                 375                 380
Ala Ile Thr Val Phe Cys Ser Trp Asp Tyr Lys Val Thr Glu Lys Arg
385                 390                 395                 400
```

Ala Ser Arg Leu Gln Gln Asp Asn Ile Arg Thr Gln Leu Lys Glu Leu
            405                 410                 415

Leu Ala Glu Trp Gln Leu His Arg Ser Pro Gln Ser Leu Arg Gly Arg
        420                 425                 430

Leu Arg Gln Ala Val Leu Leu Gly Leu Ala Trp Leu Leu Cys Leu Gly
        435                 440                 445

Thr Met Leu Gly Cys Ser Val Ala Val Phe Val Phe Ser Glu Val Met
        450                 455                 460

Ile Gln Ser Pro Val Ser Ala Gly Gln Glu Ala Arg Leu Leu Ala Leu
465                 470                 475                 480

Pro Leu Val Val Ser Leu Leu Asn Leu Gly Ala Ser Tyr Leu Phe Arg
                485                 490                 495

Gly Leu Ala Ala Leu Glu Arg His Glu Ser Pro Gly Leu Glu Val Tyr
            500                 505                 510

Val Ala Ile Cys Arg Asn Leu Ile Leu Lys Met Ala Ile Leu Gly Ile
            515                 520                 525

Leu Cys Tyr His Trp Leu Gly Arg Arg Val Ala Ala Leu Gln Gly Gln
        530                 535                 540

Cys Trp Glu Asp Phe Val Gly Gln Glu Leu Tyr Arg Phe Met Val Met
545                 550                 555                 560

Asp Phe Val Phe Ala Leu Leu Asp Thr Leu Phe Gly Glu Leu Val Trp
                565                 570                 575

Arg Leu Ile Ser Glu Arg Lys Leu Lys Arg Arg Lys Pro Glu Phe
            580                 585                 590

Asp Ile Ala Arg Asn Val Leu Asp Leu Ile Tyr Gly Gln Thr Leu Thr
            595                 600                 605

Trp Leu Gly Val Leu Phe Ser Pro Leu Leu Pro Ala Val Gln Val Leu
        610                 615                 620

Arg Leu Leu Leu Leu Phe Leu Val Lys Lys Ala Ser Leu Met Ala Asn
625                 630                 635                 640

Cys Gln Ala Pro Arg Arg Pro Trp Leu Ala Ser His Met Ser Thr Val
                645                 650                 655

Phe Leu Thr Leu Leu Cys Phe Pro Ser Phe Leu Gly Ala Ala Ile Phe
            660                 665                 670

Leu Cys Tyr Ala Val Trp Gln Val Lys Pro Ser Ser Thr Cys Gly Pro
        675                 680                 685

Phe Arg Thr Leu Asp Thr Met Tyr Glu Ala Gly Arg Val Trp Val Arg
        690                 695                 700

His Leu Glu Ser Ala Gly Pro Gly Ala Ser Trp Val Pro Trp Leu His
705                 710                 715                 720

Arg Tyr Leu Val Asp Ser Thr Phe Phe Leu Phe Leu Ala Ser Ala Leu
                725                 730                 735

Leu Leu Ala Ile Ile Tyr Phe Asn Ile Gln Val Val Lys Gly Gln Arg
            740                 745                 750

Lys Val Ile Ser Leu Leu Lys Glu Gln Ile Arg Asn Glu Gly Glu Asp
            755                 760                 765

Lys Ile Phe Leu Ile Asn Arg Leu His Ser Val Tyr Glu Arg Lys Glu
        770                 775                 780

Arg Ser Arg Ala His Arg Asn Glu Glu Ala Val Thr Pro Ser Ala Leu
785                 790                 795                 800

Leu Ala Asp Gly Gly Asp Ser Trp Trp Asp Ser Glu Gly Pro Gly Arg
                805                 810                 815

Leu Pro Gln His Pro Gln Leu Arg Ser Val Thr Thr Ser Trp Gln Ala

Glu Thr Arg Ile
        835

<210> SEQ ID NO 30
<211> LENGTH: 524
<212> TYPE: PRT
<213> ORGANISM: Marmota marmota marmot

<400> SEQUENCE: 30

Met Ala Gln Pro Leu Ala Leu Val Leu Asn Val Pro Glu Ala Leu Gly
1               5                   10                  15

Asp Gln Asp Gln Glu Pro Ser Pro Tyr Glu Gly Ser Glu Val His Asp
            20                  25                  30

Ser Phe His Gln Leu Ile Gln Gln Ser Gln Leu Ala Glu Glu Glu
        35                  40                  45

Leu Glu Leu Gln Gln Arg Gln Leu Val Ala Gly Thr Leu Gly Val Pro
    50                  55                  60

Gly Ser Gly His Gln Thr Leu Leu Gly Pro Glu Gly Ala Pro Val His
65                  70                  75                  80

Ser Ala Ala Thr Leu Arg Ile Leu Ala Ser Met Pro Ser Arg Thr Ile
                85                  90                  95

Gly Arg Ser Arg Gly Ala Ile Ile Ser Gln Tyr Tyr Asn Arg Thr Val
            100                 105                 110

Lys Leu Arg Arg Arg Gly Ser Arg Pro Leu Leu Gly Asp Leu Val Arg
        115                 120                 125

Ser Ala Arg Pro Ser Leu Arg Leu Tyr Asp Leu Glu Leu Gly Pro Arg
    130                 135                 140

Ala Leu Glu Glu Asp Gly Asp Ala Leu Gln Ser Pro Val Ser Ala Gly
145                 150                 155                 160

Gln Glu Ala Arg Leu Leu Ala Leu Pro Leu Val Val Ser Leu Leu Asn
                165                 170                 175

Leu Gly Ala Ser Tyr Leu Phe Arg Gly Leu Ala Ala Leu Glu Arg His
            180                 185                 190

Glu Ser Pro Gly Leu Glu Val Tyr Val Ser Ile Cys Arg Asn Leu Ile
        195                 200                 205

Leu Lys Met Ala Ile Leu Gly Ile Leu Cys Tyr His Trp Leu Gly Arg
    210                 215                 220

Arg Val Ala Ala Leu Gln Gly Gln Cys Trp Glu Asp Phe Val Gly Gln
225                 230                 235                 240

Glu Leu Tyr Arg Phe Met Val Met Asp Phe Leu Phe Ala Leu Leu Asp
                245                 250                 255

Thr Leu Phe Gly Glu Leu Val Trp Arg Leu Ile Ser Glu Arg Lys Leu
            260                 265                 270

Lys Arg Arg Arg Lys Pro Glu Phe Asp Ile Ala Arg Asn Val Leu Asp
        275                 280                 285

Leu Ile Tyr Gly Gln Thr Leu Thr Trp Leu Gly Val Leu Phe Ala Pro
    290                 295                 300

Leu Leu Pro Ala Val Gln Val Leu Arg Leu Leu Leu Phe Leu Val
305                 310                 315                 320

Lys Lys Ala Ser Leu Met Ala Asn Cys Gln Ala Pro Arg Arg Pro Trp
                325                 330                 335

Leu Ala Ser His Met Ser Thr Val Phe Leu Thr Leu Leu Cys Phe Pro
            340                 345                 350

```
Ser Phe Leu Gly Ala Ala Ile Phe Leu Cys Tyr Ala Val Trp Gln Val
        355                 360                 365

Lys Pro Ser Ser Thr Cys Gly Pro Phe Arg Thr Leu Asp Thr Met Tyr
370                 375                 380

Glu Ala Gly Arg Val Trp Val Arg His Leu Glu Ser Ala Gly Pro Arg
385                 390                 395                 400

Ala Ser Trp Val Pro Trp Leu His Arg Tyr Leu Val Glu Ser Thr Phe
                405                 410                 415

Phe Leu Phe Leu Ala Ser Ala Leu Leu Ala Ile Ile Tyr Phe Asn
                420                 425                 430

Ile Gln Val Val Lys Gly Gln Arg Lys Val Ile Ser Leu Leu Lys Glu
        435                 440                 445

Gln Ile Arg Asn Glu Gly Glu Asp Lys Ile Phe Leu Ile Asn Arg Leu
        450                 455                 460

His Ser Val Tyr Glu Arg Lys Glu Arg Ser Arg Ala His Arg Asn Glu
465                 470                 475                 480

Glu Ala Val Thr Pro Ser Ala Leu Leu Ala Asp Gly Gly Asp Ser Trp
                485                 490                 495

Trp Asp Ser Glu Gly Pro Cys Arg Leu Pro Gln His Pro Gln Leu Arg
                500                 505                 510

Ser Val Thr Thr Ser Trp Gln Ala Glu Thr Arg Ile
        515                 520

<210> SEQ ID NO 31
<211> LENGTH: 857
<212> TYPE: PRT
<213> ORGANISM: Galeopterus variegatus

<400> SEQUENCE: 31

Met Ala Gln Pro Leu Ala Phe Val Leu Asp Val Pro Glu Thr Pro Gly
1               5                   10                  15

Asp Gln Gly Cys Glu Ser Ser Pro Gln Asp Asp Glu Ser Glu Val His
                20                  25                  30

His Ser Phe Cys Gln Leu Ile Gln Glu Gln Ser Gln Trp Ala Ala Glu
            35                  40                  45

Glu Gly Leu Glu Leu Gln Gln Arg Glu Pro Ala Pro Gly Ala Trp Gly
        50                  55                  60

Ala Pro Asp Asp Ser His Gln Ala Leu Leu Gly Pro Glu Val Ala Pro
65                  70                  75                  80

Ala His Ser Thr Ala Thr Leu Arg Ile Leu Ala Ser Met Pro Ser Arg
                85                  90                  95

Thr Ile Gly Arg Ser Arg Gly Ala Val Ile Ser Gln Tyr Tyr Asn Arg
                100                 105                 110

Thr Val Arg Leu Arg Arg Arg Ser Ser Arg Pro Leu Leu Gly Glu Met
            115                 120                 125

Ser Arg Ser Ala Arg Pro Ser Leu Arg Leu Tyr Asp Leu Glu Leu Asp
        130                 135                 140

Pro Ala Ala Gly Glu Glu Glu Lys Leu Asn Leu Leu Val Lys Glu
145                 150                 155                 160

Leu Gln Gly Leu Ser Val Ala Gln Arg Asp His Met Leu Arg Gly Met
                165                 170                 175

Pro Val Asn Leu Ala Glu Lys Arg Cys Leu Arg Asp Lys Ser Gln Thr
                180                 185                 190

Leu Arg Gly Met Arg Arg Gly Gln Gln His Arg Gly Gly Val Cys Ser
            195                 200                 205
```

```
Cys Cys Ser Arg Leu Gly Tyr Ala Cys Val Leu Ala Ser His Ser Leu
    210                 215                 220

Gly Leu Val Leu Leu Ser Gly Leu His Ala Leu Ala Pro Trp Arg Phe
225                 230                 235                 240

Ala Leu Lys Gln Ile Gly Gly Gln Phe Gly Ser Ser Val Leu Ser Tyr
                245                 250                 255

Phe Leu Phe Leu Lys Thr Leu Leu Val Phe Asn Ala Leu Leu Leu Leu
            260                 265                 270

Leu Leu Leu Ala Phe Ile Val Gly Pro Gln Ala Ala Phe Pro Gln Gly
        275                 280                 285

Pro Val Pro Thr Ala Phe Met Gly Leu Glu Leu Thr Gly Gly Gly
290                 295                 300

Gly Phe Ala His Thr Val Met Tyr Tyr Gly Tyr Tyr Ser Asn Ala Thr
305                 310                 315                 320

Leu Asn Gln Pro Cys Ala Pro Gln Pro Asn Gly Ser Gln Cys Thr Pro
                325                 330                 335

Arg Ala Gly Ser Leu Pro Tyr Asn Met Pro Leu Ala Tyr Leu Phe Thr
                340                 345                 350

Val Gly Ala Ala Ala Phe Ile Thr Cys Ile Thr Leu Val Tyr Ser Met
                355                 360                 365

Ser His Ser Phe Gly Glu Ser Tyr Arg Val Gly Ser Thr Ser Gly Val
370                 375                 380

His Ala Ile Thr Ala Phe Cys Ser Trp Asp Tyr Lys Val Thr Gln Lys
385                 390                 395                 400

Trp Ala Ser Arg Leu Gln His Asp Asn Ile Arg Thr Arg Leu Lys Glu
                405                 410                 415

Leu Leu Ala Ala Trp Gln Leu Gln Gln Glu Pro Arg Ser Met Cys Gly
                420                 425                 430

Arg Leu Arg Gln Val Ala Val Leu Val Leu Trp Leu Leu Cys Leu
                435                 440                 445

Gly Thr Thr Leu Gly Cys Ala Ala Ala Val His Val Phe Ser Glu Val
    450                 455                 460

Met Leu Glu Ser Pro Val Ala Ala Gly Gln Glu Ala Ala Leu Leu Ala
465                 470                 475                 480

Leu Pro Leu Val Val Cys Leu Leu His Leu Ala Ala Pro Tyr Leu Tyr
                485                 490                 495

Arg Gly Leu Ala Ala Leu Glu Arg His Gly Ser Pro Val Leu Glu Val
                500                 505                 510

Tyr Met Ala Ile Phe Arg Asn Leu Val Leu Lys Met Ala Ile Leu Gly
            515                 520                 525

Val Leu Cys Tyr His Trp Leu Gly Arg Val Ala Ala Leu Arg Asp
530                 535                 540

Gln Cys Trp Glu Asp Phe Val Gly Gln Glu Leu Tyr Arg Phe Val Val
545                 550                 555                 560

Met Asp Phe Ile Phe Ala Leu Leu Asp Thr Leu Phe Gly Glu Leu Val
                565                 570                 575

Trp Arg Phe Ile Ser Glu Lys Lys Leu Lys Arg Arg Lys Pro Glu
                580                 585                 590

Phe Asp Ile Ala Arg Asn Val Leu Asp Leu Ile Tyr Gly Gln Thr Leu
                595                 600                 605

Ile Trp Leu Gly Val Leu Phe Ser Pro Leu Leu Pro Ala Ile Gln Ile
    610                 615                 620
```

Ile Lys Leu Leu Leu Phe Tyr Val Lys Lys Thr Ser Leu Leu Ala
625                 630                 635                 640

Asn Cys Gln Ala Pro Arg Arg Pro Trp Leu Ala Ser His Met Ser Thr
            645                 650                 655

Leu Phe Leu Thr Leu Leu Cys Phe Pro Ser Phe Leu Gly Ala Ala Val
                660                 665                 670

Phe Leu Ser Tyr Val Val Trp Gln Val Lys Pro Ser Ser Thr Cys Gly
            675                 680                 685

Pro Phe Arg Thr Leu Asp Ser Met Tyr Glu Ala Gly Arg Leu Trp Val
            690                 695                 700

Arg Gln Leu Glu Thr Ala Gly Ser Ser Val Ser Trp Leu Ser Trp Leu
705                 710                 715                 720

Tyr Gln His Leu Val Glu Asp Thr Val Phe Ile Phe Leu Val Ser Ala
                725                 730                 735

Leu Leu Leu Ala Val Ile Tyr Leu Asn Ile Gln Val Val Lys Gly Gln
                740                 745                 750

Arg Lys Val Ile Cys Leu Leu Lys Glu Gln Ile Ser Asn Val Thr Arg
            755                 760                 765

Ile Met Arg Gly Ile Trp Ile Arg Trp Trp His Arg His Ala Thr Ala
770                 775                 780

Gly Leu Ala Ile Cys Arg Ala Leu Pro Ala Gly Thr Gly Ser Pro Arg
785                 790                 795                 800

Gly Gly Asp Ser Ser Pro Arg Gln Asp Thr Trp Arg Val Leu Gly Arg
            805                 810                 815

Ala Ala Pro Cys Gly Tyr Arg Gln Ser Leu Arg Ile Phe Ala Ile Leu
            820                 825                 830

Glu Val Ala Phe Gly Leu Pro Pro Ala Gly Gly Thr His Val Gly Thr
            835                 840                 845

Arg Thr Leu Leu Ser Ala Leu Ile Leu
850                 855

<210> SEQ ID NO 32
<211> LENGTH: 775
<212> TYPE: PRT
<213> ORGANISM: Otolemur garnettii

<400> SEQUENCE: 32

Met Ala Gln Pro Leu Ser Phe Phe Leu Asp Val Pro Glu Thr Pro Gly
1               5                   10                  15

Asp Gln Asp Gln Glu Pro Ser Pro Tyr Asp Glu Ser Glu Val His Asp
            20                  25                  30

Ser Phe His Gln Leu Ile Gln Glu Gln Ser Gln Trp Val Thr Glu Glu
        35                  40                  45

Gly Leu Glu Leu Gln Pro Arg Glu Gln Glu Thr Pro Gly Ser Gly His
    50                  55                  60

Glu Thr Phe Leu Gly Pro Glu Ser Ala Pro Val His Ser Thr Ala Thr
65                  70                  75                  80

Leu Arg Ile Leu Ala Ser Met Pro Ser Arg Thr Ile Gly Arg Ser Arg
                85                  90                  95

Gly Ala Ile Ile Ser Gln Tyr Tyr Ser Arg Thr Met Arg Leu Arg Arg
            100                 105                 110

Arg Ser Gly Arg Pro Leu Leu Gly Asp Val Val Ala Arg Ser Ala Arg
        115                 120                 125

Pro Ser Leu Arg Leu Tyr Asp Leu Glu Leu Asp Pro Met Ala Gln Glu
    130                 135                 140

-continued

```
Glu Glu Glu Lys Gln Asn Leu Leu Val Lys Glu Leu Gln Gly Leu Ser
145                 150                 155                 160

Ala Ala Gln Arg Asp His Met Leu Arg Gly Met Pro Leu Ser Leu Ala
                165                 170                 175

Glu Lys Arg Ser Leu Arg Glu Lys Ser Gln Thr Ser His Arg Lys Trp
            180                 185                 190

Lys Gly Gln Ser Ser Arg Val Gly Val Phe Ser Cys Cys Ser Arg Leu
        195                 200                 205

Gly Tyr Ala Cys Ile Leu Thr Ser Arg Ser Leu Gly Leu Thr Leu Leu
    210                 215                 220

Ser Gly Leu Gln Ala Leu Thr Pro Trp His Tyr Thr Leu Lys Arg Ile
225                 230                 235                 240

Gly Gly Gln Phe Gly Ser Ser Val Leu Ser Tyr Phe Leu Phe Leu Lys
                245                 250                 255

Thr Leu Val Ala Phe Asn Gly Leu Leu Leu Pro Leu Leu Ala Phe
                260                 265                 270

Val Val Gly Val Gln Ala Ala Phe Pro Pro Asp Pro Gly Pro Gly Ser
            275                 280                 285

Gly Pro Ala Cys Thr Gly Leu Glu Leu Leu Thr Gly Ala Gly Cys Phe
290                 295                 300

Thr Asn Thr Val Met Tyr Tyr Gly Tyr Tyr Ser Asn Ala Thr Val Gly
305                 310                 315                 320

Trp Pro Cys Asp His Pro Leu Glu Gly Gly Pro Cys Arg Pro Arg Ala
                325                 330                 335

Gly Gly Leu Ser Tyr His Met Pro Leu Ala Tyr Leu Phe Thr Leu Gly
            340                 345                 350

Val Ala Phe Phe Val Thr Cys Ile Thr Leu Val Tyr Ser Met Ala His
        355                 360                 365

Ala Phe Gly Glu Ser Tyr Arg Val Gly Ser Thr Ser Gly Val His Ala
    370                 375                 380

Leu Thr Val Phe Cys Ser Trp Asp Tyr Lys Val Thr Gln Lys Arg Ala
385                 390                 395                 400

Val Arg Leu Gln His Gly Asn Ile Arg Thr Arg Leu Lys Ser Cys Cys
                405                 410                 415

Leu Cys Trp Arg Leu Gln Gln Ala Ala Val Leu Gly Leu Val Trp Leu
            420                 425                 430

Leu Cys Leu Gly Thr Val Leu Gly Cys Ala Val Ala Val Tyr Thr Phe
        435                 440                 445

Ser Glu Leu Val Ile Gln Gly Pro Val Ala Ala Gly Gln Glu Val Thr
    450                 455                 460

Leu Leu Ala Leu Pro Leu Val Val Cys Leu Leu Asn Leu Met Ala Pro
465                 470                 475                 480

Tyr Leu Tyr Arg Gly Leu Ala Thr Leu Glu Pro His Asp Ser Pro Val
                485                 490                 495

Leu Glu Val Tyr Val Ala Ile Cys Arg Asn Leu Ile Leu Lys Thr Val
            500                 505                 510

Ile Met Gly Val Leu Cys Tyr His Trp Leu Gly Arg Arg Val Gly Ala
        515                 520                 525

Leu Gln Asp Arg Cys Trp Glu Asp Phe Val Gly Gln Glu Leu Tyr Arg
    530                 535                 540

Phe Met Val Val Asp Phe Leu Phe Ala Leu Leu Asp Thr Leu Phe Gly
545                 550                 555                 560
```

```
Glu Leu Val Trp Arg Val Ile Ser Glu Lys Met Arg Arg Lys Arg
                565                 570                 575

Lys Pro Glu Phe Asp Ile Ala Arg Asn Val Leu Glu Leu Ile Tyr Gly
            580                 585                 590

Gln Thr Leu Thr Trp Leu Gly Val Leu Phe Ser Pro Leu Leu Pro Ala
            595                 600                 605

Val Gln Met Val Lys Leu Leu Leu Phe Tyr Val Lys Lys Thr Ser
        610                 615                 620

Leu Leu Ala Asn Cys Gln Ala Pro Arg Arg Pro Trp Leu Ala Ser His
625                 630                 635                 640

Met Ser Thr Val Phe Leu Ser Leu Leu Cys Phe Pro Ser Phe Leu Gly
                645                 650                 655

Ala Ala Val Phe Leu Cys Tyr Ala Val Trp Gln Val Lys Pro Ser Ser
                660                 665                 670

Leu Cys Gly Pro Phe Arg Ser Leu Asp Ser Met Tyr Glu Ala Gly Leu
            675                 680                 685

Met Trp Val His Arg Leu Glu Glu Ala Gly Pro Gly Leu Ser Trp Leu
            690                 695                 700

Pro Trp Val His Arg His Leu Leu Glu Asn Thr Phe Phe Ile Phe Leu
705                 710                 715                 720

Leu Ser Ala Leu Leu Leu Ala Val Ile Tyr Phe Asn Ile Gln Val Val
                725                 730                 735

Arg Gly Gln Gln Lys Val Ile Gly Leu Leu Lys Glu Gln Ile Ser His
                740                 745                 750

Glu Gly Glu Asp Lys Ile Phe Leu Ile Asn Lys Leu His Ser Val Tyr
            755                 760                 765

Glu Arg Lys Glu Arg Ser Arg
        770                 775

<210> SEQ ID NO 33
<211> LENGTH: 802
<212> TYPE: PRT
<213> ORGANISM: Propithecus coquereli

<400> SEQUENCE: 33

Met Ala Gln Pro Leu Asp Phe Val Leu Asp Val Pro Glu Thr Pro Gly
1               5                   10                  15

Asp Gln Gly Gln Glu Pro Ser Pro Tyr Asp Glu Ser Glu Val His Asp
            20                  25                  30

Ser Phe His Gln Leu Ile Gln Glu Gln Ser Arg Trp Val Ala Glu Glu
        35                  40                  45

Gly Leu Glu Leu Gln Gln Arg Glu Pro Gly Asp Pro Gly Arg Gly His
    50                  55                  60

Glu Thr Leu Leu Gly Glu Gly Ala Pro Val His Ser Met Ala Thr
65                  70                  75                  80

Leu Arg Ile Leu Ala Ser Met Pro Ser Arg Thr Ile Gly Arg Ser Arg
                85                  90                  95

Gly Ala Ile Ile Ser Gln Tyr Tyr Asn Arg Thr Val Arg Leu Arg Arg
            100                 105                 110

Arg Ser Gly Arg Pro Leu Leu Gly Asp Val Val Thr Ser Ala Arg
        115                 120                 125

Pro Ser Leu Arg Leu Tyr Asp Leu Glu Leu Asp Pro Met Ala Gln Glu
    130                 135                 140

Glu Glu Glu Lys Arg Asn Leu Leu Val Lys Glu Leu Gln Gly Leu Ser
145                 150                 155                 160
```

-continued

Ala Ala Gln Arg Asp His Met Leu Arg Gly Met Pro Leu Ser Leu Gly
            165                 170                 175

Glu Lys Arg Gly Leu Arg Glu Lys Ser Gln Thr Pro His Gly Lys Arg
            180                 185                 190

Arg Gly Gln Pro Gly Arg Gly Gly Leu Phe Ser Cys Cys Ser Arg Leu
            195                 200                 205

Arg Tyr Ala Cys Val Leu Ala Leu His Ser Leu Gly Leu Ala Leu Leu
            210                 215                 220

Ser Gly Leu His Ala Leu Thr Pro Trp Arg Tyr Ala Leu Lys Arg Ile
225                 230                 235                 240

Gly Gly Gln Phe Gly Ser Ser Val Leu Ser Tyr Phe Leu Phe Leu Lys
            245                 250                 255

Thr Leu Val Ala Phe Asn Ala Leu Leu Leu Pro Leu Leu Ala Phe
            260                 265                 270

Val Val Gly Val Gln Ala Ala Phe Pro Pro Asp Pro Gly Pro Gly Pro
            275                 280                 285

Arg Pro Thr Cys Thr Gly Leu Glu Phe Leu Thr Gly Ala Gly Cys Phe
            290                 295                 300

Thr His Thr Val Met Tyr Tyr Gly Tyr Tyr Ser Asn Ala Thr Leu Asn
305                 310                 315                 320

Gln Pro Cys Gly Gln Pro Leu Glu Gly Gly Gln Cys Arg Pro Arg Ala
            325                 330                 335

Gly Gly Leu Pro Tyr Asn Met Pro Leu Ala Tyr Leu Phe Thr Val Gly
            340                 345                 350

Val Ala Phe Phe Ile Thr Cys Ile Thr Leu Val Tyr Ser Met Ala His
            355                 360                 365

Ala Phe Gly Glu Ser Tyr Arg Val Gly Ser Thr Ser Gly Val His Ala
            370                 375                 380

Ile Thr Val Phe Cys Ser Trp Asp Tyr Lys Val Thr Gln Lys Arg Ala
385                 390                 395                 400

Ser Arg Leu Gln His Asp Asn Ile Arg Thr Arg Leu Lys Glu Leu Leu
            405                 410                 415

Ala Glu Trp Gln Leu Arg Gln Ser Thr Arg Ser Leu Cys Gly Arg Leu
            420                 425                 430

Gln Gln Ala Ala Val Leu Gly Leu Val Trp Leu Leu Cys Leu Gly Thr
            435                 440                 445

Val Ser Gly Cys Ala Ala Ala Val His Ala Phe Ser Glu Phe Val Ile
450                 455                 460

Gln Gly Pro Val Ala Ala Gly Gln Glu Val Ala Leu Leu Ala Leu Pro
465                 470                 475                 480

Val Val Val Cys Leu Leu Asn Leu Gly Ala Pro Tyr Leu Tyr Arg Gly
            485                 490                 495

Leu Ala Ala Leu Glu Pro Gln Asp Ser Pro Val Leu Glu Val Tyr Val
            500                 505                 510

Ala Ile Cys Arg Asn Leu Val Leu Lys Met Val Ile Leu Gly Val Leu
            515                 520                 525

Cys Tyr His Trp Leu Gly Arg Arg Val Gly Ala Leu Gln Asp Gln Cys
            530                 535                 540

Trp Glu Asp Phe Val Gly Gln Glu Leu Tyr Arg Phe Val Val Leu Asp
545                 550                 555                 560

Phe Leu Phe Thr Leu Leu Asp Thr Leu Phe Gly Glu Leu Ala Trp Arg
            565                 570                 575

-continued

Val Ile Ser Glu Lys Lys Thr Lys Thr Arg Arg Lys Pro Glu Phe Asp
              580             585             590

Ile Ala Arg Asn Val Leu Glu Leu Ile Tyr Gly Gln Thr Leu Thr Trp
          595             600             605

Leu Gly Val Leu Phe Ser Pro Leu Leu Pro Ala Val Gln Ile Val Lys
      610             615             620

Leu Leu Leu Leu Phe Gln Val Lys Lys Thr Ser Leu Leu Ala Asn Cys
625             630             635             640

Gln Ala Pro Arg Arg Pro Trp Leu Ser Ser His Met Ser Thr Val Phe
              645             650             655

Leu Ser Leu Leu Cys Phe Pro Ser Phe Leu Gly Ala Ala Val Phe Leu
          660             665             670

Cys Tyr Ala Val Trp Gln Val Lys Pro Ser Ser Met Cys Gly Pro Phe
      675             680             685

Arg Ser Leu Asp Thr Met Tyr Arg Ala Gly Thr Ala Trp Val Arg His
      690             695             700

Leu Glu Ala Ala Gly Pro Arg Leu Ser Trp Leu Pro Trp Val His Arg
705             710             715             720

His Leu Val Glu Asn Thr Phe Phe Ile Phe Leu Leu Ser Ala Leu Leu
              725             730             735

Leu Ala Val Ile Tyr Phe Asn Ile Gln Val Val Arg Gly Gln Arg Lys
          740             745             750

Val Ile Cys Leu Leu Lys Glu Gln Ile Ser His Glu Gly Glu Asp Lys
      755             760             765

Ile Phe Leu Ile Asn Lys Leu His Ser Ile Tyr Glu Lys Lys Glu Arg
      770             775             780

Lys Glu Gly Glu Glu Arg Ser Arg Cys Ala Gly Arg Ser Gly Lys Glu
785             790             795             800

Glu Ser

<210> SEQ ID NO 34
<211> LENGTH: 807
<212> TYPE: PRT
<213> ORGANISM: Tarsius syrichta

<400> SEQUENCE: 34

Met Ala Gln Pro Leu Ala Phe Ile Leu Asp Val Pro Glu Thr Pro Gly
1               5                   10                  15

Asn Gln Gly Gln Glu Pro Ser Pro Tyr Asp Glu Ser Glu Val His Asp
              20              25                  30

Ser Phe His Gln Leu Ile Gln Glu Gln Ser Gln Arg Ala Ala Gln Glu
          35                  40                  45

Gly Leu Glu Leu Gln Pro Arg Glu Pro Gly Ala Ser Gly Ser Asp His
      50                  55                  60

Gln Thr Leu Arg Gln Pro Glu Gly Val Pro Ala His Ser Thr Ala Thr
65                  70                  75                  80

Leu Arg Ile Leu Ala Ser Met Pro Ser Arg Thr Ile Gly Arg Ser Arg
              85                  90                  95

Gly Ala Ile Ile Ser Gln Tyr Tyr Asn Arg Thr Val Gln Leu Arg Arg
          100                 105                 110

Arg Gly Ser Arg Pro Leu Leu Gly Asp Met Val Arg Ser Ala Arg Pro
      115                 120                 125

Ser Leu Arg Leu Tyr Asp Leu Glu Leu Asp Pro Met Ala Arg Gly Glu
      130                 135                 140

```
Glu Glu Lys Gln Ser Leu Leu Val Lys Glu Leu Gln Gly Leu Ser Val
145                 150                 155                 160

Ala Gln Arg Asp His Met Leu Arg Gly Met Pro Leu Ser Leu Ala Glu
            165                 170                 175

Lys Arg Cys Leu Arg Glu Lys Ser Arg Thr Pro Arg Gly Arg Arg Arg
            180                 185                 190

Gly Gln Gln Gly His Gly Gly Phe Ser Cys Cys Ser Arg Leu Arg
            195                 200                 205

Tyr Ala Cys Ile Leu Ala Leu His Ser Leu Gly Val Ala Leu Leu Ser
            210                 215                 220

Arg Leu His Ala Leu Met Pro Trp Arg Tyr Ala Leu Lys Arg Ile Gly
225                 230                 235                 240

Gly Gln Phe Gly Ser Ser Val Leu Ser Tyr Phe Leu Phe Leu Lys Thr
            245                 250                 255

Leu Leu Val Phe Asn Ala Leu Leu Leu Pro Leu Leu Ala Phe Ile
            260                 265                 270

Val Gly Ala Gln Ala Ala Phe Pro Ala Ala Pro Ser Ala Thr Ala Ser
            275                 280                 285

Ala Cys Thr Gly Leu Glu Leu Leu Thr Gly Thr Val Arg Ser Cys Pro
290                 295                 300

Leu Thr Gly Asp Gln Cys Thr Pro Arg Val Gly Gly Leu Pro Tyr Asn
305                 310                 315                 320

Met Pro Leu Ala Tyr Leu Phe Thr Met Gly Val Ala Phe Phe Ile Thr
            325                 330                 335

Cys Ile Ala Leu Val Tyr Ser Met Ala His Ser Phe Gly Glu Ser Tyr
            340                 345                 350

Arg Val Gly Ser Ala Ser Gly Val His Ala Ile Thr Val Phe Cys Ser
            355                 360                 365

Trp Asp Tyr Lys Val Thr Gln Lys Arg Ala Ser Arg Leu Gln His Asp
            370                 375                 380

Ser Val Arg Thr Arg Leu Lys Glu Leu Leu Ala Glu Trp Arg Leu Arg
385                 390                 395                 400

Gln Glu Pro Arg Ser Val Cys Gly Lys Met Arg Gln Ala Ala Val Leu
            405                 410                 415

Gly Ile Val Trp Leu Leu Cys Leu Gly Thr Val Leu Gly Cys Ala Val
            420                 425                 430

Ala Val His Ala Phe Ser Glu Leu Met Leu Gln Ser Pro Val Val Ala
            435                 440                 445

Gly Arg Glu Val Ala Leu Leu Ala Leu Pro Leu Val Val Ser Leu Leu
450                 455                 460

Asn Leu Gly Ala Pro Tyr Leu Cys Arg Gly Leu Ala Ala Leu Glu Gln
465                 470                 475                 480

His Asp Ser Pro Val Leu Glu Val Tyr Val Ala Val Cys Arg Asn Leu
            485                 490                 495

Phe Leu Lys Met Val Val Leu Gly Thr Leu Cys Tyr His Trp Leu Gly
            500                 505                 510

Arg Arg Val Gly Ala Leu Gln Gly Gln Cys Trp Glu Asp Phe Val Gly
            515                 520                 525

Gln Glu Leu Tyr Arg Phe Met Val Met Asp Phe Val Phe Ala Leu Leu
            530                 535                 540

Asp Thr Leu Phe Gly Glu Leu Val Trp Arg Ala Ile Ser Glu Lys Lys
545                 550                 555                 560

Leu Lys Arg Arg Arg Lys Pro Glu Phe Asp Ile Ala Arg Asn Val Leu
```

```
                565                 570                 575
Glu Leu Ile Tyr Gly Gln Thr Leu Thr Trp Leu Gly Val Leu Phe Ser
            580                 585                 590

Pro Leu Leu Pro Ala Val Gln Ile Ile Lys Leu Leu Leu Leu Phe Tyr
            595                 600                 605

Val Lys Lys Thr Ser Leu Leu Ala Asn Cys Gln Ala Pro Arg Arg Pro
            610                 615                 620

Trp Leu Ala Ser His Met Ser Thr Val Phe Leu Thr Leu Leu Cys Phe
625                 630                 635                 640

Pro Ser Phe Leu Gly Ala Ala Ile Phe Phe Cys Tyr Ala Val Trp Gln
                645                 650                 655

Val Lys Pro Ser Ser Ile Cys Gly Pro Phe Arg Thr Leu Asp Thr Met
                660                 665                 670

Tyr Gln Ala Gly Thr Val Trp Val Arg Leu Leu Glu Arg Ala Gly Pro
                675                 680                 685

Arg Val Ser Trp Leu Pro Trp Val His Arg Asn Leu Val Glu Asn Thr
            690                 695                 700

Phe Phe Ile Phe Leu Val Ser Ala Leu Leu Leu Ala Val Ile Tyr Leu
705                 710                 715                 720

Asn Ile Gln Val Val Arg Gly Gln Arg Lys Val Ile Cys Leu Leu Lys
                725                 730                 735

Glu Gln Ile Ser Asn Glu Gly Asp Lys Ile Phe Leu Ile Asn Lys
                740                 745                 750

Leu His Ser Val Tyr Glu Arg Lys Glu Arg Lys Glu Lys Ala Arg Ser
                755                 760                 765

Arg Ala Gly Gly Thr Glu Glu Ala Thr Pro Ala Leu Leu Thr
            770                 775                 780

Glu Gly Arg Asp Ala Arg Trp Asp Gly Asn Gly Pro Arg Leu Thr
785                 790                 795                 800

Leu Gln Pro Glu Leu Leu Ala
                805

<210> SEQ ID NO 35
<211> LENGTH: 805
<212> TYPE: PRT
<213> ORGANISM: Homo sapiens

<400> SEQUENCE: 35

Met Ala Gln Pro Leu Ala Phe Ile Leu Asp Val Pro Glu Thr Pro Gly
1               5                   10                  15

Asp Gln Gly Gln Gly Pro Ser Pro Tyr Asp Glu Ser Glu Val His Asp
            20                  25                  30

Ser Phe Gln Gln Leu Ile Gln Glu Gln Ser Gln Cys Thr Ala Gln Glu
        35                  40                  45

Gly Leu Glu Leu Gln Gln Arg Glu Arg Glu Val Thr Gly Ser Ser Gln
    50                  55                  60

Gln Thr Leu Trp Arg Pro Glu Gly Thr Gln Ser Thr Ala Thr Leu Arg
65                  70                  75                  80

Ile Leu Ala Ser Met Pro Ser Arg Thr Ile Gly Arg Ser Arg Gly Ala
                85                  90                  95

Ile Ile Ser Gln Tyr Tyr Asn Arg Thr Val Gln Leu Arg Cys Arg Ser
            100                 105                 110

Ser Arg Pro Leu Leu Gly Asn Phe Val Arg Ser Ala Trp Pro Ser Leu
        115                 120                 125
```

```
Arg Leu Tyr Asp Leu Glu Leu Asp Pro Thr Ala Leu Glu Glu Glu
    130                 135                 140
Lys Gln Ser Leu Leu Val Lys Glu Leu Gln Ser Leu Ala Val Ala Gln
145                 150                 155                 160
Arg Asp His Met Leu Arg Gly Met Pro Leu Ser Leu Ala Glu Lys Arg
                165                 170                 175
Ser Leu Arg Glu Lys Ser Arg Thr Pro Arg Gly Lys Trp Arg Gly Gln
            180                 185                 190
Pro Gly Ser Gly Gly Val Cys Ser Cys Cys Gly Arg Leu Arg Tyr Ala
        195                 200                 205
Cys Val Leu Ala Leu His Ser Leu Gly Leu Ala Leu Leu Ser Ala Leu
210                 215                 220
Gln Ala Leu Met Pro Trp Arg Tyr Ala Leu Lys Arg Ile Gly Gly Gln
225                 230                 235                 240
Phe Gly Ser Ser Val Leu Ser Tyr Phe Leu Phe Leu Lys Thr Leu Leu
                245                 250                 255
Ala Phe Asn Ala Leu Leu Leu Leu Leu Val Ala Phe Ile Met Gly
            260                 265                 270
Pro Gln Val Ala Phe Pro Pro Ala Leu Pro Gly Pro Ala Pro Val Cys
        275                 280                 285
Thr Gly Leu Glu Leu Leu Thr Gly Ala Gly Cys Phe Thr His Thr Val
290                 295                 300
Met Tyr Tyr Gly His Tyr Ser Asn Ala Thr Leu Asn Gln Pro Cys Gly
305                 310                 315                 320
Ser Pro Leu Asp Gly Ser Gln Cys Thr Pro Arg Val Gly Gly Leu Pro
                325                 330                 335
Tyr Asn Met Pro Leu Ala Tyr Leu Ser Thr Val Gly Val Ser Phe Phe
            340                 345                 350
Ile Thr Cys Ile Thr Leu Val Tyr Ser Met Ala His Ser Phe Gly Glu
        355                 360                 365
Ser Tyr Arg Val Gly Ser Thr Ser Gly Ile His Ala Ile Thr Val Phe
370                 375                 380
Cys Ser Trp Asp Tyr Lys Val Thr Gln Lys Arg Ala Ser Arg Leu Gln
385                 390                 395                 400
Gln Asp Asn Ile Arg Thr Arg Leu Lys Glu Leu Leu Ala Glu Trp Gln
                405                 410                 415
Leu Arg His Ser Pro Arg Ser Val Cys Gly Arg Leu Arg Gln Ala Ala
            420                 425                 430
Val Leu Gly Leu Val Trp Leu Leu Cys Leu Gly Thr Ala Leu Gly Cys
        435                 440                 445
Ala Val Ala Val His Val Phe Ser Glu Phe Met Ile Gln Ser Pro Glu
450                 455                 460
Ala Ala Gly Gln Glu Ala Val Leu Leu Val Leu Pro Leu Val Val Gly
465                 470                 475                 480
Leu Leu Asn Leu Gly Ala Pro Tyr Leu Cys Arg Val Leu Ala Ala Leu
                485                 490                 495
Glu Pro His Asp Ser Pro Val Leu Glu Val Tyr Val Ala Ile Cys Arg
            500                 505                 510
Asn Leu Ile Leu Lys Leu Ala Ile Leu Gly Thr Leu Cys Tyr His Trp
        515                 520                 525
Leu Gly Arg Arg Val Gly Val Leu Gln Gly Gln Cys Trp Glu Asp Phe
530                 535                 540
Val Gly Gln Glu Leu Tyr Arg Phe Leu Val Met Asp Phe Val Leu Met
```

```
              545                 550                 555                 560

Leu Leu Asp Thr Leu Phe Gly Glu Leu Val Trp Arg Ile Ile Ser Glu
                        565                 570                 575

Lys Lys Leu Lys Arg Arg Lys Pro Glu Phe Asp Ile Ala Arg Asn
                    580                 585                 590

Val Leu Glu Leu Ile Tyr Gly Gln Thr Leu Thr Trp Leu Gly Val Leu
                        595                 600                 605

Phe Ser Pro Leu Leu Pro Ala Val Gln Ile Ile Lys Leu Leu Leu Val
                    610                 615                 620

Phe Tyr Val Lys Lys Thr Ser Leu Leu Ala Asn Cys Gln Ala Pro Arg
        625                 630                 635                 640

Arg Pro Trp Leu Ala Ser His Met Ser Thr Val Phe Leu Thr Leu Leu
                        645                 650                 655

Cys Phe Pro Ala Phe Leu Gly Ala Ala Val Phe Leu Cys Tyr Ala Val
                        660                 665                 670

Trp Gln Val Lys Pro Ser Ser Thr Cys Gly Pro Phe Arg Thr Leu Asp
                    675                 680                 685

Thr Met Tyr Glu Ala Gly Arg Val Trp Val Arg His Leu Glu Ala Ala
                690                 695                 700

Gly Pro Arg Val Ser Trp Leu Pro Trp Val His Arg Tyr Leu Met Glu
        705                 710                 715                 720

Asn Thr Phe Phe Val Phe Leu Val Ser Ala Leu Leu Leu Ala Val Ile
                        725                 730                 735

Tyr Leu Asn Ile Gln Val Val Arg Gly Gln Arg Lys Val Ile Cys Leu
                    740                 745                 750

Leu Lys Glu Gln Ile Ser Asn Glu Gly Glu Asp Lys Ile Phe Leu Ile
                    755                 760                 765

Asn Lys Leu His Ser Ile Tyr Glu Arg Lys Glu Arg Glu Glu Arg Ser
                    770                 775                 780

Arg Val Gly Thr Thr Glu Glu Ala Ala Ala Pro Pro Ala Leu Leu Thr
        785                 790                 795                 800

Asp Glu Gln Asp Ala
                    805

<210> SEQ ID NO 36
<211> LENGTH: 805
<212> TYPE: PRT
<213> ORGANISM: Pan paniscus

<400> SEQUENCE: 36

Met Ala Gln Pro Leu Ala Phe Ile Leu Asp Val Pro Glu Thr Pro Gly
1               5                   10                  15

Asp Gln Gly Arg Asp Pro Ser Pro Tyr Asp Glu Ser Glu Val His Asp
            20                  25                  30

Ser Phe Gln Gln Leu Ile Gln Glu Gln Ser Gln Cys Ala Ala Gln Glu
        35                  40                  45

Gly Leu Glu Leu Gln Gln Arg Glu Arg Glu Val Thr Gly Ser Ser Gln
    50                  55                  60

Gln Thr Leu Trp Arg Pro Glu Gly Thr Gln Ser Thr Ala Thr Leu Arg
65                  70                  75                  80

Ile Leu Ala Ser Met Pro Ser Arg Thr Ile Gly Arg Ser Arg Gly Ala
                85                  90                  95

Ile Ile Ser Gln Tyr Tyr Asn Arg Thr Val Gln Leu Arg Arg Arg Ser
            100                 105                 110
```

-continued

Ser Arg Pro Leu Leu Gly Asn Phe Val His Ser Ala Arg Pro Ser Leu
        115                 120                 125

Arg Leu Tyr Asp Leu Glu Leu Asp Pro Thr Ala Arg Glu Glu Glu
130                 135                 140

Lys Gln Ser Leu Leu Val Lys Glu Leu Gln Ser Leu Ala Val Ala Gln
145                 150                 155                 160

Arg Asp His Met Leu Arg Gly Met Pro Leu Ser Leu Ala Glu Lys Arg
                165                 170                 175

Ser Leu Arg Glu Lys Ser Arg Thr Pro Arg Gly Lys Trp Arg Gly Gln
            180                 185                 190

Pro Gly Ser Gly Gly Val Cys Ser Cys Cys Gly Arg Leu Arg Tyr Ala
        195                 200                 205

Cys Val Leu Ala Leu His Ser Leu Gly Leu Ala Leu Leu Ser Ala Leu
        210                 215                 220

Gln Ala Leu Met Pro Trp Arg Tyr Ala Leu Lys Arg Ile Gly Gly Gln
225                 230                 235                 240

Phe Gly Ser Ser Val Leu Ser Tyr Phe Leu Phe Leu Lys Thr Leu Leu
                245                 250                 255

Ala Phe Asn Ala Leu Leu Leu Leu Leu Val Ala Phe Ile Met Gly
            260                 265                 270

Pro Gln Val Ala Phe Pro Pro Ala Leu Pro Gly Pro Ala Pro Val Cys
        275                 280                 285

Thr Gly Leu Glu Leu Leu Thr Gly Ala Gly Cys Phe Thr His Thr Val
        290                 295                 300

Met Tyr Tyr Gly His Tyr Ser Asn Ala Thr Leu Asn Gln Pro Cys Gly
305                 310                 315                 320

Ser Pro Leu Asp Gly Ser Gln Cys Thr Pro Arg Val Gly Gly Leu Pro
                325                 330                 335

Tyr Asn Met Pro Leu Ala Tyr Leu Ser Thr Val Gly Val Ser Phe Phe
            340                 345                 350

Ile Thr Cys Ile Thr Leu Val Tyr Ser Met Ala His Ser Phe Gly Glu
        355                 360                 365

Ser Tyr Arg Val Gly Ser Thr Ser Gly Ile His Ala Ile Thr Val Phe
370                 375                 380

Cys Ser Trp Asp Tyr Lys Val Thr Gln Lys Arg Ala Ser Arg Leu Gln
385                 390                 395                 400

Gln Asp Asn Ile Arg Thr Arg Leu Lys Glu Leu Leu Ala Glu Trp Gln
                405                 410                 415

Leu Arg His Ser Pro Arg Ser Val Cys Gly Arg Leu Arg Gln Ala Ala
            420                 425                 430

Val Leu Gly Leu Val Trp Leu Leu Cys Leu Gly Thr Ala Leu Ala Cys
        435                 440                 445

Ala Val Ala Val His Val Phe Ser Glu Phe Met Ile Gln Ser Pro Glu
450                 455                 460

Ala Val Gly Gln Glu Ala Val Leu Leu Val Leu Pro Leu Val Val Gly
465                 470                 475                 480

Leu Leu Asn Leu Gly Ala Pro Tyr Leu Cys Arg Val Leu Ala Ala Leu
                485                 490                 495

Glu Pro His Asp Ser Pro Val Leu Glu Val Tyr Val Ala Ile Cys Arg
            500                 505                 510

Asn Leu Ile Leu Lys Leu Ala Ile Leu Gly Thr Leu Cys Tyr His Trp
        515                 520                 525

Leu Gly Arg Arg Val Gly Val Leu Gln Gly Gln Cys Trp Glu Asp Phe

```
                        530                 535                 540
Val Gly Gln Glu Leu Tyr Arg Phe Leu Val Met Asp Phe Val Leu Met
545                 550                 555                 560

Leu Leu Asp Thr Leu Phe Gly Glu Leu Val Trp Arg Ile Ile Ser Glu
                565                 570                 575

Lys Lys Leu Lys Arg Arg Lys Pro Glu Phe Asp Ile Ala Arg Asn
                580                 585                 590

Val Leu Glu Leu Ile Tyr Gly Gln Thr Leu Thr Trp Leu Gly Val Leu
                595                 600                 605

Phe Ser Pro Leu Leu Pro Ala Val Gln Ile Ile Lys Leu Leu Leu Val
610                 615                 620

Phe Tyr Val Lys Lys Thr Ser Leu Leu Ala Asn Cys Gln Ala Pro Arg
625                 630                 635                 640

Arg Pro Trp Leu Ala Ser His Met Ser Thr Val Phe Leu Thr Leu Leu
                645                 650                 655

Cys Phe Pro Ala Phe Leu Gly Ala Ala Val Phe Leu Cys Tyr Ala Val
                660                 665                 670

Trp Gln Val Lys Pro Ser Ser Thr Cys Gly Pro Phe Arg Thr Leu Asp
                675                 680                 685

Thr Met Tyr Glu Ala Gly Arg Val Trp Val Arg His Leu Glu Ala Ala
                690                 695                 700

Gly Pro Arg Val Ser Trp Leu Pro Trp Val His Arg Tyr Leu Val Glu
705                 710                 715                 720

Asn Thr Phe Phe Val Phe Leu Val Ser Ala Leu Leu Leu Ala Val Ile
                725                 730                 735

Tyr Leu Asn Ile Gln Val Val Arg Gly Gln Arg Lys Val Ile Cys Leu
                740                 745                 750

Leu Lys Glu Gln Ile Ser Asn Glu Gly Glu Asp Lys Ile Phe Leu Ile
                755                 760                 765

Asn Lys Leu His Ser Ile Tyr Glu Arg Lys Glu Arg Glu Arg Ser
                770                 775                 780

Arg Val Gly Thr Thr Glu Glu Ala Ala Ala Pro Pro Ala Leu Leu Thr
785                 790                 795                 800

Asp Glu Gln Asp Ala
                805

<210> SEQ ID NO 37
<211> LENGTH: 805
<212> TYPE: PRT
<213> ORGANISM: Pan troglodytes

<400> SEQUENCE: 37

Met Ala Gln Pro Leu Ala Phe Ile Leu Asp Val Pro Glu Thr Pro Gly
1               5                   10                  15

Asp Gln Gly Gln Asp Leu Ser Pro Tyr Asp Glu Ser Glu Val His Asp
                20                  25                  30

Ser Phe Gln Gln Leu Ile Gln Glu Gln Ser Gln Cys Thr Ala Gln Glu
            35                  40                  45

Gly Leu Glu Leu Gln Gln Arg Glu Arg Glu Val Thr Gly Ser Ser Gln
        50                  55                  60

Gln Thr Leu Trp Arg Pro Glu Gly Thr Gln Ser Thr Ala Thr Leu Arg
65              70                  75                  80

Ile Leu Ala Ser Met Pro Ser Arg Thr Ile Gly Arg Ser Arg Gly Ala
                85                  90                  95
```

-continued

```
Ile Ile Ser Gln Tyr Tyr Asn Arg Thr Val Gln Leu Arg Arg Arg Ser
            100                 105                 110

Ser Arg Pro Leu Leu Gly Asn Phe Val His Ser Ala Arg Pro Ser Leu
        115                 120                 125

Arg Leu Tyr Asp Leu Glu Leu Asp Pro Thr Ala Arg Glu Glu Glu Glu
    130                 135                 140

Lys Gln Ser Leu Leu Val Lys Glu Leu Gln Ser Leu Ala Val Ala Gln
145                 150                 155                 160

Arg Asp His Met Leu Arg Gly Met Pro Leu Ser Leu Ala Glu Lys Arg
                165                 170                 175

Ser Leu Arg Glu Lys Ser Arg Thr Pro Arg Gly Lys Trp Arg Gly Gln
            180                 185                 190

Pro Gly Ser Gly Gly Val Cys Ser Cys Gly Arg Leu Arg Tyr Ala
        195                 200                 205

Cys Val Leu Ala Leu His Ser Leu Gly Leu Val Leu Leu Ser Ala Leu
    210                 215                 220

Gln Ala Leu Met Pro Trp Arg Tyr Ala Leu Lys Arg Ile Gly Gly Gln
225                 230                 235                 240

Phe Gly Ser Ser Val Leu Ser Tyr Phe Leu Phe Leu Lys Thr Leu Leu
                245                 250                 255

Ala Phe Asn Ala Leu Leu Leu Leu Leu Val Ala Phe Ile Met Gly
            260                 265                 270

Pro Gln Val Ala Phe Pro Pro Ala Leu Pro Gly Pro Ala Pro Val Cys
        275                 280                 285

Thr Gly Leu Glu Leu Leu Thr Gly Ala Gly Cys Phe Thr His Thr Val
    290                 295                 300

Met Tyr Tyr Gly His Tyr Ser Asn Ala Thr Leu Asn Gln Pro Cys Gly
305                 310                 315                 320

Ser Pro Leu Asp Gly Ser Gln Cys Thr Pro Arg Val Gly Gly Leu Pro
                325                 330                 335

Tyr Asn Met Pro Leu Ala Tyr Leu Ser Thr Val Gly Val Ser Phe Phe
            340                 345                 350

Ile Thr Cys Ile Thr Leu Val Tyr Ser Met Ala His Ser Phe Gly Glu
        355                 360                 365

Ser Tyr Arg Val Gly Ser Thr Ser Gly Ile His Ala Ile Thr Val Phe
    370                 375                 380

Cys Ser Trp Asp Tyr Lys Val Thr Gln Lys Arg Ala Ser Arg Leu Gln
385                 390                 395                 400

Gln Asp Asn Ile Arg Thr Arg Leu Lys Glu Leu Leu Ala Glu Trp Gln
                405                 410                 415

Leu Arg His Ser Pro Arg Ser Val Cys Gly Arg Leu Arg Gln Ala Ala
            420                 425                 430

Val Leu Gly Leu Val Trp Leu Leu Cys Leu Gly Thr Ala Leu Gly Cys
        435                 440                 445

Ala Val Ala Val His Val Phe Ser Glu Phe Met Ile Gln Ser Pro Glu
    450                 455                 460

Ala Val Gly Gln Glu Ala Ala Leu Leu Val Leu Pro Leu Val Val Gly
465                 470                 475                 480

Leu Leu Asn Leu Gly Ala Pro Tyr Leu Cys Arg Val Leu Ala Ala Leu
                485                 490                 495

Glu Pro His Asp Ser Pro Val Leu Glu Val Tyr Val Ala Ile Cys Arg
            500                 505                 510

Asn Leu Ile Leu Lys Leu Ala Ile Leu Gly Thr Leu Cys Tyr His Trp
```

```
            515                 520                 525
Leu Gly Arg Arg Val Gly Val Leu Gln Gly Gln Cys Trp Glu Asp Phe
        530                 535                 540

Val Gly Gln Glu Leu Tyr Arg Phe Leu Val Met Asp Phe Val Leu Met
545                 550                 555                 560

Leu Leu Asp Thr Leu Phe Gly Glu Leu Val Trp Arg Ile Ile Ser Glu
                565                 570                 575

Lys Lys Leu Lys Arg Arg Lys Pro Glu Phe Asp Ile Ala Arg Asn
            580                 585                 590

Val Leu Glu Leu Ile Tyr Gly Gln Thr Leu Thr Trp Leu Gly Val Leu
            595                 600                 605

Phe Ser Pro Leu Leu Pro Ala Val Gln Ile Ile Lys Leu Leu Leu Val
        610                 615                 620

Phe Tyr Val Lys Lys Thr Ser Leu Leu Ala Asn Cys Gln Ala Pro Arg
625                 630                 635                 640

Arg Pro Trp Leu Ala Ser His Met Ser Thr Val Phe Leu Thr Leu Leu
                645                 650                 655

Cys Phe Pro Ala Phe Leu Gly Ala Ala Val Phe Leu Cys Tyr Ala Val
                660                 665                 670

Trp Gln Val Lys Pro Ser Ser Thr Cys Gly Pro Phe Arg Thr Leu Asp
            675                 680                 685

Thr Met Tyr Glu Ala Gly Arg Val Trp Val Arg His Leu Glu Ala Ala
        690                 695                 700

Gly Pro Arg Val Ser Trp Leu Pro Trp Val His Arg Tyr Leu Gly Glu
705                 710                 715                 720

Asn Thr Phe Phe Val Phe Leu Val Ser Ala Leu Leu Ala Val Ile
                725                 730                 735

Tyr Leu Asn Ile Gln Val Val Arg Gly Gln Arg Lys Val Ile Cys Leu
            740                 745                 750

Leu Lys Glu Gln Ile Ser Asn Glu Gly Glu Asp Lys Ile Phe Leu Ile
            755                 760                 765

Asn Lys Leu His Ser Ile Tyr Glu Arg Lys Glu Arg Glu Arg Ser
        770                 775                 780

Arg Val Gly Thr Thr Glu Glu Ala Ala Ala Pro Ala Leu Leu Thr
785                 790                 795                 800

Asp Glu Gln Asp Ala
            805

<210> SEQ ID NO 38
<211> LENGTH: 805
<212> TYPE: PRT
<213> ORGANISM: Pongo abelii

<400> SEQUENCE: 38

Met Ala Gln Pro Leu Ala Phe Ile Leu Asp Val Pro Glu Thr Pro Gly
1               5                   10                  15

Asp Gln Gly Gln Asp Pro Ser Pro Tyr Asp Glu Ser Glu Val His Asp
            20                  25                  30

Ser Phe Gln Gln Leu Ile Gln Glu Gln Ser Arg Cys Ala Ala Gln Glu
        35                  40                  45

Gly Leu Glu Leu Gln Gln Arg Glu Arg Glu Ala Thr Gly Ser Gly Gln
    50                  55                  60

Gln Thr Leu Trp Arg Pro Glu Gly Thr Gln Ser Thr Ala Thr Leu Arg
65                  70                  75                  80
```

```
Ile Leu Ala Ser Met Pro Ser Arg Thr Ile Gly Arg Ser Arg Gly Ala
                85                  90                  95
Ile Ile Ser Gln Tyr Tyr Asn Arg Thr Val Gln Leu Arg Arg Arg Ser
            100                 105                 110
Ser Arg Pro Leu Leu Gly Asn Phe Val Arg Ser Ala Arg Pro Ser Leu
            115                 120                 125
Arg Leu Tyr Asp Leu Glu Leu Asp Pro Met Ala Arg Glu Glu Glu Glu
            130                 135                 140
Lys Gln Ser Leu Leu Val Lys Glu Leu Gln Ser Leu Ala Val Ala Gln
145                 150                 155                 160
Arg Asp His Met Leu Arg Gly Met Pro Leu Ser Leu Ala Glu Lys Arg
                165                 170                 175
Ser Leu Arg Glu Lys Ser Arg Thr Leu Arg Gly Lys Trp Arg Gly Gln
            180                 185                 190
Pro Gly Ser Gly Gly Val Cys Ser Cys Gly Gln Leu Arg Tyr Ala
            195                 200                 205
Cys Val Leu Ala Leu His Ser Leu Gly Leu Ala Leu Leu Ser Ala Leu
    210                 215                 220
Gln Ala Leu Thr Pro Trp Arg Tyr Ala Leu Lys Arg Ile Gly Gly Gln
225                 230                 235                 240
Phe Gly Ser Ser Val Leu Ser Tyr Phe Leu Phe Leu Lys Thr Leu Leu
                245                 250                 255
Ala Phe Asn Ala Leu Leu Leu Leu Leu Val Ala Phe Ile Thr Gly
            260                 265                 270
Pro Gln Val Ala Phe Pro Pro Ala Leu Leu Gly Pro Val Pro Val Cys
            275                 280                 285
Thr Gly Leu Glu Leu Leu Thr Gly Ala Gly Cys Phe Thr His Thr Val
    290                 295                 300
Met Tyr Tyr Gly His Tyr Ser Asn Ala Thr Leu Asn Gln Pro Cys Gly
305                 310                 315                 320
Ser Pro Leu Asp Gly Ser Gln Cys Thr Pro Arg Ala Gly Gly Leu Pro
                325                 330                 335
Tyr Asn Met Pro Leu Ala Tyr Leu Ser Thr Val Gly Val Ser Phe Phe
            340                 345                 350
Val Thr Cys Ile Thr Leu Val Tyr Ser Met Ala His Ser Phe Gly Glu
            355                 360                 365
Ser Tyr Arg Val Gly Ser Thr Ser Gly Ile His Ala Ile Thr Val Phe
            370                 375                 380
Cys Ser Trp Asp Tyr Lys Val Thr Gln Lys Arg Ala Ser Arg Leu Gln
385                 390                 395                 400
Gln Asp Asn Ile Arg Thr Arg Leu Lys Glu Leu Leu Ala Glu Trp Gln
                405                 410                 415
Leu Arg Gln Ser Pro Arg Ser Val Cys Gly Thr Leu Arg Gln Ala Ala
            420                 425                 430
Val Leu Gly Leu Val Trp Leu Leu Cys Leu Gly Thr Ala Leu Gly Cys
            435                 440                 445
Ala Val Ala Val His Val Phe Ser Glu Phe Met Ile Gln Ser Pro Glu
    450                 455                 460
Ala Ala Gly Gln Glu Ala Leu Leu Val Leu Pro Leu Val Val Gly
465                 470                 475                 480
Leu Leu Asn Leu Gly Ala Pro Tyr Leu Cys Arg Val Leu Ala Ala Leu
                485                 490                 495
Glu Pro His Asp Ser Pro Val Met Glu Val Tyr Val Ala Ile Cys Arg
```

```
                500             505                 510
Asn Leu Ile Leu Lys Leu Ala Ile Leu Gly Thr Leu Cys Tyr His Trp
            515                 520                 525

Leu Asp His Arg Val Gly Val Leu Gln Gly Gln Cys Trp Glu Asp Phe
            530                 535             540

Val Gly Gln Glu Leu Tyr Arg Phe Leu Val Met Asp Phe Val Leu Met
545                 550                 555                 560

Leu Leu Asp Thr Leu Phe Gly Glu Leu Val Trp Arg Ile Ile Ser Glu
                565                 570                 575

Lys Lys Leu Lys Arg Arg Lys Pro Glu Phe Asp Ile Ala Arg Asn
            580                 585                 590

Val Leu Glu Leu Ile Tyr Gly Gln Thr Leu Thr Trp Leu Gly Val Leu
            595                 600                 605

Phe Ser Pro Leu Leu Pro Ala Val Gln Ile Ile Lys Leu Leu Leu Val
            610                 615                 620

Phe Tyr Val Lys Lys Thr Ser Leu Leu Ala Asn Cys Gln Ala Pro Arg
625                 630                 635                 640

Arg Pro Trp Leu Ala Ser His Met Ser Thr Ile Phe Leu Thr Leu Leu
                645                 650                 655

Cys Phe Pro Ala Phe Leu Gly Ala Ala Val Phe Leu Cys Tyr Ala Val
                660                 665                 670

Trp Gln Val Lys Pro Ser Ser Thr Cys Gly Pro Phe Arg Thr Leu Asp
            675                 680                 685

Thr Met Tyr Glu Ala Gly Arg Val Trp Val Arg His Leu Glu Thr Ala
            690                 695                 700

Gly Pro Arg Val Ser Trp Leu Pro Trp Val His Arg Tyr Leu Val Glu
705                 710                 715                 720

Asn Thr Phe Phe Val Phe Leu Val Ser Ala Leu Leu Leu Ala Val Ile
                725                 730                 735

Tyr Leu Asn Ile Gln Val Val Arg Gly Gln Arg Lys Val Ile Cys Leu
                740                 745                 750

Leu Lys Glu Gln Ile Ser Asn Glu Gly Glu Asp Lys Ile Phe Leu Ile
            755                 760                 765

Asn Lys Leu His Ser Ile Tyr Glu Arg Lys Glu Arg Glu Arg Ser
            770                 775                 780

Arg Val Gly Thr Thr Glu Glu Ala Val Ala Pro Ser Ala Leu Leu Thr
785                 790                 795                 800

Asp Glu Gln Asp Ala
                805

<210> SEQ ID NO 39
<211> LENGTH: 770
<212> TYPE: PRT
<213> ORGANISM: Nomascus leucogenys

<400> SEQUENCE: 39

Met Ala Gln Pro Leu Ala Phe Ile Leu Asp Val Pro Glu Thr Pro Gly
1               5                   10                  15

Asp Gln Gly Gln Asp Pro Ser Pro Tyr Asp Glu Ser Glu Val His Asp
            20                  25                  30

Ser Phe Gln Gln Leu Ile Gln Glu Gln Ser Gln Cys Glu Ala Gln Glu
        35                  40                  45

Gly Leu Glu Leu Gln Gln Arg Glu Arg Glu Ala Thr Gly Ser Gly Gln
    50                  55                  60
```

```
Gln Thr Leu Trp Arg Pro Glu Gly Thr Gln Ser Ala Ala Thr Leu Arg
 65                  70                  75                  80

Ile Leu Ala Ser Met Pro Ser Arg Thr Ile Gly Arg Ser Arg Gly Ala
                 85                  90                  95

Ile Ile Ser Gln Tyr Tyr Asn Arg Thr Val Gln Leu Arg Arg Arg Ser
            100                 105                 110

Ser Arg Pro Leu Leu Gly Asn Phe Val Arg Ser Ala Arg Pro Ser Leu
        115                 120                 125

Arg Leu Tyr Asp Leu Glu Leu Asp Pro Val Ala Arg Glu Glu Glu Glu
    130                 135                 140

Lys Gln Ser Leu Leu Val Lys Glu Leu Gln Ser Leu Ala Val Ala Gln
145                 150                 155                 160

Arg Asp His Met Leu Arg Gly Met Pro Leu Ser Leu Ala Glu Lys Arg
                165                 170                 175

Ser Leu Arg Glu Lys Ser Arg Thr Leu Arg Gly Lys Trp Arg Gly Gln
            180                 185                 190

Pro Gly Ser Gly Gly Val Cys Ser Cys Cys Gly Arg Leu Arg Tyr Ala
        195                 200                 205

Cys Val Leu Ala Leu His Ser Leu Gly Leu Ala Leu Leu Ser Ala Leu
    210                 215                 220

Gln Ala Leu Thr Pro Trp Arg Tyr Ala Leu Lys Arg Ile Gly Gly Gln
225                 230                 235                 240

Phe Gly Ser Ser Val Leu Ser Tyr Phe Leu Phe Leu Lys Thr Leu Leu
                245                 250                 255

Ala Phe Asn Ala Leu Leu Leu Leu Leu Val Ala Phe Ile Met Gly
            260                 265                 270

Pro Gln Val Ala Phe Pro Pro Thr Leu Pro Gly Pro Ala Pro Val Cys
        275                 280                 285

Thr Gly Leu Glu Leu Leu Thr Gly Ala Gly Cys Phe Thr His Thr Val
    290                 295                 300

Met Tyr Tyr Gly His Tyr Ser Asn Ala Thr Leu Asn Gln Pro Cys Gly
305                 310                 315                 320

Ser Pro Leu Asp Gly Ser Gln Cys Thr Pro Arg Ala Gly Gly Leu Pro
                325                 330                 335

Tyr Asn Met Pro Leu Ala Tyr Leu Ser Thr Val Gly Met Ser Phe Phe
            340                 345                 350

Ile Thr Cys Ile Thr Leu Val Tyr Ser Met Ala His Ser Phe Gly Glu
        355                 360                 365

Ser Tyr Arg Val Gly Ser Thr Ser Gly Ile His Ala Leu Thr Val Phe
    370                 375                 380

Cys Ser Trp Asp Tyr Lys Val Thr Gln Lys Arg Ala Ser Arg Leu Gln
385                 390                 395                 400

Gln Asp Asn Ile Arg Thr Arg Leu Lys Glu Leu Leu Ala Glu Trp Gln
                405                 410                 415

Leu Arg Gln Ser Pro Arg Ser Val Cys Gly Arg Leu Arg Gln Ala Ala
            420                 425                 430

Val Leu Gly Leu Val Trp Leu Leu Cys Leu Gly Thr Ala Leu Gly Cys
        435                 440                 445

Ala Val Ala Ile His Val Phe Ser Glu Phe Met Ile Gln Ser Pro Glu
    450                 455                 460

Ala Ala Gly Gln Glu Ala Ala Leu Leu Val Leu Pro Leu Val Val Gly
465                 470                 475                 480

Leu Leu Asn Leu Gly Ala Pro Tyr Leu Cys Arg Val Leu Ala Ala Leu
```

```
                485                 490                 495
Glu Pro His Asp Ser Pro Val Leu Glu Val Tyr Val Ala Ile Cys Arg
            500                 505                 510

Asn Leu Ile Leu Lys Leu Ala Ile Leu Gly Thr Leu Cys Tyr His Trp
            515                 520                 525

Leu Gly Arg Arg Val Gly Val Leu Gln Gly Gln Cys Trp Glu Asp Phe
            530                 535                 540

Val Gly Gln Glu Leu Tyr Arg Phe Leu Val Met Asp Phe Ile Leu Met
545                 550                 555                 560

Leu Leu Asp Thr Leu Phe Gly Glu Leu Val Trp Arg Ile Ile Ser Glu
            565                 570                 575

Lys Lys Leu Lys Arg Arg Lys Pro Glu Phe Asp Ile Ala Arg Asn
            580                 585                 590

Val Leu Glu Leu Ile Tyr Gly Gln Thr Leu Thr Trp Leu Gly Val Leu
            595                 600                 605

Phe Ser Pro Leu Leu Pro Ala Val Gln Ile Ile Lys Leu Leu Leu Val
            610                 615                 620

Phe Tyr Ile Lys Lys Thr Ser Leu Leu Ala Asn Cys Gln Ala Pro Arg
625                 630                 635                 640

Arg Pro Trp Leu Ala Ser His Met Ser Thr Val Phe Leu Thr Leu Leu
            645                 650                 655

Cys Phe Pro Ala Phe Leu Gly Thr Ala Val Phe Leu Cys Tyr Ala Val
            660                 665                 670

Trp Gln Val Lys Pro Ser Ser Thr Cys Gly Pro Phe Arg Thr Leu Asp
            675                 680                 685

Thr Met Tyr Glu Ala Gly Arg Val Ser Phe His Ser Gly Ala Val Gly
            690                 695                 700

Ala Arg Ile Gln Gly Ser Arg Gln Leu Val Pro Val Cys Pro Lys His
705                 710                 715                 720

Ser Trp Asp Gly Ser His Ile Ala Trp Val Val Asn Thr Glu Glu Gly
            725                 730                 735

Glu Asp Lys Ile Phe Leu Ile Asn Lys Leu His Ser Ile Tyr Glu Arg
            740                 745                 750

Lys Glu Arg Glu Glu Arg Ser Arg Val Gly Thr Thr Glu Glu Ala Ala
            755                 760                 765

His Arg
    770

<210> SEQ ID NO 40
<211> LENGTH: 805
<212> TYPE: PRT
<213> ORGANISM: Rhinopithecus roxellana

<400> SEQUENCE: 40

Met Ala Gln Pro Leu Ala Phe Ile Leu Asp Val Pro Glu Thr Pro Gly
1               5                  10                  15

Asp Gln Gly Gln Glu Pro Ser Pro Tyr Asp Glu Ser Glu Val His His
            20                  25                  30

Ser Phe His Gln Leu Ile Gln Glu Gln Ser Gln Trp Val Ala Gln Glu
        35                  40                  45

Gly Leu Glu Leu Gln Gln Arg Glu Gln Glu Ala Thr Gly Ser Gly Gln
    50                  55                  60

Gln Thr Leu Arg Arg Pro Glu Gly Thr Gln Ser Thr Ala Thr Leu Arg
65                  70                  75                  80
```

```
Ile Leu Ala Ser Met Pro Ser Arg Thr Ile Gly Arg Ser Arg Gly Ala
                85                  90                  95

Ile Ile Ser Gln Tyr Tyr Ser Arg Thr Val Gln Leu Arg Arg Arg Ser
            100                 105                 110

Ser Arg Pro Leu Leu Gly Asn Leu Val Leu Ser Ala Arg Pro Ser Leu
            115                 120                 125

Arg Leu Tyr Asp Leu Glu Leu Asp Pro Thr Ala Arg Glu Glu Glu Glu
            130                 135                 140

Lys Gln Ser Leu Leu Val Lys Glu Leu Gln Ser Leu Ala Val Ala Gln
145                 150                 155                 160

Arg Asp His Met Leu Arg Gly Met Pro Leu Ser Leu Ala Glu Lys Arg
                165                 170                 175

Ser Leu Arg Glu Lys Ser Arg Thr Pro Thr Gly Lys Trp Arg Gly Gln
            180                 185                 190

Arg Gly Gly Gly Gly Val Phe Ser Cys Cys Gly Arg Leu Arg Tyr Ala
            195                 200                 205

Cys Val Leu Ala Leu His Ser Leu Gly Leu Ala Leu Leu Ser Gly Leu
            210                 215                 220

Gln Ala Leu Thr Pro Trp Arg Tyr Ala Leu Lys Arg Ile Gly Gly Gln
225                 230                 235                 240

Phe Gly Ser Ser Val Leu Ser Tyr Phe Leu Phe Leu Lys Thr Leu Leu
                245                 250                 255

Ala Phe Asn Ala Leu Leu Leu Leu Leu Val Ala Phe Ile Met Gly
                260                 265                 270

Pro Gln Val Ala Phe Leu Pro Thr Leu Pro Gly Pro Ala Pro Val Cys
                275                 280                 285

Thr Gly Leu Glu Leu Leu Thr Gly Ala Gly Cys Phe Thr His Thr Val
                290                 295                 300

Met Phe Tyr Gly His Tyr Ser Asn Ala Thr Leu Asn Gln Pro Cys Gly
305                 310                 315                 320

Ser Pro Leu Asp Gly Ser Gln Cys Thr Pro Arg Ala Gly Gly Leu Pro
                325                 330                 335

Tyr Asn Met Pro Leu Ala Tyr Leu Tyr Thr Val Gly Ala Gly Phe Phe
                340                 345                 350

Ile Thr Cys Ile Thr Leu Val Tyr Ser Met Ala His Ser Phe Gly Glu
                355                 360                 365

Ser Tyr Arg Val Gly Ser Thr Ser Gly Ile His Ala Ile Thr Val Phe
                370                 375                 380

Cys Ser Trp Asp Tyr Lys Val Thr Gln Lys Arg Ala Ser Arg Leu Gln
385                 390                 395                 400

Gln Asp Asn Ile Arg Thr Arg Leu Lys Glu Leu Leu Ala Glu Trp Gln
                405                 410                 415

Leu Arg Gln Ser Pro Arg Ser Val Cys Gly Arg Leu Arg Gln Ala Ala
                420                 425                 430

Ala Leu Gly Leu Ala Trp Leu Leu Cys Leu Gly Thr Ala Leu Gly Cys
                435                 440                 445

Ala Val Ala Val His Val Phe Ser Glu Phe Leu Ile Gln Ser Pro Glu
            450                 455                 460

Ala Ala Gly Gln Glu Ala Leu Leu Val Leu Pro Leu Val Val Gly
465                 470                 475                 480

Leu Leu Asn Leu Gly Ala Pro Tyr Leu Cys Arg Val Leu Ala Ala Leu
                485                 490                 495

Glu Pro His Asp Ser Pro Val Leu Glu Val Tyr Val Ala Ile Cys Arg
```

```
                    500                 505                 510
Asn Leu Ile Leu Lys Leu Ala Ile Leu Gly Thr Leu Cys Tyr His Trp
                515                 520                 525

Leu Gly Arg Arg Val Ala Val Leu Gln Gly Gln Cys Trp Glu Asp Phe
            530                 535                 540

Val Gly Gln Glu Leu Tyr Arg Phe Leu Val Met Asp Phe Val Leu Met
545                 550                 555                 560

Leu Leu Asp Thr Leu Phe Gly Glu Leu Val Trp Arg Ile Ile Ser Glu
                565                 570                 575

Lys Lys Leu Lys Arg Arg Lys Pro Glu Phe Asp Ile Ala Arg Asn
            580                 585                 590

Val Leu Glu Leu Ile Tyr Gly Gln Thr Leu Thr Trp Leu Gly Val Leu
                595                 600                 605

Phe Ser Pro Leu Leu Pro Ala Val Gln Ile Ile Lys Leu Leu Leu Val
            610                 615                 620

Phe Tyr Val Lys Lys Thr Ser Leu Leu Ala Asn Cys Gln Ala Pro Arg
625                 630                 635                 640

Gln Pro Trp Leu Ala Ser His Met Ser Thr Val Phe Leu Thr Leu Leu
                645                 650                 655

Cys Phe Pro Ala Phe Leu Gly Ala Ala Val Phe Leu Cys Tyr Ala Val
            660                 665                 670

Trp Gln Val Lys Pro Ser Ser Thr Cys Gly Pro Phe Arg Thr Leu Asp
            675                 680                 685

Ser Met Tyr Glu Ala Ser Arg Val Trp Val Arg Tyr Leu Glu Ala Ala
            690                 695                 700

Gly Pro Arg Val Ser Trp Leu Pro Trp Val His Arg Tyr Leu Val Glu
705                 710                 715                 720

Asn Thr Phe Phe Val Phe Leu Val Ser Ala Leu Leu Leu Ala Val Ile
                725                 730                 735

Tyr Leu Asn Ile Gln Val Val Arg Gly Gln Arg Arg Val Ile Cys Leu
                740                 745                 750

Leu Lys Glu Gln Ile Ser Asn Glu Gly Glu Asp Lys Ile Phe Leu Ile
                755                 760                 765

Asn Lys Leu His Ser Ile Tyr Glu Arg Lys Glu Arg Glu Glu Arg Ser
            770                 775                 780

Arg Val Gly Thr Thr Glu Glu Thr Ala Ala Pro Pro Ala Leu Leu Thr
785                 790                 795                 800

Glu Glu Arg Gly Asp
            805

<210> SEQ ID NO 41
<211> LENGTH: 805
<212> TYPE: PRT
<213> ORGANISM: Chlorocebus sabaeus

<400> SEQUENCE: 41

Met Ala Gln Pro Leu Ala Phe Ile Leu Asp Val Pro Glu Thr Pro Gly
1               5                   10                  15

Glu Gln Gly Gln Glu Pro Ser Pro Tyr Asp Glu Ser Glu Val His His
                20                  25                  30

Ser Phe His Gln Leu Ile Gln Glu Gln Ser Gln Trp Ala Ala Gln Glu
            35                  40                  45

Gly Leu Glu Leu Gln Gln Arg Glu Gln Glu Ala Thr Gly Ser Gly Gln
50                  55                  60
```

-continued

```
Gln Thr Leu Arg Arg Pro Glu Gly Thr Gln Ser Thr Ala Thr Leu Arg
 65                  70                  75                  80

Ile Leu Ala Ser Met Pro Ser Arg Thr Ile Gly Arg Ser Arg Gly Ala
                 85                  90                  95

Ile Ile Ser Gln Tyr Tyr Ser Arg Thr Val Gln Leu Arg Arg Arg Ser
            100                 105                 110

Ser Arg Pro Leu Leu Gly Ser Phe Val Leu Ser Ala Arg Pro Ser Leu
        115                 120                 125

Arg Leu Tyr Asp Leu Glu Leu Asp Pro Thr Ala Arg Glu Glu Glu Glu
    130                 135                 140

Lys Gln Ser Leu Leu Val Lys Glu Leu Gln Ser Leu Ala Val Ala Gln
145                 150                 155                 160

Arg Asp His Met Leu Arg Gly Met Pro Leu Ser Leu Ala Glu Lys Arg
                165                 170                 175

Ser Leu Arg Glu Lys Ser Arg Thr Pro Arg Gly Lys Trp Arg Gly Gln
            180                 185                 190

Gln Gly Ser Gly Gly Val Cys Ser Cys Cys Gly Arg Leu Arg Tyr Ala
        195                 200                 205

Cys Val Leu Ala Leu His Ser Leu Gly Leu Ala Leu Leu Ser Gly Leu
    210                 215                 220

Gln Ala Leu Thr Pro Trp Arg Tyr Ala Leu Lys Arg Ile Gly Gly Gln
225                 230                 235                 240

Phe Gly Ser Ser Val Leu Ser Tyr Phe Leu Phe Leu Lys Thr Leu Leu
                245                 250                 255

Ala Phe Asn Ala Leu Leu Leu Leu Leu Val Ala Phe Ile Met Gly
            260                 265                 270

Pro Gln Val Ala Phe Pro Pro Ala Leu Pro Gly Pro Ala Pro Ile Cys
            275                 280                 285

Thr Gly Leu Glu Leu Leu Thr Gly Ala Gly Cys Phe Thr His Thr Val
        290                 295                 300

Met Phe Tyr Gly His Tyr Ser Asn Ala Thr Leu Asn Gln Pro Cys Gly
305                 310                 315                 320

Ser Pro Leu Asp Gly Ser Gln Cys Thr Pro Arg Ala Gly Gly Leu Pro
                325                 330                 335

Tyr Asn Met Pro Leu Ala Tyr Leu Tyr Thr Val Gly Ala Gly Phe Phe
            340                 345                 350

Ile Ser Cys Ile Thr Leu Val Tyr Ser Met Ala His Ser Phe Gly Glu
        355                 360                 365

Ser Tyr Arg Val Gly Ser Thr Ser Gly Ile His Ala Ile Thr Val Phe
    370                 375                 380

Cys Ser Trp Asp Tyr Lys Val Thr Gln Lys Arg Ala Ser Arg Leu Gln
385                 390                 395                 400

Gln Asp Asn Ile Arg Thr Arg Leu Lys Glu Leu Leu Ala Glu Trp Gln
                405                 410                 415

Leu Arg Gln Ser Pro Arg Ser Val Cys Gly Arg Leu Arg Gln Ala Ala
            420                 425                 430

Ala Leu Gly Leu Ala Trp Leu Leu Cys Leu Gly Thr Ala Leu Gly Cys
        435                 440                 445

Ala Val Ala Ile His Val Phe Ser Glu Phe Leu Ile Gln Ser Pro Glu
    450                 455                 460

Ala Ala Gly Gln Glu Ala Ser Leu Leu Val Leu Pro Leu Val Val Gly
465                 470                 475                 480

Leu Leu Asn Leu Gly Ala Pro Tyr Leu Cys Arg Val Leu Ala Ala Leu
```

```
                485                 490                 495
Glu Pro His Asp Ser Pro Val Leu Glu Val Tyr Val Ala Ile Cys Arg
                500                 505                 510

Asn Leu Ile Leu Lys Leu Ala Ile Leu Gly Thr Leu Cys Tyr His Trp
                515                 520                 525

Leu Gly Arg Arg Val Ala Val Leu Gln Ser Gln Cys Trp Glu Asp Phe
            530                 535                 540

Val Gly Gln Glu Leu Tyr Arg Phe Leu Val Met Asp Phe Val Leu Met
545                 550                 555                 560

Leu Leu Asp Thr Leu Phe Gly Glu Leu Val Trp Arg Ile Ile Ser Glu
                565                 570                 575

Lys Lys Leu Lys Arg Arg Lys Pro Glu Phe Asp Ile Ala Arg Asn
            580                 585                 590

Val Leu Glu Leu Ile Tyr Gly Gln Thr Leu Thr Trp Leu Gly Val Leu
                595                 600                 605

Phe Ser Pro Leu Leu Pro Ala Val Gln Ile Ile Lys Leu Leu Leu Val
            610                 615                 620

Phe Tyr Val Lys Lys Thr Ser Leu Leu Ala Asn Cys Gln Ala Pro Arg
625                 630                 635                 640

Arg Pro Trp Leu Ala Ser His Met Ser Thr Val Phe Leu Thr Leu Leu
                645                 650                 655

Cys Phe Pro Ala Phe Leu Gly Ala Ala Ile Phe Leu Cys Tyr Ala Val
                660                 665                 670

Trp Gln Val Lys Pro Ser Ser Thr Cys Gly Pro Phe Arg Thr Leu Asp
            675                 680                 685

Ser Met Tyr Glu Ala Gly Arg Val Trp Val Arg Tyr Leu Glu Ala Ala
690                 695                 700

Gly Pro Arg Val Ser Trp Leu Pro Trp Val His Arg Tyr Leu Val Glu
705                 710                 715                 720

Asn Thr Phe Phe Val Phe Leu Val Ser Ala Leu Leu Leu Ala Val Ile
                725                 730                 735

Tyr Leu Asn Ile Gln Val Val Arg Gly Gln Arg Arg Val Ile Cys Leu
            740                 745                 750

Leu Lys Glu Gln Ile Ser Asn Glu Gly Glu Asp Lys Ile Phe Leu Ile
            755                 760                 765

Asn Lys Leu His Ser Ile Tyr Glu Arg Lys Arg Glu Glu Arg Ser
            770                 775                 780

Arg Val Gly Thr Thr Glu Glu Thr Ala Ala Pro Pro Ala Leu Leu Thr
785                 790                 795                 800

Asp Glu Arg Asp Asp
                805

<210> SEQ ID NO 42
<211> LENGTH: 806
<212> TYPE: PRT
<213> ORGANISM: Macaca fascicularis

<400> SEQUENCE: 42

Met Ala Gln Pro Leu Ala Phe Ile Leu Asp Val Pro Glu Thr Pro Gly
1               5                   10                  15

Asp Gln Gly Ser Gln Glu Pro Ser Pro Tyr Asp Glu Ser Glu Val His
                20                  25                  30

Asp Ser Phe His Gln Leu Ile Gln Glu Gln Ser Gln Trp Ala Ala Gln
            35                  40                  45
```

```
Glu Gly Leu Glu Leu Gln Gln Arg Glu Gln Glu Ala Thr Gly Ser Gly
 50                  55                  60

Gln Gln Thr Leu Arg Arg Pro Glu Gly Thr Gln Ser Thr Ala Thr Leu
 65                  70                  75                  80

Arg Ile Leu Ala Ser Met Pro Ser Arg Thr Ile Gly Arg Ser Arg Gly
                 85                  90                  95

Ala Ile Ile Ser Gln Tyr Tyr Ser Arg Thr Val Gln Leu Arg Arg Arg
            100                 105                 110

Ser Ser Arg Pro Leu Leu Gly Asn Phe Val Leu Ser Ala Arg Pro Ser
            115                 120                 125

Leu Arg Leu Tyr Asp Leu Glu Leu Asp Pro Thr Ala Arg Glu Glu Glu
130                 135                 140

Glu Lys Gln Ser Leu Leu Val Lys Glu Leu Gln Ser Leu Ala Val Ala
145                 150                 155                 160

Gln Arg Asp His Met Leu Arg Gly Met Pro Leu Ser Leu Ala Glu Lys
                165                 170                 175

Arg Ser Leu Arg Glu Lys Ser Arg Thr Pro Arg Gly Lys Trp Arg Gly
            180                 185                 190

Gln Gln Gly Ser Gly Gly Val Cys Ser Cys Cys Gly Arg Leu Arg Tyr
            195                 200                 205

Ala Cys Val Leu Ala Leu His Ser Leu Gly Leu Ala Leu Leu Ser Gly
210                 215                 220

Leu Gln Ala Leu Thr Pro Trp Arg Tyr Ala Leu Lys Arg Ile Gly Gly
225                 230                 235                 240

Gln Phe Gly Ser Ser Val Leu Ser Tyr Phe Leu Phe Leu Lys Thr Leu
                245                 250                 255

Leu Ala Phe Asn Ala Leu Leu Gln Leu Leu Val Ala Phe Ile Val
            260                 265                 270

Gly Pro Gln Val Ala Phe Pro Pro Ala Leu Pro Gly Pro Ala Pro Ile
            275                 280                 285

Cys Thr Gly Leu Glu Leu Leu Thr Gly Ala Gly Cys Phe Thr His Thr
            290                 295                 300

Val Met Phe Tyr Gly His Tyr Ser Asn Ala Thr Leu Asn Gln Pro Cys
305                 310                 315                 320

Gly Ser Pro Leu Asp Gly Ser Gln Cys Thr Pro Arg Ala Gly Gly Leu
                325                 330                 335

Pro Tyr Asn Met Pro Leu Ala Tyr Leu Tyr Thr Val Gly Ala Gly Phe
            340                 345                 350

Phe Ile Thr Cys Ile Thr Leu Val Tyr Ser Met Ala His Ser Phe Gly
            355                 360                 365

Glu Ser Tyr Arg Val Gly Ser Thr Ser Gly Ile His Ala Ile Thr Val
370                 375                 380

Phe Cys Ser Trp Asp Tyr Lys Val Thr Gln Lys Arg Ala Ser Arg Leu
385                 390                 395                 400

Gln Gln Asp Asn Ile Arg Thr Arg Leu Lys Glu Leu Leu Ala Glu Trp
                405                 410                 415

Gln Leu Arg Gln Ser Pro Arg Ser Val Cys Gly Arg Leu Arg Gln Ala
            420                 425                 430

Ala Ala Leu Gly Leu Ala Trp Leu Cys Leu Gly Thr Ala Leu Gly
            435                 440                 445

Cys Ala Val Ala Ile His Val Phe Ser Glu Phe Leu Ile Gln Ser Pro
450                 455                 460

Glu Ala Ala Gly Gln Glu Ala Ala Leu Leu Val Leu Pro Leu Val Val
```

```
              465                 470                 475                 480
    Gly Leu Leu Asn Leu Gly Ala Pro Tyr Leu Cys Arg Val Leu Ala Ala
                    485                 490                 495

Leu Glu Pro His Asp Ser Pro Val Leu Glu Val Tyr Val Ala Ile Cys
                500                 505                 510

Arg Asn Leu Ile Leu Lys Leu Ala Ile Leu Gly Thr Leu Cys Tyr His
                515                 520                 525

Trp Leu Gly Arg Arg Val Ala Val Leu Gln Asp Gln Cys Trp Glu Asp
                530                 535                 540

Phe Val Gly Gln Glu Leu Tyr Arg Phe Leu Val Met Asp Phe Val Leu
    545                 550                 555                 560

Met Leu Leu Asp Thr Leu Phe Gly Glu Leu Val Trp Arg Ile Ile Ser
                565                 570                 575

Glu Lys Lys Leu Lys Arg Arg Lys Pro Glu Phe Asp Ile Ala Arg
                580                 585                 590

Asn Val Leu Glu Leu Ile Tyr Gly Gln Thr Leu Thr Trp Leu Gly Val
                595                 600                 605

Leu Phe Ser Pro Leu Leu Pro Ala Val Gln Ile Ile Lys Leu Leu Leu
                610                 615                 620

Val Phe Tyr Val Lys Lys Thr Ser Leu Leu Ala Asn Cys Gln Ala Pro
    625                 630                 635                 640

Arg Arg Pro Trp Leu Ala Ser His Met Ser Thr Ile Phe Leu Thr Leu
                645                 650                 655

Leu Cys Phe Pro Ala Phe Leu Gly Ala Ala Ile Phe Leu Cys Tyr Ala
                660                 665                 670

Val Trp Gln Val Lys Pro Ser Ser Thr Cys Gly Pro Phe Arg Thr Leu
                675                 680                 685

Asp Ser Met Tyr Glu Ala Gly Arg Val Trp Val Arg Tyr Leu Glu Ala
                690                 695                 700

Ala Gly Pro Arg Val Ser Trp Leu Pro Trp Val His Arg Tyr Leu Val
    705                 710                 715                 720

Glu Asn Thr Phe Phe Val Phe Leu Val Ser Ala Leu Leu Ala Val
                725                 730                 735

Ile Tyr Leu Asn Ile Gln Val Val Arg Gly Gln Arg Val Ile Cys
                740                 745                 750

Leu Leu Lys Glu Gln Ile Ser Asn Glu Gly Asp Lys Ile Phe Leu
                755                 760                 765

Ile Asn Lys Leu His Ser Ile Tyr Glu Arg Lys Glu Arg Glu Arg
                770                 775                 780

Ser Arg Val Gly Thr Thr Glu Glu Thr Ala Ala Pro Pro Thr Leu Leu
    785                 790                 795                 800

Thr Asp Glu Arg Asp Asp
                805
```

<210> SEQ ID NO 43
<211> LENGTH: 806
<212> TYPE: PRT
<213> ORGANISM: Macaca mulatta

<400> SEQUENCE: 43

```
    Met Ala Gln Pro Leu Ala Phe Ile Leu Asp Val Pro Glu Thr Pro Gly
    1                   5                  10                  15

Asp Gln Gly Ser Gln Glu Pro Ser Pro Tyr Asp Glu Ser Glu Val His
                20                  25                  30
```

-continued

Asp Ser Phe His Gln Leu Ile Gln Glu Gln Ser Gln Trp Ala Ala Gln
            35                  40                  45
Glu Gly Leu Glu Leu Gln Gln Arg Glu Gln Ala Thr Gly Ser Gly
 50                  55                  60
Gln Gln Thr Leu Arg Arg Pro Glu Gly Thr Gln Ser Thr Ala Thr Leu
 65                  70                  75                  80
Arg Ile Leu Ala Ser Met Pro Ser Arg Thr Ile Gly Arg Ser Arg Gly
                 85                  90                  95
Ala Ile Ile Ser Gln Tyr Tyr Ser Arg Thr Val Gln Leu Arg Arg Arg
                100                 105                 110
Ser Ser Arg Pro Leu Leu Gly Asn Phe Val Leu Ser Ala Arg Pro Ser
                115                 120                 125
Leu Arg Leu Tyr Asp Leu Glu Leu Asp Pro Thr Ala Arg Glu Glu Glu
                130                 135                 140
Glu Lys Gln Ser Leu Leu Val Lys Glu Leu Gln Ser Leu Ala Val Ala
145                 150                 155                 160
Gln Arg Asp His Met Leu Arg Gly Met Pro Leu Ser Leu Ala Glu Lys
                165                 170                 175
Arg Ser Leu Arg Glu Lys Ser Arg Thr Pro Arg Gly Lys Trp Arg Gly
                180                 185                 190
Gln Gln Gly Ser Gly Gly Val Cys Ser Cys Cys Gly Arg Leu Arg Tyr
                195                 200                 205
Ala Cys Val Leu Ala Leu His Ser Leu Gly Leu Ala Leu Leu Ser Gly
                210                 215                 220
Leu Gln Ala Leu Thr Pro Trp Arg Tyr Ala Leu Lys Arg Ile Gly Gly
225                 230                 235                 240
Gln Phe Gly Ser Ser Val Leu Ser Tyr Phe Leu Phe Leu Lys Thr Leu
                245                 250                 255
Leu Ala Phe Asn Ala Leu Leu Gln Leu Leu Val Ala Phe Ile Val
                260                 265                 270
Gly Pro Gln Val Ala Phe Pro Pro Ala Leu Pro Gly Pro Ala Pro Ile
                275                 280                 285
Cys Thr Gly Leu Glu Leu Leu Thr Gly Ala Gly Cys Phe Thr His Thr
290                 295                 300
Val Met Phe Tyr Gly His Tyr Ser Asn Ala Thr Leu Asn Gln Pro Cys
305                 310                 315                 320
Gly Ser Pro Leu Asp Gly Ser Gln Cys Thr Pro Arg Ala Gly Gly Leu
                325                 330                 335
Pro Tyr Asn Met Pro Leu Ala Tyr Leu Tyr Thr Val Gly Ala Gly Phe
                340                 345                 350
Phe Ile Thr Cys Ile Thr Leu Val Tyr Ser Met Ala His Ser Phe Gly
                355                 360                 365
Glu Ser Tyr Arg Val Gly Ser Thr Gly Ile His Ala Ile Thr Val
                370                 375                 380
Phe Cys Ser Trp Asp Tyr Lys Val Thr Gln Lys Arg Ala Ser Arg Leu
385                 390                 395                 400
Gln Gln Asp Asn Ile Arg Thr Arg Leu Lys Glu Leu Leu Ala Glu Trp
                405                 410                 415
Gln Leu Arg Gln Ser Pro Arg Ser Val Cys Gly Arg Leu Arg Gln Ala
                420                 425                 430
Ala Ala Leu Gly Leu Ala Trp Leu Cys Leu Gly Thr Ala Leu Gly
                435                 440                 445
Cys Ala Val Ala Ile His Val Phe Ser Glu Phe Leu Ile Gln Ser Pro

```
                450                 455                 460
Glu Ala Gly Gln Glu Ala Leu Leu Val Leu Pro Leu Val Val
465                 470                 475                 480

Gly Leu Leu Asn Leu Gly Ala Pro Tyr Leu Cys Arg Val Leu Ala Ala
                485                 490                 495

Leu Glu Pro His Asp Ser Pro Val Leu Glu Val Tyr Val Ala Ile Cys
                500                 505                 510

Arg Asn Leu Ile Leu Lys Leu Ala Ile Leu Gly Thr Leu Cys Tyr His
                515                 520                 525

Trp Leu Gly Arg Arg Val Ala Val Leu Gln Asp Gln Cys Trp Glu Asp
                530                 535                 540

Phe Val Gly Gln Glu Leu Tyr Arg Phe Leu Val Met Asp Phe Val Leu
545                 550                 555                 560

Met Leu Leu Asp Thr Leu Phe Gly Glu Leu Val Trp Arg Ile Ile Ser
                565                 570                 575

Glu Lys Lys Leu Lys Arg Arg Lys Pro Glu Phe Asp Ile Ala Arg
                580                 585                 590

Asn Val Leu Glu Leu Ile Tyr Gly Gln Thr Leu Thr Trp Leu Gly Val
                595                 600                 605

Leu Phe Ser Pro Leu Leu Pro Ala Val Gln Ile Ile Lys Leu Leu Leu
                610                 615                 620

Val Phe Tyr Val Lys Lys Thr Ser Leu Leu Ala Asn Cys Gln Ala Pro
625                 630                 635                 640

Arg Arg Pro Trp Leu Ala Ser His Met Ser Thr Ile Phe Leu Thr Leu
                645                 650                 655

Leu Cys Phe Pro Ala Phe Leu Gly Ala Ala Ile Phe Leu Cys Tyr Ala
                660                 665                 670

Val Trp Gln Val Lys Pro Ser Ser Thr Cys Gly Pro Phe Arg Thr Leu
                675                 680                 685

Asp Ser Met Tyr Glu Ala Gly Arg Val Trp Val Arg Tyr Leu Glu Ala
                690                 695                 700

Ala Gly Pro Arg Val Ser Trp Leu Pro Trp Val His Arg Tyr Leu Val
705                 710                 715                 720

Glu Asn Thr Phe Phe Val Phe Leu Val Ser Ala Leu Leu Leu Ala Val
                725                 730                 735

Ile Tyr Leu Asn Ile Gln Val Val Arg Gly Gln Arg Val Ile Cys
                740                 745                 750

Leu Leu Lys Glu Gln Ile Ser Asn Glu Gly Glu Asp Lys Ile Phe Leu
                755                 760                 765

Ile Asn Lys Leu His Ser Ile Tyr Glu Arg Lys Glu Arg Glu Arg
                770                 775                 780

Ser Arg Val Gly Thr Thr Glu Glu Thr Ala Ala Pro Pro Thr Leu Leu
785                 790                 795                 800

Thr Asp Glu Arg Asp Asp
                805

<210> SEQ ID NO 44
<211> LENGTH: 675
<212> TYPE: PRT
<213> ORGANISM: Macaca nemestrina

<400> SEQUENCE: 44

Met Ala Gln Pro Leu Ala Phe Ile Leu Asp Val Pro Glu Thr Pro Gly
1               5                   10                  15
```

```
Asp Gln Gly Ser Gln Glu Pro Ser Pro Tyr Asp Glu Ser Glu Val His
            20              25                  30

Asp Ser Phe His Gln Leu Ile Gln Glu Gln Ser Gln Trp Ala Ala Gln
        35              40                  45

Glu Gly Leu Glu Leu Gln Gln Arg Glu Gln Glu Ala Thr Gly Ser Gly
50              55                  60

Gln Gln Thr Leu Arg Arg Pro Glu Gly Thr Gln Ser Thr Ala Thr Leu
65              70                  75                  80

Arg Ile Leu Ala Ser Met Pro Ser Arg Thr Ile Gly Arg Ser Arg Gly
                85                  90                  95

Ala Ile Ile Ser Gln Tyr Tyr Ser Arg Thr Val Gln Leu Arg Arg Arg
            100                 105                 110

Ser Ser Arg Pro Leu Leu Gly Asp Phe Val Leu Ser Ala Arg Pro Ser
        115                 120                 125

Leu Arg Leu Tyr Asp Leu Glu Leu Asp Pro Thr Ala Arg Glu Glu Glu
    130                 135                 140

Glu Lys Gln Ser Leu Leu Val Lys Glu Leu Gln Ser Leu Ala Val Ala
145                 150                 155                 160

Gln Arg Asp His Met Leu Arg Gly Met Pro Leu Ser Leu Ala Glu Lys
                165                 170                 175

Arg Ser Leu Arg Glu Lys Ser Arg Thr Pro Arg Gly Lys Trp Arg Gly
            180                 185                 190

Gln Gln Gly Ser Gly Val Cys Ser Cys Gly Arg Leu Arg Tyr
        195                 200                 205

Ala Cys Val Leu Ala Leu His Ser Leu Gly Leu Ala Leu Leu Ser Gly
210                 215                 220

Leu Gln Ala Leu Thr Pro Trp Arg Tyr Ala Leu Lys Arg Ile Gly Gly
225                 230                 235                 240

Gln Phe Gly Ser Ser Val Leu Ser Tyr Phe Leu Phe Leu Lys Thr Leu
            245                 250                 255

Leu Ala Phe Asn Ala Leu Leu Gln Leu Leu Val Ala Cys Ile Val
            260                 265                 270

Gly Pro Gln Val Ala Phe Pro Pro Ala Leu Pro Gly Pro Ala Pro Ile
        275                 280                 285

Cys Thr Gly Leu Glu Leu Leu Thr Gly Ala Gly Cys Phe Thr His Thr
    290                 295                 300

Val Met Phe Tyr Gly His Tyr Ser Asn Ala Thr Leu Asn Gln Pro Cys
305                 310                 315                 320

Gly Ser Pro Leu Asp Gly Ser Gln Cys Thr Pro Arg Ala Gly Gly Leu
                325                 330                 335

Pro Tyr Asn Met Pro Leu Ala Tyr Leu Tyr Thr Val Gly Ala Gly Phe
            340                 345                 350

Phe Ile Thr Cys Ile Thr Leu Val Tyr Ser Met Ala His Ser Phe Gly
        355                 360                 365

Glu Ser Tyr Arg Val Gly Ser Thr Ser Gly Val His Ala Ile Thr Val
    370                 375                 380

Phe Cys Ser Trp Asp Tyr Lys Val Thr Gln Lys Arg Ala Ser Arg Leu
385                 390                 395                 400

Gln Gln Asp Asn Ile Arg Thr Arg Leu Lys Glu Leu Leu Ala Glu Trp
                405                 410                 415

Gln Leu Arg Gln Ser Pro Arg Ser Val Cys Gly Arg Leu Arg Gln Ala
            420                 425                 430

Ala Ala Leu Gly Leu Ala Trp Leu Leu Cys Leu Gly Thr Ala Leu Gly
```

```
                    435                 440                 445
        Cys Ala Val Ala Ile His Val Phe Ser Glu Phe Leu Ile Gln Ser Pro
        450                 455                 460
        Glu Ala Ala Gly Gln Glu Ala Ala Leu Leu Val Leu Pro Leu Val Val
        465                 470                 475                 480
        Gly Leu Leu Asn Leu Gly Ala Pro Tyr Leu Cys Arg Val Leu Ala Ala
                            485                 490                 495
        Leu Glu Pro His Asp Ser Pro Val Leu Glu Val Tyr Val Ala Ile Cys
                        500                 505                 510
        Arg Asn Leu Ile Leu Lys Leu Ala Ile Leu Gly Thr Leu Cys Tyr His
                        515                 520                 525
        Trp Leu Gly Arg Arg Val Ala Val Leu Gln Asp Gln Cys Trp Glu Asp
        530                 535                 540
        Phe Val Gly Gln Glu Leu Tyr Arg Phe Leu Val Met Asp Phe Val Leu
        545                 550                 555                 560
        Met Leu Leu Asp Thr Leu Phe Gly Glu Leu Val Trp Arg Ile Ile Ser
                        565                 570                 575
        Glu Lys Lys Leu Lys Arg Arg Lys Pro Glu Phe Asp Ile Ala Arg
                        580                 585                 590
        Asn Val Leu Glu Leu Ile Tyr Gly Gln Thr Leu Thr Trp Leu Gly Val
                        595                 600                 605
        Leu Phe Ser Pro Leu Leu Pro Ala Val Gln Ile Ile Lys Leu Leu Leu
                        610                 615                 620
        Val Phe Tyr Val Lys Lys Thr Ser Leu Leu Ala Asn Cys Gln Ala Pro
        625                 630                 635                 640
        Arg Arg Pro Trp Leu Ala Ser His Met Ser Thr Ile Phe Leu Thr Leu
                            645                 650                 655
        Leu Cys Phe Pro Ala Phe Leu Gly Ala Ala Ile Phe Leu Cys Tyr Ala
                        660                 665                 670
        Val Trp Gln
                675

<210> SEQ ID NO 45
<211> LENGTH: 810
<212> TYPE: PRT
<213> ORGANISM: Cercocebus atys

<400> SEQUENCE: 45

Met Ala Gln Pro Leu Ala Phe Ile Leu Asp Val Pro Glu Thr Pro Gly
        1               5                   10                  15
        Asp Gln Gly Ser Gln Glu Pro Ser Pro Tyr Asp Glu Ser Glu Val His
                        20                  25                  30
        Asp Ser Phe His Gln Leu Ile Gln Glu Gln Ser Gln Trp Ala Ala Gln
                    35                  40                  45
        Glu Gly Leu Glu Leu Gln Gln Arg Glu Gln Glu Ala Thr Gly Ser Gly
        50                  55                  60
        Gln Gln Thr Leu Arg Arg Pro Glu Gly Thr Gln Ser Thr Ala Thr Leu
        65                  70                  75                  80
        Arg Ile Leu Ala Ser Met Pro Ser Arg Thr Ile Gly Arg Ser Arg Gly
                            85                  90                  95
        Ala Ile Ile Ser Gln Tyr Tyr Ser Arg Thr Val Gln Leu Arg Arg Arg
                        100                 105                 110
        Ser Ser Arg Pro Leu Leu Gly Asn Phe Val Leu Ser Ala Arg Pro Ser
                        115                 120                 125
```

-continued

```
Leu Arg Leu Tyr Asp Leu Glu Leu Asp Pro Thr Ala Arg Glu Glu
    130                 135                 140

Glu Lys Gln Ser Leu Leu Val Lys Glu Leu Gln Ser Leu Ala Val Ala
145                 150                 155                 160

Gln Arg Asp His Met Leu Arg Gly Met Pro Leu Ser Leu Ala Glu Lys
                165                 170                 175

Arg Ser Leu Arg Glu Lys Ser Arg Thr Pro Arg Gly Lys Trp Arg Gly
        180                 185                 190

Gln Gln Gly Ser Gly Val Cys Ser Cys Gly Arg Leu Arg Tyr
                195                 200                 205

Ala Cys Val Leu Ala Leu His Ser Leu Gly Leu Ala Leu Ser Gly
210                 215                 220

Leu Gln Ala Leu Thr Pro Trp Arg Tyr Ala Leu Lys Arg Ile Gly Gly
225                 230                 235                 240

Gln Phe Gly Ser Ser Val Leu Ser Tyr Phe Leu Phe Leu Lys Thr Leu
                245                 250                 255

Leu Ala Phe Asn Ala Leu Leu Gln Leu Leu Leu Val Ala Phe Ile Val
                260                 265                 270

Gly Pro Gln Val Ala Phe Pro Pro Ala Leu Pro Gly Pro Ala Pro Ile
                275                 280                 285

Cys Thr Gly Leu Glu Leu Leu Thr Gly Ala Gly Cys Phe Thr His Thr
290                 295                 300

Val Met Phe Tyr Gly His Tyr Ser Asn Ala Thr Leu Asn Gln Pro Cys
305                 310                 315                 320

Gly Ser Pro Leu Asp Gly Ser Gln Cys Thr Pro Arg Ala Gly Gly Leu
                325                 330                 335

Pro Tyr Asn Met Pro Leu Ala Tyr Leu Tyr Thr Val Gly Ala Gly Phe
                340                 345                 350

Phe Ile Thr Cys Ile Thr Leu Val Tyr Ser Met Ala His Ser Phe Gly
                355                 360                 365

Glu Ser Tyr Arg Val Gly Ser Thr Ser Gly Ile His Ala Ile Thr Val
                370                 375                 380

Phe Cys Ser Trp Asp Tyr Lys Val Met Gln Lys Arg Ala Ser Arg Leu
385                 390                 395                 400

Gln Gln Asp Asn Ile Arg Thr Arg Leu Lys Glu Leu Leu Ala Glu Trp
                405                 410                 415

Gln Leu Arg Gln Ser Pro Arg Ser Val Cys Gly Arg Leu Arg Gln Val
                420                 425                 430

Ala Ala Leu Gly Leu Ala Trp Leu Leu Cys Leu Gly Thr Ala Leu Gly
                435                 440                 445

Cys Ala Val Ala Ile His Val Phe Ser Glu Phe Leu Ile Gln Ser Pro
450                 455                 460

Glu Ala Ala Gly Gln Glu Ala Ala Leu Leu Val Leu Pro Leu Val Val
465                 470                 475                 480

Gly Leu Leu Asn Leu Gly Ala Pro Tyr Leu Cys Arg Val Leu Ala Ala
                485                 490                 495

Leu Glu Pro His Asp Ser Pro Val Leu Glu Val Tyr Val Ala Ile Cys
                500                 505                 510

Arg Asn Leu Ile Leu Lys Leu Ala Ile Leu Gly Thr Leu Cys Tyr His
                515                 520                 525

Trp Leu Gly Arg Arg Val Ala Val Leu Gln Gly Gln Cys Trp Glu Asn
530                 535                 540

Phe Val Gly Gln Glu Leu Tyr Arg Phe Leu Val Met Asp Phe Val Leu
```

```
                545                 550                 555                 560
Met Leu Leu Asp Thr Leu Phe Gly Glu Leu Val Trp Arg Ile Ile Ser
                565                 570                 575

Glu Lys Lys Leu Lys Arg Arg Lys Pro Glu Phe Asp Ile Ala Arg
                580                 585                 590

Asn Val Leu Glu Leu Ile Tyr Gly Gln Thr Leu Thr Trp Leu Gly Val
                595                 600                 605

Leu Phe Ser Pro Leu Leu Pro Thr Val Gln Ile Ile Lys Leu Leu
        610                 615                 620

Val Phe Tyr Val Lys Lys Thr Ser Leu Leu Ala Asn Cys Gln Ala Pro
625                 630                 635                 640

Arg Arg Pro Trp Leu Ala Ser His Met Ser Thr Val Phe Leu Thr Leu
                645                 650                 655

Leu Cys Phe Pro Ala Phe Leu Gly Ala Ala Ile Phe Leu Cys Tyr Ala
                660                 665                 670

Val Trp His Leu Phe Pro Arg Val Lys Pro Ser Ser Thr Cys Gly Pro
                675                 680                 685

Phe Arg Thr Leu Asp Ser Met Tyr Glu Ala Gly Arg Val Trp Val Arg
        690                 695                 700

Tyr Leu Glu Ala Ala Gly Pro Arg Val Ser Trp Leu Pro Trp Val His
705                 710                 715                 720

Arg Tyr Leu Val Glu Asn Thr Phe Phe Val Phe Leu Val Ser Ala Leu
                725                 730                 735

Leu Leu Ala Val Ile Tyr Leu Asn Ile Gln Val Val Arg Gly Gln Arg
                740                 745                 750

Arg Val Ile Cys Leu Leu Lys Glu Gln Ile Ser Asn Glu Gly Lys Asp
                755                 760                 765

Lys Ile Phe Leu Ile Asn Lys Leu His Ser Ile Tyr Glu Arg Lys Glu
        770                 775                 780

Arg Glu Glu Arg Ser Arg Val Gly Thr Thr Glu Glu Thr Ala Ala Pro
785                 790                 795                 800

Pro Ala Val Leu Thr Asp Glu Arg Asp Asp
                805                 810

<210> SEQ ID NO 46
<211> LENGTH: 805
<212> TYPE: PRT
<213> ORGANISM: Mandrillus leucophaeus
<220> FEATURE:
<221> NAME/KEY: misc_feature
<222> LOCATION: (513)..(518)
<223> OTHER INFORMATION: Xaa can be any naturally occurring amino acid

<400> SEQUENCE: 46

Met Ala Gln Pro Leu Ala Phe Ile Leu Asp Val Pro Glu Thr Pro Gly
1               5                   10                  15

Asp Gln Gly Gln Glu Pro Ser Pro Tyr Asp Glu Ser Glu Val His Asp
                20                  25                  30

Ser Phe His Gln Leu Ile Gln Glu Gln Ser Gln Trp Ala Ala Arg Glu
        35                  40                  45

Gly Leu Glu Leu Gln Gln Arg Glu Gln Glu Ala Thr Gly Ser Gly Gln
    50                  55                  60

Gln Thr Leu Arg Arg Pro Glu Gly Thr Gln Ser Thr Ala Thr Leu Arg
65                  70                  75                  80

Ile Leu Ala Ser Met Pro Ser Arg Thr Ile Gly Arg Ser Arg Gly Ala
                85                  90                  95
```

```
Ile Ile Ser Gln Tyr Tyr Ser Arg Thr Val Gln Leu Arg Arg Arg Ser
                100                 105                 110

Ser Arg Pro Leu Leu Gly Asn Phe Val Leu Ser Ala Arg Pro Ser Leu
            115                 120                 125

Arg Leu Tyr Asp Leu Glu Leu Asp Pro Thr Ala Arg Glu Glu Glu Glu
        130                 135                 140

Lys Gln Ser Leu Leu Val Lys Glu Leu Gln Ser Leu Ala Val Ala Gln
145                 150                 155                 160

Arg Asp His Met Leu Arg Gly Met Pro Leu Ser Leu Ala Glu Lys Arg
                165                 170                 175

Ser Leu Arg Glu Lys Ser Arg Thr Pro Arg Gly Lys Trp Arg Gly Gln
            180                 185                 190

Gln Gly Ser Gly Gly Val Cys Ser Cys Cys Gly Arg Leu Arg Tyr Ala
        195                 200                 205

Cys Val Leu Ala Leu His Ser Leu Gly Leu Ala Leu Leu Ser Gly Leu
    210                 215                 220

Gln Ala Leu Thr Pro Trp Arg Tyr Ala Leu Lys Arg Ile Gly Gly Gln
225                 230                 235                 240

Phe Gly Ser Ser Val Leu Ser Tyr Phe Leu Phe Leu Lys Thr Leu Leu
                245                 250                 255

Ala Phe Asn Ala Leu Leu Gln Leu Leu Leu Val Ala Phe Ile Val Gly
            260                 265                 270

Pro Gln Val Ala Phe Pro Pro Ala Leu Pro Gly Pro Ala Pro Ile Cys
        275                 280                 285

Thr Gly Leu Glu Leu Leu Thr Gly Ala Gly Cys Phe Thr Asp Thr Val
    290                 295                 300

Met Phe Tyr Gly His Tyr Ser Asn Ala Thr Leu Asn Gln Pro Cys Gly
305                 310                 315                 320

Ser Pro Leu Asp Gly Ser Gln Cys Thr Pro Arg Ala Gly Gly Leu Pro
                325                 330                 335

Tyr Asn Met Pro Leu Ala Tyr Leu Tyr Thr Val Gly Ala Gly Phe Phe
            340                 345                 350

Ile Thr Cys Ile Thr Leu Val Tyr Ser Met Ala His Ser Phe Gly Glu
        355                 360                 365

Ser Tyr Arg Val Gly Ser Thr Ser Gly Ile His Ala Ile Thr Val Phe
    370                 375                 380

Cys Ser Trp Asp Tyr Lys Val Met Gln Lys Arg Ala Ser Arg Leu Gln
385                 390                 395                 400

Gln Asp Asn Ile Arg Thr Arg Leu Lys Glu Leu Leu Ala Glu Trp Gln
                405                 410                 415

Leu Arg Gln Ser Pro Arg Ser Val Cys Gly Arg Leu Arg Gln Ala Ala
            420                 425                 430

Ala Leu Gly Leu Ala Trp Leu Leu Cys Leu Gly Thr Ala Leu Gly Cys
        435                 440                 445

Ala Val Ala Ile His Val Phe Ser Glu Phe Leu Ile Gln Ser Pro Glu
    450                 455                 460

Ala Ala Gly Gln Glu Ala Ala Leu Leu Val Leu Pro Leu Val Val Gly
465                 470                 475                 480

Leu Leu Asn Leu Gly Ala Pro Tyr Leu Cys Arg Val Leu Ala Ala Leu
                485                 490                 495

Glu Pro His Asp Ser Pro Val Leu Glu Val Tyr Val Ala Ile Cys Arg
            500                 505                 510
```

```
Xaa Xaa Xaa Xaa Xaa Ala Ile Leu Gly Thr Leu Cys Tyr His Trp
            515                 520                 525

Leu Gly Arg Arg Val Ala Val Leu Gln Gly Gln Cys Trp Glu Asp Phe
530                 535                 540

Val Gly Gln Glu Leu Tyr Arg Phe Leu Val Met Asp Phe Val Leu Met
545                 550                 555                 560

Leu Leu Asp Thr Leu Phe Gly Glu Leu Val Trp Arg Ile Ile Ser Glu
                565                 570                 575

Lys Lys Leu Lys Arg Arg Arg Lys Pro Glu Phe Asp Ile Ala Arg Asn
                580                 585                 590

Val Leu Glu Leu Ile Tyr Gly Gln Thr Leu Thr Trp Leu Gly Val Leu
                595                 600                 605

Phe Ser Pro Leu Leu Pro Ala Val Gln Ile Ile Lys Leu Leu Leu Val
                610                 615                 620

Phe Tyr Val Lys Lys Thr Ser Leu Leu Ala Asn Cys Gln Ala Pro Arg
625                 630                 635                 640

Arg Pro Trp Leu Ala Ser His Met Ser Thr Val Phe Leu Thr Leu Leu
                645                 650                 655

Cys Phe Pro Ala Phe Leu Gly Ala Ala Ile Phe Leu Cys Tyr Ala Val
                660                 665                 670

Trp Gln Val Lys Pro Ser Ser Thr Cys Gly Pro Phe Arg Thr Leu Asp
                675                 680                 685

Ser Met Tyr Glu Ala Gly Arg Val Trp Val Arg Tyr Leu Glu Ala Ala
                690                 695                 700

Gly Pro Arg Val Ser Trp Leu Pro Trp Val His Arg Tyr Leu Val Glu
705                 710                 715                 720

Asn Thr Phe Phe Val Phe Leu Val Ser Ala Leu Leu Leu Ala Val Ile
                725                 730                 735

Tyr Leu Asn Ile Gln Val Val Arg Gly Gln Arg Arg Val Ile Cys Leu
                740                 745                 750

Leu Lys Glu Gln Ile Ser Asn Glu Gly Glu Asp Lys Ile Phe Leu Ile
                755                 760                 765

Asn Lys Leu His Ser Ile Tyr Glu Arg Lys Glu Arg Glu Glu Arg Ser
                770                 775                 780

Arg Val Gly Thr Thr Glu Glu Thr Ala Ala Pro Pro Ala Leu Leu Thr
785                 790                 795                 800

Asp Glu Arg Asp Asp
                805

<210> SEQ ID NO 47
<211> LENGTH: 805
<212> TYPE: PRT
<213> ORGANISM: Papio Anubis

<400> SEQUENCE: 47

Met Ala Gln Pro Leu Ala Phe Ile Leu Asp Val Pro Glu Thr Pro Gly
1                 5                  10                  15

Asp Gln Gly Ser Gln Glu Pro Ser Pro Tyr Asp Glu Ser Glu Val His
                20                  25                  30

Asp Ser Phe His Gln Leu Ile Gln Glu Gln Ser Gln Trp Ala Ala Gln
                35                  40                  45

Glu Gly Leu Glu Leu Gln Gln Arg Glu Gln Glu Ala Thr Gly Ser Gly
            50                  55                  60

Gln Gln Met Leu Arg Arg Pro Glu Gly Thr Gln Ser Thr Ala Thr Leu
65                  70                  75                  80
```

```
Arg Ile Leu Ala Ser Met Pro Ser Arg Thr Ile Gly Arg Ser Arg Gly
                85                  90                  95

Ala Ile Ile Ser Gln Tyr Tyr Ser Arg Thr Val Gln Leu Arg Arg Arg
            100                 105                 110

Ser Ser Arg Pro Leu Leu Gly Asn Phe Val Leu Ser Ala Arg Pro Ser
        115                 120                 125

Leu Arg Leu Tyr Asp Leu Glu Leu Asp Pro Thr Ala Arg Glu Glu Glu
    130                 135                 140

Glu Lys Gln Ser Leu Leu Val Lys Glu Leu Gln Ser Leu Ala Val Ala
145                 150                 155                 160

Gln Arg Asp His Met Leu Arg Gly Met Pro Leu Ser Leu Ala Glu Lys
                165                 170                 175

Arg Ser Leu Arg Glu Lys Ser Arg Thr Pro Arg Gly Lys Trp Arg Gly
            180                 185                 190

Gln Gln Gly Ser Gly Gly Val Cys Ser Cys Cys Gly Arg Leu Arg Tyr
        195                 200                 205

Ala Cys Val Leu Ala Leu His Ser Leu Gly Leu Ala Leu Leu Ser Gly
    210                 215                 220

Leu Gln Ala Leu Thr Pro Trp Arg Tyr Ala Leu Lys Arg Ile Gly Gly
225                 230                 235                 240

Gln Phe Gly Ser Ser Val Leu Ser Tyr Phe Leu Phe Leu Lys Thr Leu
                245                 250                 255

Leu Ala Phe Asn Ala Leu Leu Gln Leu Leu Val Ala Phe Ile Val
            260                 265                 270

Gly Pro Gln Val Ala Phe Leu Pro Ala Leu Pro Gly Pro Ala Pro Ile
        275                 280                 285

Cys Thr Gly Leu Glu Leu Leu Thr Gly Ala Gly Cys Phe Thr His Thr
    290                 295                 300

Val Met Phe Tyr Gly His Tyr Ser Asn Ala Thr Leu Asn Gln Pro Cys
305                 310                 315                 320

Gly Ser Pro Leu Asp Ser Ser Gln Cys Thr Pro Arg Ala Gly Gly Leu
                325                 330                 335

Pro Tyr Asn Met Pro Leu Ala Tyr Leu Tyr Thr Val Gly Ala Gly Phe
            340                 345                 350

Phe Ile Thr Cys Ile Thr Leu Val Tyr Ser Met Ala His Ser Phe Gly
        355                 360                 365

Glu Ser Tyr Arg Val Gly Ser Thr Ser Gly Ile His Ala Ile Thr Val
    370                 375                 380

Phe Cys Ser Trp Asp Tyr Lys Val Met Gln Lys Arg Ala Ser Arg Leu
385                 390                 395                 400

Gln Gln Asp Asn Ile Arg Thr Arg Leu Lys Glu Leu Leu Ala Glu Trp
                405                 410                 415

Gln Leu Arg Gln Ser Pro Arg Ser Val Cys Gly Arg Leu Arg Gln Ala
            420                 425                 430

Val Ala Leu Gly Leu Ala Trp Leu Cys Leu Gly Thr Ala Leu Gly
        435                 440                 445

Cys Ala Val Ala Ile His Val Phe Ser Glu Phe Leu Ile Gln Ser Pro
    450                 455                 460

Glu Ala Ala Gly Gln Glu Ala Ala Leu Leu Val Leu Pro Leu Val Val
465                 470                 475                 480

Gly Leu Leu Asn Leu Gly Ala Pro Tyr Leu Cys Arg Val Leu Ala Ala
                485                 490                 495
```

-continued

```
Leu Glu Pro His Asp Ser Pro Val Leu Val Tyr Val Ala Ile Cys
            500                 505                 510
Arg Asn Leu Ile Leu Lys Leu Ala Ile Leu Gly Thr Leu Cys Tyr His
        515                 520                 525
Trp Leu Gly Arg Arg Val Ala Val Leu Gln Gly Gln Cys Trp Glu Asp
    530                 535                 540
Phe Val Gly Gln Glu Leu Tyr Arg Phe Leu Val Met Asp Phe Val Leu
545                 550                 555                 560
Met Leu Leu Asp Thr Leu Phe Gly Glu Leu Val Trp Arg Ile Ile Ser
                565                 570                 575
Glu Lys Lys Leu Lys Arg Lys Pro Glu Phe Asp Ile Ala Arg Asn
            580                 585                 590
Ala Leu Glu Leu Ile Tyr Gly Gln Thr Leu Ala Trp Leu Gly Val Leu
        595                 600                 605
Phe Ser Pro Leu Leu Pro Ala Val Gln Ile Ile Lys Leu Leu Leu Val
    610                 615                 620
Phe Tyr Val Lys Lys Thr Ser Leu Leu Ala Asn Cys Gln Ala Pro Arg
625                 630                 635                 640
Arg Pro Trp Leu Ala Ser His Met Ser Thr Val Phe Leu Thr Leu Leu
                645                 650                 655
Cys Phe Pro Ala Phe Leu Gly Ala Ala Ile Phe Leu Cys Tyr Ala Val
            660                 665                 670
Trp Gln Val Lys Pro Ser Ser Thr Cys Gly Pro Phe Arg Thr Leu Asp
        675                 680                 685
Ser Met Tyr Glu Ala Gly Arg Val Trp Val Arg Tyr Leu Glu Ala Ala
    690                 695                 700
Gly Pro Arg Val Ser Trp Leu Pro Trp Val His Arg Tyr Leu Val Glu
705                 710                 715                 720
Asn Thr Phe Phe Val Phe Leu Val Ser Ala Leu Leu Ala Val Ile
                725                 730                 735
Tyr Leu Asn Ile Gln Val Val Arg Gly Gln Arg Val Ile Cys Leu
            740                 745                 750
Leu Lys Glu Gln Ile Ser Asn Glu Gly Glu Asp Lys Ile Phe Leu Ile
        755                 760                 765
Asn Lys Leu His Ser Ile Tyr Glu Arg Lys Glu Arg Glu Arg Ser
    770                 775                 780
Arg Val Gly Thr Thr Glu Glu Thr Ala Ala Pro Ala Leu Leu Thr
785                 790                 795                 800
Asp Glu Arg Asp Asp
            805

<210> SEQ ID NO 48
<211> LENGTH: 23
<212> TYPE: DNA
<213> ORGANISM: Mus musculus

<400> SEQUENCE: 48
agcatgccca gccgtaccat tgg                                              23

<210> SEQ ID NO 49
<211> LENGTH: 23
<212> TYPE: DNA
<213> ORGANISM: Mus musculus

<400> SEQUENCE: 49
cagctggaag tatcaccacg ggg                                              23
```

<210> SEQ ID NO 50
<211> LENGTH: 23
<212> TYPE: DNA
<213> ORGANISM: Mus musculus

<400> SEQUENCE: 50
gtcgcaagcg ttgtagccgt agg                                              23

<210> SEQ ID NO 51
<211> LENGTH: 42
<212> TYPE: DNA
<213> ORGANISM: Artificial Sequence
<220> FEATURE:
<223> OTHER INFORMATION: V5 epitope

<400> SEQUENCE: 51
ggtaagccta tccctaaccc tctgctgggc ctggattcta cc                          42

<210> SEQ ID NO 52
<211> LENGTH: 7897
<212> TYPE: DNA
<213> ORGANISM: Artificial Sequence
<220> FEATURE:
<223> OTHER INFORMATION: YC2.60-pcDNA

<400> SEQUENCE: 52
acgcgccctg tagcggcgca ttaagcgcgg cgggtgtggt ggttacgcgc agcgtgaccg      60
ctacacttgc cagcgcccta gcgcccgctc ctttcgcttt cttcccttcc tttctcgcca     120
cgttcgccgg ctttccccgt caagctctaa atcgggggct ccctttaggg ttccgattta     180
gtgctttacg gcacctcgac cccaaaaaac ttgattaggg tgatggttca cgtagtgggc     240
catcgccctg atagacggtt tttcgccctt tgacgttgga gtccacgttc tttaatagtg     300
gactcttgtt ccaaactgga acaacactca accctatctc ggtctattct tttgatttat     360
aagggatttt gccgatttcg gcctattggt taaaaaatga gctgatttaa caaaaattta     420
acgcgaatta attctgtgga atgtgtgtca gttagggtgt ggaaagtccc caggctcccc     480
agcaggcaga agtatgcaaa gcatgcatct caattagtca gcaaccaggt gtggaaagtc     540
cccaggctcc ccagcaggca gaagtatgca aagcatgcat ctcaattagt cagcaaccat     600
agtcccgccc ctaactccgc ccatcccgcc cctaactccg cccagttccg cccattctcc     660
gccccatggc tgactaattt ttttatttta tgcagaggcc gaggccgcct ctgcctctga     720
gctattccag aagtagtgag gaggcttttt tggaggccta ggcttttgca aaaagctccc     780
gggagcttgt atatccattt tcggatctga tcaagagaca ggatgaggat cgtttcgcat     840
gattgaacaa gatggattgc acgcaggttc tccggccgct tgggtggaga ggctattcgg     900
ctatgactgg gcacaacaga caatcggctg ctctgatgcc gccgtgttcc ggctgtcagc     960
gcaggggcgc ccggttcttt ttgtcaagac cgacctgtcc ggtgccctga atgaactgca    1020
ggacgaggca gcgcggctat cgtggctggc cacgacgggc gttccttgcg cagctgtgct    1080
cgacgttgtc actgaagcgg gaagggactg gctgctattg ggcgaagtgc cggggcagga    1140
tctcctgtca tctcaccttg ctcctgccga gaaagtatcc atcatggctg atgcaatgcg    1200
gcggctgcat acgcttgatc cggctacctg cccattcgac caccaagcga aacatcgcat    1260
cgagcgagca cgtactcgga tggaagccgg tcttgtcgat caggatgatc tggacgaaga    1320
gcatcagggg ctcgcgccag ccgaactgtt cgccaggctc aaggcgcgca tgcccgacgg    1380

```
cgaggatctc gtcgtgaccc atggcgatgc ctgcttgccg aatatcatgg tggaaaatgg    1440
ccgcttttct ggattcatcg actgtggccg gctgggtgtg gcggaccgct atcaggacat    1500
agcgttggct acccgtgata ttgctgaaga gcttggcggc gaatgggctg accgcttcct    1560
cgtgctttac ggtatcgccg ctcccgattc gcagcgcatc gccttctatc gccttcttga    1620
cgagttcttc tgagcgggac tctggggttc gaaatgaccg accaagcgac gcccaacctg    1680
ccatcacgag atttcgattc caccgccgcc ttctatgaaa ggttgggctt cggaatcgtt    1740
ttccgggacg ccggctggat gatcctccag cgcggggatc tcatgctgga gttcttcgcc    1800
caccccaact tgtttattgc agcttataat ggttacaaat aaagcaatag catcacaaat    1860
ttcacaaata aagcattttt ttcactgcat tctagttgtg gtttgtccaa actcatcaat    1920
gtatcttatc atgtctgtat accgtcgacc tctagctaga gcttggcgta atcatggtca    1980
tagctgtttc ctgtgtgaaa ttgttatccg ctcacaattc cacacaacat acgagccgga    2040
agcataaagt gtaaagcctg gggtgcctaa tgagtgagct aactcacatt aattgcgttg    2100
cgctcactgc ccgctttcca gtcgggaaac ctgtcgtgcc agctgcatta tgaatcggc    2160 caacgcgcgg ggagaggcgg tttgcgtatt gggcgctctt ccgcttcctc gctcactgac    2220
tcgctgcgct cggtcgttcg gctgcggcga gcggtatcag ctcactcaaa ggcggtaata    2280
cggttatcca cagaatcagg ggataacgca ggaaagaaca tgtgagcaaa aggccagcaa    2340
aaggccagga accgtaaaaa ggccgcgttg ctggcgtttt tccataggct ccgcccccct    2400
gacgagcatc acaaaaatcg acgctcaagt cagaggtggc gaaacccgac aggactataa    2460
agataccagg cgtttccccc tggaagctcc ctcgtgcgct ctcctgttcc gaccctgccg    2520
cttaccggat acctgtccgc ctttctccct tcgggaagcg tggcgctttc tcatagctca    2580
cgctgtaggt atctcagttc ggtgtaggtc gttcgctcca agctgggctg tgtgcacgaa    2640
ccccccgttc agcccgaccg ctgcgcctta tccggtaact atcgtcttga gtccaacccg    2700
gtaagacacg acttatcgcc actggcagca gccactggta acaggattag cagagcgagg    2760
tatgtaggcg gtgctacaga gttcttgaag tggtggccta actacggcta cactagaaga    2820
acagtatttg gtatctgcgc tctgctgaag ccagttacct tcggaaaaag agttggtagc    2880
tcttgatccg gcaaacaaac caccgctggt agcggttttt ttgtttgcaa gcagcagatt    2940
acgcgcagaa aaaaggatc tcaagaagat cctttgatct tttctacggg gtctgacgct    3000
cagtggaacg aaaactcacg ttaagggatt ttggtcatga gattatcaaa aaggatcttc    3060
acctagatcc ttttaaatta aaatgaagt tttaaatcaa tctaaagtat atatgagtaa    3120
acttggtctg acagttacca atgcttaatc agtgaggcac ctatctcagc gatctgtcta    3180
tttcgttcat ccatagttgc ctgactcccc gtcgtgtaga taactacgat acgggagggc    3240
ttaccatctg gccccagtgc tgcaatgata ccgcgagacc cacgctcacc ggctccagat    3300
ttatcagcaa taaaccagcc agccggaagg gccgagcgca gaagtggtcc tgcaacttta    3360
tccgcctcca tccagtctat taattgttgc cgggaagcta gagtaagtag ttcgccagtt    3420
aatagtttgc gcaacgttgt tgccattgct acaggcatcg tggtgtcacg ctcgtcgttt    3480
ggtatggctt cattcagctc cggttcccaa cgatcaaggc gagttacatg atcccccatg    3540
ttgtgcaaaa aagcggttag ctccttcggt cctccgatcg ttgtcagaag taagttggcc    3600
gcagtgttat cactcatggt tatggcagca ctgcataatt ctcttactgt catgccatcc    3660
gtaagatgct tttctgtgac tggtgagtac tcaaccaagt cattctgaga atagtgtatg    3720
cggcgaccga gttgctcttg cccggcgtca atacgggata ataccgcgcc acatagcaga    3780
```

```
actttaaaag tgctcatcat tggaaaacgt tcttcggggc gaaaactctc aaggatctta   3840
ccgctgttga gatccagttc gatgtaaccc actcgtgcac ccaactgatc ttcagcatct   3900
tttactttca ccagcgtttc tgggtgagca aaaacaggaa ggcaaaatgc cgcaaaaaag   3960
ggaataaggg cgacacggaa atgttgaata ctcatactct tcctttttca atattattga   4020
agcatttatc agggttattg tctcatgagc ggatacatat ttgaatgtat ttagaaaaat   4080
aaacaaatag gggttccgcg cacatttccc cgaaaagtgc cacctgacgt cgacggatcg   4140
ggagatctcc cgatcccta tggtgcactc tcagtacaat ctgctctgat gccgcatagt   4200
taagccagta tctgctccct gcttgtgtgt tggaggtcgc tgagtagtgc gcgagcaaaa   4260
tttaagctac aacaaggcaa ggcttgaccg acaattgcat gaagaatctg cttagggtta   4320
ggcgttttgc gctgcttcgc gatgtacggg ccagatatac gcgttgacat tgattattga   4380
ctagttatta atagtaatca attacgggt cattagttca tagcccatat atggagttcc   4440
gcgttacata acttacggta atggcccgc ctggctgacc gcccaacgac ccccgcccat   4500
tgacgtcaat aatgacgtat gttcccatag taacgccaat agggactttc cattgacgtc   4560
aatgggtgga gtatttacgg taaactgccc acttggcagt acatcaagtg tatcatatgc   4620
caagtacgcc ccctattgac gtcaatgacg gtaaatggcc cgcctggcat tatgcccagt   4680
acatgacctt atgggactt cctacttggc agtacatcta cgtattagtc atcgctatta   4740
ccatggtgat gcggttttgg cagtacatca atgggcgtgg atagcggttt gactcacggg   4800
gatttccaag tctccacccc attgacgtca atgggagttt gttttggcac caaaatcaac   4860
gggactttcc aaaatgtcgt aacaactccg ccccattgac gcaaatgggc ggtaggcgtg   4920
tacggtggga ggtctatata agcagagctc tctggctaac tagagaaccc actgcttact   4980
ggcttatcga aattaatacg actcactata gggagaccca agctggctag cgccaccatg   5040
ggactgcaga acgagctggc tctgaagctg gctggactgg atattaacaa gactggaggc   5100
tccatggtct ccaagggcga ggagctgttc accggggtgg tgcccatcct ggtcgagctg   5160
gacggcgacg taaacggcca caggttcagc gtgtccggcg agggcgaggg cgatgccacc   5220
tacggcaagc tgaccctgaa gttcatctgc accaccggca agctgcccgt gccctggccc   5280
accctcgtga ccaccctgac ctggggcgtg cagtgcttca gccgctaccc cgaccacatg   5340
aagcagcacg acttcttcaa gtccgccatg cccgaaggct acgtccagga gcgtaccatc   5400
ttcttcaagg acgacggcaa ctacaagacc cgcgccgagg tgaagttcga gggcgacacc   5460
ctggtgaacc gcatcgagct gaagggcatc gacttcaagg aggacggcaa catcctgggg   5520
cacaagctgg agtacaacta catcagccac aacgtctata tcaccgccga caagcagaag   5580
aacggcatca aggcccactt caagatccgc cacaacatcg aggacggcag cgtgcagctc   5640
gccgaccact accagcagaa cacccccatc ggcgacggcc ccgtgctgct gcccgacaac   5700
cactacctga gcacccagtc cgccctgagc aagaccccca acgagaagcg cgatcacatg   5760
gtcctgctgg agttcgtgac cgccgcccgc atgcatgacc aactgacaga agagcagatt   5820
gcagagttca agaagccttt ctcattattc gacaaggatg ggacggcac catcaccaca   5880
aaggaacttg gcaccgttat gaggtcgctt ggacaaaacc caacgaaagc agaattgcag   5940
gatatgatca atgaagtcga tgctgatggc aatggaacga tttactttcc tgaatttctt   6000
actatgatgc taaaaaat gaaggacaca gacagcgaag aggaaatccg agaagcattc   6060
cgtgttttg acaaggatgg gaacggctac atcagcgctg ctgaattacg tcacgtcatg   6120
```

|                                                            |      |
| ---------------------------------------------------------- | ---- |
| acaaacctcg gggagaagtt aacagatgaa gaagttgatg aaatgataag ggaagcagat | 6180 |
| atcgatggtg atggccaagt aaactatgaa gagtttgtac aaatgatgac agcaaagggg | 6240 |
| gggaagaggc gctggaagaa aaacttcatt gccgtcagcg ctgccaaccg gttcaagaag | 6300 |
| atctccagct ccggggcact ggagctcatg gacggcggcg tgcagctcgc cgaccactac | 6360 |
| cagcagaaca cccccatcgg cgacggcccc gtgctgctgc ccgacaacca ctacctgagc | 6420 |
| taccagtccg ccctgagcaa agaccccaac gagaagcgcg atcacatggt cctgctggag | 6480 |
| ttcgtgaccg ccgccgggat cactctcggc atggacgagc tgtacaaggg tggcagcggt | 6540 |
| ggcatggtct ccaagggcga ggagctgttc accggggtgg tgcccatcct ggtcgagctg | 6600 |
| gacggcgacg taaacggcca agttcagc gtgtccggcg agggcgaggg cgatgccacc | 6660 |
| tacggcaagc tgaccctgaa gctgatctgc accaccggca agctgcccgt gccctggccc | 6720 |
| accctcgtga ccaccctggg ctacggcctg cagtgcttcg cccgctaccc cgaccacatg | 6780 |
| aagcagcacg acttcttcaa gtccgccatg cccgaaggct acgtccagga gcgcaccatc | 6840 |
| ttcttcaagg acgacggcaa ctacaagacc cgcgccgagg tgaagttcga gggcgacacc | 6900 |
| ctggtgaacc gcatcgagct gaagggcatc gacttcaagg aggacggcaa catcctgggg | 6960 |
| cacaagctgg agtacaacta caacagccac aacgtctata tcatggccga caagcagaag | 7020 |
| aacggcatca aggccaactt caagatccgc cacaacatcg agtaagaatt cactcctcag | 7080 |
| gtgcaggctg cctatcagaa ggtggtggct ggtgtggcca atgccctggc tcacaaatac | 7140 |
| cactgagatc ttttcccctc tgccaaaaat tatggggaca tcatgaagcc ccttgagcat | 7200 |
| ctgacttctg gctaataaag gaaatttatt tcattgcaa tagtgtgttg gaattttttg | 7260 |
| tgtctctcac tcggaaggac atatgggagg gcaaatcatt taaaacatca gaatgagtat | 7320 |
| ttggtttaga gtttggcaac atatgccat atgctggctg ccatgaacaa aggttggcta | 7380 |
| taaagaggtc atcagtatat gaaacagccc cctgctgtcc attccttatt ccatagaaaa | 7440 |
| gccttgactt gaggttagat atctgcagaa ttccaccaca ctggactagt ggatccacag | 7500 |
| gtaccacaaa gcttgaaggt aagcctatcc ctaaccctct gctgggcctg gattctacca | 7560 |
| agtagaccgg tagcttctat agtgtcacct aaatatagct taagttttaaa ccgctgatca | 7620 |
| gcctcgactg tgccttctag ttgccagcca tctgttgttt gcccctcccc cgtgccttcc | 7680 |
| ttgacccctgg aagtgccac tcccactgtc ctttcctaat aaaatgagga aattgcatcg | 7740 |
| cattgtctga gtaggtgtca ttctattctg ggggtgggg tggggcagga cagcaagggg | 7800 |
| gaggattggg aagacaatag caggcatgct ggggatgcgg tgggctctat ggcttctgag | 7860 |
| gcggaaagaa ccagctgggg ctctaggggg tatcccc | 7897 |

```
<210> SEQ ID NO 53
<211> LENGTH: 29
<212> TYPE: DNA
<213> ORGANISM: Artificial Sequence
<220> FEATURE:
<223> OTHER INFORMATION: primer

<400> SEQUENCE: 53
```

| | |
|---|---|
| cctaggtctg cagggtatag cacagccat | 29 |

```
<210> SEQ ID NO 54
<211> LENGTH: 29
<212> TYPE: DNA
<213> ORGANISM: Artificial Sequence
<220> FEATURE:
<223> OTHER INFORMATION: primer
```

<400> SEQUENCE: 54 tttaatagggg ggtgcacacc tctggtttc                                29

<210> SEQ ID NO 55
<211> LENGTH: 7877
<212> TYPE: DNA
<213> ORGANISM: Artificial Sequence
<220> FEATURE:
<223> OTHER INFORMATION: TMC6-pcDNA3.1

<400> SEQUENCE: 55

| | |
|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gccgccatgg ctcagtcact ggctttagcc ctcgatgtcc cggagaccac gggagacgaa | 960 |
| ggcctggagc ccagccccta tgaagaaagt gaagtccatg actccttcca ccagctcatt | 1020 |
| caagagcaaa gccttcgggt ggcggaggag gggctggagc tactgccctt gggtctaggc | 1080 |
| agaggtgacc agaccctccc aggacttgaa ggtgctcctg cccttagctc ggccactctc | 1140 |
| cgcatcctgg ccagcatgcc cagccgtacc attggtcgca gccgtgggc catcatctcc | 1200 |
| caatactaca accgcacagt gaggcttcgg cgcaggagca gccggccctt gctgggcaat | 1260 |
| gtggtgccct ctgccggcc cagccttcgc ctgtatgacc tggagctgga ctccacaatc | 1320 |
| ttggaggagg atgagaagcg gagcctgcta gtaaaggagc ttcaaggtct gtcggcggcc | 1380 |
| cagagggacc acatggtgcg gaacatgccc ttgagtctgg gtgagaagcg ctgtcttcga | 1440 |
| gagaaaagtt ggagcccaaa gggaaagcgg cggcacctgc agggtcgaag cggggccttc | 1500 |
| tcctgctgta gccggctcag atacacctgc atgctggctc ttcatagcct ggggctggca | 1560 |
| ctgctctcag gcctgtatgc tgccaggccg tggcgctatg ctctgaagca gatcggtggc | 1620 |
| cagtttggct ccagcgtcct ctcctacttc ctcttcctca agaccctgtt ggccttcaac | 1680 |
| gcgctgatgt tgctgccttt gctggccttc ctcgtgggtg ttcaggctgc cttttccacct | 1740 |
| gacccagcag gccccgtgcc tacgttttct ggtctggaac tcctcacagg cgggggccgg | 1800 |
| ttcacacaca cagttatgta ctacggctac tacagtaaca gcacgctgag cccgtcatgt | 1860 |
| gacgcccctc gggaaggtgg ccagtgcagt cccaggctgg gcagcctgcc ctataacatg | 1920 |

-continued

```
ccgctggcct acctcttcac aatgggggcc accttcttcc ttacctgcat cattctggta    1980
tacagcatgt cccactcctt tggggagagc taccggggttg gcagtaccaa gggtatccat   2040
gcccttacgg tcttctgctc ctgggactac aaggtgacac agaagagggc ttcccgtgtc    2100
caacaggaca gcatctgcac tcagctgaag gagctgttgg ctgaatggca ccttcgaaag    2160
cgccctcgga gtgtgtgcgg gcagctgagg caggtcgtcg ttctaggtct ggggtggctg    2220
ctgtgtctgg gctccacaat gggctgcacg gtggctgtcc tcaccttctc agaggtaatg    2280
attcagagac ctgcttctgg tggccagggg gtggaggcgt tggccttgcc cctggtggtc    2340
agtgtcctta acctgggtgc ctcctacctg ttccgtggtc tagccactct ggagcgacat    2400
gactcccctg tgttggaggt atacatggcc atctgcagga acctcatcct gaagatggcc    2460
gtcctgggtg tgcttgcta tcactggctg ggccgcaggg tggccaccct gcagggtcag    2520
tgctgggagg actttgtggg ccaggagctg taccgcttca tggtcgtgga tttcatcttc    2580
atgctcttgg actcccttt tggagagttg gtgtggaggc tcatctcaga aagaagctc     2640 aagaggggc agaagcctga gtttgacatt gccaggaatg tgctggacct gatttatgga    2700
cagacactga cctggctggg cgtcctgttc tcaccgctcc tgcctgcagt acagattctc    2760
cggctgctct tccttttcca catcaagaag gccagcctga tggccaactg ccaggcacca    2820
cgccgaccct ggctggcctc gcacatgagc actgtcttcc tcaccttgct ctgcttcccg    2880
tcgttcctgg gcgctgctgt tttcctctgc tatgctgtct ggcaggtgag gccctcgagc    2940
acttgtggcc ctttccggac tctgaacacc atgtatgaag caggcacggt ctgggtgcgt    3000
cgcctggagc atgcaggctc cggagcctcc tggctgccct ggctgcacca cttcctggtg    3060
gagaacactt tcttcctctt cctggcttca gccctgctgc tggctgtcat ctacttcaac    3120
atccaggtgg tgaaaggaca acggaaggtc atctgcctgc tcaaggagca gatccggaat    3180
gaaggagagg acaagatctt cctgatcaac aagcttcact ctgtttacga ggaggaggga   3240
aggagcaggc ctggcagaac ccaggacact actgaaccac ctgcctggca tgaggatgga   3300
ggggaccaga aggaaccctg taacccccgg tcaccaggag gatccacagg taccacaaag   3360
cttgaaggta agcctatccc taaccctctg ctgggcctgg attctaccaa gtagaccggt   3420
agcttctata gtgtcaccta aatatagctt aagtttaaac cgctgatcag cctcgactgt   3480
gccttctagt tgccagccat ctgttgtttg cccctccccc gtgccttcct tgaccctgga   3540
aggtgccact cccactgtcc tttcctaata aaatgaggaa attgcatcgc attgtctgag   3600
taggtgtcat tctattctgg ggggtggggt ggggcaggac agcaagggg aggattggga   3660 agacaatagc aggcatgctg gggatgcggt gggctctatg gcttctgagg cggaaagaac   3720
cagctggggc tctaggggt atccccacgc gccctgtagc ggcgcattaa gcgcggcggg    3780
tgtggtggtt acgcgcagcg tgaccgctac acttgccagc gccctagcgc ccgctccttt   3840
cgctttcttc ccttcctttc tcgccacgtt cgccggcttt cccgtcaag ctctaaatcg    3900 gggctccct ttagggttcc gatttagtgc tttacggcac ctcgacccca aaaaacttga    3960
ttagggtgat ggttcacgta gtgggccatc gccctgatag acggttttc gccctttgac    4020 gttggagtcc acgttcttta atagtggact cttgttccaa actggaacaa cactcaaccc   4080
tatctcggtc tattctttg atttataagg gattttgccg atttcggcct attggttaaa    4140
aaatgagctg atttaacaaa aatttaacgc gaattaattc tgtggaatgt gtgtcagtta   4200
gggtgtggaa agtccccagg ctccccagca ggcagaagta tgcaaagcat gcatctcaat   4260
tagtcagcaa ccaggtgtgg aaagtcccca ggctccccag caggcagaag tatgcaaagc   4320
```

```
atgcatctca attagtcagc aaccatagtc ccgcccctaa ctccgcccat cccgcccta    4380
actccgccca gttccgccca ttctccgccc catggctgac taattttttt tatttatgca   4440
gaggccgagg ccgcctctgc ctctgagcta ttccagaagt agtgaggagg cttttttgga   4500
ggcctaggct tttgcaaaaa gctcccggga gcttgtatat ccattttcgg atctgatcaa   4560
gagacaggat gaggatcgtt tcgcatgatt gaacaagatg gattgcacgc aggttctccg   4620
gccgcttggg tggagaggct attcggctat gactgggcac aacagacaat cggctgctct   4680
gatgccgccg tgttccggct gtcagcgcag gggcgcccgg ttcttttttgt caagaccgac   4740
ctgtccggtg ccctgaatga actgcaggac gaggcagcgc ggctatcgtg gctggccacg   4800
acgggcgttc cttgcgcagc tgtgctcgac gttgtcactg aagcgggaag gactggctg    4860
ctattgggcg aagtgccggg gcaggatctc ctgtcatctc accttgctcc tgccgagaaa   4920
gtatccatca tggctgatgc aatgcggcgg ctgcatacgc ttgatccggc tacctgccca   4980
ttcgaccacc aagcgaaaca tcgcatcgag cgagcacgta ctcggatgga agccggtctt   5040
gtcgatcagg atgatctgga cgaagagcat caggggctcg cgccagccga actgttcgcc   5100
aggctcaagg cgcgcatgcc cgacggcgag gatctcgtcg tgacccatgg cgatgcctgc   5160
ttgccgaata tcatggtgga aaatggccgc ttttctggat tcatcgactg tggccggctg   5220
ggtgtggcgg accgctatca ggacatagcg ttggctaccc gtgatattgc tgaagagctt   5280
ggcggcgaat gggctgaccg cttcctcgtg ctttacggta tcgccgctcc cgattcgcag   5340
cgcatcgcct tctatcgcct tcttgacgag ttcttctgag cgggactctg gggttcgaaa   5400
tgaccgacca agcgacgccc aacctgccat cacgagattt cgattccacc gccgccttct   5460
atgaaaggtt gggcttcgga atcgttttcc gggacgccgg ctggatgatc ctccagcgcg   5520
gggatctcat gctggagttc ttcgcccacc ccaacttgtt tattgcagct tataatggtt   5580
acaaataaag caatagcatc acaaatttca caaataaagc atttttttca ctgcattcta   5640
gttgtggttt gtccaaactc atcaatgtat cttatcatgt ctgtataccg tcgacctcta   5700
gctagagctt ggcgtaatca tggtcatagc tgtttcctgt gtgaaattgt tatccgctca   5760
caattccaca acaacatacga gccggaagca taaagtgtaa agcctggggt gcctaatgag   5820
tgagctaact cacattaatt gcgttgcgct cactgcccgc tttccagtcg gaaacctgt    5880
cgtgccagct gcattaatga atcggccaac gcgcggggag aggcggtttg cgtattgggc   5940
gctcttccgc ttcctcgctc actgactcgc tgcgctcggt cgttcggctg cggcgagcgg   6000
tatcagctca ctcaaaggcg gtaatacggt tatccacaga atcaggggat aacgcaggaa   6060
agaacatgtg agcaaaaggc cagcaaaagg ccaggaaccg taaaaaggcc gcgttgctgg   6120
cgttttccca taggctccgc cccctgacg agcatcacaa aaatcgacgc tcaagtcaga   6180
ggtggcgaaa cccgacagga ctataaagat accaggcgtt tccccctgga agctccctcg   6240
tgcgctctcc tgttccgacc ctgccgctta ccggatacct gtccgccttt ctcccttcgg   6300
gaagcgtggc gctttctcat agctcacgct gtaggtatct cagttcggtg taggtcgttc   6360
gctccaagct gggctgtgtg cacgaacccc ccgttcagcc cgaccgctgc gccttatccg   6420
gtaactatcg tcttgagtcc aacccggtaa gacacgactt atcgccactg gcagcagcca   6480
ctggtaacag gattagcaga gcgaggtatg taggcggtgc tacagagttc ttgaagtggt   6540
ggcctaacta cggctacact agaagaacag tatttggtat ctgcgctctg ctgaagccag   6600
ttaccttcgg aaaaagagtt ggtagctctt gatccggcaa acaaaccacc gctggtagcg   6660
```

-continued

```
gttttttgt ttgcaagcag cagattacgc gcagaaaaaa aggatctcaa gaagatcctt    6720 tgatctttc tacggggtct gacgctcagt ggaacgaaaa ctcacgttaa gggattttgg    6780
tcatgagatt atcaaaaagg atcttcacct agatcctttt aaattaaaaa tgaagtttta    6840
aatcaatcta agtatatat gagtaaactt ggtctgacag ttaccaatgc ttaatcagtg    6900
aggcacctat ctcagcgatc tgtctatttc gttcatccat agttgcctga ctccccgtcg    6960
tgtagataac tacgatacgg gagggcttac catctggccc cagtgctgca atgataccgc    7020
gagacccacg ctcaccggct ccagatttat cagcaataaa ccagccagcc ggaagggccg    7080
agcgcagaag tggtcctgca actttatccg cctccatcca gtctattaat tgttgccggg    7140
aagctagagt aagtagttcg ccagttaata gtttgcgcaa cgttgttgcc attgctacag    7200
gcatcgtggt gtcacgctcg tcgtttggta tggcttcatt cagctccggt tcccaacgat    7260
caaggcgagt tacatgatcc cccatgttgt gcaaaaaagc ggttagctcc ttcggtcctc    7320
cgatcgttgt cagaagtaag ttggccgcag tgttatcact catggttatg gcagcactgc    7380
ataattctct tactgtcatg ccatccgtaa gatgcttttc tgtgactggt gagtactcaa    7440
ccaagtcatt ctgagaatag tgtatgcggc gaccgagttg ctcttgcccg gcgtcaatac    7500
gggataatac cgcgccacat agcagaactt taaaagtgct catcattgga aaacgttctt    7560
cggggcgaaa actctcaagg atcttaccgc tgttgagatc cagttcgatg taacccactc    7620
gtgcacccaa ctgatcttca gcatctttta ctttcaccag cgtttctggg tgagcaaaaa    7680
caggaaggca aaatgccgca aaaaagggaa taagggcgac acggaaatgt tgaatactca    7740
tactcttcct ttttcaatat tattgaagca tttatcaggg ttattgtctc atgagcggat    7800
acatatttga atgtatttag aaaaataaac aaataggggt tccgcgcaca tttccccgaa    7860
aagtgccacc tgacgtc                                                   7877
```

<210> SEQ ID NO 56
<211> LENGTH: 23
<212> TYPE: DNA
<213> ORGANISM: Artificial Sequence
<220> FEATURE:
<223> OTHER INFORMATION: primer

<400> SEQUENCE: 56
gccaccatgg cccagccact ggc                                             23

<210> SEQ ID NO 57
<211> LENGTH: 22
<212> TYPE: DNA
<213> ORGANISM: Artificial Sequence
<220> FEATURE:
<223> OTHER INFORMATION: primer

<400> SEQUENCE: 57
caggctctgg agctccttca cc                                              22

<210> SEQ ID NO 58
<211> LENGTH: 22
<212> TYPE: DNA
<213> ORGANISM: Artificial Sequence
<220> FEATURE:
<223> OTHER INFORMATION: primer

<400> SEQUENCE: 58
ggtgaaggag ctccagagcc tg                                              22

<210> SEQ ID NO 59
<211> LENGTH: 19
<212> TYPE: DNA
<213> ORGANISM: Artificial Sequence
<220> FEATURE:
<223> OTHER INFORMATION: primer

<400> SEQUENCE: 59
ggcatcctgt tcatctgtg                                                19

<210> SEQ ID NO 60
<211> LENGTH: 7826
<212> TYPE: DNA
<213> ORGANISM: Artificial Sequence
<220> FEATURE:
<223> OTHER INFORMATION: hTMC6-pcDNA3.1

<400> SEQUENCE: 60
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggccacc     900
atggcccagc cactggcctt catcctcgat gtccctgaga ccccagggga ccagggccag     960
ggccccagcc cctatgatga agcgaagtg cacgactcct tccagcagct catccaggag    1020
cagagccagt gcacggccca gaggggctg gagctgcagc agagagagcg ggaggtgaca    1080
ggaagtagcc agcagacact ctggcggccc gagggcaccc agagcacggc cacactccgc    1140
atcctggcca gcatgcccag ccgcaccatt ggccgcagcc gaggtgccat catctcccag    1200
tactacaacc gcacggtgca gcttcggtgc aggagcagcg ggcccctgct cgggaacttt    1260
gtccgctccg cctggcccag cctccgcctg tacgacctgg agctggaccc cacggccctg    1320
gaggaggagg agaagcagag cctcctggtg aaggagctcc agagcctggc agtggcacag    1380
cgggaccaca tgcttcgcgg gatgccctta agcctggctg agaaacgcag cctgcgagag    1440
aagagcagga ccccgagggg gaagtggagg ggccagccgg gcagcggcgg ggtctgctcc    1500
tgctgtggcc ggctcagata tgcctgcgtg ctggccttgc acagcctggg cctggcgctg    1560
ctctccgccc tgcaggccct gatgccgtgg cgctacgccc tgaagcgcat cggggggccag    1620 ttcggctcca gcgtgctctc ctacttcctc tttctcaaga ccctgctggc tttcaatgcc    1680
ctcctgctgc tgctgctggt ggccttcatc atgggccctc aggtcgcctt cccacccgcc    1740

```
ctgccgggcc ctgcccccgt ctgcacaggc ctggagctcc tcacaggcgc gggttgcttc    1800
acccacaccg tcatgtacta cggccactac agtaacgcca cgctgaacca gccgtgtggc    1860
agcccctgg atgcagcca gtgcacaccc agggtgggtg gcctgcccta caacatgccc     1920
ctggcctacc tctccactgt gggcgtgagc ttctttatca cctgcatcac cctggtgtac   1980
agcatggctc actctttcgg ggagagctac cgggtgggca gcacctctgg catccacgcc   2040
atcaccgtct tctgctcctg ggactacaag gtgacgcaga agcgggcctc ccgcctccag   2100
caggacaata ttcgcacccg gctgaaggag ctgctggccg agtggcagct gcggcacagc   2160
cccaggagcg tgtgcgggag gctgcggcag gcggctgtgc tggggcttgt gtggctgctg   2220
tgtctgggga ccgcgctggg ctgcgccgtg gccgtccacg tcttctcgga gttcatgatc   2280
cagagtccag aggctgctgg ccaggaggct gtgctgctgg tcctgcccct ggtggttggc   2340
ctcctcaacc tggggccccc ctacctgtgc cgtgtcctgg ccgccctgga gccgcatgac   2400
tccccggtac tggaggtgta cgtggccatc tgcaggaacc tcatcctcaa gctggccatc   2460
ctggggacac tgtgctacca ctggctgggc cgcagggtgg cgtcctgca gggccagtgc    2520
tgggaggatt tgtgggcca ggagctgtac cggttcctgg tgatggactt cgtcctcatg    2580
ttgctggaca cgcttttggg ggaactggtg tggaggatta tctccgagaa gaagctgaag   2640
aggaggcgga agccggagtt tgacattgcc cggaatgtcc tggagctgat ttatgggcag   2700
actctgacct ggctggggt gctcttctcg cccctcctcc ccgccgtgca gatcatcaag    2760
ctgctgctcg tcttctatgt caagaagacc agccttctgg ccaactgcca ggcgccgcgc   2820
cggccctggc tggcctcaca catgagcacc gtcttcctca cgctgctctg cttccccgcc   2880
ttcctgggcg ccgctgtctt cctctgctac gccgtctggc aggtgaagcc ctcgagcacc   2940
tgcggcccct tccggaccct ggacaccatg tacgaggccg gcagggtgtg ggtgcgccac   3000
ctggaggcgg caggccccag ggtctcctgg ctgccctggg tgcaccggta cctgatggaa   3060
aacaccttct tgtcttcct ggtgtcagcc ctgctgctgg ccgtgatcta cctcaacatc    3120
caggtggtgc ggggccagcg caaggtcatc tgcctgctca aggagcagat cagcaatgag   3180
ggtgaggaca aaatcttctt aatcaacaag cttcactcca tctacgagag gaaggagagg   3240
gaggagagga gcagggttgg gacaaccgag gaggctgcgg caccccctgc cctgctcaca   3300
gatgaacagg atgccggtaa gcctatccct aaccctctgc tgggcctgga ttctaccaag   3360
tagaccggta gcttctatag tgtcacctaa atatagctta agtttaaacc gctgatcagc   3420
ctcgactgtg ccttctagtt gccagccatc tgttgtttgc ccctcccccg tgccttcctt   3480
gaccctggaa ggtgccactc ccactgtcct ttcctaataa aatgaggaaa ttgcatcgca   3540
ttgtctgagt aggtgtcatt ctattctggg ggtggggtg gggcaggaca gcaaggggga   3600
ggattgggaa gacaatagca ggcatgctgg ggatgcggtg gctctatgg cttctgaggc    3660
ggaaagaacc agctggggct ctaggggta tccccacgcg ccctgtagcg cgcattaag    3720
cgcggcgggt gtggtggtta cgcgcagcgt gaccgctaca cttgccagcg ccctagcgcc   3780
cgctcctttc gctttcttcc cttcctttct cgccacgttc gccggctttc cccgtcaagc   3840
tctaaatcgg gggctccctt tagggttccg atttagtgct ttacggcacc tcgaccccaa   3900
aaaacttgat tagggtgatg gttcacgtag tgggccatcg ccctgataga cggtttttcg   3960
ccctttgacg ttggagtcca cgttctttaa tagtggactc ttgttccaaa ctggaacaac   4020
actcaaccct atctcggtct attctttga tttataaggg attttgccga tttcggccta   4080
ttggttaaaa aatgagctga tttaacaaaa atttaacgcg aattaattct gtggaatgtg   4140
```

```
tgtcagttag ggtgtggaaa gtccccaggc tccccagcag gcagaagtat gcaaagcatg    4200
catctcaatt agtcagcaac caggtgtgga aagtccccag gctccccagc aggcagaagt    4260
atgcaaagca tgcatctcaa ttagtcagca accatagtcc cgcccctaac tccgcccatc    4320
ccgcccctaa ctccgcccag ttccgcccat tctccgcccc atggctgact aatttttttt    4380
atttatgcag aggccgaggc cgcctctgcc tctgagctat tccagaagta gtgaggaggc    4440
ttttttggag gcctaggctt ttgcaaaaag ctcccgggag cttgtatatc cattttcgga    4500
tctgatcaag agacaggatg aggatcgttt cgcatgattg aacaagatgg attgcacgca    4560
ggttctccgg ccgcttgggt ggagaggcta ttcggctatg actgggcaca acagacaatc    4620
ggctgctctg atgccgccgt gttccggctg tcagcgcagg ggcgcccggt tctttttgtc    4680
aagaccgacc tgtccggtgc cctgaatgaa ctgcaggacg aggcagcgcg gctatcgtgg    4740
ctggccacga cgggcgttcc ttgcgcagct gtgctcgacg ttgtcactga agcgggaagg    4800
gactggctgc tattgggcga agtgccgggg caggatctcc tgtcatctca ccttgctcct    4860
gccgagaaag tatccatcat ggctgatgca atgcggcggc tgcatacgct tgatccggct    4920
acctgcccat tcgaccacca agcgaaacat cgcatcgagc gagcacgtac tcggatggaa    4980
gccggtcttg tcgatcagga tgatctggac gaagagcatc aggggctcgc gccagccgaa    5040
ctgttcgcca ggctcaaggc gcgcatgccc gacggcgagg atctcgtcgt gacccatggc    5100
gatgcctgct tgccgaatat catggtggaa aatggccgct tttctggatt catcgactgt    5160
ggccggctgg gtgtggcgga ccgctatcag gacatagcgt tggctacccg tgatattgct    5220
gaagagcttg gcggcgaatg ggctgaccgc ttcctcgtgc tttacggtat cgccgctccc    5280
gattcgcagc gcatcgcctt ctatcgcctt cttgacgagt tcttctgagc gggactctgg    5340
ggttcgaaat gaccgaccaa gcgacgccca acctgccatc acgagatttc gattccaccg    5400
ccgccttcta tgaaaggttg gcttcggaa tcgttttccg gacgccggc tggatgatcc    5460 tccagcgcgg ggatctcatg ctggagttct tcgcccaccc caacttgttt attgcagctt    5520
ataatggtta caaataaagc aatagcatca caaatttcac aaataaagca tttttttcac    5580
tgcattctag ttgtggtttg tccaaactca tcaatgtatc ttatcatgtc tgtataccgt    5640
cgacctctag ctagagcttg gcgtaatcat ggtcatagct gtttcctgtg tgaaattgtt    5700
atccgctcac aattccacac aacatacgag ccggaagcat aaagtgtaaa gcctggggtg    5760
cctaatgagt gagctaactc acattaattg cgttgcgctc actgcccgct ttccagtcgg    5820
gaaacctgtc gtgccagctg cattaatgaa tcggccaacg cgcggggaga ggcggtttgc    5880
gtattgggcg ctcttccgct tcctcgctca ctgactcgct gcgctcggtc gttcggctgc    5940
ggcgagcggt atcagctcac tcaaaggcgg taatacggtt atccacagaa tcaggggata    6000
acgcaggaaa gaacatgtga gcaaaaggcc agcaaaaggc caggaaccgt aaaaaggccg    6060
cgttgctggc gtttttccat aggctccgcc cccctgacga gcatcacaaa aatcgacgct    6120
caagtcagag gtggcgaaac ccgacaggac tataaagata ccaggcgttt cccctggaa    6180 gctccctcgt gcgctctcct gttccgaccc tgccgcttac cggatacctg tccgcctttc    6240
tcccttcggg aagcgtggcg ctttctcata gctcacgctg taggtatctc agttcggtgt    6300
aggtcgttcg ctccaagctg ggctgtgtgc acgaacccc cgttcagccc gaccgctgcg    6360
ccttatccgg taactatcgt cttgagtcca acccggtaag acacgactta tcgccactgg    6420
cagcagccac tggtaacagg attagcagag cgaggtatgt aggcggtgct acagagttct    6480
```

```
tgaagtggtg gcctaactac ggctacacta aagaacagt atttggtatc tgcgctctgc   6540
tgaagccagt taccttcgga aaaagagttg gtagctcttg atccggcaaa caaaccaccg   6600
ctggtagcgg ttttttttgtt tgcaagcagc agattacgcg cagaaaaaaa ggatctcaag   6660
aagatccttt gatcttttct acggggtctg acgctcagtg aacgaaaac tcacgttaag    6720 ggattttggt catgagatta tcaaaaagga tcttcaccta gatcctttta aattaaaaat   6780
gaagttttaa atcaatctaa agtatatatg agtaaacttg gtctgacagt taccaatgct   6840
taatcagtga ggcacctatc tcagcgatct gtctatttcg ttcatccata gttgcctgac   6900
tccccgtcgt gtagataact acgatacggg agggcttacc atctggcccc agtgctgcaa   6960
tgataccgcg agacccacgc tcaccggctc cagatttatc agcaataaac cagccagccg   7020
gaagggccga gcgcagaagt ggtcctgcaa ctttatccgc ctccatccag tctattaatt   7080
gttgccggga agctagagta agtagttcgc cagttaatag tttgcgcaac gttgttgcca   7140
ttgctacagg catcgtggtg tcacgctcgt cgtttggtat ggcttcattc agctccggtt   7200
cccaacgatc aaggcgagtt acatgatccc ccatgttgtg caaaaaagcg gttagctcct   7260
tcggtcctcc gatcgttgtc agaagtaagt tggccgcagt gttatcactc atggttatgg   7320
cagcactgca taattctctt actgtcatgc catccgtaag atgcttttct gtgactggtg   7380
agtactcaac caagtcattc tgagaatagt gtatgcggcg accgagttgc tcttgcccgg   7440
cgtcaatacg ggataatacc gcgccacata gcagaacttt aaaagtgctc atcattggaa   7500
aacgttcttc ggggcgaaaa ctctcaagga tcttaccgct gttgagatcc agttcgatgt   7560
aacccactcg tgcacccaac tgatcttcag catcttttac tttcaccagc gtttctgggt   7620
gagcaaaaac aggaaggcaa aatgccgcaa aaaagggaat aagggcgaca cggaaatgtt   7680
gaatactcat actcttcctt tttcaatatt attgaagcat ttatcagggt tattgtctca   7740
tgagcggata catatttgaa tgtatttaga aaaataaaca aataggggtt ccgcgcacat   7800
ttccccgaaa agtgccacct gacgtc                                         7826

<210> SEQ ID NO 61
<211> LENGTH: 9857
<212> TYPE: DNA
<213> ORGANISM: Artificial Sequence
<220> FEATURE:
<223> OTHER INFORMATION: Macaca mulatta TMC6-2A-YC260TM in pcDNA3.1(-)

<400> SEQUENCE: 61
gacggatcgg gagatctccc gatccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
```

-continued

```
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gccaccatgg cccaaccccct tgccttcatt cttgacgtcc ctgaaactcc cggagatcag     960
ggaagccagg aacccagccc atacgacgaa agcgaggtac atgattcctt ccaccaattg     1020
atccaggaac agtcccagtg ggctgctcag gaaggccttg aactgcaaca gcgggaacaa     1080
gaggccaccg gctccgggca gcagacactt cgcagaccag agggcacgca gagtaccgca     1140
acccttagaa ttctggcatc aatgccttca cgtactattg gcaggagtcg tggtgccatc     1200
atctctcagt attactctag gacagtgcaa cttcgaaggc gctccagcag accctcctg      1260
gggaattttg tcctttccgc acggcccagc ctgaggctct acgatctgga attggaccca     1320
actgctcgtg aggaggaaga aaagcagtct ctcctcgtga aggaactgca gagcctcgca     1380
gtggcacaga gagatcacat gctgaggggc atgcctctct ctttggctga aaagaggagc     1440
ctgagagaaa agagtcggac tcctcgggga aaatggcgcg ccagcaagg ctccggaggg      1500
gtgtgcagtt gttgtgggcg gttgagatac gcctgtgtcc ttgccctgca ttccctgggt     1560
ctggctctgc tttccgggtt gcaagccctc acgccttgga gatatgctct gaaaaggatc     1620
ggaggtcagt tcgggagtag cgtgctttct tatttcttgt tccttaagac actgctggcc     1680
ttcaatgcgt tgcttcagct tctgctggtg gcctttatcg tgggtcctca gtagctttc      1740
cctccagcgc tgcccggtcc tgctcccatt gcaccggcc tggaacttct gaccggagct      1800
ggctgtttta cccacaccgt gatgttttac ggacattact caaacgccac cctgaatcag     1860
ccatgcggct ctcccctgga tggttcacag tgtactccga gagccggagg cctgccatat     1920
aatatgcccc tggcatacct ctatactgtc ggggctggct tcttcattac gtgcatcact     1980
ttggtctaca gcatggccca ttcctttggg gagagttacc gagtcgggag tacaagtggg     2040
atacacgcta taaccgtgtt ttgcagctgg gactacaaag taacccagaa gcgagcgtcc     2100
cggctgcagc aggacaacat tcggacacgc ctgaaggagt tgctggcaga gtggcagctc     2160
cgacagagcc ctaggtctgt ttgtggccgc ctgagacagg cagcagccct gggcctggct     2220
tggttgctgt gtctgggaac tgctctgggt tgtgctgtgg ccatccacgt tttcagcgag     2280
ttcttgattc aatctcccga ggctgccggt caagaggctg ctctgctggt cctgccattg     2340
gtcgtaggcc tgcttaacct gggcgctccc tatctgtgca gagtgctggc ggccctggag     2400
cctcatgaca gcccggttct tgaggtctac gtggccatct gccggaacct gatcctcaaa     2460
ctggcaattc tgggcacact gtgctatcac tggctgggta cacgggtcgc cgtgctccag     2520
gatcagtgct gggaggactt cgtggggcag gagctgtaca gatttctggt gatggacttt     2580
gtcctgatgc tgctggacac actctttggg gaactggtgt ggcgcatcat cagcgagaag     2640
aaattgaaga ggaggcgtaa gcccgagttt gacatcgccc ggaatgtcct cgagctcatt     2700
tatggacaga cattgacctg gctgggagtt ctgttttcac cactgctccc ggcggtgcag     2760
atcatcaaac tcctcctggt gttctacgtg aagaaaacca gtttgctcgc caactgtcag     2820
gccccacgac gaccatggct ggcatctcac atgtccacga tatttctgac actcttgtgc     2880
tttcctgcgt tcctcggagc cgcaatcttc ctgtgctatg ccgtgtggca agtaaaacct     2940
tcatcaactt gtgggccatt cagaacccctc gacagcatgt acgaagccgg ccgggttggg     3000
gtaagatatc tggaggcagc tggacccagg gtttcctggc tgccgtgggt acatcgctac     3060
```

```
ctggtggaaa acactttctt tgtgtttctg gtttctgctc ttctcttggc cgtgatatat    3120
ctcaacattc aagttgttcg cggtcagagg agggtgattt gtctgctcaa ggaacagata    3180
tctaacgagg gagaggataa gatcttcctg atcaataagc tgcacagcat ttatgagcgc    3240
aaagagcgtg aggagaggtc acgagtcgga acaaccgagg aaacagcagc acctccaaca    3300
ctcctgaccg atgagcgcga tgacgggagt ggtgaaggtc gtggctcact gttgacttgt    3360
ggcgatgtag aagagaatcc tggccctgca acgatgggac tccagaacga actagcccta    3420
aaactggctg gcctggacat caacaagact ggaggaagca tggtctccaa gggtgaggaa    3480
cttttcaccg gcgtagtgcc cattcttgtg gagctggacg gagatgtcaa cggacatcgg    3540
ttttctgtga gtggtgaggg ggaaggcgat gccacctatg gtaaactgac cttaaagttc    3600
atttgcacca ctggcaagct tcctgtccca tggcccacac tggtgaccac tctcacctgg    3660
ggagtgcagt gcttctcacg ctaccctgat cacatgaagc aacatgactt ctttaaatcc    3720
gctatgccag aggggtatgt tcaggaaagg accatcttct ttaaggacga tgggaactat    3780
aagacccgag ctgaagtgaa gttcgaggga gatacactgg tgaataggat cgagctcaaa    3840
gggatcgatt tcaaagagga tggaaacatt ctcggtcaca aactggaata caactacatt    3900
agccataacg tgtacatcac cgccgacaag caaaagaatg gatcaaggc ccatttcaaa    3960
atccggcaca acatcgagga cggctctgtg caactcgctg accactatca gcagaatacg    4020
cccattggcg acggccccgt tctgttgcct gacaaccact acctgtctac tcagtcagct    4080
cttttccaagg acccaaacga gaaacgagac cacatggtgc ttttagagtt cgtgacggca    4140
gccaggatgc atgaccaact aactgaggag cagatcgcag agtttaaaga ggcttttttcc    4200
ctcttcgaca agatggtgga tggaaccatc actacaaaag agctgggcac agtgatgaga    4260
agtcttggcc agaatccgac cgaagcgaa ctccaggaca tgattaacga agtagacgcg    4320
gatggtaacg gaacaatcta cttccccgaa tttctgacaa tgatggcacg gaaaatgaag    4380
gacacagact cggaagagga gattcgggag gcattcaggg tcttcgataa ggacggtaac    4440
ggttacatct ctgccgcaga actaagacac gtgatgacaa ccttggggga aaagctgacc    4500
gatgaggagg tggacgagat gatacgtgaa gctgatattg acggggacgg ccaagtcaat    4560
tacgaggaat ttgttcagat gatgacagcc aagggggga aaaggcgatg aagaaaaac    4620
tttatagccg tgagcgctgc aaatcggttc aagaagatct cctctagcgg tgcactggag    4680
ctgatggatg ggggcgtcca gttagccgat cattaccaac agaatactcc aatcggcgat    4740
ggacctgtac tgctgcccga taatcattat ctcagttatc agtcggcttt gagcaaagat    4800
cccaatgaga agcgcgatca catggtgttg ttggaatttg tcaccgctgc cggaataacc    4860
ctaggaatgg acgagctgta caaagcggt tcaggcggga tggttagcaa ggggggaggag    4920
ttatttacag gagtggtgcc aatactggta gaactggatg gagatgttaa tggccacaag    4980
ttttccgtct ctggggaggg agagggagac gccacatatg gaagctgac tctcaagctg    5040
atttgtacca ctgggaaatt gccagttccg tggccaacac tcgtgacaac gctgggatat    5100
ggcctccagt gcttcgccag atatccggat catatgaagc agcacgattt ctttaagagt    5160
gcgatgcctg agggtacgt tcaggaacgc acgatctttt tcaaagacga cggcaattac    5220
aagacaagag ccgaggtcaa gtttgaggga gacactttgg tcaatagaat cgaattgaaa    5280
ggcatagact tcaaggaaga cggcaacata cttgggcata aactcgagta caactataat    5340
agccacaacg tctacattat ggctgacaag cagaagaacg gcatcaaggc caactttaag    5400
attcgccaca atattgaatg atctaaggcc cgtttaaacc cgctgatcag cctcgactgt    5460
```

```
gccttctagt tgccagccat ctgttgtttg cccctccccc gtgccttcct tgaccctgga    5520
aggtgccact cccactgtcc tttcctaata aaatgaggaa attgcatcgc attgtctgag    5580
taggtgtcat tctattctgg ggggtggggt ggggcaggac agcaaggggg aggattggga    5640
agacaatagc aggcatgctg gggatgcggt gggctctatg gcttctgagg cggaaagaac    5700
cagctggggc tctagggggt atccccacgc gccctgtagc ggcgcattaa gcgcggcggg    5760
tgtggtggtt acgcgcagcg tgaccgctac acttgccagc gccctagcgc ccgctccttt    5820
cgctttcttc ccttcctttc tcgccacgtt cgccggcttt ccccgtcaag ctctaaatcg    5880
ggggctccct ttagggttcc gatttagtgc tttacggcac ctcgacccca aaaaacttga    5940
ttagggtgat ggttcacgta gtgggccatc gccctgatag acggttttc gccctttgac     6000 gttggagtcc acgttcttta atagtggact cttgttccaa actggaacaa cactcaaccc    6060
tatctcggtc tattcttttg atttataagg gattttgccg atttcggcct attggttaaa   6120
aaatgagctg atttaacaaa aatttaacgc gaattaattc tgtggaatgt gtgtcagtta    6180
gggtgtggaa agtccccagg ctccccagca ggcagaagta tgcaaagcat gcatctcaat    6240
tagtcagcaa ccaggtgtgg aaagtcccca ggctccccag caggcagaag tatgcaaagc    6300
atgcatctca attagtcagc aaccatagtc ccgcccctaa ctccgcccat cccgccccta    6360
actccgccca gttccgccca ttctccgccc catggctgac taatttttt tatttatgca    6420 gaggccgagg ccgcctctgc ctctgagcta ttccagaagt agtgaggagg cttttttgga    6480
ggcctaggct tttgcaaaaa gctcccggga gcttgtatat ccattttcgg atctgatcaa    6540
gagacaggat gaggatcgtt tcgcatgatt gaacaagatg gattgcacgc aggttctccg    6600
gccgcttggg tggagaggct attcggctat gactgggcac aacagacaat cggctgctct    6660
gatgccgccg tgttccggct gtcagcgcag gggcgcccgg ttcttttgt caagaccgac     6720 ctgtccggtg ccctgaatga actgcaggac gaggcagcgc ggctatcgtg gctggccacg    6780
acgggcgttc cttgcgcagc tgtgctcgac gttgtcactg aagcgggaag ggactggctg    6840
ctattgggcg aagtgccggg gcaggatctc ctgtcatctc accttgctcc tgccgagaaa    6900
gtatccatca tggctgatgc aatgcggcgg ctgcatacgc ttgatccggc tacctgccca    6960
ttcgaccacc aagcgaaaca tcgcatcgag cgagcacgta ctcggatgga agccggtctt    7020
gtcgatcagg atgatctgga cgaagagcat caggggctcg cgccagccga actgttcgcc    7080
aggctcaagg cgcgcatgcc cgacggcgag gatctcgtcg tgacccatgg cgatgcctgc    7140
ttgccgaata tcatggtgga aaatggccgc ttttctggat tcatcgactg tggccggctg    7200
ggtgtggcgg accgctatca ggacatagcg ttggctaccc gtgatattgc tgaagagctt    7260
ggcggcgaat gggctgaccg cttcctcgtg ctttacggta tcgccgctcc cgattcgcag    7320
cgcatcgcct tctatcgcct tcttgacgag ttcttctgag cgggactctg gggttcgaaa    7380
tgaccgacca agcgacgccc aacctgccat cacgagattt cgattccacc gccgccttct    7440
atgaaaggtt gggcttcgga atcgttttcc gggacgccgg ctggatgatc ctccagcgcg    7500
gggatctcat gctggagttc ttcgcccacc ccaacttgtt tattgcagct tataatggtt    7560
acaaataaag caatagcatc acaaatttca caaataaagc atttttttca ctgcattcta    7620
gttgtggttt gtccaaactc atcaatgtat cttatcatgt ctgtataccg tcgacctcta    7680
gctagagctt ggcgtaatca tggtcatagc tgtttcctgt gtgaaattgt tatccgctca    7740
caattccaca acatacga gccggaagca taaagtgtaa agcctggggt gcctaatgag    7800
```

```
tgagctaact cacattaatt gcgttgcgct cactgcccgc tttccagtcg ggaaacctgt   7860
cgtgccagct gcattaatga atcggccaac gcgcggggag aggcggtttg cgtattgggc   7920
gctcttccgc ttcctcgctc actgactcgc tgcgctcggt cgttcggctg cggcgagcgg   7980
tatcagctca ctcaaaggcg gtaatacggt tatccacaga atcaggggat aacgcaggaa   8040
agaacatgtg agcaaaaggc cagcaaaagg ccaggaaccg taaaaaggcc gcgttgctgg   8100
cgtttttcca taggctccgc ccccctgacg agcatcacaa aaatcgacgc tcaagtcaga   8160
ggtggcgaaa cccgacagga ctataaagat accaggcgtt tccccctgga agctccctcg   8220
tgcgctctcc tgttccgacc ctgccgctta ccggatacct gtccgccttt ctcccttcgg   8280
gaagcgtggc gctttctcat agctcacgct gtaggtatct cagttcggtg taggtcgttc   8340
gctccaagct gggctgtgtg cacgaacccc ccgttcagcc cgaccgctgc gccttatccg   8400
gtaactatcg tcttgagtcc aacccggtaa gacacgactt atcgccactg gcagcagcca   8460
ctggtaacag gattagcaga gcgaggtatg taggcggtgc tacagagttc ttgaagtggt   8520
ggcctaacta cggctacact agaagaacag tatttggtat ctgcgctctg ctgaagccag   8580
ttaccttcgg aaaaagagtt ggtagctctt gatccggcaa acaaaccacc gctggtagcg   8640
gttttttttgt ttgcaagcag cagattacgc gcagaaaaaa aggatctcaa gaagatcctt   8700
tgatcttttc tacggggtct gacgctcagt ggaacgaaaa ctcacgttaa gggattttgg   8760
tcatgagatt atcaaaaagg atcttcacct agatcctttt aaattaaaaa tgaagtttta   8820
aatcaatcta agtatatat gagtaaactt ggtctgacag ttaccaatgc ttaatcagtg   8880
aggcacctat ctcagcgatc tgtctatttc gttcatccat agttgcctga ctccccgtcg   8940
tgtagataac tacgatacgg gagggcttac catctggccc cagtgctgca atgataccgc   9000
gagacccacg ctcaccggct ccagatttat cagcaataaa ccagccagcc ggaagggccg   9060
agcgcagaag tggtcctgca actttatccg cctccatcca gtctattaat tgttgccggg   9120
aagctagagt aagtagttcg ccagttaata gtttgcgcaa cgttgttgcc attgctacag   9180
gcatcgtggt gtcacgctcg tcgtttggta tggcttcatt cagctccggt tcccaacgat   9240
caaggcgagt tacatgatcc cccatgttgt gcaaaaaagc ggttagctcc ttcggtcctc   9300
cgatcgttgt cagaagtaag ttggccgcag tgttatcact catggttatg gcagcactgc   9360
ataattctct tactgtcatg ccatccgtaa gatgcttttc tgtgactggt gagtactcaa   9420
ccaagtcatt ctgagaatag tgtatgcggc gaccgagttg ctcttgcccg gcgtcaatac   9480
gggataatac cgcgccacat agcagaactt taaaagtgct catcattgga aaacgttctt   9540
cggggcgaaa actctcaagg atcttaccgc tgttgagatc cagttcgatg taacccactc   9600
gtgcacccaa ctgatcttca gcatctttta ctttcaccag cgtttctggg tgagcaaaaa   9660
caggaaggca aaatgccgca aaaaagggaa taagggcgac acggaaatgt tgaatactca   9720
tactcttcct ttttcaatat tattgaagca tttatcaggg ttattgtctc atgagcggat   9780
acatatttga atgtatttag aaaaataaac aaataggggt tccgcgcaca tttccccgaa   9840
aagtgccacc tgacgtc                                                  9857
```

<210> SEQ ID NO 62
<211> LENGTH: 9854
<212> TYPE: DNA
<213> ORGANISM: Artificial Sequence
<220> FEATURE:
<223> OTHER INFORMATION: Pongo abelii TMC6-2A-YC260TM in pcDNA3.1(-)

<400> SEQUENCE: 62

-continued

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gccaccatgg ctcagcctct ggcgtttata ctcgacgtgc ccgagacacc aggcgaccaa     960
ggccaggatc cctcacccta tgacgagagt gaggttcatg attcattcca gcagctcata    1020
caagaacagt ctaggtgtgc agcccaggag ggactcgaac tccagcagcg cgaacgggag    1080
gctaccggtt ccgggcagca aaccctgtgg cgtcccgaag ggactcaaag tactgctacc    1140
ctccgaatac tggcctccat gccatcaagg acgatcgggc gcagtcgcgg agccattatt    1200
tcccagtact acaacaggac agtacagctg cgacgtcggt cctctcggcc gctcctcggg    1260
aacttcgtgc gaagcgcaag accttccctt agactgtacg acctggaact tgatcccatg    1320
gctcgggagg aagaggaaaa gcagagcctt ctggttaagg agctgcagtc tttggccgtt    1380
gcgcagcggg atcacatgct caggggaatg cctctcagtc tggctgaaaa gagaagcctg    1440
cgggagaagt ccagaaccct tagagggaag tggcggggcc agcctggcag cggaggcgtg    1500
tgtagctgtt gtgggcaact gcgttatgca tgcgtcctcg cactgcacag cctgggcctt    1560
gccctgttgt ccgcactcca ggccctcact ccttggagat atgctctgaa gagaattggc    1620
ggccaatttg gtagctccgt attgtcttac ttccttttcc tgaaaacatt gttggctttc    1680
aacgcactgc tgctgttgct gctggtcgct ttcatcacgg gccacaggt ggcttttcca    1740 ccagctctgt tgggtcctgt cccagtgtgt acaggactcg agcttctgac aggcgcaggg    1800
tgtttcactc acactgtgat gtactatggc cactattcta atgctactct gaatcagccc    1860
tgtgggtccc ctctggatgg tagccaatgc accccaaggg ccggtggcct gccgtataat    1920
atgccccttg cgtacttgtc aaccgtcggg gttagcttct tcgtgacttg cattacgttg    1980
gtgtattcaa tggcacatag tttcggcgag agctataggg ttggatccac tagcgggata    2040
cacgcaatca cggtgttctg ttcttgggac tacaaagtga cacagaaaag agctagcagg    2100
ctgcagcaag ataacattag aaccagactg aaagagttgc tggcagagtg gcagctgagg    2160
cagagtccgc gcagtgtttg cggaaccttg cggcaggctg ccgtcctggg cctcgtttgg    2220
ttgctctgct tgggaacagc gctgggatgt gccgtcgcag tgcacgtttt ctccgagttt    2280
atgatccaga gtcctgaagc cgctggccag gaagccgctc tgctggtgct gcccctcgtt    2340
```

```
gtcggcctcc tgaatctcgg ggcaccatac ctgtgccgtg tgctggccgc cttggaacct    2400
catgactccc ctgtcatgga ggtgtatgtg gccatctgca ggaacctgat cctgaagctg    2460
gccattctgg gaacactttg ttaccattgg cttgatcata gggtcggtgt actccaggga    2520
cagtgctggg aggacttcgt gggtcaggaa ctgtatagat ttctcgtcat ggacttcgta    2580
cttatgctgc tggatacccT gtttggcgaa cttgtctggc gcatcataag cgagaagaaa    2640
ctgaagcgac gccggaagcc agaatttgac attgcacgga atgtgctgga gctgatctac    2700
ggtcagacct tgacttggct cggcgtgctc ttctctccgc tgctgcccgc cgtgcagatc    2760
atcaagctgc tgctcgtgtt ttacgtgaag aaaaccagcc tgttggccaa ttgccaggcc    2820
ccacgcaggc cttggctcgc atcacacatg agcactatct ttcttacact gctgtgcttt    2880
ccagcctttc ttggggctgc tgtattcctt tgctacgctg tgtggcaagt gaaacctagt    2940
tcaacatgtg gacccTttag aactctggac accatgtatg aggccggtcg cgtgtgggtg    3000
aggcacctgg aaacagccgg accccgtgtt tcatggcttc cctgggtgca tcgctacctg    3060
gtcgagaaca ccttctttgt cttTctggtg tctgcgcttc tgctggcagt tatctacctg    3120
aacatccaag tggtacgcgg gcagcggaaa gtcatttgcc tgttgaagga gcagattagc    3180
aatgagggag aggacaaaat cttcctcatt aacaagctgc actctatcta cgagcgaaag    3240
gaaagggaag agcgatctcg agtcggtacc accgaagagg ccgtagcgcc atctgccctg    3300
ctgacagacg agcaagatgc cgggagtggt gaaggtcgtg gctcactgtt gacttgtggc    3360
gatgtagaag agaatcctgg ccctgcaacg atgggactcc agaacgaact agccctaaaa    3420
ctggctggcc tggacatcaa caagactgga ggaagcatgg tctccaaggg tgaggaactt    3480
ttcaccggcg tagtgcccat tcttgtggag ctggacggag atgtcaacgg acatcggttt    3540
tctgtgagtg gtgaggggga aggcgatgcc acctatggta aactgacctt aaagttcatt    3600
tgcaccactg gcaagcttcc tgtcccatgg cccacactgg tgaccactct cacctgggga    3660
gtgcagtgct tctcacgcta ccctgatcac atgaagcaac atgacttctt taaatccgct    3720
atgccagagg ggtatgttca ggaaaggacc atcttcttta aggacgatgg gaactataag    3780
acccgagctg aagtgaagtt cgagggagat accctggtga ataggatcga gctcaaaggg    3840
atcgatttca agaggatgg aaacattctc ggtcacaaac tggaatacaa ctacattagc    3900
cataacgtgt acatcaccgc cgacaagcaa aagaatggga tcaaggccca tttcaaaatc    3960
cggcacaaca tcgaggacgg ctctgtgcaa ctcgctgacc actatcagca gaatacgccc    4020
attggcgacg gccccgttct gttgcctgac aaccactacc tgtctactca gtcagctctt    4080
tccaaggacc caaacgagaa acgagaccac atggtgcttt tagagttcgt gacggcagcc    4140
aggatgcatg accaactaac tgaggagcag atcgcagagt ttaaagaggc tttttcccTc    4200
ttcgacaaag atggtgatgg aaccatcact acaaaagagc tgggcacagt gatgagaagt    4260
cttggccaga atccgaccga gcggaactc aggacatga ttaacgaagt agacgcggat    4320
ggtaacggaa caatctactt ccccgaattt ctgacaatga tggcacggaa aatgaaggac    4380
acagactcgg aagaggagat tcgggaggca ttcagggtct tcgataagga cggtaacggt    4440
tacatctctg ccgcagaact aagacacgtg atgacaaacc tggggaaaa gctgaccgat    4500 gaggaggtgg acgagatgat acgtgaagct gatattgacg gggacggcca agtcaattac    4560
gaggaatttg ttcagatgat gacagccaaa ggggggaaaa ggcgatggaa gaaaaacttt    4620
atagccgtga gcgctgcaaa tcggttcaag aagatctcct ctagcggtgc actggagctg    4680
atggatgggg gcgtccagtt agccgatcat taccaacaga atactccaat cggcgatgga    4740
```

```
cctgtactgc tgcccgataa tcattatctc agttatcagt cggctttgag caaagatccc    4800
aatgagaagc gcgatcacat ggtgttgttg gaatttgtca ccgctgccgg aataacccta    4860
ggaatggacg agctgtacaa aggcggttca ggcgggatgg ttagcaaggg ggaggagtta    4920
tttacaggag tggtgccaat actggtagaa ctggatggag atgttaatgg ccacaagttt    4980
tccgtctctg gggagggaga gggagacgcc acatatggga agctgactct caagctgatt    5040
tgtaccactg ggaaattgcc agttccgtgg ccaacactcg tgacaacgct gggatatggc    5100
ctccagtgct tcgccagata tccggatcat atgaagcagc acgatttctt taagagtgcg    5160
atgcctgagg gttacgttca ggaacgcacg atcttttttca aagacgacgg caattacaag    5220
acaagagccg aggtcaagtt tgagggagac actttggtca atagaatcga attgaaaggc    5280
atagacttca aggaagacgg caacatactt gggcataaac tcgagtacaa ctataatagc    5340
cacaacgtct acattatggc tgacaagcag aagaacggca tcaaggccaa ctttaagatt    5400
cgccacaata ttgaatgatc taaggcccgt ttaaacccgc tgatcagcct cgactgtgcc    5460
ttctagttgc cagccatctg ttgtttgccc ctccccgtg ccttccttga ccctggaagg    5520
tgccactccc actgtccttt cctaataaaa tgaggaaatt gcatcgcatt gtctgagtag    5580
gtgtcattct attctggggg gtggggtggg gcaggacagc aaggggggag attgggaaga    5640
caatagcagg catgctgggg atgcggtggg ctctatggct tctgaggcgg aaagaaccag    5700
ctggggctct aggggggtatc cccacgcgcc ctgtagcggc gcattaagcg cggcgggtgt    5760
ggtggttacg cgcagcgtga ccgctacact tgccagcgcc ctagcgcccg ctccctttcgc    5820
tttcttccct tcctttctcg ccacgttcgc cggctttccc cgtcaagctc taaatcgggg    5880
gctcccttta gggttccgat ttagtgcttt acggcacctc gaccccaaaa aacttgatta    5940
gggtgatggt tcacgtagtg ggccatcgcc ctgatagacg ttttttcgcc ctttgacgtt    6000
ggagtccacg ttctttaata gtggactctt gttccaaact ggaacaacac tcaaccctat    6060
ctcggtctat tcttttgatt tataagggat tttgccgatt tcggcctatt ggttaaaaaa    6120
tgagctgatt taacaaaaat ttaacgcgaa ttaattctgt ggaatgtgtg tcagttaggg    6180
tgtggaaagt ccccaggctc cccagcaggc agaagtatgc aaagcatgca tctcaattag    6240
tcagcaacca ggtgtggaaa gtccccaggc tccccagcag gcagaagtat gcaaagcatg    6300
catctcaatt agtcagcaac catagtcccg cccctaactc cgcccatccc gcccctaact    6360
ccgcccagtt ccgcccattc tccgccccat ggctgactaa ttttttttat ttatgcagag    6420
gccgaggccg cctctgcctc tgagctattc cagaagtagt gaggaggctt ttttggaggc    6480
ctaggctttt gcaaaaagct cccgggagct gtatatcca ttttcggatc tgatcaagag    6540
acaggatgag gatcgtttcg catgattgaa caagatggat tgcacgcagg ttctccggcc    6600
gcttgggtgg agaggctatt cggctatgac tgggcacaac agacaatcgg ctgctctgat    6660
gccgccgtgt tccggctgtc agcgcagggg cgcccggttc ttttttgtcaa gaccgacctg    6720
tccggtgccc tgaatgaact gcaggacgag gcagcgcggc tatcgtggct ggccacgacg    6780
ggcgttcctt gcgcagctgt gctcgacgtt gtcactgaag cgggaaggga ctggctgcta    6840
ttgggcgaag tgccggggca ggatctcctg tcatctcacc ttgctcctgc cgagaaagta    6900
tccatcatgg ctgatgcaat gcggcggctg catacgcttg atccggctac ctgcccattc    6960
gaccaccaag cgaaacatcg catcgagcga gcacgtactc ggatggaagc cggtcttgtc    7020
gatcaggatg atctggacga agagcatcag gggctcgcgc cagccgaact gttcgccagg    7080
```

```
ctcaaggcgc gcatgcccga cggcgaggat ctcgtcgtga cccatggcga tgcctgcttg    7140
ccgaatatca tggtggaaaa tggccgcttt tctggattca tcgactgtgg ccggctgggt    7200
gtggcggacc gctatcagga catagcgttg gctacccgtg atattgctga agagcttggc    7260
ggcgaatggg ctgaccgctt cctcgtgctt tacggtatcg ccgctcccga ttcgcagcgc    7320
atcgccttct atcgccttct tgacgagttc ttctgagcgg gactctgggg ttcgaaatga    7380
ccgaccaagc gacgcccaac ctgccatcac gagatttcga ttccaccgcc gccttctatg    7440
aaaggttggg cttcggaatc gttttccggg acgccggctg gatgatcctc cagcgcgggg    7500
atctcatgct ggagttcttc gcccacccca acttgtttat tgcagcttat aatggttaca    7560
aataaagcaa tagcatcaca aatttcacaa ataaagcatt ttttcactg cattctagtt     7620 gtggtttgtc caaactcatc aatgtatctt atcatgtctg tataccgtcg acctctagct    7680
agagcttggc gtaatcatgg tcatagctgt ttcctgtgtg aaattgttat ccgctcacaa    7740
ttccacacaa catacgagcc ggaagcataa agtgtaaagc ctggggtgcc taatgagtga    7800
gctaactcac attaattgcg ttgcgctcac tgcccgcttt ccagtcggga aacctgtcgt    7860
gccagctgca ttaatgaatc ggccaacgcg cggggagagg cggtttgcgt attgggcgct    7920
cttccgcttc ctcgctcact gactcgctgc gctcggtcgt tcggctgcgg cgagcggtat    7980
cagctcactc aaaggcggta atacggttat ccacagaatc aggggataac gcaggaaaga    8040
acatgtgagc aaaaggccag caaaaggcca ggaaccgtaa aaaggccgcg ttgctggcgt    8100
ttttccatag gctccgcccc cctgacgagc atcacaaaaa tcgacgctca agtcagaggt    8160
ggcgaaaccc gacaggacta taaagatacc aggcgtttcc ccctggaagc tccctcgtgc    8220
gctctcctgt tccgaccctg ccgcttaccg gatacctgtc cgcctttctc ccttcgggaa    8280
gcgtggcgct ttctcatagc tcacgctgta ggtatctcag ttcggtgtag tcgttcgct    8340 ccaagctggg ctgtgtgcac gaaccccccg ttcagcccga ccgctgcgcc ttatccggta    8400
actatcgtct tgagtccaac ccggtaagac acgacttatc gccactggca gcagccactg    8460
gtaacaggat tagcagagcg aggtatgtag gcggtgctac agagttcttg aagtggtggc    8520
ctaactacgg ctacactaga agaacagtat tggtatctg cgctctgctg aagccagtta     8580
ccttcggaaa aagagttggt agctcttgat ccggcaaaca accaccgct ggtagcggtt     8640 tttttgtttg caagcagcag attacgcgca gaaaaaaagg atctcaagaa gatcctttga    8700
tcttttctac ggggtctgac gctcagtgga acgaaaactc acgttaaggg attttggtca    8760
tgagattatc aaaaaggatc ttcacctaga tccttttaaa ttaaaaatga gttttaaat     8820 caatctaaag tatatatgag taaacttggt ctgacagtta ccaatgctta atcagtgagg    8880
cacctatctc agcgatctgt ctatttcgtt catccatagt tgcctgactc cccgtcgtgt    8940
agataactac gatacgggag ggcttaccat ctggccccag tgctgcaatg ataccgcgag    9000
acccacgctc accggctcca gatttatcag caataaacca gccagccgga agggccgagc    9060
gcagaagtgg tcctgcaact ttatccgcct ccatccagtc tattaattgt tgccgggaag    9120
ctagagtaag tagttcgcca gttaatagtt tgcgcaacgt tgttgccatt gctacaggca    9180
tcgtggtgtc acgctcgtcg tttggtatgg cttcattcag ctccggttcc caacgatcaa    9240
ggcgagttac atgatccccc atgttgtgca aaaaagcggt tagctccttc ggtcctccga    9300
tcgttgtcag aagtaagttg gccgcagtgt tatcactcat ggttatggca gcactgcata    9360
attctcttac tgtcatgcca tccgtaagat gcttttctgt gactggtgag tactcaacca    9420
agtcattctg agaatagtgt atgcggcgac cgagttgctc ttgcccggcg tcaatacggg    9480
```

```
ataataccgc gccacatagc agaactttaa aagtgctcat cattggaaaa cgttcttcgg    9540
ggcgaaaact ctcaaggatc ttaccgctgt tgagatccag ttcgatgtaa cccactcgtg    9600
cacccaactg atcttcagca tcttttactt tcaccagcgt ttctgggtga gcaaaaacag    9660
gaaggcaaaa tgccgcaaaa aagggaataa gggcgacacg gaaatgttga atactcatac    9720
tcttcctttt tcaatattat tgaagcattt atcagggtta ttgtctcatg agcggataca    9780
tatttgaatg tatttagaaa aataaacaaa taggggttcc gcgcacattt ccccgaaaag    9840
tgccacctga cgtc                                                     9854
```

<210> SEQ ID NO 63
<211> LENGTH: 9854
<212> TYPE: DNA
<213> ORGANISM: Artificial Sequence
<220> FEATURE:
<223> OTHER INFORMATION: Mouse-Aotus nancymaae chimera TMC6 2A-YC260TM
      in pcDNA3.1(-)

<400> SEQUENCE: 63

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180 ttaggggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gccaccatgg ctcagtcact ggctttagcc ctcgatgtcc cggagaccac agaggatcag    960
ggatctcagg agccttctcc ctacgatgag agcgaggtcc atgactcttt ccaccagctg   1020
atccaggaac agtcccgatg ggccgctcaa gaaggtctgg aactgcagca acgtgcaagg   1080
ggtgcgactg gctctgggca gcataccctg agcgggtcag agggagcaca ctctaccgcc   1140
acactccgga ttctggccag catgcctagt aggactattg tcggagccg tggcgctatc   1200 atatcacagt actataatcg gaccgtccag ctccggagaa ggtcctccag gccccttctg   1260
ggaaaccttg tgcggagtgc tcggccctca cttagaatgt acgacctgga gttggaccca   1320
agagctcaag aggaggagga gaaacagagc ctgctggtta agaattgca gagcctggct   1380 gtggcccaga gggaccatat gctgcgaggc atgccactgt cattggctga agcggtcc    1440 ctgagggaaa agtcacggac tcctcgcggg aagtggcgtg gccaaagagg acatggaggt   1500
gtgtgctctt gttgtggctg gctgcgttac gcctgcgttc tgacattgca ctctctgggc   1560
ctggctctcc tcagctcact ccaggcattg accccgtgga gggatgcact caagagaatc   1620
```

```
ggtggacagt tgggagcag cgtactgtcc tacttcctgt ttctgaaaac tctgctcgct   1680
ttcaatgctc tgctgctgtt gcttctcctg gctttcattg tggggccaca ggccgccttt   1740
ccacccgccc ttccggggcc cgtcccagtg tgtaccggct tggaattgct gacaggggcc   1800
ggatgtttca cccacacagt gatgtactat ggccactata gcaatgccac tctgaatcag   1860
ccctgtggtg gacctctgga gggcggaaga tgttctccac gcgctggagg tctgccctat   1920
aacatgcccc ttgcatacct gtttacggta ggtgtggggt tcttcataac ttgcatctcc   1980
ttggtgtaca gtatggcgca ctcctttggg gagtcatacc gagtcgacag cacatccgga   2040
atacacgcta ttaccgtgtt ctgcagctgg gactgcaaag tgacacagaa acgagctagt   2100
agactgcagc aggacaacat ccgcacccga ctcaaggaac ttctggccga gtggcaactc   2160
aggcaaggcc ctaggtctgt ttgcagacgg cttcgtcagg ccgccgccct cgggctggtc   2220
tggcttctgt gtctgggtac ggccctgggc tgtgcagtgg cagtccacgt gttctccgaa   2280
tttatgatcc agagtcctga aacagctgga caagaggctg cactgctcgt actgcctctt   2340
gtggtgggtc tgcttaacct gggtgcccct tatctgtgca gaatactggc agcactcgaa   2400
cctcacgact ctccagtttt ggaggtgtac atggccatct gtcgaaacct gattttgaag   2460
ctggccgtgc tggggactct gtgctatcac tggcttggcc ggagggtcgg cgtgctccaa   2520
ggccagtgct gggaggactt cgtcggccag gaactgtaca gatttcttgt aatggatttt   2580
gttctcaccc tcctggacac actgtttggc gaactggtct ggagaatcat tagtgagaag   2640
aagctgaagc gccgacgaaa gcccgagttt gacattgcta gaaatgtcct ggagctgatt   2700
tatgggcaga ctctggcctg gctgggagta ttgtttagcc cacttttgcc agcagttcag   2760
atcatcaagc tcttgctggt gttctacatc aagaaaacta gtctccttgc taattgtcag   2820
gctcctaggc gccctggct ggcctccac atgtctacag tgttcctcac gctgctgtgc   2880
ttcccagcgt ttctcggcgc agccgtgttc ctctgttatg ccgtttggca agtcaagccg   2940
agtggaatat gcgggcccct taggacgttg gacaccatgt acgaagcagg gcgcgtctgg   3000
gtgcgccatt tggaggcggc gggacccaga gtgtcctggc tgccttgggt gcatcgctat   3060
ctggtcgaga ataccttctt cgtattcctg gtgagcgccc tcctgcttgc agtgatttac   3120
ctgaacatcc aggttgtacg cggccagcgg aaagtgattt gcctgctcaa gaacagatc   3180 agcaacgaag gcgaagataa aatctttctg attaacaagc ttcatagcat ctatgagcgc   3240
aaggaaaggg aggagagatc aaggtttcgc acatcccaag ccgcggttcc tccgaccctc   3300
ttcacagatg agcgggatgc agggagtggt gaaggtcgtg gctcactgtt gacttgtggc   3360
gatgtagaag agaatcctgg ccctgcaacg atgggactcc agaacgaact agccctaaaa   3420
ctggctggcc tggacatcaa caagactgga ggaagcatgg tctccaaggg tgaggaactt   3480
ttcaccggcg tagtgcccat tcttgtggag ctggacggag atgtcaacgg acatcggttt   3540
tctgtgagtg gtgaggggga aggcgatgcc acctatggta aactgaccct aaagttcatt   3600
tgcaccactg gcaagcttcc tgtcccatgg cccacactgg tgaccactct cacctgggga   3660
gtgcagtgct tctcacgcta ccctgatcac atgaagcaac atgacttctt taaatccgct   3720
atgccagagg ggtatgttca ggaaaggacc atcttcttta aggacgatgg gaactataag   3780
acccgagctg aagtgaagtt cgagggagat accctggtga ataggatcga gctcaaaggg   3840
atcgatttca agaggatgg aaacattctc ggtcacaaac tggaatacaa ctacattagc   3900
cataacgtgt acatcaccgc cgacaagcaa aagaatggga tcaaggccca tttcaaaatc   3960
```

-continued

```
cggcacaaca tcgaggacgg ctctgtgcaa ctcgctgacc actatcagca gaatacgccc    4020
attggcgacg gccccgttct gttgcctgac aaccactacc tgtctactca gtcagctctt    4080
tccaaggacc caaacgagaa acgagaccac atggtgcttt tagagttcgt gacggcagcc    4140
aggatgcatg accaactaac tgaggagcag atcgcagagt ttaaagaggc ttttcccctc    4200
ttcgacaaag atggtgatgg aaccatcact acaaaagagc tgggcacagt gatgagaagt    4260
cttggccaga atccgaccga agcggaactc caggacatga ttaacgaagt agacgcggat    4320
ggtaacggaa caatctactt ccccgaattt ctgacaatga tggcacggaa aatgaaggac    4380
acagactcgg aagaggagat tcgggaggca ttcagggtct tcgataagga cggtaacggt    4440
tacatctctg ccgcagaact aagacacgtg atgacaaacc ttggggaaaa gctgaccgat    4500
gaggaggtgg acgagatgat acgtgaagct gatattgacg gggacggcca agtcaattac    4560
gaggaatttg ttcagatgat gacagccaaa ggggggaaaa ggcgatggaa gaaaaacttt    4620
atagccgtga gcgctgcaaa tcggttcaag aagatctcct ctagcggtgc actggagctg    4680
atggatgggg gcgtccagtt agccgatcat taccaacaga atactccaat cggcgatgga    4740
cctgtactgc tgcccgataa tcattatctc agttatcagt cggctttgag caaagatccc    4800
aatgagaagc gcgatcacat ggtgttgttg gaatttgtca ccgctgccgg aataacccta    4860
ggaatggacg agctgtacaa aggcggttca ggcgggatgg ttagcaaggg ggaggagtta    4920
tttacaggag tggtgccaat actggtagaa ctggatggag atgttaatgg ccacaagttt    4980
tccgtctctg ggagggaga gggagacgcc acatatggga agctgactct caagctgatt    5040
tgtaccactg gaaaattgcc agttccgtgg ccaacactcg tgacaacgct gggatatggc    5100
ctccagtgct cgccagata tccggatcat atgaagcagc acgatttctt taagagtgcg    5160
atgcctgagg gttacgttca ggaacgcacg atctttttca aagacgacgg caattacaag    5220
acaagagccg aggtcaagtt tgagggagac actttggtca atagaatcga attgaaaggc    5280
atagacttca aggaagacgg caacatactt gggcataaac tcgagtacaa ctataatagc    5340
cacaacgtct acattatggc tgacaagcag aagaacggca tcaaggccaa ctttaagatt    5400
cgccacaata ttgaatgatc taaggcccgt ttaaacccgc tgatcagcct cgactgtgcc    5460
ttctagttgc cagccatctg ttgtttgccc ctcccccgtg ccttccttga ccctggaagg    5520
tgccactccc actgtccttt cctaataaaa tgaggaaatt gcatcgcatt gtctgagtag    5580
gtgtcattct attctggggg gtggggtggg gcaggacagc aaggggggagg attgggaaga    5640
caatagcagg catgctgggg atgcggtggg ctctatggct tctgaggcgg aaagaaccag    5700
ctggggctct aggggtatc cccacgcgcc ctgtagcggc gcattaagcg cggcgggtgt    5760
ggtggttacg cgcagcgtga ccgctacact tgccagcgcc ctagcgcccg ctccttttcgc    5820
tttcttccct tcctttctcg ccacgttcgc cggctttccc cgtcaagctc taaatcgggg    5880
gctcccttta gggttccgat ttagtgcttt acggcacctc gaccccaaaa aacttgatta    5940
gggtgatggt tcacgtagtg ggccatcgcc ctgatagacg gtttttcgcc ctttgacgtt    6000
ggagtccacg ttctttaata gtggactctt gttccaaact ggaacaacac tcaaccctat    6060
ctcggtctat tcttttgatt tataagggat tttgccgatt tcggcctatt ggttaaaaaa    6120
tgagctgatt taacaaaaat ttaacgcgaa ttaattctgt ggaatgtgtg tcagttaggg    6180
tgtggaaagt ccccaggctc cccagcaggc agaagtatgc aaagcatgca tctcaattag    6240
tcagcaacca ggtgtggaaa gtccccaggc tccccagcag gcagaagtat gcaaagcatg    6300
catctcaatt agtcagcaac catagtcccg cccctaactc cgcccatccc gcccctaact    6360
```

```
ccgcccagtt ccgcccattc tccgccccat ggctgactaa ttttttttat ttatgcagag    6420
gccgaggccg cctctgcctc tgagctattc cagaagtagt gaggaggctt ttttggaggc    6480
ctaggctttt gcaaaaagct cccgggagct tgtatatcca ttttcggatc tgatcaagag    6540
acaggatgag gatcgtttcg catgattgaa caagatggat tgcacgcagg ttctccggcc    6600
gcttgggtgg agaggctatt cggctatgac tgggcacaac agacaatcgg ctgctctgat    6660
gccgccgtgt tccggctgtc agcgcagggg cgcccggttc tttttgtcaa gaccgacctg    6720
tccggtgccc tgaatgaact gcaggacgag gcagcgcggc tatcgtggct ggccacgacg    6780
ggcgttcctt gcgcagctgt gctcgacgtt gtcactgaag cgggaaggga ctggctgcta    6840
ttgggcgaag tgccggggca ggatctcctg tcatctcacc ttgctcctgc cgagaaagta    6900
tccatcatgg ctgatgcaat gcggcggctg catacgcttg atccggctac ctgcccattc    6960
gaccaccaag cgaaacatcg catcgagcga gcacgtactc ggatggaagc cggtcttgtc    7020
gatcaggatg atctggacga agagcatcag gggctcgcgc cagccgaact gttcgccagg    7080
ctcaaggcgc gcatgcccga cggcgaggat ctcgtcgtga cccatggcga tgcctgcttg    7140
ccgaatatca tggtggaaaa tggccgcttt tctggattca tcgactgtgg ccggctgggt    7200
gtggcggacc gctatcagga catagcgttg gctacccgtg atattgctga agagcttggc    7260
ggcgaatggg ctgaccgctt cctcgtgctt tacggtatcg ccgctcccga ttcgcagcgc    7320
atcgccttct atcgccttct tgacgagttc ttctgagcgg gactctgggg ttcgaaatga    7380
ccgaccaagc gacgcccaac ctgccatcac gagatttcga ttccaccgcc gccttctatg    7440
aaaggttggg cttcggaatc gttttccggg acgccggctg gatgatcctc cagcgcgggg    7500
atctcatgct ggagttcttc gcccacccca acttgtttat tgcagcttat aatggttaca    7560
aataaagcaa tagcatcaca aatttcacaa ataaagcatt ttttcactg cattctagtt    7620 gtggtttgtc caaactcatc aatgtatctt atcatgtctg tataccgtcg acctctagct    7680
agagcttggc gtaatcatgg tcatagctgt ttcctgtgtg aaattgttat ccgctcacaa    7740
ttccacacaa catacgagcc ggaagcataa agtgtaaagc ctggggtgcc taatgagtga    7800
gctaactcac attaattgcg ttgcgctcac tgcccgcttt ccagtcggga aacctgtcgt    7860
gccagctgca ttaatgaatc ggccaacgcg cggggagagg cggtttgcgt attgggcgct    7920
cttccgcttc ctcgctcact gactcgctgc gctcggtcgt tcggctgcgg cgagcggtat    7980
cagctcactc aaaggcggta atacggttat ccacagaatc aggggataac gcaggaaaga    8040
acatgtgagc aaaaggccag caaaaggcca ggaaccgtaa aaaggccgcg ttgctggcgt    8100
ttttccatag gctccgcccc cctgacgagc atcacaaaaa tcgacgctca agtcagaggt    8160
ggcgaaaccc gacaggacta taaagatacc aggcgtttcc ccctggaagc tccctcgtgc    8220
gctctcctgt tccgaccctg ccgcttaccg gatacctgtc cgcctttctc ccttcgggaa    8280
gcgtggcgct ttctcatagc tcacgctgta ggtatctcag ttcggtgtag tcgttcgct    8340 ccaagctggg ctgtgtgcac gaaccccccg ttcagcccga ccgctgcgcc ttatccggta    8400
actatcgtct tgagtccaac ccggtaagac acgacttatc gccactggca gcagccactg    8460
gtaacaggat tagcagagcg aggtatgtag gcggtgctac agagttcttg aagtggtggc    8520
ctaactacgg ctacactaga agaacagtat ttggtatctg cgctctgctg aagccagtta    8580
ccttcggaaa aagagttggt agctcttgat ccggcaaaca aaccaccgct ggtagcggtt    8640
tttttgtttg caagcagcag attacgcgca gaaaaaaagg atctcaagaa gatcctttga    8700
```

-continued

| | |
|---|---|
| tcttttctac ggggtctgac gctcagtgga acgaaaactc acgttaaggg attttggtca | 8760 |
| tgagattatc aaaaaggatc ttcacctaga tccttttaaa ttaaaaatga agttttaaat | 8820 |
| caatctaaag tatatatgag taaacttggt ctgacagtta ccaatgctta atcagtgagg | 8880 |
| cacctatctc agcgatctgt ctatttcgtt catccatagt tgcctgactc cccgtcgtgt | 8940 |
| agataactac gatacgggag ggcttaccat ctggccccag tgctgcaatg ataccgcgag | 9000 |
| acccacgctc accggctcca gatttatcag caataaacca gccagccgga agggccgagc | 9060 |
| gcagaagtgg tcctgcaact ttatccgcct ccatccagtc tattaattgt tgccgggaag | 9120 |
| ctagagtaag tagttcgcca gttaatagtt tgcgcaacgt tgttgccatt gctacaggca | 9180 |
| tcgtggtgtc acgctcgtcg tttggtatgg cttcattcag ctccggttcc caacgatcaa | 9240 |
| ggcgagttac atgatccccc atgttgtgca aaaaagcggt tagctccttc ggtcctccga | 9300 |
| tcgttgtcag aagtaagttg gccgcagtgt tatcactcat ggttatggca gcactgcata | 9360 |
| attctcttac tgtcatgcca tccgtaagat gcttttctgt gactggtgag tactcaacca | 9420 |
| agtcattctg agaatagtgt atgcggcgac cgagttgctc ttgcccggcg tcaatacggg | 9480 |
| ataataccgc gccacatagc agaactttaa aagtgctcat cattggaaaa cgttcttcgg | 9540 |
| ggcgaaaact ctcaaggatc ttaccgctgt tgagatccag ttcgatgtaa cccactcgtg | 9600 |
| cacccaactg atcttcagca tcttttactt tcaccagcgt ttctgggtga gcaaaaacag | 9660 |
| gaaggcaaaa tgccgcaaaa aagggaataa gggcgacacg gaaatgttga atactcatac | 9720 |
| tcttcctttt tcaatattat tgaagcattt atcagggtta ttgtctcatg agcggataca | 9780 |
| tatttgaatg tatttagaaa aataaacaaa taggggttcc gcgcacattt ccccgaaaag | 9840 |
| tgccacctga cgtc | 9854 |

<210> SEQ ID NO 64
<211> LENGTH: 12102
<212> TYPE: DNA
<213> ORGANISM: Artificial Sequence
<220> FEATURE:
<223> OTHER INFORMATION: m-Tmc6 6xHis in pVL1392

<400> SEQUENCE: 64

| | |
|---|---|
| aagctttact cgtaaagcga gttgaaggat catatttagt tgcgtttatg agataagatt | 60 |
| gaaagcacgt gtaaaatgtt tcccgcgcgt tggcacaact atttacaatg cggccaagtt | 120 |
| ataaaagatt ctaatctgat atgttttaaa acacctttgc ggcccgagtt gtttgcgtac | 180 |
| gtgactagcg aagaagatgt gtggaccgca gaacagatag taaaacaaaa ccctagtatt | 240 |
| ggagcaataa tcgatttaac caacacgtct aaatattatg atggtgtgca tttttttgcgg | 300 |
| gcgggcctgt tatacaaaaa aattcaagta cctggccaga cttttgccgcc tgaaagcata | 360 |
| gttcaagaat ttattgacac ggtaaaagaa tttacagaaa agtgtcccgg catgttggtg | 420 |
| ggcgtgcact gcacacacgg tattaatcgc accggttaca tggtgtgcag atatttaatg | 480 |
| cacaccctgg gtattgcgcc gcaggaagcc atagatagat cgaaaaagc cagaggtcac | 540 |
| aaaattgaaa gacaaaatta cgttcaagat ttattaattt aattaatatt atttgcattc | 600 |
| tttaacaaat actttatcct attttcaaat tgttgcgctt cttccagcga accaaaacta | 660 |
| tgcttcgctt gctccgttta gcttgtagcc gatcagtggc gttgttccaa tcgacggtag | 720 |
| gattaggccg atattctcc accacaatgt tggcaacgtt gatgttacgt ttatgctttt | 780 |
| ggttttccac gtacgtcttt tggccggtaa tagccgtaaa cgtagtgccg tcgcgcgtca | 840 |
| cgcacaacac cggatgtttg cgcttgtccg cggggtattg aaccgcgcga tccgacaaat | 900 |

```
ccaccacttt ggcaactaaa tcggtgacct gcgcgtcttt tttctgcatt atttcgtctt      960
tcttttgcat ggtttcctgg aagccggtgt acatgcggtt tagatcagtc atgacgcgcg     1020
tgacctgcaa atctttggcc tcgatctgct tgtccttgat ggcaacgatg cgttcaataa     1080
actcttgttt tttaacaagt tcctcggttt tttgcgccac caccgcttgc agcgcgtttg     1140
tgtgctcggt gaatgtcgca atcagcttag tcaccaactg tttgctctcc tcctcccgtt     1200
gtttgatcgc gggatcgtac ttgccggtgc agagcacttg aggaattact tcttctaaaa     1260
gccattcttg taattctatg gcgtaaggca atttggactt cataatcagc tgaatcacgc     1320
cggatttagt aatgagcact gtatgcggct gcaaatacag cgggtcgccc cttttcacga     1380
cgctgttaga ggtagggccc ccatttggaa tggtctgctc aaataacgat ttgtatttat     1440
tgtctacatg aacacgtata gctttatcac aaactgtata ttttaaactg ttagcgacgt     1500
ccttggccac gaaccggacc tgttggtcgc gctctagcac gtaccgcagg ttgaacgtat     1560
cttctccaaa tttaaattct ccaatttaa cgcgagccat tttgatacac gtgtgtcgat      1620
tttgcaacaa ctattgtttt ttaacgcaaa ctaaacttat tgtggtaagc aataattaaa     1680
tatgggggaa catgcgccgc tacaacactc gtcgttatga acgcagacgg cgccggtctc     1740
ggcgcaagcg gctaaaacgt gttgcgcgtt caacgcggca acatcgcaa aagccaatag       1800
tacagttttg atttgcatat taacggcgat tttttaaatt atcttattta ataaatagtt     1860
atgacgccta caactccccg cccgcgttga ctcgctgcac ctcgagcagt tcgttgacgc     1920
cttcctccgt gtggccgaac acgtcgagcg ggtggtcgat gaccagcggc gtgccgcacg     1980
cgacgcacaa gtatctgtac accgaatgat cgtcgggcga aggcacgtcg gcctccaagt     2040
ggcaatattg gcaaattcga aaatatatac agttgggttg tttgcgcata tctatcgtgg     2100
cgttgggcat gtacgtccga acgttgattt gcatgcaagc cgaaattaaa tcattgcgat     2160
tagtgcgatt aaaacgttgt acatcctcgc ttttaatcat gccgtcgatt aaatcgcgca     2220
atcgagtcaa gtgatcaaag tgtggaataa tgttttcttt gtattcccga gtcaagcgca     2280
gcgcgtattt taacaaacta gccatcttgt aagttagttt catttaatgc aactttatcc     2340
aataatatat tatgtatcgc acgtcaagaa ttaacaatgc gcccgttgtc gcatctcaac     2400
acgactatga tagagatcaa ataaagcgcg aattaaatag cttgcgacgc aacgtgcacg     2460
atctgtgcac gcgttccggc acgagctttg attgtaataa gttttacga agcgatgaca      2520
tgaccccccgt agtgacaacg atcacgccca aaagaactgc cgactacaaa attaccgagt    2580
atgtcggtga cgttaaaaact attaagccat ccaatcgacc gttagtcgaa tcaggaccgc    2640
tggtgcgaga agccgcgaag tatggcgaat gcatcgtata acgtgtggag tccgctcatt     2700
agagcgtcat gtttagacaa gaaagctaca tatttaattg atcccgatga ttttattgat     2760
aaattgaccc taactccata cacggtattc tacaatggcg gggttttggt caaaatttcc     2820
ggactgcgat tgtacatgct gttaacggct ccgcccacta ttaatgaaat taaaaattcc     2880
aattttaaaa aacgcagcaa gagaaacatt tgtatgaaag aatgcgtaga aggaaagaaa     2940
aatgtcgtcg acatgctgaa caacaagatt aatatgcctc cgtgtataaa aaaaatattg     3000
aacgatttga agaaaacaa tgtaccgcgc ggcggtatgt acaggaagag gtttatacta      3060
aactgttaca ttgcaaacgt ggtttcgtgt gccaagtgtg aaaaccgatg tttaatcaag     3120
gctctgacgc atttctacaa ccacgactcc aagtgtgtgg gtgaagtcat gcatctttta    3180
atcaaatccc aagatgtgta taaaccacca aactgccaaa aaatgaaaac tgtcgacaag    3240
```

```
ctctgtccgt tgctggcaa ctgcaagggt ctcaatccta tttgtaatta ttgaataata    3300
aaacaattat aaatgctaaa tttgtttttt attaacgata caaaccaaac gcaacaagaa    3360
catttgtagt attatctata attgaaaacg cgtagttata atcgctgagg taatatttaa    3420
aatcattttc aaatgattca cagtaatttt gcgacaatat aatttttattt tcacataaac    3480
tagacgcctt gtcgtcttct tcttcgtatt ccttctcttt ttcattttc tcctcataaa    3540
aattaacata gttattatcg tatccatata tgtatctatc gtatagagta aattttttgt    3600
tgtcataaat atatatgtct tttttaatgg ggtgtatagt accgctgcgc atagttttc     3660
tgtaatttac aacagtgcta ttttctggta gttcttcgga gtgtgttgct ttaattatta    3720
aatttatata atcaatgaat ttgggatcgt cggttttgta caatatgttg ccggcatagt    3780
acgcagcttc ttctagttca attacaccat tttttagcag caccggatta acataacttt    3840
ccaaaatgtt gtacgaaccg ttaaacaaaa acagttcacc tccctttct atactattgt     3900
ctgcgagcag ttgtttgttg ttaaaaataa cagccattgt aatgagacgc acaaactaat    3960
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atcagatctg    4140
cagcggccgc tcctgccacc atggctcagt cactggcttt agccctcgat gtcccggaga    4200
ccacgggaga cgaaggcctg gagcccagcc cctatgaaga aagtgaagtc catgactcct    4260
tccaccagct cattcaagag caaagccttc gggtggcgga ggaggggctg gagctactgc    4320
ccttgggtct aggcagaggt gaccagaccc tcccaggact tgaaggtgct cctgcccta     4380
gctcggccac tctccgcatc ctggccagca tgcccagccg taccattggt cgcagccgtg    4440
gggccatcat ctcccaatac tacaaccgca cagtgaggct tcggcgcagg agcagccggc    4500
ccttgctggg caatgtggtg ccctctgccc ggcccagcct tcgcctgtat gacctggagc    4560
tggactccac aatcttggag gaggatgaga agccgagcct gctagtaaag gagcttcaag    4620
gtctgtcggc ggcccagagg gaccacatgg tgcggaacat gcccttgagt ctgggtgaga    4680
agcgctgtct tcgagagaaa agttggagcc caaagggaaa gcggcggcac ctgcagggtc    4740
gaagcggggc cttctcctgc tgtagccggc tcagatacac ctgcatgctg gctcttcata    4800
gcctggggct ggcactgctc tcaggcctgt atgctgccag gccgtggcgc tatgctctga    4860
agcagatcgg tggccagttt ggctccagcg tcctctccta cttcctcttc ctcaagaccc    4920
tgttggcctt caacgcgctg atgttgctgc ctttgctggc cttcctcgtg ggtgttcagg    4980
ctgccttcc acctgaccca gcaggccccg tgcctacgtt ttctggtctg gaactcctca    5040
caggcggggg ccggttcaca cacacagtta tgtactacgg ctactacagt aacagcacgc    5100
tgagcccgtc atgtgacgcc cctcgggaag gtggccagtg cagtcccagg ctgggcagcc    5160
tgccctataa catgccgctg gcctacctct tcacaatggg ggccaccttc ttccttacct    5220
gcatcattct ggtatacagc atgtcccact cctttgggga gagctaccgg gttggcagta    5280
ccaagggtat ccatgccctt acggtcttct gctcctggga ctacaaggtg acacagaaga    5340
gggcttcccg tgtccaacag gacagcatct gcactcagct gaaggagctg ttggctgaat    5400
ggcaccttcg aaagcgccct cggagtgtgt gcgggcagct gaggcaggtc gtcgttctag    5460
gtctggggtg gctgctgtgt ctgggctcca caatgggctg cacggtggct gtcctcacct    5520
tctcagaggt aatgattcag agacctgctt ctggtgccca ggggtggag gcgttggcct    5580
tgccctggt ggtcagtgtc cttaacctgg gtgcctccta cctgttccgt ggtctagcca    5640
```

```
ctctggagcg acatgactcc cctgtgttgg aggtatacat ggccatctgc aggaacctca    5700
tcctgaagat ggccgtcctg ggtgtgcttt gctatcactg gctgggccgc agggtggcca    5760
ccctgcaggg tcagtgctgg gaggactttg tgggccagga gctgtaccgc ttcatggtcg    5820
tggatttcat cttcatgctc ttggactccc ttttggaga gttggtgtgg aggctcatct    5880
cagagaagaa gctcaagagg gggcagaagc ctgagtttga cattgccagg aatgtgctgg    5940
acctgattta tggacagaca ctgacctggc tgggcgtcct gttctcaccg ctcctgcctg    6000
cagtacagat tctccggctg ctcttccttt tccacatcaa gaaggccagc ctgatggcca    6060
actgccaggc accacgccga ccctggctgg cctcgcacat gagcactgtc ttcctcacct    6120
tgctctgctt cccgtcgttc ctgggcgctg ctgttttcct ctgctatgct gtctggcagg    6180
tgaggccctc gagcacttgt ggcccttttcc ggactctgaa caccatgtat gaagcaggca    6240
cggtctgggt gcgtcgcctg gagcatgcag gctccggagc ctcctggctg ccctggctgc    6300
accacttcct ggtggagaac actttcttcc tcttcctggc ttcagccctg ctgctggctg    6360
tcatctactt caacatccag gtggtgaaag acaacggaa ggtcatctgc ctgctcaagg    6420
agcagatccg gaatgaagga gaggacaaga tcttcctgat caacaagctt cactctgttt    6480
acgaggagga gggaaggagc aggcctggca gaacccagga cactactgaa ccacctgcct    6540
ggcatgagga tggagggggac cagaaggaac cctgtaaccc ccggtcacca ggaggacatc    6600
accatcacca tcactgagaa ttctagaagg tacccgggat cctttcctgg gacccggcaa    6660
gaaccaaaaa ctcactctct tcaaggaaat ccgtaatgtt aaacccgaca cgatgaagct    6720
tgtcgttgga tggaaaggaa aagagttcta cagggaaact tggaccccgct tcatggaaga    6780 cagcttcccc attgttaacg accaagaagt gatggatgtt ttccttgttg tcaacatgcg    6840
tcccactaga cccaaccgtt gttacaaatt cctggcccaa cacgctctgc gttgcgaccc    6900
cgactatgta cctcatgacg tgattaggat cgtcgagcct tcatgggtgg gcagcaacaa    6960
cgagtaccgc atcagcctgg ctaagaaggg cggcggctgc ccaataatga accttcactc    7020
tgagtacacc aactcgttcg aacagttcat cgatcgtgtc atctgggaga acttctacaa    7080
gcccatcgtt tacatcggta ccgactctgc tgaagaggag gaaattctcc ttgaagtttc    7140
cctggtgttc aaagtaaagg agtttgcacc agacgcacct ctgttcactg gtccggcgta    7200
ttaaaacacg atacattgtt attagtacat ttattaagcg ctagattctg tgcgttgttg    7260
atttacagac aattgttgta cgtattttaa taattcatta aatttataat ctttagggtg    7320
gtatgttaga gcgaaaatca aatgattttc agcgtcttta tatctgaatt taaatattaa    7380
atcctcaata gatttgtaaa ataggtttcg attagtttca aacaagggtt gtttttccga    7440
accgatggct ggactatcta atggattttc gctcaacgcc acaaaacttg ccaaatcttg    7500
tagcagcaat ctagctttgt cgatattcgt ttgtgttttg ttttgtaata aaggttcgac    7560
gtcgttcaaa atattatgcg cttttgtatt tctttcatca ctgtcgttag tgtacaattg    7620
actcgacgta aacacgttaa ataaagcttg gacatattta acatcgggcg tgttagcttt    7680
attaggccga ttatcgtcgt cgtcccaacc ctcgtcgtta agagttgctt ccgaagacga    7740
ttttgccata gccacacgac gcctattaat tgtgtcggct aacacgtccg cgatcaaatt    7800
tgtagttgag cttttggaa ttatttctga ttgcgggcgt ttttgggcgg gtttcaatct    7860
aactgtgccc gattttaatt cagacaacac gttagaaagc gatggtgcag gcggtggtaa    7920
catttcagac ggcaaatcta ctaatggcgg cggtggtgga gctgatgata aatctaccat    7980
```

```
cggtggaggc gcaggcgggg ctggcggcgg aggcggaggc ggaggtggtg gcggtgatgc    8040
agacggcggt ttaggctcaa atgtctcttt aggcaacaca gtcggcacct caactattgt    8100
actggtttcg ggcgccgttt ttggtttgac cggtctgaga cgagtgcgat tttttcgtt     8160
tctaatagct tccaacaatt gttgtctgtc gtctaaaggt gcagcgggtt gaggttccgt    8220
cggcattggt ggagcgggcg gcaattcaga catcgatggt ggtggtggtg gtggaggcgc    8280
tggaatgtta ggcacgggag aaggtggtgg cggcggtgcc gccggtataa tttgttctgg    8340
tttagtttgt tcgcgcacga ttgtgggcac cggcgcaggc gccgctggct gcacaacgga    8400
aggtcgtctg cttcgaggca gcgcttgggg tggtggcaat tcaatattat aattggaata    8460
caaatcgtaa aaatctgcta taagcattgt aatttcgcta tcgtttaccg tgccgatatt    8520
taacaaccgc tcaatgtaag caattgtatt gtaaagagat tgtctcaagc tccgcacgcc    8580
gataacaagc ttttcatttt ttactacagc attgtagtgg cgagacactt cgctgtcgtc    8640
gacgtacatg tatgctttgt tgtcaaaaac gtcgttggca agctttaaaa tatttaaaag    8700
aacatctctg ttcagcacca ctgtgttgtc gtaaatgttt tttttgataa tttgcgcttc    8760
cgcagtatcg acacgttcaa aaaattgatg cgcatcaatt ttgttgttcc tattattgaa    8820
taaataagat tgtacagatt catatctacg attcgtcatg ccaccacaa atgctacgct     8880
gcaaacgctg gtacaatttt acgaaaactg caaaaacgtc aaaactcggt ataaataat     8940
caacgggcgc tttggcaaaa tatctatttt atcgcacaag cccactagca aattgtattt    9000
gcagaaaaca atttcggcgc acaattttaa cgctgacgaa ataaaagttc accagttaat    9060
gagcgaccac ccaaattta taaaaatcta ttttaatcac ggttccatca acaaccaagt     9120
gatcgtgatg gactacattg actgtcccga tttatttgaa acactacaaa ttaaaggcga    9180
gctttcgtac caacttgtta gcaatattat tagacagctg tgtgaagcgc tcaacgattt    9240
gcacaagcac aatttcatac acaacgacat aaaactcgaa aatgtcttat atttcgaagc    9300
acttgatcgc gtgtatgttt gcgattacgg attgtgcaaa cacgaaaact cacttagcgt    9360
gcacgacggc acgttggagt attttagtcc ggaaaaaatt cgacacacaa ctatgcacgt    9420
ttcgtttgac tggtacgcgg cgtgttaaca tacaagttgc taaccggcgg ttcgtaatca    9480
tggtcatagc tgtttcctgt gtgaaattgt tatccgctca caattccaca caacatacga    9540
gccgaagca taaagtgtaa agcctggggt gcctaatgag tgagctaact cacattaatt     9600
gcgttgcgct cactgcccgc tttccagtcg ggaaacctgt cgtgccagct gcattaatga    9660
atcggccaac gcgcgggag aggcggtttg cgtattgggc gctcttccgc ttcctcgctc     9720
actgactcgc tgcgctcggt cgttcggctg cggcgagcgg tatcagctca ctcaaaggcg    9780
gtaatacggt tatccacaga atcagggat aacgcaggaa agaacatgtg agcaaaaggc     9840
cagcaaaagg ccaggaaccg taaaaaggcc gcgttgctgg cgttttccca taggctccgc    9900
cccccctgacg agcatcacaa aaatcgacgc tcaagtcaga ggtggcgaaa cccgacagga    9960
ctataaagat accaggcgtt tccccctgga agctccctcg tgcgctctcc tgttccgacc   10020
ctgccgctta ccggatacct gtccgccttt ctcccttcgg aagcgtggc gctttctcat    10080
agctcacgct gtaggtatct cagttcggtg taggtcgttc gctccaagct gggctgtgtg   10140
cacgaacccc ccgttcagcc cgaccgctgc gccttatccg gtaactatcg tcttgagtcc   10200
aacccggtaa gacacgactt atcgccactg gcagcagcca ctggtaacag gattagcaga   10260
gcgaggtatg taggcggtgc tacagagttc ttgaagtggt ggcctaacta cggctacact   10320
agaaggacag tatttggtat ctgcgctctg ctgaagccag ttaccttcgg aaaaagagtt   10380
```

-continued

```
ggtagctctt gatccggcaa acaaaccacc gctggtagcg gtggttttt tgtttgcaag     10440 cagcagatta cgcgcagaaa aaaggatct caagaagatc ctttgatctt ttctacgggg     10500
tctgacgctc agtggaacga aaactcacgt taagggattt tggtcatgag attatcaaaa    10560
aggatcttca cctagatcct tttaaattaa aaatgaagtt ttaaatcaat ctaaagtata    10620
tatgagtaaa cttggtctga cagttaccaa tgcttaatca gtgaggcacc tatctcagcg    10680
atctgtctat ttcgttcatc catagttgcc tgactcccg tcgtgtagat aactacgata    10740
cgggagggct taccatctgg ccccagtgct gcaatgatac cgcgagaccc acgctcaccg    10800
gctccagatt tatcagcaat aaaccagcca gccggaaggg ccgagcgcag aagtggtcct    10860
gcaactttat ccgcctccat ccagtctatt aattgttgcc gggaagctag agtaagtagt    10920
tcgccagtta atagtttgcg caacgttgtt gccattgcta caggcatcgt ggtgtcacgc    10980
tcgtcgtttg gtatggcttc attcagctcc ggttcccaac gatcaaggcg agttacatga    11040
tcccccatgt tgtgcaaaaa agcggttagc tccttcggtc ctccgatcgt tgtcagaagt    11100
aagttggccg cagtgttatc actcatggtt atggcagcac tgcataattc tcttactgtc    11160
atgccatccg taagatgctt ttctgtgact ggtgagtact caaccaagtc attctgagaa    11220
tagtgtatgc ggcgaccgag ttgctcttgc ccggcgtcaa tacgggataa taccgcgcca    11280
catagcagaa ctttaaaagt gctcatcatt ggaaaacgtt cttcggggcg aaaactctca    11340
aggatcttac cgctgttgag atccagttcg atgtaaccca ctcgtgcacc caactgatct    11400
tcagcatctt ttactttcac cagcgtttct gggtgagcaa aaacaggaag gcaaaatgcc    11460
gcaaaaaagg gaataagggc gacacggaaa tgttgaatac tcatactctt ccttttcaa    11520 tattattgaa gcatttatca gggttattgt ctcatgagcg gatacatatt tgaatgtatt    11580
tagaaaaata acaaataggg gttccgcgc acatttcccc gaaaagtgcc acctgacgtc    11640
taagaaacca ttattatcat gacattaacc tataaaaata ggcgtatcac gaggcccttt    11700
cgtctcgcgc gtttcggtga tgacggtgaa aacctctgac acatgcagct cccggagacg    11760
gtcacagctt gtctgtaagc ggatgccggg agcagacaag cccgtcaggg cgcgtcagcg    11820
ggtgttggcg ggtgtcgggg ctggcttaac tatgcggcat cagagcagat tgtactgaga    11880
gtgcaccata tgcggtgtga ataccgcac agatgcgtaa ggagaaaata ccgcatcagg    11940
cgccattcgc cattcaggct gcgcaactgt tgggaagggc gatcggtgcg ggcctcttcg    12000
ctattacgcc agctggcgaa aggggatgt gctgcaaggc gattaagttg ggtaacgcca    12060
gggttttccc agtcacgacg ttgtaaaacg acggccagtg cc                       12102
```

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
cagttcacct cccttttcta                                                20

<210> SEQ ID NO 66
<211> LENGTH: 20
<212> TYPE: DNA
<213> ORGANISM: Artificial Sequence
<220> FEATURE:
<223> OTHER INFORMATION: primer

```
<400> SEQUENCE: 66
cttcatcgtg tcgggtttaa                                              20

<210> SEQ ID NO 67
<211> LENGTH: 69
<212> TYPE: DNA
<213> ORGANISM: Artificial Sequence
<220> FEATURE:
<223> OTHER INFORMATION: TMC6 gene (wild type)

<400> SEQUENCE: 67
cactctccgc atcctggcca gcatgcccag ccgtaccatt ggtgagccgg gtcctttgtc   60
cttgtgctg                                                          69

<210> SEQ ID NO 68
<211> LENGTH: 53
<212> TYPE: DNA
<213> ORGANISM: Artificial Sequence
<220> FEATURE:
<223> OTHER INFORMATION: TMC6 gene (mutant)

<400> SEQUENCE: 68
cactctccgc atcctggcca gcatgcccag ccgggtcctt tgtccttgtg ctg          53

<210> SEQ ID NO 69
<211> LENGTH: 70
<212> TYPE: DNA
<213> ORGANISM: Artificial Sequence
<220> FEATURE:
<223> OTHER INFORMATION: TMC3 gene (wild-type)

<400> SEQUENCE: 69
tagttggaca tatcagcagc cccgtggtga tacttccagc tgtgctgctt ctgttgtgag   60
tgctacacct                                                         70

<210> SEQ ID NO 70
<211> LENGTH: 65
<212> TYPE: DNA
<213> ORGANISM: Artificial Sequence
<220> FEATURE:
<223> OTHER INFORMATION: TMC3 gene (mutant)

<400> SEQUENCE: 70
tagttggaca tatcagcagc cccgatactt ccagctgtgc tgcttctgtt gtgagtgcta   60
cacct                                                              65

<210> SEQ ID NO 71
<211> LENGTH: 63
<212> TYPE: DNA
<213> ORGANISM: Artificial Sequence
<220> FEATURE:
<223> OTHER INFORMATION: TMC8 gene (wild-type)

<400> SEQUENCE: 71
ggcagaaaca agaccagctg cgagtcctac ggctacaacg cttgcgacta ccaggtggcc   60
tac                                                                63

<210> SEQ ID NO 72
<211> LENGTH: 70
<212> TYPE: DNA
<213> ORGANISM: Artificial Sequence
<220> FEATURE:
<223> OTHER INFORMATION: TMC8 gene (mutant)
```

```
<400> SEQUENCE: 72
ggcagaaaca agaccagctg cgagtcctac gctacaacgc tacaacgctt gcgactacca      60
ggtggcctac                                                             70
```

METHOD OF USING TRANSMEMBRANE CHANNEL-LIKE PROTEIN 6 (TMC6) PROTEIN TO IDENTIFY SUBSTANCES AFFECTING SALTY TASTE

CROSS-REFERENCE TO RELATED APPLICATIONS

The present application is a continuation of U.S. Ser. No. 15/654,162, filed Jul. 19, 2017, and claims priority to JP 2016-141446, filed Jul. 19, 2016, the entire contents of which is incorporated herein by reference.

TECHNICAL FIELD

The present invention relates to a method for screening an objective substance such as a salty-taste modifying substance.

BACKGROUND ART

In the art of the present invention, there has been a consensus that an epithelial sodium channel (also referred to as "ENaC") is a salty-taste receptor (Non-patent document 1). In addition, it has been known that mice have a salty-taste reception system via ENaC and another unknown salty-taste reception system (Non-patent document 2). It has been considered that ENaC is responsible for approximately half of salty-taste reception (taste nerve responses to salty taste) in mice (Non-patent document 1).

It has been reported that the Kv3.2 protein generates sodium current, i.e. functions as a sodium channel (Patent document 1). In addition, an activator substance of the Kv3.2 protein slightly showed a salty-taste enhancing effect in sensory evaluation (Patent document 1).

The TMC6 protein, which is encoded by the TMC6 gene, has been predicted to be a ten-pass transmembrane protein and an ion channel on the basis of the amino acid sequence thereof. In addition, it has been known that disruption of the TMC6 gene results in a decrease in immune functions (Non-patent documents 3-4). However, the actual function of the TMC6 protein has not been identified.

PRIOR ART REFERENCES

Patent Documents

Patent document 1: WO2011/040475

Non-Patent Documents

Non-patent document 1: Chandrashekar J. et al., The cells and peripheral representation of sodium taste in mice. Nature. 2010 Mar. 11; 464(7286):297-301.

Non-patent document 2: Roper S D, The taste of table salt. Eur J Physiol. 2015 March; 467(3):457-63.

Non-patent document 3: Kurima K. et al., Characterization of the transmembrane channel-like (TMC) gene family: functional clues from hearing loss and epidermodysplasia verruciformis. Genomics. 2003 September; 82(3):300-8.

Non-patent document 4: Keresztes G. et al., TMC and EVER genes belong to a larger novel family, the TMC gene family encoding transmembrane proteins. BMC Genomics. 2003 Jun. 17; 4(1):24.

SUMMARY OF THE INVENTION

Object to be Achieved by the Invention

An object of the present invention is to provide a method for screening an objective substance such as a salty-taste modifying substance.

Means for Achieving the Object

The inventors of the present invention conducted various researches in order to achieve the aforementioned object. As a result, the inventors found that the TMC6 gene encodes a salty-taste receptor, and accomplished the present invention.

The present invention can be thus embodied, for example, as follows.

[1] A method for screening an objective substance, the method comprising:
a step of identifying an objective substance by using a TMC6 protein.

[2] The method mentioned above, wherein the objective substance is a substance that acts on the TMC6 protein.

[3] The method mentioned above, wherein the substance that acts on the TMC6 protein is a substance that activates or inactivates the TMC6 protein.

[4] The method mentioned above, wherein the objective substance is a salty-taste modifying substance.

[5] The method mentioned above, wherein the salty-taste modifying substance is a salty-taste alternative substance, a salty-taste enhancing substance, or a salty-taste reducing substance.

[6] The method mentioned above, wherein the objective substance is an active ingredient of a prophylactic or therapeutic agent for a disease relating to the TMC6 protein.

[7] The method mentioned above, wherein the step comprises the following steps (A) to (C):
(A) a step of bringing the TMC6 protein and a test substance into contact with each other;
(B) a step of measuring an action of the test substance on the TMC6 protein upon the contact; and
(C) a step of identifying the objective substance on the basis of the action.

[8] The method mentioned above, wherein the action is binding of the test substance to the TMC6 protein, or activation or inactivation of the TMC6 protein by the test substance.

[9] The method mentioned above, wherein the steps (B) and (C) are the following steps (B1) and (C1), respectively:
(B1) a step of measuring an activation degree D1, the activation degree D1 being the degree of activation of the TMC6 protein upon the contact;
(C1) a step of identifying the objective substance on the basis of the activation degree D1.

[10] The method mentioned above, wherein the wherein the step (C1) is the following step (C2),
(C2) a step of identifying the objective substance on the basis of a difference between the activation degree D1 and an activation degree D2, the activation degree D2 being the degree of activation of the TMC6 protein under a control condition.

[11] The method mentioned above, wherein the control condition is the following condition (C2-1) or (C2-2):
(C2-1) a condition of not bringing the TMC6 protein and the test substance into contact with each other;

(C2-2) a condition of bringing the TMC6 protein and the test substance into contact with each other, where the concentration of the test substance is lower than that in the step (A).

[12] The method mentioned above, wherein the TMC6 protein is used in a form carried by a cell or a cell membrane.

[13] The method mentioned above, wherein the activation or inactivation of the TMC6 protein is measured by using activation or inactivation of the cell as an index.

[14] The method mentioned above, wherein the activation or inactivation of the TMC6 protein is measured by using one or more parameters selected from the membrane potential of the cell or of the cell membrane, the membrane current of the cell or of the cell membrane, and the cation concentration in the cell or in one of spaces separated by the cell membrane as an index or indices.

[15] The method mentioned above, wherein the cation is a sodium ion or a calcium ion.

[16] The method mentioned above, wherein the step (A) is carried out in the presence of a salty-taste substance.

[17] The method mentioned above, wherein if activation of the TMC6 protein by the test substance is observed, the test substance is identified as a salty-taste enhancing substance.

[18] The method mentioned above, wherein if inactivation of the TMC6 protein by the test substance is observed, the test substance is identified as a salty-taste reducing substance.

[19] The method mentioned above, wherein the step (A) is carried out in the absence of a salty-taste substance.

[20] The method mentioned above, wherein if activation of the TMC6 protein by the test substance is observed, the test substance is identified as a salty-taste alternative substance.

[21] The method mentioned above, wherein the salty-taste substance is a substance that provides a sodium ion in an aqueous medium.

[22] The method mentioned above, wherein the salty-taste substance is sodium chloride.

[23] The method mentioned above, wherein the TMC6 protein is a protein defined in (A) or (B) mentioned below:
(A) a TMC6 protein of a mammal;
(B) a chimeric TMC6 protein of two or more kinds of mammals.

[24] The method mentioned above, wherein the TMC6 protein is a protein defined in (a), (b), or (c) mentioned below:
(a) a protein comprising the amino acid sequence of any one of SEQ ID NOS: 1-47, or comprising a chimeric sequence of two or more kinds of amino acid sequences selected from the amino acid sequences of SEQ ID NOS: 1-47;
(b) a protein comprising the amino acid sequence of any one of SEQ ID NOS: 1-47, or comprising a chimeric sequence of two or more kinds of amino acid sequences selected from the amino acid sequences of SEQ ID NOS: 1-47, but which includes substitution, deletion, insertion, and/or addition of 1 to 10 amino acid residues, and having a function of salty-taste receptor;
(c) a protein comprising an amino acid sequence showing an identity of 90% or higher to the amino acid sequence of any one of SEQ ID NOS: 1-47, or to a chimeric sequence of two or more kinds of amino acid sequences selected from the amino acid sequences of SEQ ID NOS: 1-47, and having a function of salty-taste receptor.

[25] The method mentioned above, wherein the cell is a cell of an organism.

[26] The method mentioned above, wherein the cell is an animal cell.

[27] A cell introduced with a TMC6 gene.

The present invention can be further embodied, for example, as follows.

[1] A method for identifying a substance that affects salty taste, comprising:
contacting a test substance with a TMC6 protein;
measuring an action of said test substance on the TMC6 protein upon contact;
identifying said substance as a substance that affects salty taste on the basis of the action measured, wherein said action is binding of the test substance to the TMC6 protein, activation of the TMC6 protein by the test substance, or inactivation of the TMC6 protein by the test substance.

[2] The method mentioned above, wherein said action is binding of the test substance to the TMC6 protein.

[3] The method mentioned above, wherein the substance that acts on the TMC6 protein is a substance that activates or inactivates the TMC6 protein.

[4] The method mentioned above, wherein the substance that affects salty taste is a salty-taste alternative substance.

[5] The method mentioned above, wherein substance that affects salty taste is a salty-taste enhancing substance.

[6] The method mentioned above, wherein substance that affects salty taste is a salty-taste reducing substance.

[7] The method mentioned above, wherein the test substance is an active ingredient of a prophylactic or therapeutic agent for a disease relating to the TMC6 protein.

[8] The method mentioned above, further comprising: following said measuring, determining an activation degree D1, the activation degree D1 being the degree of activation of the TMC6 protein upon the contact; and following said identifying, further identifying the test substance on the basis of the activation degree D1.

[9] The method mentioned above, further comprising: following said further identifying, classifying the test substance on the basis of a difference between the activation degree D1 and an activation degree D2, the activation degree D2 being the degree of activation of the TMC6 protein under a control condition.

[10] The method mentioned above, wherein the control condition comprises:
a condition of not bringing the TMC6 protein and the test substance into contact with each other; and
a condition of bringing the TMC6 protein and the test substance into contact with each other, where the concentration of the test substance is lower than that in said contacting a test substance with a TMC6 protein.

[11] The method mentioned above, wherein the TMC6 protein is in a form isolated from its native host cell.

[12] The method mentioned above, wherein the TMC6 protein is carried by a cell or a cell membrane.

[13] The method mentioned above, wherein the activation or inactivation of the TMC6 protein is measured by using activation or inactivation of the cell as an index.

[14] The method mentioned above, wherein the activation or inactivation of the TMC6 protein is measured by using one or more parameters selected from the group consisting of the membrane potential of the cell or of the cell membrane, the membrane current of the cell or of the cell membrane, and the cation concentration in the cell or in one of spaces separated by the cell membrane as an index or indices.

[15] The method mentioned above, wherein the cation is a sodium ion or a calcium ion.

[16] The method mentioned above, wherein the cell is a cell of an organism.

[17] The method mentioned above, wherein the cell is an animal cell.

[18] The method mentioned above, wherein said contacting is performed in the presence of a salty-taste substance.
[19] The method mentioned above, wherein if activation of the TMC6 protein by the test substance is observed, the test substance is identified as a salty-taste enhancing substance.
[20] The method mentioned above, wherein if inactivation of the TMC6 protein by the test substance is observed, the test substance is identified as a salty-taste reducing substance.
[21] The method mentioned above, wherein the salty-taste substance is a substance that provides a sodium ion in an aqueous medium.
[22] The method mentioned above, wherein the salty-taste substance is sodium chloride.
[23] The method mentioned above, wherein said contacting is carried out in the absence of a salty-taste substance.
[24] The method mentioned above, wherein if activation of the TMC6 protein by the test substance is observed, the test substance is identified as a salty-taste alternative substance.
[25] The method mentioned above, wherein the TMC6 protein is a protein defined in (A) or (B):
(A) a mammalian TMC6 protein;
(B) a chimeric TMC6 protein of two or more kinds of mammalian TMC6 proteins.
[26] The method mentioned above, wherein the TMC6 protein is a protein defined in (a), (b), or (c):
(a) a protein comprising the amino acid sequence of any one of SEQ ID NOs: 1-47, or comprising a chimeric sequence of two or more kinds of amino acid sequences selected from the amino acid sequences of SEQ ID NOs: 1-47;
(b) a protein comprising the amino acid sequence of any one of SEQ ID NOS: 1-47, or comprising a chimeric sequence of two or more kinds of amino acid sequences selected from the amino acid sequences of SEQ ID NOs: 1-47, but which includes substitution, deletion, insertion, and/or addition of 1 to 10 amino acid residues, and having a function of a salty-taste receptor;
(c) a protein comprising an amino acid sequence showing an identity of 90% or higher to the amino acid sequence of any one of SEQ ID NOs: 1-47, or to a chimeric sequence of two or more kinds of amino acid sequences selected from the amino acid sequences of SEQ ID NOs: 1-47, and having a function of salty-taste receptor.
[27] A host cell comprising a heterologous TMC6 gene.
[28] A cell which has been modified to overexpress a TMC6 gene.

The above objects highlight certain aspects of the invention. Additional objects, aspects and embodiments of the invention are found in the following detailed description of the invention.

According to the present invention, an objective substance such as a salty-taste modifying substance can be screened (e.g., identified).

BRIEF DESCRIPTION OF DRAWINGS

A more complete appreciation of the invention and many of the attendant advantages thereof will be readily obtained as the same becomes better understood by reference to the following Figures in conjunction with the detailed description below.

FIG. 1 A diagram showing a phylogenetic tree of TMC6 proteins of mammals.

FIG. 2A and FIG. 2B A diagram showing an alignment of TMC6 proteins of mammals. In FIG. 2A and FIG. 2B, the sequences correspond to a portion of SEQ ID NOs: 1-47, respectively in descending order, as illustrated in the table below. FIGS. 2A-7B mutually connected in this order serve as a diagram showing an alignment of full-length TMC6 proteins from N-termini to C-termini as set forth in SEQ ID NOs: 1-47, respectively in descending order, as illustrated in the table below.

FIG. 3A and FIG. 3B A diagram showing an alignment of TMC6 proteins of mammals. In FIG. 3A and FIG. 3B, the sequences correspond to a portion of SEQ ID NOs: 1-47, respectively in descending order, as illustrated in the table below. As stated above, FIGS. 2A-7B mutually connected in this order serve as a diagram showing an alignment of full-length TMC6 proteins from N-termini to C-termini as set forth in SEQ ID NOs: 1-47, respectively in descending order, as illustrated in the table below.

FIG. 4A and FIG. 4B A diagram showing an alignment of TMC6 proteins of mammals. In FIG. 4A and FIG. 4B, the sequences correspond to a portion of SEQ ID NOs: 1-47, respectively in descending order, as illustrated in the table below. As stated above, FIGS. 2A-7B mutually connected in this order serve as a diagram showing an alignment of full-length TMC6 proteins from N-termini to C-termini as set forth in SEQ ID NOs: 1-47, respectively in descending order, as illustrated in the table below.

FIG. 5A and FIG. 5B A diagram showing an alignment of TMC6 proteins of mammals. In FIG. 5A and FIG. 5B, the sequences correspond to a portion of SEQ ID NOs: 1-47, respectively in descending order, as illustrated in the table below. As stated above, FIGS. 2A-7B mutually connected in this order serve as a diagram showing an alignment of full-length TMC6 proteins from N-termini to C-termini as set forth in SEQ ID NOs: 1-47, respectively in descending order, as illustrated in the table below.

FIG. 6A and FIG. 6B A diagram showing an alignment of TMC6 proteins of mammals. In FIG. 6A and FIG. 6B, the sequences correspond to a portion of SEQ ID NOs: 1-47, respectively in descending order, as illustrated in the table below. As stated above, FIGS. 2A-7B mutually connected in this order serve as a diagram showing an alignment of full-length TMC6 proteins from N-termini to C-termini as set forth in SEQ ID NOs: 1-47, respectively in descending order, as illustrated in the table below.

FIG. 7A and FIG. 7B A diagram showing an alignment of TMC6 proteins of mammals. In FIG. 7A and FIG. 7B, the sequences correspond to a portion of SEQ ID NOs: 1-47, respectively in descending order, as illustrated in the table below. As stated above, FIGS. 2A-7B mutually connected in this order serve as a diagram showing an alignment of full-length TMC6 proteins from N-termini to C-termini as set forth in SEQ ID NOs: 1-47, respectively in descending order, as illustrated in the table below.

Figure 2A:
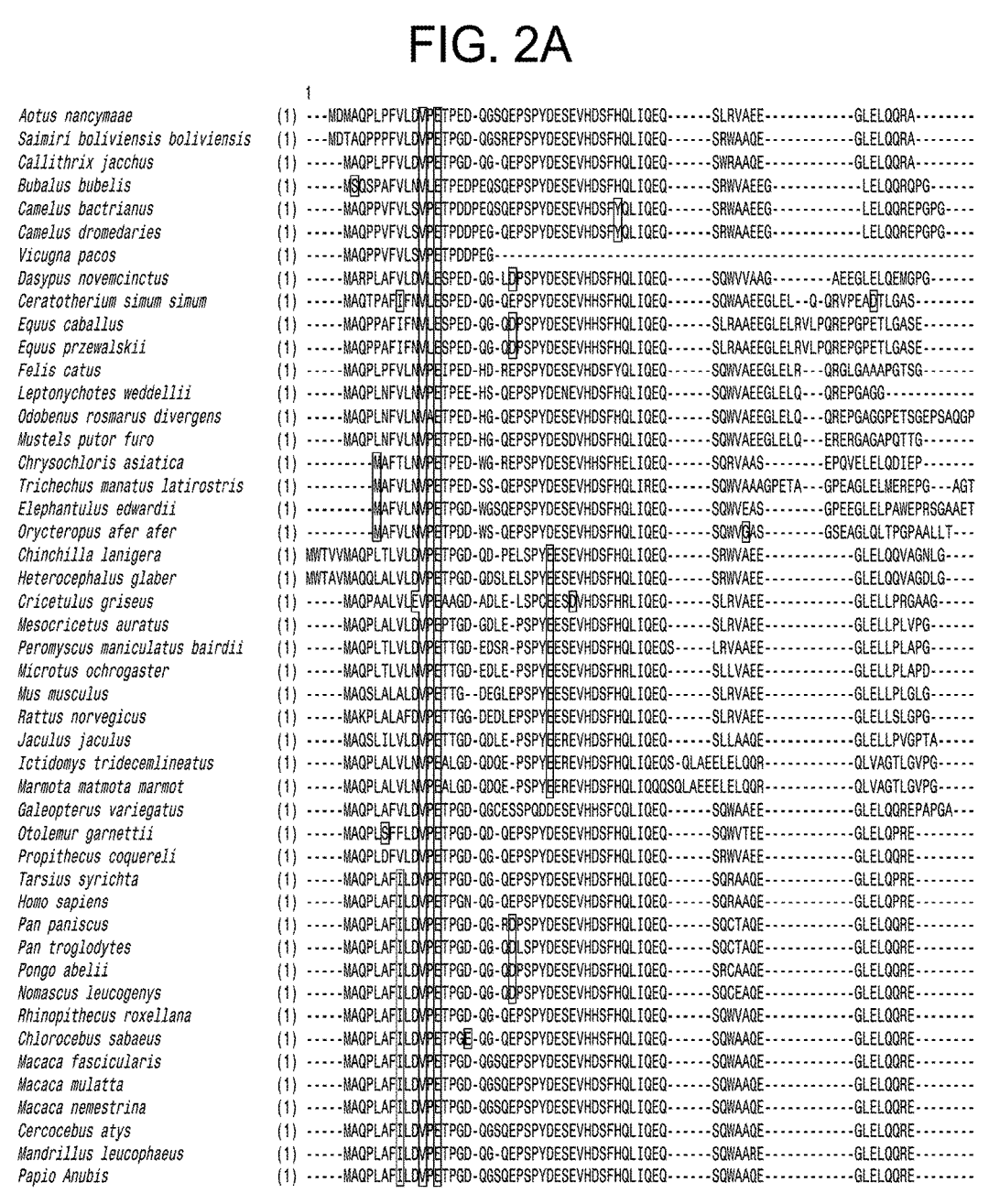
Figure 6B:
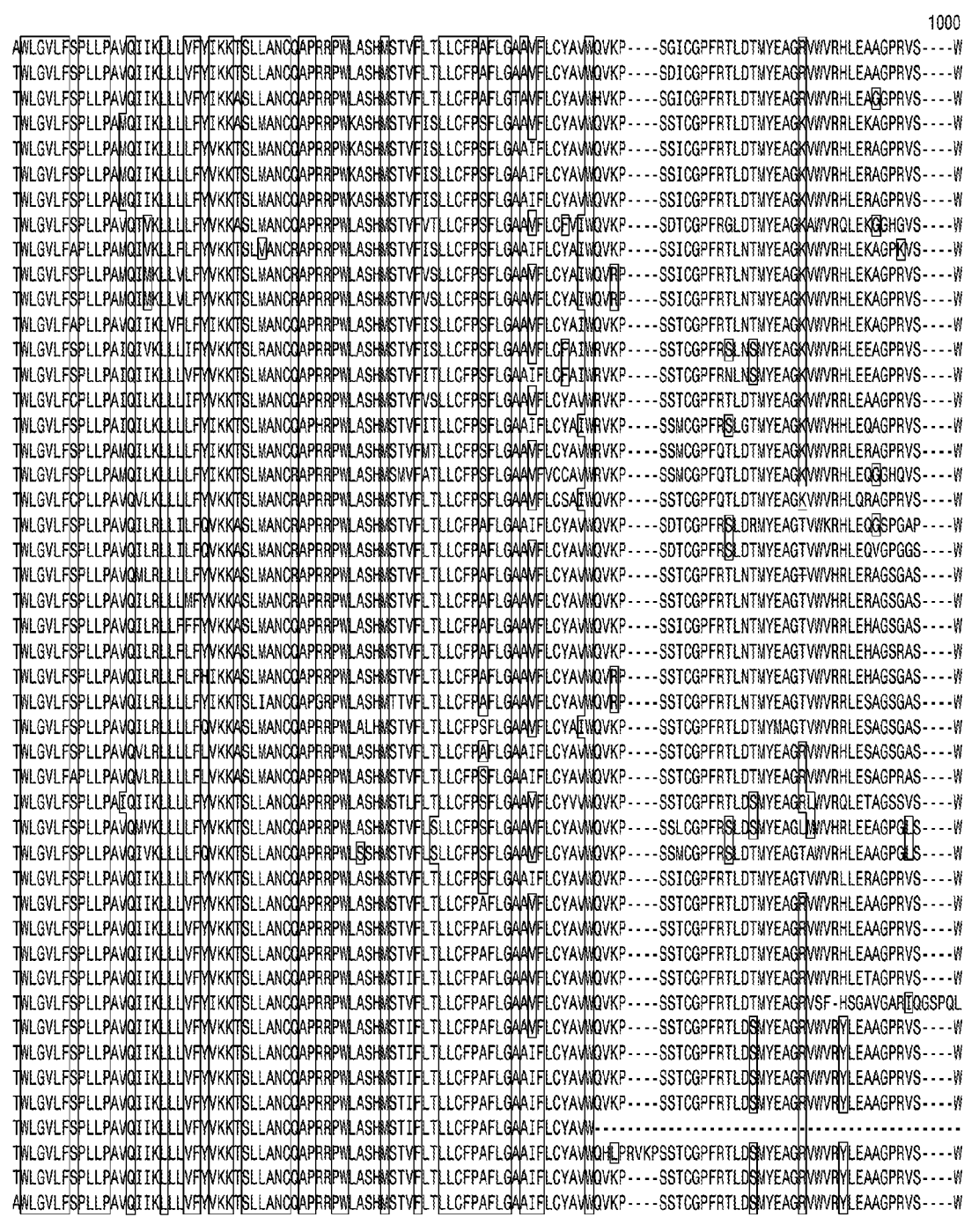

In the alignments of the amino acid sequences of the TMC6 proteins of those mammals appearing in FIGS. 2-7, the following table provides the corresponding NCBI accession numbers of mRNAs thereof and SEQ ID NOS of the amino acid sequences thereof.

| Organism | NCBI accessoion NO. | Amino acid sequence SEQ ID NO. |
| --- | --- | --- |
| *Aotus nancymaae* | XM_012453598 | 1 |
| *Saimiri boliviensis boliviensis* | XM_010342356 | 2 |
| *Callithrix jacchus* | XM_008997836 | 3 |
| *Bubalus bubalis* | XP_006064158 | 4 |
| *Camelus bactrianus* | XM_010950966 | 5 |
| *Camelus dromedaries* | XM_010983819 | 6 |
| *Vicugna pacos* | XM_015235096 | 7 |

-continued

| Organism | NCBI accessoion NO. | Amino acid sequence SEQ ID NO. |
|---|---|---|
| Dasypus novemcinctus | XM_012525900 | 8 |
| Ceratotherium simum simum | XM_014789319 | 9 |
| Equus caballus | XM_014736492 | 10 |
| Equus przewalskii | XM_008524861 | 11 |
| Felis catus | XM_011289443 | 12 |
| Leptonychotes weddellii | XM_006734272 | 13 |
| Odobenus rosmarus divergens | XM_012560260 | 14 |
| Mustela putorius furo | XM_013054374 | 15 |
| Chrysochloris asiatica | XM_006869659 | 16 |
| Trichechus manatus latirostris | XM_004374113 | 17 |
| Elephantulus edwardii | XM_006886352 | 18 |
| Orycteropus afer afer | XM_007959612 | 19 |
| Chinchilla lanigera | XP_005407445 | 20 |
| Heterocephalus glaber | XP_012933678 | 21 |
| Cricetulus griseus | XM_007633914 | 22 |
| Mesocricetus auratus | XM_005070196 | 23 |
| Peromyscus maniculatus bairdii | XP_006990317 | 24 |
| Microtus ochrogaster | XM_005350799 | 25 |
| Mus musculus | NP_663414 | 26 |
| Rattus norvegicus | EDM06725 | 27 |
| Jaculus jaculus | XP_012803507 | 28 |
| Ictidomys tridecemlineatus | XP_005332669 | 29 |
| Marmota marmota marmot | XP_015359755 | 30 |
| Galeopterus variegatus | XM_008579513 | 31 |
| Otolemur garnettii | XM_012802837 | 32 |
| Propithecus coquereli | XP_012516798 | 33 |
| Tarsius syrichta | XM_008060478 | 34 |
| Homo sapiens | NP_009198 | 35 |
| Pan paniscus | XM_008971553 | 36 |
| Pan troglodytes | XM_009433381 | 37 |
| Pongo abelii | XM_002827886 | 38 |
| Nomascus leucogenys | XM_012512408 | 39 |
| Rhinopithecus roxellana | XM_010381913 | 40 |
| Chlorocebus sabaeus | XP_008009756 | 41 |
| Macaca fascicularis | XM_005585117 | 42 |
| Macaca mulatta | XM_015120470 | 43 |
| Macaca nemestrina | XM_011720034 | 44 |
| Cercocebus atys | XM_012042275 | 45 |
| Mandrillus leucophaeus | XM_011988387 | 46 |
| Papio Anubis | XM_009191346 | 47 |

FIG. 8 Diagrams showing the nucleotide sequences of mutation sites of genes and adjacent regions thereof in knockout mice. (A) TMC6 gene (SEQ ID NO: 67 wild-type and SEQ ID NO: 68 mutant). (B) TMC3 gene (SEQ ID NO: 69 wild-type and SEQ ID NO: 70 mutant), and (C) TMC8 gene (SEQ ID NO: 71 wild-type and SEQ ID NO: 72 mutant).

FIG. 9 A diagram showing test results of NaCl palatability of wild-type C57BL/6J mouse and various knockout mice.

FIG. 10 A diagram showing test results of palatability of wild-type C57BL/6J mouse and homo knockout mouse of TMC6 gene for taste substances other than NaCl.

FIG. 11 Diagrams (photographs) showing slice images of circumvallate papillae of mice. (A) wild-type C57BL/6J mouse, (B) hetero knockout mouse of TMC6 gene, and (C) homo knockout mouse of TMC6 gene.

FIG. 12 Diagrams showing change of the intracellular calcium concentration by stimulation with a high-concentration NaCl solution. The vertical axis represents a relative YFP/CFP value. (A) TMC6-expressing cells (CHO-K1 cells expressing mouse TMC6 gene and YC2.60 gene), and (B) control cells (CHO-K1 cells expressing YC2.60 gene).

FIG. 13 Diagrams (photographs) showing change of the intracellular calcium concentration in a TMC6-expressing cell by stimulation with a high concentration NaCl solution. (A) photograph of YFP fluorescence intensity, (B) photograph of YFP/CFP value (FRET value), and (C) graph of YFP/CFP value (FRET value).

FIG. 14 Diagrams (photographs) showing change of the intracellular calcium concentration in a TMC6-expressing cell by stimulation with a high concentration NaCl solution (frames 1-108).

FIG. 15 Diagrams (photographs) showing change of the intracellular calcium concentration in a TMC6-expressing cell by stimulation with a high concentration NaCl solution (frames 109-216).

FIG. 16 Diagrams (photographs) showing change of the intracellular calcium concentration in a TMC6-expressing cell by stimulation with a high concentration NaCl solution (frames 217-324).

FIG. 17 Diagrams showing change of the intracellular calcium concentration by stimulation with a high-concentration NaCl solution. The vertical axis represents a relative YFP/CFP value. (A) TMC6-expressing cells (CHO-K1 cells expressing human TMC6 gene and YC2.60 gene), and (B) control cells (CHO-K1 cells expressing YC2.60 gene).

FIG. 18 Diagrams showing change of the intracellular calcium concentration by stimulation with a high-concentration NaCl solution. The vertical axis represents an average YFP/CFP value. (A) Cells expressing mouse/*Aotus nancymaae* chimeric TMC6 gene, (B) cells expressing *Macaca mulatta* TMC6 gene, (C) cells expressing *Pongo abelii* TMC6 gene, and (D) control cells.

FIG. 19 Diagrams (photographs) showing immunofluorescence images of cells expressing the mouse TMC6 protein added with 6×His at the C-terminus. (A) The anti-His antibody (Alexa488), (B) the anti-TMC6 antibody in combination with anti-chicken IgY antibody (Alexa568), (C) a merged image of A and B, and (D) a differential interference contrast image.

FIG. 20 Diagrams showing the result of electrophysiological analysis using a roughly purified membrane fraction containing TMC6 protein.

FIG. 21 A diagram showing the result of electrophysiological analysis using a roughly purified membrane fraction not containing TMC6 protein.

MODES FOR CARRYING OUT THE INVENTION

Hereinafter, the present invention will be explained in detail. Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The method of the present invention is a method for screening an objective substance such as a salty-taste modifying substance or for identifying a substance that affects salty taste by using a TMC6 protein.

<1> TMC6 Protein

The term "TMC6 protein" refers to a protein encoded by a TMC6 gene. The TMC6 protein may specifically be a salty-taste receptor protein. The TMC6 protein may function as, for example, an ion channel such as a sodium channel.

The notational system of genes and proteins may differ depending on the species of organisms. Hence, there may be genes corresponding to the TMC6 gene with various names such as TMC6 gene, Tmc6 gene, and tmc6 gene depending on the species of organisms. However, such genes with any names may also be referred to uniformly as "TMC6 gene" in the present invention, and should be included in "TMC6 gene" of the present invention. Also, there may be proteins corresponding to the TMC6 protein with various names such as TMC6 protein, Tmc6 protein, tmc6 protein, TMC6p, Tmc6p, and tmc6p depending on the species of organisms. However, such proteins with any names may also be referred to uniformly as "TMC6 protein" in the present invention, and should be included in "TMC6 protein" of the present invention.

Examples of the TMC6 gene and the TMC6 protein include TMC6 genes and TMC6 proteins of various organisms. Examples of organisms include, for example, mammals, amphibians, fish, and brachiopods. Particular examples of organisms include mammals. Specific examples of the mammals include, for example, those shown in Table 1. The nucleotide sequences of the TMC6 genes derived from these various organisms and the amino acid sequences of the TMC6 proteins derived from these various organisms can be obtained from, for example, public databases such as NCBI. Examples of the TMC6 proteins of mammals are shown in Table 1 with NCBI accession numbers of mRNAs thereof and SEQ ID NOS of the amino acid sequences thereof. In addition, a phylogenetic tree of the TMC6 proteins of those mammals is shown as FIG. 1. In addition, an alignment of the amino acid sequences of the TMC6 proteins of those mammals is shown as FIGS. 2-7.

TABLE 1

Examples of TMC6 proteins of mammals

| Organism | NCBI accessoion NO. | Amino acid sequence SEQ ID NO. |
|---|---|---|
| Aotus nancymaae | XM_012453598 | 1 |
| Saimiri boliviensis boliviensis | XM_010342356 | 2 |
| Callithrix jacchus | XM_008997836 | 3 |
| Bubalus bubalis | XP_006064158 | 4 |
| Camelus bactrianus | XM_010950966 | 5 |
| Camelus dromedaries | XM_010983819 | 6 |
| Vicugna pacos | XM_015235096 | 7 |
| Dasypus novemcinctus | XM_012525900 | 8 |
| Ceratotherium simum simum | XM_014789319 | 9 |
| Equus caballus | XM_014736492 | 10 |
| Equus przewalskii | XM_008524861 | 11 |
| Felis catus | XM_011289443 | 12 |
| Leptonychotes weddellii | XM_006734272 | 13 |
| Odobenus rosmarus divergens | XM_012560260 | 14 |
| Mustela putorius furo | XM_013054374 | 15 |
| Chrysochloris asiatica | XM_006869659 | 16 |
| Trichechus manatus latirostris | XM_004374113 | 17 |
| Elephantulus edwardii | XM_006886352 | 18 |
| Orycteropus afer afer | XM_007959612 | 19 |
| Chinchilla lanigera | XP_005407445 | 20 |
| Heterocephalus glaber | XP_012933678 | 21 |
| Cricetulus griseus | XM_007633914 | 22 |
| Mesocricetus auratus | XM_005070196 | 23 |
| Peromyscus maniculatus bairdii | XP_006990317 | 24 |
| Microtus ochrogaster | XM_005350799 | 25 |
| Mus musculus | NP_663414 | 26 |
| Rattus norvegicus | EDM06725 | 27 |
| Jaculus jaculus | XP_012803507 | 28 |
| Ictidomys tridecemlineatus | XP_005332669 | 29 |
| Marmota marmota marmot | XP_015359755 | 30 |
| Galeopterus variegatus | XM_008579513 | 31 |
| Otolemur garnettii | XM_012802837 | 32 |
| Propithecus coquereli | XP_012516798 | 33 |

TABLE 1-continued

Examples of TMC6 proteins of mammals

| Organism | NCBI accessoion NO. | Amino acid sequence SEQ ID NO. |
|---|---|---|
| Tarsius syrichta | XM_008060478 | 34 |
| Homo sapiens | NP_009198 | 35 |
| Pan paniscus | XM_008971553 | 36 |
| Pan troglodytes | XM_009433381 | 37 |
| Pongo abelii | XM_002827886 | 38 |
| Nomascus leucogenys | XM_012512408 | 39 |
| Rhinopithecus roxellana | XM_010381913 | 40 |
| Chlorocebus sabaeus | XP_008009756 | 41 |
| Macaca fascicularis | XM_005585117 | 42 |
| Macaca mulatta | XM_015120470 | 43 |
| Macaca nemestrina | XM_011720034 | 44 |
| Cercocebus atys | XM_012042275 | 45 |
| Mandrillus leucophaeus | XM_011988387 | 46 |
| Papio Anubis | XM_009191346 | 47 |

That is, the TMC6 gene may be, for example, a gene having a nucleotide sequence encoding the amino acid sequence of any of the TMC6 proteins exemplified above (e.g. nucleotide sequences encoding the amino acid sequences shown as SEQ ID NOS: 1-47). Also, the TMC6 protein may be, for example, a protein having the amino acid sequence of any of the TMC6 proteins exemplified above (e.g. the amino acid sequences shown as SEQ ID NOS: 1-47). The expression "a gene or protein has a nucleotide or amino acid sequence" encompasses cases where a gene or protein comprises the nucleotide or amino acid sequence, and cases where a gene or protein consists of the nucleotide or amino acid sequence.

Examples of the TMC6 protein also include a chimeric TMC6 protein. The term "chimeric TMC6 protein" refers to a chimeric protein of TMC6 proteins, i.e. a chimeric protein of two or more kinds of TMC6 proteins. In other words, the term "chimeric TMC6 protein" refers to a protein having a chimeric sequence of TMC6 proteins, i.e. a protein having a chimeric sequence of two or more kinds of TMC6 proteins. The term "chimeric sequence of TMC6 proteins" refers to a chimeric sequence of the amino acid sequences of TMC6 proteins, i.e. a chimeric sequence of the amino acid sequences of two or more kinds of TMC6 proteins. The term "chimeric sequence of TMC6 proteins" specifically refers to the amino acid sequence of a certain TMC6 protein, a part of which has been replaced with a part of the amino acid sequence of other one or more kinds of TMC6 proteins. Substitution of an amino acid sequence in construction of the chimeric TMC6 protein can be carried out between portions corresponding to each other in the amino acid sequences of TMC6 proteins. The term "portions corresponding to each other in the amino acid sequences of TMC6 proteins" refers to portions aligned at positions corresponding to each other in an alignment of the amino acid sequences of those TMC6 proteins. Examples of the chimeric TMC6 protein includes, for example, a chimeric TMC6 protein of the TMC6 proteins exemplified above, specifically, a chimeric protein of two or more kinds of TMC6 proteins selected from the TMC6 proteins exemplified above. Specific examples of the chimeric TMC6 protein includes, for example, a chimeric TMC6 protein of mammals, specifically, a chimeric protein of two or more kinds of TMC6 proteins selected from the TMC6 proteins of mammals. That is, the TMC6 protein may also be, for example, a protein having a chimeric sequence of the amino acid sequences of the TMC6 proteins exemplified above, specifically, a chimeric sequence of two or more kinds of amino acid sequences selected from the amino acid sequences of the TMC6 proteins exemplified above. Specific examples of the chimeric sequence include, for example, a chimeric sequence of the amino acid sequences shown as SEQ ID NOS: 1 and 26 or a chimeric sequence of the amino acid sequences shown as SEQ ID NOS: 26 and 35. Specific examples of the chimeric sequence of the amino acid sequences shown as SEQ ID NOS: 1 and 26 include, for example, the amino acid sequence consisting of the amino acid sequence of positions 1 to 15 of SEQ ID NO: 26 and the amino acid sequence of positions 18 to 807 of SEQ ID NO: 1. As the chimeric TMC6 protein, there can be selected those having a function as a salty-taste receptor protein.

The number of kinds of the TMC6 proteins constituting the chimeric TMC6 protein is not particularly limited. The number of kinds of the TMC6 proteins constituting the chimeric TMC6 protein may be two, or may be three or more.

The constitution ratio of each TMC6 protein in the chimeric TMC6 protein is not particularly limited. The constitution ratio of each TMC6 protein can be appropriately set within a range in which the sum of the constitution ratios of the TMC6 proteins constituting the chimeric TMC6 protein does not exceed 100%. The constitution ratio of each TMC6 protein, for example, may be 1% or more, 3% or more, 5% or more, 10% or more, 20% or more, 40% or more, 50% or more, 60% or more, 70% or more, 80% or more, 90% or more, 95% or more, 97% or more, or 99% or more, may be 99% or less, 97% or less, 95% or less, 90% or less, 80% or less, 70% or less, 60% or less, 50% or less, 40% or less, 30% or less, 20% or less, 10% or less, 5% or less, 3% or less, or 1% or less, or may be a range defined as a non-contradictory combination thereof. The term "constitution ratio of each TMC6 protein" refers to a ratio of the number of amino acid residue(s) derived from each TMC6 protein with respect to the total number of amino acid residues constituting the chimeric TMC6 protein. Incidentally, among the amino acid residues constituting the chimeric TMC6 protein, amino acid residue(s) identical to that/those of a conservative sequence of the TMC6 proteins constituting the chimeric TMC6 protein may each be regarded as one derived from any of those TMC6 proteins.

The distribution pattern of the portion derived from each TMC6 protein in the chimeric TMC6 protein is not particularly limited. In the chimeric TMC6 protein, the portion derived from each TMC6 protein may be present collectively at one position, or may be present dispersedly at two or more positions. For example, when an internal amino acid sequence of a certain TMC6 protein (TMC6 protein A) is replaced with an amino acid sequence of another TMC6 protein (TMC6 protein B) to design the chimeric TMC6 protein, the amino acid sequence of the TMC6 protein A remains dispersedly at N-terminus and C-terminus in the chimeric TMC6 protein.

Similarly, examples of the TMC6 gene also include a chimeric TMC6 gene. The descriptions concerning the chimeric TMC6 protein can be applied mutatis mutandis to the chimeric TMC6 gene.

The TMC6 gene may be a variant of any of the TMC6 genes exemplified above, such as a gene having a nucleotide sequence encoding any of the amino acid sequences shown as SEQ ID NOS: 1-47 or a chimeric sequence thereof, so long as the original function thereof is maintained. Similarly, the TMC6 protein may be a variant of any of the TMC6 proteins exemplified above, such as a protein having any of the amino acid sequences shown as SEQ ID NOS: 1-47 or a chimeric sequence thereof, so long as the original function thereof is maintained. The term "TMC6 gene" includes not only the TMC6 genes exemplified above, but also includes conservative variants thereof. Similarly, the term "TMC6 protein" includes not only the TMC6 proteins exemplified above, but also includes conservative variants thereof. Examples of the conservative variants include, for example, homologues and artificially modified versions of the TMC6 genes and TMC6 proteins exemplified above.

Furthermore, the TMC6 gene defined with the name of an organism from which the TMC6 gene is derived includes not only the TMC6 gene found in the organism, but also includes genes having the nucleotide sequence of the TMC6 gene found in the organism and conservative variants thereof. Similarly, the TMC6 protein defined with the name of an organism from which the TMC6 protein is derived includes not only the TMC6 protein found in the organism, but also includes proteins having the amino acid sequence of the TMC6 protein found in the organism and conservative variants thereof. These conservative variants may be or may not be found in the organism. For example, the term "TMC6 protein of a mammal" includes proteins having the amino acid sequence of the TMC6 protein found in a mammal (e.g. the amino acid sequences shown as SEQ ID NOS: 1-47) and conservative variants thereof. Also, for example, the term "chimeric TMC6 protein of mammals" includes proteins having a chimeric sequence of the amino acid sequences of the TMC6 proteins found in mammals and conservative variants thereof. In other words, the TMC6 proteins constituting "chimeric TMC6 protein of mammals" are not limited to the TMC6 proteins found in the mammals, but may also be conservative variants thereof.

The expression "the original function is maintained" means that a variant of gene or protein has a function (such as activity or property) corresponding to the function (such as activity or property) of the original gene or protein. The expression "the original function is maintained" used for a gene means that a variant of the gene encodes a protein that maintains the original function. That is, the expression "the original function is maintained" used for the TMC6 gene means that a variant of the gene encodes a protein having a function as a salty-taste receptor protein. Furthermore, the expression "the original function is maintained" used for the TMC6 protein means that a variant of the protein has a function as a salty-taste receptor protein.

Whether a protein has a function as a salty-taste receptor protein can be confirmed by confirming activation of cells having (expressing) the protein upon allowing the cells to be in contact with a salty-taste substance such as NaCl. The activation may be confirmed, for example, under a condition where a salty-taste receptor other than the protein (herein also referred to as "other salty-taste receptor") does not function. Examples of such a condition include a condition of using cells not having the other salty-taste receptor, and a condition of inhibiting the function of the other salty-taste receptor by an inhibitor. For other conditions, the descriptions concerning the method of the present invention described later can be applied, mutatis mutandis.

Hereinafter, examples of the conservative variants will be explained.

Homologues of the TMC6 genes or homologues of the TMC6 proteins can be easily obtained from public databases by, for example, BLAST search or FASTA search using any of the nucleotide sequences of the TMC6 genes exemplified above or any of the amino acid sequences of the TMC6 proteins exemplified above as a query sequence. Furthermore, homologues of the TMC6 genes can be obtained by, for example, PCR using a chromosome of various organisms as the template, and oligonucleotides prepared on the basis of any of the nucleotide sequences of these known TMC6 genes as primers.

The TMC6 gene may be a gene encoding a protein having any of the aforementioned amino acid sequences (e.g. the amino acid sequences shown as SEQ ID NOS: 1-47 and chimeric sequences thereof), but which includes substitution, deletion, insertion, and/or addition of one or several amino acid residues at one or several positions, so long as the original function is maintained. For example, the N-terminus and/or the C-terminus of the encoded protein may be elongated or shortened. Although the number meant by the term "one or several" mentioned above may differ depending on the positions of amino acid residues in the three-dimensional structure of the protein or the types of amino acid residues, specifically, it is, for example, 1 to 50, 1 to 40, or 1 to 30, preferably 1 to 20, more preferably 1 to 10, still more preferably 1 to 5, particularly preferably 1 to 3.

The aforementioned substitution, deletion, insertion, and/or addition of one or several amino acid residues are/is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, inversion, or the like of amino acid residues as mentioned above includes a naturally occurring mutation due to an individual difference, or a difference of species of the organism from which the gene is derived (mutant or variant).

The TMC6 gene may be a gene encoding a protein having an amino acid sequence showing a homology of, for example, 50% or more, 65% or more, or 80% or more, preferably 90% or more, more preferably 95% or more, still more preferably 97% or more, particularly preferably 99% or more, to the total amino acid sequence of any of the aforementioned amino acid sequences, so long as the original function is maintained. In this description, "homology" means "identity".

The TMC6 gene may also be a gene, such as DNA, that is able to hybridize under stringent conditions with a probe that can be prepared from any of the aforementioned nucleotide sequences (e.g. nucleotide sequences encoding amino acid sequences shown as SEQ ID NOS: 1-47 and chimeric sequences thereof), such as a sequence complementary to a partial or entire sequence of any of the aforementioned nucleotide sequences, so long as the original function is maintained. The term "stringent conditions" refers to conditions under which a so-called specific hybrid is formed, and a non-specific hybrid is not formed. Examples of the stringent conditions include those under which highly homologous DNAs hybridize to each other, for example, DNAs not less than 50%, 65%, or 80% homologous, preferably not less than 90% homologous, more preferably not less than 95% homologous, still more preferably not less than 97% homologous, particularly preferably not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., preferably 0.1× SSC, 0.1% SDS at 60° C., more preferably 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Furthermore, since the degeneracy of codons differs depending on the host, arbitrary codons in the TMC6 gene may be replaced with respective equivalent codons. That is, the TMC6 gene may be a variant of any of the TMC6 genes exemplified above due to the degeneracy of the genetic code. For example, the TMC6 gene may be a gene modified so that it has optimal codons according to codon frequencies in a host to be used.

In the present invention, the term "gene" is not limited to DNA, but may include an arbitrary polynucleotide, so long as it encodes a target protein. That is, the term "TMC6 gene" may mean an arbitrary polynucleotide encoding the TMC6 protein. The TMC6 gene may be DNA, RNA, or a combination thereof. The TMC6 gene may be single-stranded or double-stranded. The TMC6 gene may be single-stranded DNA or single-stranded RNA. The TMC6 gene may be double-stranded DNA, double-stranded RNA, or a hybrid strand consisting of a DNA strand and an RNA strand. The TMC6 gene may contain both a DNA residue and an RNA residue in a single polynucleotide chain. When the TMC6 gene contains RNA, the aforementioned descriptions concerning DNA, such as those concerning nucleotide sequences exemplified above, may be applied to RNA with appropriately changing wordings to those for RNA as required. The TMC6 gene may or may not contain an intron. The mode of the TMC6 gene can be appropriately selected according to various conditions such as use mode thereof.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See http://www.ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

Furthermore, the TMC6 protein may also have a part or the whole of a conservative sequence of the TMC6 proteins, i.e. a part or the whole of a conservative sequence of the amino acid sequences of two or more kinds of TMC6 proteins. The TMC6 protein may also have, for example, a part or the whole of a conservative sequence of the TMC6 proteins exemplified above, i.e. a part or the whole of a conservative sequence of the amino acid sequences of two or more kinds of TMC6 proteins selected from the TMC6 proteins exemplified above. Specifically, the TMC6 protein may also have, for example, a part or the whole of a conservative sequence of a chimeric TMC6 protein of mammals, i.e. a part or the whole of a conservative sequence of the amino acid sequences of two or more kinds of TMC6 proteins selected from the TMC6 proteins of mammals. Furthermore, the TMC6 protein may also have a part or the whole of an amino acid sequence conserved in 10 or more, 20 or more, or 30 or more amino acid sequences upon aligning the total 47 amino acid sequences shown as SEQ ID NOS: 1-47. The conservative sequence can be determined by alignment of target amino acid sequences.

Furthermore, the TMC6 protein may also contain another amino acid sequence, as well as such an amino acid sequence of the TMC6 protein as mentioned above. That is, the TMC6 protein may also be a fused protein of such an amino acid sequence of the TMC6 protein as mentioned above and the other amino acid sequence. The other amino acid sequence is not particularly limited, so long as the TMC6 protein does not lose the function as a salty-taste receptor. Examples of the other amino acid sequence include, for example, tag sequences such as His tag and V5 epitope tag. The other amino acid sequence may be fused to, for example, N-terminus, C-terminus, or both termini of the TMC6 protein.

<2> Production of TMC6 Protein

The TMC6 protein can be produced and used in any form usable for screening of the objective substance. The form of the TMC6 protein to be produced and used can be appropriately selected according to various conditions such as the mode for carrying out the method of the present invention.

The TMC6 protein can be produced by, for example, expressing the TMC6 gene. The expression of the TMC6 gene may be carried out, for example, by using a cell, or by using a cell-free protein synthesis system. For the expression of the TMC6 gene by using a cell, the descriptions for a cell having the TMC6 protein described later can be referenced. The expressed TMC6 protein can be obtained in a form usable for screening of the objective substance, such as those described later, as required, to be used for the method of the present invention.

The TMC6 protein may be used, for example, in a form isolated at a desired degree, such as a purified product or a roughly purified product, or in a form contained in a material. Specifically, the TMC6 protein may be used, for example, in a form carried by a structure. Examples of the structure include, for example, a cell and a cell membrane. In other words, the TMC6 protein may be used, for example, in the form of a structure having (carrying) the TMC6 protein, such as a cell having the TMC6 protein and a cell membrane having the TMC6 protein. These structures having the TMC6 protein each may also be used, for example, in a form isolated at a desired degree, or in a form contained in a material.

A cell having the TMC6 protein is also referred to as "cell of the present invention". The TMC6 protein may be localized to, for example, a cell membrane, to function. Hence, the cell of the present invention may have the TMC6 protein, for example, on a cell membrane.

The TMC6 protein is expressed from a gene encoding it (TMC6 gene). Hence, the cell of the present invention may have the TMC6 gene. Specifically, the cell of the present invention may have the TMC6 gene so that the gene can be expressed. Incidentally, it is sufficient that the cell of the present invention has the TMC6 gene till expressing the TMC6 protein. That is, the cell of the present invention may or may not have the TMC6 gene after expressing the TMC6 protein. Furthermore, in other words, the cell of the present invention may be a cell expressing the TMC6 gene, and may be a cell expressing the TMC6 protein. The terms "expression of the TMC6 gene" and "expression of the TMC6 protein" may be used synonymously with each other.

The cell of the present invention may have one copy of the TMC6 gene, or two or more copies of the TMC6 gene. Also, the cell of the present invention may have one kind of TMC6 gene, or two or more kinds of TMC6 genes. Also, the cell of the present invention may have one kind of TMC6 protein, or two or more kinds of TMC6 proteins.

The cell of the present invention may be a cell inherently having the TMC6 gene, or may be a cell modified so as to have the TMC6 gene. In other words, the cell of the present invention may be one in which TMC6 is naturally found in which case the cell may be engineered to overproduce the native TMC6 or may be engineered such that one or more additional kinds of TMC6 genes may be introduced. To this end, the additional kinds of TMC6 may be a non-native or heterologous TMC6 gene or it may be a modified version of the native TMC6 gene as described herein. It is also envisioned within the scope of the present invention that the cell may be a cell that has been modified to include a heterolougous TMC6 gene. As used "heterlougous TMC6 gene" is understood to be a TMC6 gene that is native to one organism or is a modified version of a TMC6 gene that is native to one organism, but is introduced into a different organism from which it was originally obtained and/or derived.

Examples of the cell inherently having the TMC6 gene include a cell of an organism from which the TMC6 gene is derived, e.g. taste cells of mammals such as human and mouse. The cell inherently having the TMC6 gene can be obtained from, for example, an organism or a tissue containing the cell.

Examples of the cell modified so as to have the TMC6 gene include a cell introduced with the TMC6 gene. That is, the present invention also provides a cell introduced with the TMC6 gene.

The cell of the present invention and cells to be used for obtaining the same (e.g. a cell to be introduced with the TMC6 gene and a cell having been introduced with the TMC6 gene) were also collectively referred to as "host cell".

The host cell is not particularly limited, so long as it can express a functional TMC6 protein and is thereby usable for screening of the objective substance. Specifically, it is sufficient that the host cell is activated due to contact with a salty-taste substance such as NaCl upon expressing the TMC6 protein. Examples of the host cell include, for example, bacterial cells, fungal cells, plant cells, insect cells, and animal cells. Preferred examples of the host cell include eukaryotic cells such as fungal cells, plant cells, insect cells, and animal cells. More preferred examples of the host cell include animal cells. Examples of the animals include, for example, mammals, birds, and amphibians. Examples of the mammals include, for example, rodents and primates. Examples of the rodents include, for example, Chinese hamster, hamster, mouse, rat, guinea pig. Examples of the primates include, for example, human, monkey, chimpanzee. Examples of the birds include, for example, chicken. Examples of the amphibians include, for example, *Xenopus laevis*. In addition, the tissue or cell from which the host cell is derived is not particularly limited. Examples of the tissue or cell from which the host cell is derived include, for example, ovary, kidney, adrenal gland, tongue epithelium, pineal body, thyroid gland, and melanocyte. Examples of the cells of Chinese hamster include, for example, Chinese hamster ovary-derived cell line (CHO). Specific examples of CHO include, for example, CHO-DG44 and CHO-K1. Examples of the cells of human include, for example, human embryonic kidney cell-derived cell line (HEK). Specific examples of HEK include, for example, HEK293 and HEK293T. Examples of the cells of monkey include, for example, African green monkey kidney cell-derived cell line (COS). Specific examples of COS include, for example, COS-1. Examples of the cells of *Xenopus laevis* include, for example, *Xenopus laevis* oocyte. Examples of the insect cells include, for example, cells derived from *Spodoptera frugiperda* such as Sf9, Sf21, SF+, and cells derived from *Trichoplusia ni* such as High-Five. The host cells may be free cells (independent cells) or organized cells. The host cell may be an independent individual cell, such as a free cell, or may constitute an aggregate of cells, such as a tissue.

The TMC6 gene can be obtained by cloning from an organism having the TMC6 gene. For cloning, for example, nucleotides containing the gene, such as genomic DNA and cDNA, can be used. The TMC6 gene can also be obtained by chemical synthesis (Gene, 60(1), 115-127 (1987)).

The obtained TMC6 gene can be used as it is, or after being modified as required. That is, the TMC6 gene can be modified to obtain a variant thereof. A gene can be modified by a known technique. For example, an objective mutation can be introduced into an objective site of DNA by the site-specific mutation method. That is, the coding region of a gene can be modified by the site-specific mutation method so that a specific site of the encoded protein include substitution, deletion, insertion, and/or addition of amino acid residues. Examples of the site-specific mutation method include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of the TMC6 gene may also be obtained directly by chemical synthesis.

Modes of introducing TMC6 gene into the host cell are not particularly limited. It is sufficient that the TMC6 gene is expressibly harbored by the host cell. Specifically, for example, in cases of introducing the TMC6 gene in a form requiring transcription, such as DNA, it is sufficient that the TMC6 gene is expressibly harbored by the host cell under control of a promoter that functions in the host cell. In the host cell, the TMC6 gene may be present outside the chromosome, or may have been integrated into the chromosome. In cases of introducing two or more genes, it is sufficient that the genes each are expressibly harbored by the host cell.

The promoter for expressing the TMC6 gene is not particularly limited so long as it functions in the host cell. The term "promoter that functions in a host cell" refers to a promoter that shows a promoter activity in the host cell. The promoter may be a promoter derived from the host cell, or a heterogenous promoter. The promoter may be the native promoter of the TMC6 gene, or a promoter of another gene. The promoter may also be a promoter stronger than the native promoter of the TMC6 gene. For example, examples of promoters that function in animal cells include SV40 promoter, EF1a promoter, RSV promoter, CMV promoter, and SRalpha promoter. As the promoter, a highly-active type of an existing promoter may also be obtained and used by using various reporter genes. Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The TMC6 gene can be introduced into the host cell by, for example, using a vector containing the gene. The vector containing the TMC6 gene is also referred to as "expression vector for the TMC6 gene" or "recombination vector for the TMC6 gene". The expression vector for the TMC6 gene can be constructed by, for example, ligating a DNA fragment containing the TMC6 gene with a vector. By introducing the expression vector for the TMC6 gene into the host cell, the gene can be introduced into the host cell. The vector may contain a marker such as a drug resistance gene. Furthermore, the vector may contain an expression control sequence, such as a promoter, for expressing the inserted gene. The vector can be appropriately selected according to various conditions such as the type of the host cell and the mode of introducing the TMC6 gene. For example, examples of vectors usable for gene introduction into mammalian cells include plasmid vectors and viral vectors. Examples of the viral vectors include, for example, retroviral vectors and adenoviral vectors. Examples of the plasmid vectors include, for example, pcDNA series vectors (e.g. pcDNA3.1; Thermo Fisher Scientific), pBApo-CMV series vectors (TAKARA BIO), and pCI-neo (Promega). Depending on the type and structure of the vector, the vector can be integrated into the chromosome of the host cell, autonomously replicated outside the chromosome of the host cell, or temporarily held outside the chromosome of the host cell. For example, a vector having a viral replication origin, such as SV40 replication origin, can be autonomously replicated outside the chromosome in animal cells. Specifically, for example, the pcDNA series vectors have the SV40 replication origin, and hence can be autonomously replicated outside the chromosome in the host cell expressing the SV40 large T antigen, such as COS-1 and HEK293T.

Alternatively, by introducing a nucleotide fragment containing the TMC6 gene into the host cell, the gene can be introduced into the host cell. The nucleotide fragment containing the TMC6 gene is also referred to as "TMC6 gene fragment". Examples of such a fragment include linear DNA and linear RNA. Examples of the linear RNA include, for example, mRNA and cRNA.

Methods for introducing a nucleotide such as a vector and nucleotide fragment into the host cell can be appropriately selected according to various conditions such as the type of the host cell. For example, examples of methods for introducing a nucleotide such as a vector and nucleotide fragment into animal cells include the DEAE dextran method, the calcium phosphate method, the lipofection method, the electroporation method, and the microinjection method. When the vector is a viral vector, the vector can be introduced into the host cell by infecting the host cell with the vector (virus).

Furthermore, a host cell inherently having the TMC6 gene may be modified so that the expression of the TMC6 gene is increased, and then used. The expression "the expression of a gene is increased" means that the expression amount of the gene per cell is increased as compared with that of a non-modified cell (i.e., overexpressed). The term "non-modified cell" used herein refers to a control cell that has not been modified so that the expression of an objective gene is increased. Examples of the non-modified cell include a wild-type cell and a cell from which the host cell is obtained though modification. Examples of methods for increasing the expression of the TMC6 gene include increasing the copy number of the TMC6 gene, and improving the transcription efficiency and/or translation efficiency of the TMC6 gene. The copy number of the TMC6 gene can be increased by introducing the gene into the host cell. Introduction of the TMC6 gene can be carried out as described above. The TMC6 gene to be introduced may be one derived from the host cell, or a heterogenous one. The transcription efficiency and/or translation efficiency of the TMC6 gene can be improved by modifying an expression control sequence of the gene, such as a promoter. For example, the transcription efficiency of the TMC6 gene can be improved by replacing the promoter of the TMC6 gene with a stronger promoter.

The cell of the present invention may have any other characteristics, so long as it is usable for screening of the objective substance. For example, the cell of the present invention may or may not have a taste receptor other than a salty-taste receptor. In addition, in some cases, it can be preferred that the cell of the present invention does not have a salty-taste receptor other than the TMC6 protein (herein also referred to as "other salty-taste receptor"). Examples of cells not having the other salty-taste receptor include cells not having a gene encoding the other salty-taste receptor, and cells having a gene encoding the other salty-taste receptor but not expressing the gene. For example, the cell of the present invention may be a cell inherently not having the other salty-taste receptor, or may be a cell modified so as not to have the other salty-taste receptor. A cell can be modified so as not to have the other salty-taste receptor by, for example, knockout of a gene encoding the other salty-taste receptor. In addition, the cell of the present invention may also have a probe for screening of the objective substance, such as genetically encoded calcium indicators (Chem Rev. 2008 May; 108(5):1550-64.). Examples of cells having such a probe include cells expressing a gene encoding such a probe. In addition, the cell of the present invention may also have a calcium channel. In other words, the cell of the present invention may also have a gene encoding a calcium channel.

The cell of the present invention may inherently have such characteristic(s) as exemplified above, or may have been modified so as to have such characteristic(s) as exemplified above. The descriptions concerning the modification of a cell in relation to the TMC6 gene and the TMC6 protein can be applied mutatis mutandis to the modification of a cell in relation to other characteristics.

A cell having the TMC6 gene can be used as a cell having the TMC6 protein (i.e. the cell of the present invention), as it is, or after expression of the gene as required. That is, when a cell having the TMC6 gene has already expressed the gene, the cell may be used as a cell having the TMC6 protein (i.e. the cell of the present invention) as it is. Furthermore, by allowing a cell having the TMC6 gene to express the gene, a cell having the TMC6 protein (i.e. the cell of the present invention) can be obtained. For example, by culturing a cell having the TMC6 gene, the gene can be expressed, and thereby a cell having the TMC6 protein (i.e. the cell of the present invention) can be obtained. Specifically, for example, after introduction of the TMC6 gene (e.g. transfection), culture of the host cell can be continued to express the gene. The medium composition and culture conditions are not particularly limited, so long as the cell having the TMC6 gene can be maintained (e.g. can proliferate) and the TMC6 gene is expressed. Upon cultivation, the cell having the TMC6 gene may or may not proliferate. The medium composition and culture conditions can be appropriately set according to various conditions such as the type of the host cell. Culture can be carried out by using a usual medium and usual conditions used for culturing cells such as animal cells as they are, or after modifying them as required. For example, specific examples of media usable for culturing animal cells include Opti-MEM medium (Thermo Fisher Scientific), DMEM medium, RPMI 1640 medium, and CD293 medium. Culture can be carried out, for example, as a static culture at 36° C.–38° C. under a $CO_2$-containing atmosphere such as 5% $CO_2$. As required, selection drugs and expression inducers can also be used.

The expression of the TMC6 protein can be confirmed by measuring the function of the TMC6 protein. The expression of the TMC6 protein can also be confirmed by measuring the amount of mRNA expressed from the TMC6 gene, or detecting the TMC6 protein by Western blotting using antibodies.

The cell of the present invention can be used for the method of the present invention, for example, as it is (i.e. while being contained in the culture broth), or after being collected from the culture broth. The culture broth or cells collected therefrom may also be used for the method of the present invention, for example, after being subject to a treatment such as washing, concentration, and dilution, as required. Thus, the cell of the present invention may be used, for example, in a form isolated at a desired degree, or in a form contained in a material. The same shall apply to other structures having the TMC6 protein.

Alternatively, the cell of the present invention can also be artificially prepared. That is, the term "cell" is not limited to one biotically obtained (i.e. cell of an organism), such as a cell obtained by culture, but also include one abiotically obtained, such as an artificial lipid bilayer vesicle. That is, the term "cell" may specifically refer to a lipid bilayer vesicle. The artificial lipid bilayer vesicle does not necessarily have the TMC6 gene. Methods for preparing the artificial lipid bilayer vesicle are not particularly limited. The artificial lipid bilayer vesicle having the TMC6 protein can be prepared by, for example, using the TMC6 protein. The artificial lipid bilayer vesicle may have the TMC6 protein, for example, on the membrane thereof. Examples of the artificial lipid bilayer vesicle include liposome.

The cell membrane having the TMC6 protein can be prepared from, for example, the cell of the present invention. Specifically, the cell membrane having the TMC6 protein can be obtained, for example, as a membrane fraction upon disrupting the cell of the present invention.

Alternatively, the cell membrane having the TMC6 protein can also be artificially prepared. That is, the term "cell membrane" is not limited to one biotically obtained (i.e. cell membrane of a cell of an organism), such as a cell membrane prepared from a cell obtained by culture, but also include one abiotically obtained, such as an artificially prepared lipid bilayer. That is, the term "cell membrane" may specifically refer to a lipid bilayer. Methods for preparing the artificial lipid bilayer are not particularly limited. Examples of the methods for preparing the artificial lipid bilayer include, for example, the Montal-Mueller method and the droplet contact method (Kawano R. et al., Automated Parallel Recordings of Topologically Identified Single Ion Channels, Scientific Reports, 3, No. 1995 (2013)). The artificial lipid bilayer having the TMC6 protein can be prepared by, for example, using the TMC6 protein. For example, the TMC6 protein in an appropriate form, such as a membrane fraction containing the TMC6 protein, can be incorporated into a preliminarily-prepared artificial lipid bilayer to prepare an artificial lipid bilayer having the TMC6 protein.

The cell membrane may be used, for example, so as to separate two spaces such as two wells. That is, the cell membrane may be used, for example, so as to provide a reaction system having two spaces, such as two wells, separated from each other by the cell membrane. Such a reaction system may be provided as, for example, such an apparatus as described below.

Specific examples of the material containing the TMC6 protein include, for example, a culture broth of the cell having the TMC6 gene, a cell collected from the culture broth, processed products of the cell such as a disruption product of the cell, a lysate of the cell, an extract of the cell (cell-free extract), and an immobilized cell obtained by immobilizing the cell on a carrier such as acrylamide and carrageenan, a culture supernatant collected from the culture broth, a cell membrane having the TMC6 protein, partially purified products thereof (roughly purified products), and combinations thereof.

The TMC6 protein may also constitute a part of an apparatus. That is, specific examples of the material containing the TMC6 protein also include, for example, an apparatus equipped with the TMC6 protein. In other words, specifically, the TMC6 protein can also be produced and used, for example, in the form of an apparatus equipped with the TMC6 protein. Examples of the apparatus include an apparatus for carrying out the present invention (i.e. an apparatus for screening of the objective substance). The configuration of the apparatus can be appropriately set according to various conditions such as the mode for carrying out the method of the present invention. That is, the apparatus may be configured so that an action of a test substance on the TMC6 protein can be measured. Examples of the apparatus equipped with the TMC6 protein include, for example, an apparatus with the TMC6 protein fixed thereto, and an apparatus equipped with a structure, such as a lipid bilayer, having the TMC6 protein. Specific examples of the apparatus equipped with a lipid bilayer include, for example, a chip arrayed with lipid bilayers (WO2005/000558; Watanabe R. et al., Arrayed lipid bilayer chambers allow single-molecule analysis of membrane transporter activity. Nat Commun. 2014 Jul. 24; 5:4519.; Kamiya K. et al., Preparation of artificial cell membrane and single ion channel measurement, Electrochemistry, 83, 1096-1100 (2015)) and an ion channel-recording system equipped with lipid bilayers formed by the droplet contact method (Kawano R. et al., Automated Parallel Recordings of Topologically Identified Single Ion Channels, Scientific Reports, 3, No. 1995 (2013)).

<3> Method of the Present Invention

The method of the present invention is a method for screening an objective substance by using the TMC6 protein. That is, in other words, the method of the present invention is a method for screening an objective substance, the method comprising a step of identifying an objective substance by using the TMC6 protein. This step is also referred to as "screening step". That is, in the present invention, it can be identified whether a test substance is an objective substance by using the TMC6 protein. Further, the method of the present invention allows for the identification of a substance that affects salty taste by contacting a test substance with a TMC6 and determining the action of the test substance on the TMC6 protein upon contact. From this action, an identification of the affect on salty taste can be made.

The TMC6 protein can be used for the method of the present invention in any form usable for screening of the objective substance. The TMC6 protein can be used for the method of the present invention, for example, in such a form as exemplified above. The TMC6 protein can be used for the method of the present invention, for example, specifically, in the form of a cell having the TMC6 protein. That is, the TMC6 protein to be used for the method of the present invention, for example, may be a purified protein, or may be a material containing the TMC6 protein, such as a cell having the TMC6 protein. In other words, the TMC6 protein to be used for the method of the present invention may be, for example, one contained in a material such as a cell.

The objective substance is not particularly limited, so long as it can be identified by using the TMC6 protein. Examples of the objective substance include substances that act on the TMC6 protein. Examples of the substances that act on the TMC6 protein include substances that bind to the TMC6 protein and substances that activate or inactivate the TMC6 protein.

In addition, the substance that acts on the TMC6 protein can be, for example, a candidate of a salty-taste modifying substance. Hence, examples of the objective substance also include salty-taste modifying substances. The term "salty-taste modifying substance" collectively refers to substances that affect a salty taste. Examples of the salty-taste modifying substances include salty-taste alternative substances, salty-taste enhancing substances, and salty-taste reducing substances. The term "salty-taste alternative substance" refers to a substance that per se exhibits a salty taste. A salty-taste alternative substance is also referred to as "salty-taste substance". The term "salty-taste enhancing substance" refers to a substance that enhances a salty taste in the presence of a salty-taste substance, and more specifically, may refer to a substance that enhances a salty taste of a salty-taste substance. The term "salty-taste reducing substance" refers to a substance that reduces a salty taste in the presence of a salty-taste substance, and more specifically, may refer to a substance that reduces a salty taste of a salty-taste substance. The salty-taste enhancing substance and salty-taste reducing substance each per se may or may not exhibit a salty-taste.

Furthermore, the substance that acts on the TMC6 protein can be, for example, a candidate of an active ingredient of a prophylactic or therapeutic agent for a disease relating to the TMC6 protein. Hence, examples of the objective substance also include active ingredients of prophylactic or therapeutic agents for diseases relating to the TMC6 protein.

The test substance is not particularly limited. The test substance may consist of a single component (i.e. pure substance), or may consist of a combination of two or more kinds of components (i.e. mixture). When the test substance is a mixture, the number of kinds of the components constituting the mixture and the constitution ratio of the components constituting the mixture are not particularly limited. The test substance may be a known substance or a novel substance. The test substance may be a natural substance or an artificial substance. Examples of the test substance include, for example, substances derived from natural resources, such as sugars, nucleic acids, amino acids, peptides, proteins, lipids, and organisms; compound libraries prepared using a combinatorial chemistry technique; and other various organic or inorganic substances. As the test substance, one kind of test substance may be used, or two or more kinds of test substances may be used in combination. By bringing two or more kinds of components collectively into contact with the TMC6 protein to carry out the method of the present invention, it can be identified whether the combination of those components is the objective substance as a whole. Examples of cases of "bringing two or more kinds of components collectively into contact with the TMC6 protein" include cases of bringing a test substance that is a mixture into contact with the TMC6 protein, and cases of bringing two or more kinds of test substances collectively into contact with the TMC6 protein.

In the method of the present invention, the objective substance can be identified, i.e. whether the test substance is the objective substance can be identified, for example, on the basis of an action of the test substance on the TMC6 protein. Examples of the action of the test substance on the TMC6 protein include binding of the test substance to the TMC6 protein, and activation or inactivation of the TMC6 protein by the test substance. That is, the objective substance can be identified, for example, on the basis of binding of the test substance to the TMC6 protein, or activation or inactivation of the TMC6 protein by the test substance.

Specifically, the objective substance can be identified on the basis of an action of the test substance on the TMC6 protein upon the contact between the TMC6 protein and the test substance. Hence, the screening step may comprise (A) a step of bringing the TMC6 protein and a test substance into contact with each other; (B) a step of measuring an action of the test substance on the TMC6 protein upon the contact; and (C) a step of identifying the objective substance on the basis of the action. In other words, the method of the present invention is a method for screening an objective substance, comprising the aforementioned steps (A) to (C).

The contact between the TMC6 protein and the test substance can be carried out in an appropriate liquid. A liquid in which the contact between the TMC6 protein and the test substance is carried out is also referred to as "reaction liquid". For example, by allowing the TMC6 protein and the test substance to coexist in an appropriate reaction liquid, the TMC6 protein and the test substance can be brought into contact with each other. Specifically, by dissolution, suspension, dispersion, or the like of the TMC6 protein (e.g. the TMC6 protein in such a form as exemplified above, such as a cell having the TMC6 protein) and the test substance into an appropriate reaction liquid to make them coexist, the TMC6 protein and the test substance can be brought into contact with each other. Examples of the reaction liquid include aqueous media such as water and an aqueous buffer. Reaction conditions (i.e. conditions under which the contact between the TMC6 protein and the test substance is carried out) is not particularly limited, so long as screening of the objective substance can be carried out. The Reaction conditions can be appropriately set according to various conditions such as the form of use of the TMC6 protein, the type of the test substance, and methods for measuring the action of the test substance on the TMC6 protein. As the reaction conditions, for example, known reaction conditions upon measuring an interaction between substances, such as an interaction between a protein and a ligand, can be used as they are, or after being modified as required. The concentration of the test substance may be, for example, 0.01 nM to 500 mM. The concentration of the TMC6 protein may be, for example, 1 pg/mL to 10 mg/mL. In addition, in cases of using a cell having the TMC6 protein, the concentration of the cell having the TMC6 protein may be, for example, 10 cell/mL to 10,000,000 cell/mL. The contact between the TMC6 protein and the test substance may be or may not be terminated at an appropriate timepoint. The duration of the contact between the TMC6 protein and the test substance may be, for example, 0.1 sec or more, 0.5 sec or more, 1 sec or more, 3 sec or more, 5 sec or more, 10 sec or more, 20 sec or more, 30 sec or more, or 50 sec or more. The reaction liquid may contain other component(s), as well as the TMC6 protein (e.g. the TMC6 protein in such a form as exemplified above, such as a cell having the TMC6 protein) and the test substance, so long as screening of the objective substance can be carried out. The other component(s) can be appropriately set according to various conditions such as the form of use of the TMC6 protein, the type of the test substance, and methods for measuring the action of the test substance on the TMC6 protein. Examples of the other component(s) include salts such as calcium salts, carbon sources such as glucose, and pH buffering agents.

The term "upon the contact (upon the contact between the TMC6 protein and the test substance)" is not particularly limited, so long as it represents a timepoint when the action of the test substance on the TMC6 protein is generated to such a degree that the action can be measured. The term "upon the contact" may specifically refer to an appropriate timepoint from the timepoint when the contact between the TMC6 protein and the test substance is initiated to the timepoint when the action of the test substance on the TMC6 protein disappears. Specific examples of the timepoint "upon the contact" include, for example, a timepoint when maximum action of the test substance on the TMC6 protein is obtained, such as a timepoint when the binding amount of the test substance to the TMC6 protein becomes maximum and a timepoint when the degree of activation or inactivation of the TMC6 protein by the test substance becomes maximum. The term "upon the contact" may specifically refer to, for example, a timepoint on or after 0.1 sec, 0.5 sec, 1 sec, 3 sec, 5 sec, 10 sec, 20 sec, 30 sec, or 50 sec after the timepoint of initiating the contact between the TMC6 protein and the test substance, a timepoint on or before 100 sec, 50 sec, or 20 sec after the timepoint of terminating the contact between the TMC6 protein and the test substance (in cases of terminating the contact), or a timepoint within a range defined as a non-contradictory combination thereof.

When an action of the test substance on the TMC6 protein is observed, the test substance may be identified as the objective substance.

Specifically, when binding of the test substance to the TMC6 protein is observed, the test substance may be identified as the objective substance. That is, when binding of the test substance to the TMC6 protein is observed, the test substance may be identified as, for example, a substance that binds to the TMC6 protein.

In addition, specifically, when activation or inactivation of the TMC6 protein by the test substance is observed, the test substance may be identified as the objective substance. That is, when activation of the TMC6 protein by the test substance is observed, the test substance may be identified as, for example, a substance that activates the TMC6 protein. Alternatively, that is, when inactivation of the TMC6 protein by the test substance is observed, the test substance may be identified as, for example, a substance that inactivates the TMC6 protein.

The activation or inactivation of the TMC6 protein by the test substance can be determined by using the degree of activation of the TMC6 protein upon the contact between the TMC6 protein and the test substance (activation degree D1) as an index. That is, the step (B) may be (B1) a step of measuring the activation degree D1. Also, the step (C) may be (C1) a step of identifying the objective substance on the basis of the activation degree D1.

More specifically, the activation or inactivation of the TMC6 protein by the test substance can be determined by comparing the degree of activation of the TMC6 protein upon the contact between the TMC6 protein and the test substance (activation degree D1) with the degree of activation of the TMC6 protein under a control condition (activation degree D2). That is, the step (C1) may also be (C2) a step of identifying the objective substance on the basis of a difference between the activation degree D1 and the activation degree D2.

The term "control condition" refers to the following condition (C2-1) or (C2-2):

(C2-1) a condition of not bringing the TMC6 protein and the test substance into contact with each other;

(C2-2) a condition of bringing the TMC6 protein and the test substance into contact with each other, where the concentration of the test substance is lower than that in the step (A).

In other words, the activation or inactivation of the TMC6 protein by the test substance can be determined by using, as an index, a difference in the degree of activation of the TMC6 protein due to the presence or absence of the test substance or due to a difference in the concentration of the test substance.

Examples of the condition (C2-1) include conditions before the contact between the TMC6 protein and the test substance. Examples of the condition (C2-1) also include conditions after the contact between the TMC6 protein and the test substance, where the test substance was partially or entirely removed from the reaction system and the action of the test substance on the TMC6 protein partially or entirely disappeared. The concentration of the test substance in the condition (C2-2) is not particularly limited, so long as a measurable difference between the activation degree D1 and the activation degree D2 is observed. The concentration of the test substance in the condition (C2-2) may be, for example, 90% or lower, 70% or lower, 50% or lower, 30% or lower, 20% or lower, 10% or lower, 5% or lower, or 1% or lower, of that of the step (A).

The method of the present invention may comprise a step of measuring the activation degree D2. The activation degree D1 and the activation degree D2 may be measured in turn in a single reaction system, or may be measured simultaneously or in turn in respective reaction systems. The activation degree D2 may be measured before or after the activation degree D1 is measured. For example, after the activation degree D2 is measured, the test substance may be added to the reaction system and the activation degree D1 may be measured.

When the activation degree D1 is high, it can be concluded that activation of the TMC6 protein by the test substance is observed. Specifically, when the activation degree D1 is higher than the activation degree D2, it can be concluded that activation of the TMC6 protein by the test substance is observed. Alternatively, when the activation degree D1 is low, it can be concluded that inactivation of the TMC6 protein by the test substance is observed. Specifically, when the activation degree D1 is lower than the activation degree D2, it can be concluded that inactivation of the TMC6 protein by the test substance is observed.

The method of the present invention can be carried out, and specifically the contact between the TMC6 protein and the test substance (e.g. the contact between them in the step (A) and under the control condition) can be carried out, for example, in the presence of a salty-taste substance. By carrying out the method of the present invention in the presence of a salty-taste substance, particularly, screening of a salty-taste enhancing substance or a salty-taste reducing substance can be attained. Specifically, when activation of the TMC6 protein by the test substance is observed in the presence of a salty-taste substance, the test substance may be identified as a salty-taste enhancing substance. Alternatively, specifically, when inactivation of the TMC6 protein by the test substance is observed in the presence of a salty-taste substance, the test substance may be identified as a salty-taste reducing substance.

The salty-taste substance is not particularly limited, so long as it can activates the TMC6 protein. The salty-taste substance may be a known substance or a novel substance. The salty-taste substance may be a natural substance or an artificial substance. The salty-taste substance may also be a substance identified by the method of the present invention. Examples of the salty-taste substance include, for example, substances that provide (generate) an alkaline metal cation such as a sodium ion or a potassium ion in the reaction liquid such as an aqueous medium. Specific examples of the salty-taste substance include, for example, sodium chloride and potassium chloride. As the salty-taste substance, one kind of substance may be used, or two or more kinds of substance may be used in combination. Incidentally, it is sufficient that the salty-taste substance is present in the reaction system in a form capable of acting on the TMC6 protein. The salty-taste substance may be present in the reaction system typically in an ionized form. That is, for example, the term "in the presence of sodium chloride" may mean a state that a sodium ion and a chloride ion are present. The concentration of the salty-taste substance is not particularly limited, so long as activation or inactivation of the TMC6 protein by the test substance can be measured. The concentration of the salty-taste substance can be appropriately set according to various conditions such as the type of the salty-taste substance and methods for measuring the action of the test substance on the TMC6 protein. The concentration of the salty-taste substance (e.g. the concentration of sodium chloride) may be, for example, 0.01 mM to 500 mM.

Alternatively, the method of the present invention can be carried out, and specifically the contact between the TMC6 protein and the test substance (e.g. the contact between them in the step (A) and under the control condition) can be carried out, for example, in the absence of a salty-taste substance. By carrying out the method of the present invention in the absence of a salty-taste substance, particularly, screening of a salty-taste alternative substance can be attained. Specifically, when activation of the TMC6 protein by the test substance is observed in the absence of a salty-taste substance, the test substance may be identified as a salty-taste alternative substance. The term "in the absence of a salty-taste substance" refers to a state that substantially no salty-taste substance is present. Examples of the state that substantially no salty-taste substance is present include a condition where the concentration of the salty-taste substance is a concentration at which the TMC6 protein is not activated. Specific examples of the state that substantially no salty-taste substance is present include, for example, a condition where the concentration of the salty-taste substance (e.g. the concentration of sodium chloride) is 0.1 mM or lower.

Methods for measuring the action of the test substance on the TMC6 protein are not particularly limited. The methods for measuring the action of action of the test substance on the TMC6 protein can be appropriately set according to various conditions such as the type of action to be measured. That is, the action of the test substance on the TMC6 protein can be measured, for example, by an appropriate method usable for measuring binding of the test substance to the TMC6 protein or activation or inactivation of the TMC6 protein by the test substance.

Methods for measuring binding of the test substance to the TMC6 protein are not particularly limited. Binding of the test substance to the TMC6 protein can be measured by, for example, a method for measuring binding between substances, such as binding between a protein and a ligand. Specific examples of such a method include, for example, isothermal titration calorimetry (ITC), surface plasmon resonance (SPR), nuclear magnetic resonance (NMR), and fluorescence correlation spectroscopy (FCS).

Methods for measuring activation or inactivation of the TMC6 protein by the test substance are not particularly limited. Activation or inactivation of the TMC6 protein by the test substance can be measured by, for example, using a cell having the TMC6 protein or a cell membrane having the TMC6 protein.

That is, activation or inactivation of the TMC6 protein by the test substance can be measured by, for example, using a cell having the TMC6 protein, and using activation or inactivation of the cell as an index. Activation or inactivation of a cell can be measured by, for example, using cation inflow into the cell as an index. That is, when cation inflow into a cell (i.e. cation flow from the outside of a cell into the inside of the cell) is increased or decreased as compared with that under the control condition, it can be concluded that the cell is activated or inactivated, i.e. that the activation degree D1 is higher or lower than the activation degree D2. In addition, activation or inactivation of a cell can also be measured by, for example, using one or more parameters selected from the membrane potential of the cell, the membrane current of the cell, and the cation concentration in the cell as an index or indices. That is, when the membrane potential of a cell is increased or decreased as compared with that under the control condition, i.e. when depolarization or hyperpolarization occurs, it can be concluded that the cell is activated or inactivated, i.e. that the activation degree D1 is higher or lower than the activation degree D2. Also, when the inward membrane current of a cell is increased or decreased as compared with that under the control condition, it can be concluded that the cell is activated or inactivated, i.e. that the activation degree D1 is higher or lower than the activation degree D2. Also, when the cation concentration in a cell is increased or decreased as compared with that under the control condition, it can be concluded that the cell is activated or inactivated, i.e. that the activation degree D1 is higher or lower than the activation degree D2. Examples of the cation include a sodium ion and a calcium ion. In other words, activation or inactivation of the TMC6 protein can be measured by, for example, using one or more of these parameters as an index or indices. Incidentally, the TMC6 protein may directly or indirectly affect such a parameter as exemplified above. For example, in an embodiment, sodium ions may flow into a cell through the TMC6 protein to depolarize the membrane potential of the cell, and the depolarization may induce inflow of calcium ions into the cell through a calcium channel.

Methods for measuring these parameters are not particularly limited. These parameters can be measured by, for example, known methods. For example, all the membrane potential of a cell, the membrane current of a cell, and the cation concentration in a cell are also indices of cation inflow into the cell. Hence, cation inflow into a cell can be measured by, for example, measuring the membrane potential of the cell, the membrane current of the cell, or the cation concentration in the cell. Examples of methods for measuring the membrane potential include a patch clamp method and a method of using a voltage-sensitive dye. Examples of methods for measuring the membrane current include a patch clamp method and a voltage clamp method. Examples of methods for measuring the intracellular sodium concentration include a method of using a sodium indicator such as CoroNa Green Sodium Indicator (Thermo Fisher Scientific). Examples of methods for measuring the intracellular calcium concentration include calcium imaging. In calcium imaging, the intracellular calcium concentration can be measured by using a calcium indicator. Examples of the calcium indicator include calcium-sensitive fluorescent dyes and calcium-sensitive fluorescent proteins. Examples of the calcium-sensitive fluorescent dyes include, for example, Fura 2 and Fluo 4. Examples of the calcium-sensitive fluorescent proteins include, for example, Cameleon, TN-XL, GCaMP, and G-GECO. Specific examples of Cameleon include, for example, Yellow Cameleon 2.60 (YC 2.60) (PNAS vol. 101:10554-10559 (2004)). A signal, such as fluorescence, in calcium imaging can be detected with a detector depending on the type of signal, such as a fluorescence detector. Examples of the fluorescence detector include, for example, a confocal laser microscope such as FV1200 (Olympus Corporation) and a high throughput screening system such as FDSS7000 (Hamamatsu Photonics KK). FDSS7000 supports measurement using a multi-well plate such as a 96-hole plate or 384-hole plate, and a plurality of test substances can be collectively tested with FDSS7000.

The descriptions concerning the measurement of activation or inactivation of the TMC6 protein by using a cell having the TMC6 protein can be applied mutatis mutandis to the measurement of activation or inactivation of the TMC6 protein by using a cell membrane having the TMC6 protein, particularly, in cases where the cell membrane is used so as to separate two spaces, i.e. in cases where the cell membrane is used so as to provide a reaction system having two spaces separated from each other by the cell membrane. In such cases, one of the spaces can be regarded as the inside of a cell (also referred to as "inner space"), and the other of the spaces can be regarded as the outside of the cell (also referred to as "outer space"). Of the spaces, one containing the test substance can be regarded as the outer space. In cases of using a cell membrane having the TMC6 protein, the parameters "cation inflow into a cell", "the membrane potential of a cell", "the membrane current of a cell", and "the cation concentration in the cell" can read as "cation inflow into one of spaces separated by the cell membrane (i.e. into the inner space)", "the membrane potential of a cell membrane", "the membrane current of a cell membrane", and "the cation concentration in one of spaces separated by the cell membrane (i.e. in the inner space)", respectively.

When "a parameter is measured and used as an index for measuring an action of the test substance on the TMC6 protein", it is sufficient that data reflecting the parameter is measured and used, and it is not necessary to obtain the value per se of the parameter, so long as the action can be measured, i.e. so long as it can be determined whether the action is observed. That is, when data reflecting a parameter is obtained, it is not necessary to calculate the value per se of the parameter from the data. Specifically, for example, when the intracellular calcium concentration is measured by calcium imaging and used as an index for measuring activation or inactivation of the TMC6 protein by the test substance (e.g. an index for measuring the activation degrees D1 and D2), it is sufficient that data reflecting the intracellular calcium concentration (e.g. signal intensity and signal intensity ratio derived from a calcium indicator) is measured and used, it is not necessary to calculate the intracellular calcium concentration per se from the data, so long as the activation or inactivation can be measured, i.e. so long as it can be determined whether the activation or inactivation is observed.

Thus, the objective substance can be identified. The method of the present invention may further comprise a step of evaluating the effect of the identified objective substance on salty taste, i.e. evaluating whether the identified objective substance affects (e.g. exhibits, enhances, or reduces) salty taste. Methods for the evaluation are not particularly limited. The evaluation can be carried out by, for example, known methods for evaluating a taste. Examples of such methods include sensory evaluation (evaluation by sensory test). The evaluation may be carried out in the presence or absence of a salty-taste substance.

Unless otherwise defined, all technical and scientific terms used herein have the same meaning as commonly understood by one of ordinary skill in the art to which this disclosure belongs. In case of conflict, the present specification, including definitions, will control.

The above written description of the invention as further supported by the examples provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

EXAMPLES

Having generally described this invention, a further understanding can be obtained by reference to certain specific examples, which are provided herein for purposes of illustration only, and are not intended to be limiting unless otherwise specified.

Hereinafter, the present invention will be more specifically explained with reference to examples. However, the present invention is not limited by these examples.

Example 1: Preparation of Knockout Mice

In this Example, for the purpose of analyzing the gene function of the TMC6 gene, the TMC3 gene, and the TMC8 gene, which are expressed in taste cells of mice, knockout mice of these genes were prepared.
(1) Preparation of Knockout Mouse of TMC6 Gene Genome editing was carried out on fertilized eggs of a C57BL/6J mouse by the CRISPR/Cas9 technique (Science 337:816-821 (2012)) to prepare a mouse having a mutation in the TMC6 gene (mutant mouse). The manufacturing method is described below.

Messenger RNA (mRNA) for expressing the Cas9 protein was synthesized by using a plasmid pT7-Cas9 (ORIGENE). That is, Cas9 mRNA was synthesized by transcription from the T7 promoter incorporated in pT7-Cas9. The synthesized Cas9 mRNA was purified with MEGAclear kit (Ambion) according to the supplier's protocol to obtain 100 µL of 567 ng/µL Cas9 mRNA.

A target sequence for gene mutation was designed with software CRISPR direct (Bioinformatics, 31, 1120-1123. (2015)) and Guide RNA Target Design Tool (Blue Heron). The target sequence used for preparing the mutant mouse of the TMC6 gene was "agcatgcccagccgtaccattgg" (SEQ ID NO: 48). The "tgg" at the 3'-end of the target sequence was the PAM (Proto-spacer Adjacent Motif) sequence. The target sequence was DNA-synthesized and cloned into a plasmid pT7-Guide-IVT (ORIGENE). Guide RNA (gRNA) was synthesized by transcription from the obtained plasmid. The synthesized gRNA was purified with MEGAclear kit to obtain 455 ng/μL gRNA.

Subsequently, a mixture of Cas9 mRNA and gRNA was microinjected into the pronucleus or cytoplasm of pronuclear-stage fertilized eggs (Ark Resource) of the C57BL/6J mouse (Mouse embryo manipulation manual <Third Edition> Kindai Shuppan). The concentration of RNA used for injection was 50 ng/μL for Cas9 mRNA and 40 ng/μL for gRNA. After the injection, the fertilized eggs were each transplanted into the uterus of a foster mother mouse. Genomic DNA was prepared from body tissue of an offspring mouse (mutant mouse) born after about 19 days. A nucleotide sequence of the mutation site of the TMC6 gene and adjacent regions thereof was PCR-amplified by using the genomic DNA as the template, and sequencing analysis was carried out.

Results are shown in FIG. 8A. Compared with the nucleotide sequence of the TMC6 gene of the wild type mouse, the TMC6 gene of the mutant mouse had deletion of 16 bases in one allele. The deletion site of the 16 bases was the boundary between the $4^{th}$ exon and the intron downstream thereof. Because the 5'-splice site necessary for splicing was lost due to the deletion of the 16 bases, the intron downstream of the $4^{th}$ exon was not removed by splicing, and therefore normal mature TMC6 mRNA is not produced, but mutant mRNA is produced, from nuclear mRNA transcribed from the TMC6 gene of the mutant mouse. Assuming that a protein is translated from the mutant mRNA, the stop codon exists in the un-removed intron portion, and hence, synthesis of the protein is terminated there. That is, the TMC6 protein synthesized from the mutant mRNA has the N-terminal 87 amino acids identical to those of the wild-type TMC6 protein, but has the amino acids downstream thereof different from those of the wild-type TMC6 protein, and furthermore, a stop codon appears at $15^{th}$ codon thereof and hence the amino acid residues after that are deleted. Thus, the TMC6 protein having the normal amino acid sequence is not synthesized, and that is, the TMC6 gene can be regarded as being knocked out by the deletion of the 16 bases. That is, a hetero knockout mouse of the TMC6 gene (Tmc6 +/−) was obtained.

Subsequently, a male and a female of the hetero knockout mouse of the TMC6 gene were crossed to prepare a homo knockout mouse of the TMC6 gene (Tmc6 −/−), which has the aforementioned mutation in both alleles.

(2) Preparation of Knockout Mice of TMC3 Gene and TMC8 Gene

In a similar manner, a mouse having mutation in the TMC3 gene and a mouse having mutation in the TMC8 gene (mutant mice) were prepared. The target sequences used for preparation of mutant mice were "cagctggaagtatcaccacgggg" (SEQ ID NO: 49) for the TMC3 gene and "gtcgcaagcgttgtagccgtagg" (SEQ ID NO: 50) for the TMC8 gene. The nucleotide sequences of mutation sites of the TMC3 gene and the TMC8 gene and adjacent regions thereof in knockout mice are shown in FIGS. 8B and C, respectively. Compared with the nucleotide sequence of the wild-type TMC3 gene, the mutant TMC3 gene had deletion of 5 bases. This deletion results in a frameshift of codons, and hence, the TMC3 protein having the normal amino acid sequence is not synthesized. Hence, the TMC3 gene can be regarded as being knocked out. The mutant TMC8 gene had insertion of 7 bases that are not present in the wild-type TMC8 gene. This insertion results in a frameshift of codons, and hence, the TMC8 protein having the normal amino acid sequence is not synthesized. Hence, the TMC3 gene can be regarded as being knocked out. Therefore, respective hetero knockout mice of the TMC3 gene and the TMC8 gene were obtained.

Subsequently, a male and a female of the hetero knockout mouse of each gene were crossed to prepare a homo knockout mouse of each gene (Tmc3 −/− and Tmc8 −/−), which has the aforementioned mutation in both alleles.

Example 2: Identification of Salty-Taste Receptor Gene

In this Example, palatability tests were carried out for tastes such as sodium chloride (NaCl) by using a wild-type mouse and knockout mice, to identify a salty-taste receptor gene.

(1) NaCl Palatability Test

It has been known that mice have a salty-taste reception system via an epithelial sodium channel (also referred to as "ENaC") and another unknown salty-taste reception system, specifically, a salty-taste reception system via an unknown salty-taste receptor other than ENaC (Eur J Physiol (2015) 467:457-463). The function of ENaC as a channel is inhibited by amiloride. Thus, an NaCl palatability test was carried out in the presence of amiloride, i.e. under a condition where the function of ENaC is inhibited and only the unknown salty-taste reception system functions. If a gene encodes the unknown salty-taste receptor other than ENaC, the salty-taste reception system via the unknown salty-taste receptor does not function in a homo knockout mouse of this gene, and hence, it is predicted that this knockout mouse exhibits NaCl responsiveness, such as NaCl palatability, different from that of a wild-type mouse in the presence of amiloride.

When the wild-type C57BL/6J mouse is raised by feeding D12450B (containing 0.1% sodium, RESEARCH DIETS, USA), which is a feed containing sodium in an amount approximately twice as much as a recommended amount considered to be required for normal growth (0.05% sodium), the mouse exhibits palatability for a NaCl aqueous solution slightly higher than that for water. The inventors of the present invention found that when the wild-type C57BL/6J mouse is raised by feeding water added with 30 μM amiloride, the mouse exhibits remarkable NaCl palatability. Thus, an NaCl palatability test was carried out by using the wild-type C57BL/6J mouse and the knockout mice obtained in Example 1.

The NaCl palatability test was carried out by the two-bottle choice method (abbreviated as "two-bottle method") for 96 hr. That is, two 11-mL plastic bottles (water dispenser bottles) were filled with a test aqueous solution, moisture outside of the bottles was wiped out and dried, the weights thereof (the total weight of the bottle, a water dispenser tube made of stainless, and the aqueous solution, for each bottle) were measured, and the bottles were inserted into a metal lid of a breeding cage at an angle of approximately 30 degrees. As the test aqueous solution, a test aqueous solution A (control aqueous solution; deionized water added with 30 μM amiloride) was filled into both the bottles, to be fed to the mice during the first four days. During the following four days, a test aqueous solution B (NaCl aqueous solution; 100 mM NaCl aqueous solution added with 30 μM amiloride) was filled into one bottle, and the test aqueous solution A (control aqueous solution) was filled into the other bottle, to be fed to the mice. The positions of the bottles were laterally interchanged every day. The weights of the bottles were measured every 24 hours, to calculate the reduced amounts of the aqueous solutions. Separately, four water dispenser bottles filled with deionized water were located on a vacant breeding cage, and changes of the weights were measured every day, to calculate an average value of the sum of the evaporation amount of the aqueous solution and the dropped amount of the aqueous solution due to experimental operation (approximately 0.05 g to 0.06 g). To prevent dropping of the aqueous solutions due to rocking of the lid of the breeding cage and the bottles by the mice, a transparent acryl board (10 cm×15 cm×1 cm, 180 g) was located on the bottles as a weight. The average value of the sum of the evaporation and dropped amounts of each aqueous solution was subtracted from the reduced amount of the same, and the resulting value was regarded as the intake amount of each aqueous solution. The ratio of the intake amount of the NaCl aqueous solution with respect to the total intake amount of the control aqueous solution and the NaCl aqueous solution was calculated and regarded as NaCl palatability.

Results are shown in FIG. 9. The wild-type mouse, the hetero knockout mouse of the TMC6 gene (Tmc6 +/−), and the respective homo knockout mice of the TMC3 gene and the TMC8 gene (Tmc3 −/− and Tmc8 −/−) exhibited high NaCl palatability. By contrast, the homo knockout mouse of the TMC6 gene (Tmc6 −/−) exhibited remarkably reduced NaCl palatability as compared with the other subject mice (P<0.05 or P<0.01). From these experimental results, it was indicated that the unknown salty-taste reception system other than the salty-taste reception system via ENaC did not function in the homo knockout mouse of the TMC6 gene, and hence, this knockout mouse did not normally sense salty taste. Therefore, it was indicated that the TMC6 gene is a gene encoding the unknown salty-taste receptor other than ENaC.

(2) Palatability Tests for Taste Substances Other than NaCl

In addition, palatability tests for various taste substances other than NaCl were carried out by the two-bottle method for 48 hr for the wild-type C57BL/6J mouse and the homo knockout mouse of the TMC6 gene. In the two-bottle method, deionized water was used as the test aqueous solution A (control aqueous solution), and taste substance aqueous solutions shown below were each used as the test aqueous solution B. When the taste substance aqueous solution contained amiloride, the control aqueous solution was also added with the same concentration of amiloride.
<Taste Substance Aqueous Solutions>
MSG: 100 mM monosodium glutamate
MSG+AMIL: 100 mM monosodium glutamate+30 μM amiloride
MSG+IMP: 100 mM monosodium glutamate+1 mM inosinic acid
MSG+IMP+AMIL: 100 mM monosodium glutamate+1 mM inosinic acid+30 μM amiloride
Citric Acid: 10 mM citric acid
Quinine HCl: 0.3 mM quinine hydrochloride
Glucose: 300 mM glucose
Fructose: 300 mM fructose
Sucrose: 300 mM sucrose Results are shown in FIG. 10. No difference was observed between the homo knockout mouse of the TMC6 gene (Tmc6 −/−) and the wild-type mouse regarding any of palatability for umami taste (MSG, MSG+AMIL, MSG+IMP, and MSG+IMP+AMIL) and sweet taste (Glucose, Fructose, and Sucrose) and repellency for sour taste (Citric acid) and bitter taste (Quinine HCl). From these experimental results, it was revealed that the homo knockout mouse of the TMC6 gene exhibits normal palatability for basic tastes other than salty taste. That is, it was strongly indicated that the TMC6 gene is a gene encoding a salty-taste receptor.

Example 3: Evaluation of Effects of TMC6 Gene Knockout on Taste Buds and Taste Cells In this Example, the shapes of taste buds and taste cells of the wild-type mouse and the knockout mice of the TMC6 gene were analyzed.

The wild-type C57BL/6J mouse, the hetero knockout mouse of the TMC6 gene, and the homo knockout mouse of the TMC6 gene were each killed by euthanasia. Ice-cold PBS was perfused from the ventricle at a flow rate of 5 mL/min for 2 min to remove blood. Then, ice-cold 4% paraformaldehyde-phosphate buffer (Nacalai Tesque) was perfused for 5 min to fix the whole body, and then, the tongue was isolated. A region containing circumvallate papillae was cut out from the isolated tongue into a block to prepare a sample, and incubated in 4% paraformaldehyde-phosphate buffer at 4° C. for 90 min. Then, the sample was rinsed twice with PBS, and incubated in PBS containing 10% sucrose. Then, the sucrose concentration in PBS was gradually increased from 10% to 30%, and the sample was incubated in PBS containing 30% sucrose for 2 hr. Then, the sample was embedded in Tissue-Tek O.C.T. Compound (Sakura Finetek Japan), and placed in a gas phase of liquid nitrogen to be frozen. Frozen sections having a thickness of 10 μm were cut out from the frozen sample with a cryostat (Leica Microsystems) so that the section plane was perpendicular to the long axis of the tongue. The obtained frozen sections were collected on a slide glass, rinsed with PBS, and then subjected to observation with a differential interference microscope.

Results are shown in FIG. 11. FIG. 11A shows a slice image of the circumvallate papillae of the wild-type C57BL/6J mouse. From FIG. 11A, it is observed that a plurality of taste buds are arranged along a groove of the circumvallate papillae, and each taste bud is formed as a collection of elongated taste cells. FIGS. 11B and C show slice images of the circumvallate papillae of the hetero knockout mouse of the TMC6 gene and the homo knockout mouse of the TMC6 gene, respectively. Taste buds and taste cells of the knockout mice of the TMC6 gene shown in FIGS. 11B and C were not morphologically different from those of the wild-type mouse shown in FIG. 11A, and that is, they were morphologically completely normal. This indicates that knockout of the TMC6 gene does not cause a morphological change or damage in taste buds or taste cells.

Incidentally, the fact that no difference was observed between the homo knockout mouse of the TMC6 gene and the wild-type mouse regarding palatability for any of umami taste, sweet taste, sour taste, and bitter taste (Example 2) shows that respective reception systems for umami taste, sweet taste, sour taste, and bitter taste normally function even in the homo knockout mouse of the TMC6 gene. This is consistent with the observation results showing that taste buds and taste cells of the knockout mice of the TMC6 gene are morphologically normal (FIG. 11).

Example 4: Functional Analysis of TMC6 Protein

In this Example, the TMC6 gene was expressed in animal cells, and activation of the cells by a stimulus was measured, to analyze the function of a protein encoded by the TMC6 gene (TMC6 protein).
(1) Construction of Expression Plasmids
V5-epitope sequence (ggtaagcctatccctaaccctctgctgggcctggattctacc; SEQ ID NO: 51) was totally-synthesized, and cloned into a cloning site of a plasmid pcDNA3.1 (Thermo Fisher Scientific), to obtain a plasmid pcDNA3.1-V5.

As a probe for calcium imaging used for measuring activation of cells, Yellow Cameleon 2.60 (YC2.60), which is a GECI (Genetically Encoded Calcium Indicator), was chosen. A plasmid YC2.60-pcDNA for expression of a gene encoding YC2.60 (YC2.60 gene) was constructed in the following manner. The YC2.60 gene was totally-synthesized with reference to known sequence information (GenScript). PCR was performed by using the synthesized YC2.60 gene to amplify a DNA fragment containing the YC2.60 gene. The amplified fragment was cloned downstream of CMV promoter of pcDNA3.1, to obtain YC2.60-pcDNA. The nucleotide sequence of YC2.60-pcDNA is shown as SEQ ID NO: 52. In SEQ ID NO: 52, the nucleotide sequence of positions 5104 to 7065 corresponds to the YC2.60 gene. Incidentally, while the amino acid residue at position 634 in the original YC2.60 was Thr, that amino acid residue in YC2.60 expressed from YC2.60-pcDNA has been mutated to Met.

A plasmid TMC6-pcDNA3.1 for expression of the mouse TMC6 gene was constructed in the following manner. A tissue containing circumvallate papillae was isolated from a mouse, and total RNA was prepared in the usual manner and reverse-transcribed, to obtain cDNA. PCR was performed by using the obtained cDNA as the template, and primers of SEQ ID NOS: 53 and 54, to amplify the coding sequence (CDS) of the mouse TMC6 gene. The CDS of the mouse TMC6 gene was cloned into a cloning site between CMV promoter and V5-epitope sequence of pcDNA3.1-V5 so that the CDS and V5-epitope sequence share reading frames, to obtain TMC6-pcDNA3.1. *Escherichia coli* OmniMAX (Thermo Fisher Scientific) was transformed with TMC6-pcDNA3.1, and cultured in a liquid medium in the presence of ampicillin. From cultured cells, TMC6-pcDNA3.1 (307.9 ng/µL) was purified. The nucleotide sequence of the CDS of the TMC6 gene cloned into TMC6-pcDNA3.1 was confirmed to be identical to the nucleotide sequence of mRNA transcript variant 1 of mouse (NM 145439) registered in NCBI by sequencing analysis. The nucleotide sequence of TMC6-pcDNA3.1 is shown as SEQ ID NO: 55. In SEQ ID NO: 55, the nucleotide sequence of positions 907 to 3336 corresponds to the CDS of the mouse TMC6 gene.

Similarly, a plasmid hTMC6-pcDNA3.1 for expression of the human TMC6 gene was constructed in the following manner. PCR was performed by using a cDNA clone of the human TMC6 gene (I.M.A.G.E/MGC Clone; DNAFORM) as the template, and primers of SEQ ID NOS: 56 and 57, to amplify a 5'-side fragment of the CDS of the human TMC6 gene. Separately, PCR was performed by using the cDNA clone of the human TMC6 gene (I.M.A.G.E/MGC Clone; DNAFORM) as the template, and primers of SEQ ID NOS: 58 and 59, to amplify a 3'-side fragment of the CDS of the human TMC6 gene. Both the fragments were mutually ligated by using Gibson Assembly Master Mix (New England BioLabs), and cloned into a cloning site between CMV promoter and V5-epitope sequence of pcDNA3.1-V5 so that the CDS and V5-epitope sequence share reading frames, to obtain hTMC6-pcDNA3.1, into which the full-length sequence of the CDS of the human TMC6 gene has been cloned. *Escherichia coli* OmniMAX (Thermo Fisher Scientific) was transformed with hTMC6-pcDNA3.1, and cultured in a liquid medium in the presence of ampicillin. From cultured cells, hTMC6-pcDNA3.1 (293.1 ng/µL) was purified. The nucleotide sequence of the CDS of the TMC6 gene cloned into hTMC6-pcDNA3.1 was confirmed to be identical to the nucleotide sequence of mRNA transcript variant 2 of human (NM 007267) registered in NCBI by sequencing analysis. The nucleotide sequence of hTMC6-pcDNA3.1 is shown as SEQ ID NO: 60. In SEQ ID NO: 60, the nucleotide sequence of positions 901 to 3315 corresponds to the CDS of the human TMC6 gene.

(2) Functional Analysis of Mouse TMC6 Protein

CHO-K1 cells were transfected with TMC6-pcDNA3.1 or pcDNA3.1 in combination with YC2.60-pcDNA, to prepare TMC6-expressing cells (cells expressing the mouse TMC6 gene and the YC2.60 gene) and control cells (cells expressing the YC2.60 gene). The prepared cells were stimulated, and activation of the cells was measured. The procedure was as follows.

That is, first, CHO-K1 cells (ATCC) were inoculated into a culture dish having a diameter of 60 mm while adjusting the number of the cells to obtain 60% confluence, and cultured for 8 hr. As the medium, 5 mL of Ham's F-12K (Kaighn's) (Life Technologies) containing 10% fetal bovine serum (Life Technologies) was used. A 15 µL aliquot of FuGENE 6 (Promega) was added to 235 µL of Opti-MEM (Thermo Fisher Scientific), and incubated for 5 min at a room temperature. Then, 0.625 µg of TMC6-pcDNA3.1 and 2.5 µg of YC2.60-pcDNA were further added thereto, and incubated for 15 min at a room temperature. Then, the whole of the resultant mixture was dropped into the culture broth of the CHO-K1 cells, and the culture broth was mildly stirred. Then, the cells were further cultured for 18 hr under a condition of 5% $CO_2$ at 37° C., to obtain the TMC6-expressing cells. Similarly, the control cells were obtained through transfection using pcDNA3.1 instead of TMC6-pcDNA3.1.

After the cultivation, the culture broth was removed. A low-concentration NaCl solution (27 mM NaCl, 1 mM KCl, 0.4 mM $CaCl_2$, 0.2 mM $MgCl_2$, 2 mM Hepes (pH7.3), 1 mM $NaHCO_3$, 2 mM glucose, 2 mM sodium pyruvate, and 112 mM NMDG-Cl) was added to the culture dish, incubation was carried out statically for 5 min, and then, stimulation and observation of cells were started. First, the low-concentration NaCl solution was perfused for approximately 80 sec, to provide a ground state. Then, a high-concentration NaCl solution (135 mM NaCl, 1 mM KCl, 0.4 mM $CaCl_2$, 0.2 mM $MgCl_2$, 2 mM Hepes (pH7.3), 1 mM $NaHCO_3$, 2 mM glucose, and 2 mM sodium pyruvate) was perfused instead of the low-concentration NaCl solution for approximately 60 sec, to stimulate the cells. Then, perfusion of the low-concentration NaCl solution was restarted. After the state of the cells virtually returned to the ground state, the cells were stimulated with an ATP stimulation solution (50 µM ATP, 27 mM NaCl, 1 mM KCl, 0.4 mM $CaCl_2$, 0.2 mM $MgCl_2$, 2 mM Hepes (pH7.3), 1 mM $NaHCO_3$, 2 mM glucose, 2 mM sodium pyruvate, and 112 mM NMDG-Cl). The perfusion was carried out by adding the low-concentration or high-concentration NaCl solution to the culture dish at a rate of 1 mL/min while removing a stale solution by suction from the edge of the culture dish so that the cells were always in contact with a fresh solution. The stimulation with the ATP stimulation solution was carried out by dropping 600 µL of the ATP stimulation solution near cells to be measured on the culture dish with a pipet within 3 sec.

Observation of the cells was carried out with a confocal laser microscope FV1200 (Olympus). Upon the observation of the cells, in order to minimize the phototoxicity to the cells, the output of a 440 nm laser for excitation was set to 0.3 to 4.5%, and the laser was attenuated to 1/100 with an ND filter. Activation of the cells was measured using the intracellular calcium concentration as an index. The intracellular calcium concentration was measured by calcium imaging using YC2.60. YC2.60 is one of calcium-sensitive fluorescent proteins based on fluorescence resonance energy transfer (FRET). YC2.60 contains a cyan fluorescent protein (CFP) and a yellow fluorescent protein (YFP). YC2.60 usually exhibits relatively strong CFP fluorescence and weak YFP fluorescence. When calcium ions bind to YC2.60, FRET from CFP to YFP is induced, and thereby, CFP fluorescence is attenuated and YFP fluorescence is enhanced. That is, a higher intracellular calcium concentration provides a higher YFP/CFP value of a cell, which value represents the ratio of YFP fluorescence intensity with respect to CFP fluorescence intensity. Change of the intracellular calcium concentration was measured with analysis software equipped with FV1200 according to the supplier's manual. That is, luminosity of CFP and YFP was measured for each pixel of a fluorescent image, and the ratio of the luminosity of YFP with respect to the luminosity of CFP (YFP/CFP) was obtained for each pixel. A set of pixels constituting each cell was defined as ROI (region of interest), and an average value of change values of YFP/CFP of the pixels contained in ROI was calculated and regarded as data of each cell. Because the expression amount of YC2.60 and the YFP/CFP value are different in each cell measured, data was normalized by dividing the YFP/CFP value for each cell at each measurement by an average value of the YFP/CFP value for each cell over the whole period of measurement.

Results of the mouse TMC6-expressing cells are shown in FIG. 12A, and results of the control cells are shown in FIG. 12B. In the figure, each graph line represents data of an individual cell. In the figure, the vertical axis represents a relative YFP/CFP value. A larger value of the vertical axis indicates a higher intracellular calcium concentration, and hence, indicates that cells were more activated. A smaller value of the vertical axis indicates a lower intracellular calcium concentration, and hence, indicates that cells were less activated. In the TMC6-expressing cells, there was observed an increase in the YFP/CFP value due to an increase in the intracellular calcium concentration resulting from activation of the cells by stimulation with the high-concentration NaCl solution (FIG. 12A). By contrast, in the control cells, there was not observed an increase in the YFP/CFP value by stimulation with the high-concentration NaCl solution (FIG. 12B).

In addition, detailed data of one typical cell among the TMC6-expressing cells shown in FIG. 12A is shown in FIGS. 13-16.

FIG. 13A shows a part of an observation image obtained with FV1200 at the YFP wavelength. Approximately 20 cells are observed in the field of view. The cells upon not being stimulated, which have a low intracellular calcium concentration and are in the ground state, appear white if the expression level of YC2.60 is high, appear gray if the expression level of YC2.60 is middle, or are dark and hence hardly seen if the expression level of YC2.60 is low. Detailed data of a cell that responded to stimulation with the high-concentration NaCl solution in the region selected by a square on the upper right of this field of view is shown in FIGS. 13B and C and FIGS. 14-16. This cell is one indicated with an ellipse on the upper right of FIG. 13A, and was designated as "ROI-1". FIG. 13B and FIGS. 14-16 each show an imaged YFP/CFP value (also referred to as "FRET value") for the selected region. A Dark (black) pixel indicates a small FRET value, and a bright (white) pixel indicates a large FRET value. FIG. 13B shows four frames 1, 84, 250, and 276 from 324 consecutive captured images, each indicated with the ellipse of ROI-1. FIG. 13C shows a graph of time course of the FRET value of the ROI-1 cell. In the figure, the vertical axis represents a relative value of the FRET value. A larger value of the vertical axis indicates a higher intracellular calcium concentration, and hence, indicates that cells were more activated. The frame 1 in FIG. 13B is the first one of the consecutive captured images, and shows the state of the cell before being stimulated with the high-concentration NaCl solution. The ROI-1 cell in the frame 1 was dark, which indicates that the cell was not activated. The frame 84 in FIG. 13B shows the state of the cell upon being stimulated with the high-concentration NaCl solution. The ROI-1 cell in the frame 84 was bright, which indicates that the cell was activated by stimulation with the high-concentration NaCl solution. Also in the graph of FIG. 13C, the value of the vertical axis increased to approximately 1.2 by stimulation with the high-concentration NaCl solution. The frame 250 in FIG. 13B shows the state of the cell sometime after the perfusion of the low-concentration NaCl solution was restarted. The ROI-1 cell in the frame 250 was dark, and the value of the vertical axis in FIG. 13C became 1 or below, which indicates that the state of the cell virtually returned to the ground state. The frame 276 in FIG. 13B shows the state of the cell upon being stimulated with the ATP stimulation solution. The ROI-1 cell in the frame 250 was bright, and the value of the vertical axis in FIG. 13C became 1.3 or higher, which indicates that the cell was strongly activated by stimulation with the ATP stimulation solution.

All of the frames 1 to 324 are shown in FIGS. 14-16 (FIG. 14, frames 1-108; FIG. 15, frames 109-216; and FIG. 16, frames 217-324). From FIGS. 14-16, the whole of change in the degree of activation of the ROI-1 cell is recognized.

As described above, the TMC6-expressing cells were activated by stimulation with the high-concentration NaCl solution. Hence, it was revealed that the TMC6 protein responds to stimulation with a salty-taste substance such as sodium chloride, i.e. the TMC6 protein is a salty-taste receptor. Specifically, the TMC6 protein is considered to be a sodium channel expressed on a cell membrane. That is, it is considered that when the TMC6-expressing cell was stimulated with the high-concentration NaCl solution, sodium ions flowed into the cell through the TMC6 protein to depolarize the membrane potential of the cell membrane, and thereby the cell was activated. In addition, a response of the TMC6 protein, such as a difference or change in the degree of activation of the TMC6-expressing cell, against a salty-taste substance was shown as an image or a numeral. Therefore, a substance that acts on the TMC6 protein can be screened by using a response of the TMC6 protein, such as the degree of activation of the TMC6-expressing cell, as an index.

(3) Functional Analysis of Human TMC6 Protein

CHO-K1 cells were transfected with hTMC6-pcDNA3.1 or pcDNA3.1 in combination with YC2.60-pcDNA, to prepare TMC6-expressing cells (cells expressing the human TMC6 gene and the YC2.60 gene) and control cells (cells expressing the YC2.60 gene). The prepared cells were stimulated, and activation of the cells was measured. The procedure was identical to that of the functional analysis of the mouse TMC6 protein, except that hTMC6-pcDNA3.1 was used instead of TMC6-pcDNA3.1.

Results of the human TMC6-expressing cells are shown in FIG. 17A, and results of the control cells are shown in FIG. 17B. In the TMC6-expressing cells, there was observed an increase in the YFP/CFP value due to an increase in the intracellular calcium concentration resulting from activation of the cells by stimulation with the high-concentration NaCl solution (FIG. 17A). By contrast, in the control cells, there was not observed an increase in the YFP/CFP value by stimulation with the high-concentration NaCl solution (FIG. 17B).

These experimental results indicate that the CHO-K1 cells expressing the human TMC6 gene responded to stimulation with the high-concentration NaCl solution as with the CHO-K1 cells expressing the mouse TMC6 gene. Hence, it was revealed that TMC6 proteins of a plurality of organisms have an identical function.

(4) Functional Analysis of *Macaca mulatta* Tmc6 Protein, *Pongo abelii* TMC6 Protein, and Chimeric TMC6 Protein of Mouse and *Aotus nancymaae*

The nucleotide sequences of mRNAs of the TMC6 genes of *Macaca mulatta, Pongo abelii, Aotus nancymaae*, and mouse have been registered in NCBI under accession numbers of XM_015120470, XM_002827886, XM_012453598, and NM_145439, respectively. Thus, the *Macaca mulatta* TMC6 gene, the *Pongo abelii* TMC6 gene, and a chimeric TMC6 gene of mouse and *Aotus nancymaae* (mouse/*Aotus nancymaae* chimeric TMC6 gene) were artificially synthesized according to the sequence information (Eurofins Genomics). In addition, DNA encoding YC2.60 (YC2.60 gene) and DNA encoding a 2A peptide (2A peptide gene) were artificially synthesized (Eurofins Genomics).

The synthesized DNAs were each PCR-amplified. The amplified products were cloned into the plasmid pcDNA3.1 in an appropriate combination, to obtain plasmids *Macaca mulatta* TMC6-2A-YC260TM in pcDNA3.1(-), *Pongo abelii* TMC6-2A-YC260TM in pcDNA3.1(-), and Mouse-*Aotus nancymaae* chimera TMC6 2A-YC260TM in pcDNA3.1 (-). *Escherichia coli* OmniMAX (Thermo Fisher Scientific) was transformed with each plasmid, and cultured in a liquid medium in the presence of ampicillin. From cultured cells, 246.4 ng/µL of *Macaca mulatta* TMC6-2A-YC260TM in pcDNA3.1(-), 314.2 ng/µL of *Pongo abelii* TMC6-2A-YC260TM in pcDNA3.1(-), and 335.1 ng/µL of Mouse-*Aotus nancymaae* chimera TMC6 2A-YC260TM in pcDNA3.1(-) were each purified.

The nucleotide sequence of the CDS of the TMC6 gene cloned into *Macaca mulatta* TMC6-2A-YC260TM in pcDNA3.1(-) was confirmed to be identical to the nucleotide sequence of mRNA of the *Macaca mulatta* TMC6 gene (XM_015120470) registered in NCBI by sequencing analysis. The nucleotide sequence of *Macaca mulatta* TMC6-2A-YC260TM in pcDNA3.1(-) is shown as SEQ ID NO: 61. In SEQ ID NO: 61, the nucleotide sequence of positions 907 to 3324 corresponds to the CDS of the *Macaca mulatta* TMC6 gene, the nucleotide sequence of positions 3325 to 3387 corresponds to the DNA encoding the 2A peptide, and the nucleotide sequence of positions 3388 to 5421 corresponds to the DNA encoding YC2.60.

The nucleotide sequence of the CDS of the TMC6 gene cloned into *Pongo abelii* TMC6-2A-YC260TM in pcDNA3.1(-) was confirmed to be identical to the nucleotide sequence of mRNA of the *Pongo abelii* TMC6 gene (XM_002827886) registered in NCBI by sequencing analysis. The nucleotide sequence of *Pongo abelii* TMC6-2A-YC260TM in pcDNA3.1(-) is shown as SEQ ID NO: 62. In SEQ ID NO: 62, the nucleotide sequence of positions 907 to 3321 corresponds to the CDS of the *Pongo abelii* TMC6 gene, the nucleotide sequence of positions 3322 to 3384 corresponds to the DNA encoding the 2A peptide, and the nucleotide sequence of positions 3385 to 5418 corresponds to the DNA encoding YC2.60.

The nucleotide sequence of the CDS of the chimeric TMC6 gene cloned into Mouse-*Aotus nancymaae* chimera TMC6 2A-YC260TM in pcDNA3.1(-) was confirmed to consist of an upstream part identical to positions 1 to 45 of the nucleotide sequence of mRNA of the mouse TMC6 gene (NM_145439) and a downstream part identical to positions 52 to 2421 of the nucleotide sequence of mRNA of the *Aotus nancymaae* TMC6 gene (XM_012453598) registered in NCBI by sequencing analysis. The chimeric TMC6 gene encodes a chimeric TMC6 protein consisting of the amino acid sequence of positions 1 to 15 of the mouse TMC6 protein (SEQ ID NO: 26) and the amino acid sequence of positions 18 to 807 of the *Aotus nancymaae* TMC6 protein (SEQ ID NO: 1). The nucleotide sequence of Mouse-*Aotus nancymaae* chimera TMC6 2A-YC260TM in pcDNA3.1(-) is shown as SEQ ID NO: 63. In SEQ ID NO: 63, the nucleotide sequence of positions 907 to 951 corresponds to the upstream part of the CDS of the mouse TMC6 gene, the nucleotide sequence of positions 952 to 3321 corresponds to the downstream part of the CDS of the *Aotus nancymaae* TMC6 gene, the nucleotide sequence of positions 3322 to 3384 corresponds to the DNA encoding the 2A peptide, and the nucleotide sequence of positions 3385 to 5418 corresponds to the DNA encoding YC2.60.

CHO-K1 cells were transfected with *Macaca mulatta* TMC6-2A-YC260TM in pcDNA3.1(-), *Pongo abelii* TMC6-2A-YC260TM in pcDNA3.1(-), Mouse-*Aotus nancymaae* chimera TMC6 2A-YC260TM in pcDNA3.1(-), or YC2.60-pcDNA, to prepare TMC6-expressing cells (cells expressing the *Macaca* mulatta TMC6 gene, the *Pongo abelii* TMC6 gene, or the mouse/*Aotus nancymaae* chimeric TMC6 gene, in combination with the YC2.60 gene) and control cells (cells expressing the YC2.60 gene). The prepared cells were stimulated, and activation of the cells was measured. The procedure was as follows.

First, a plurality of sterile cover glasses (18×32 mm, Matsunami Glass) were placed at the bottom of a culture dish having a diameter of 100 mm so as not to be overlapped to each other. CHO-K1 cells (ATCC) were inoculated thereto while adjusting the number of the cells to obtain 60% confluence, and cultured for 24 hr. Then, medium exchange was carried out. As the medium, 12 mL of Ham's F-12K (Kaighn's) (Life Technologies) containing 10% fetal bovine serum (Life Technologies) was used. A 30 µL aliquot of 1 mg/mL Polyethylenimine "Max" (Polysciences) was added to 460 µL of Opti-MEM (Thermo Fisher Scientific), and incubated for 5 min at a room temperature. Then, 10 µg of *Macaca mulatta* TMC6-2A-YC260TM in pcDNA3.1(-), *Pongo abelii* TMC6-2A-YC260TM in pcDNA3.1(-), or Mouse-*Aotus nancymaae* chimera TMC6 2A-YC260TM in pcDNA3.1(-) was further added thereto, and incubated for 10 min at a room temperature. Then, the whole of the resultant mixture was dropped into the culture broth of the CHO-K1 cells, and the culture broth was mildly stirred. Then, the cells were further cultured for 18 hr under a condition of 5% $CO_2$ at 37° C., to obtain the TMC6-expressing cells. Similarly, the control cells were obtained through transfection using YC2.60-pcDNA.

After the cultivation, the cover glasses inoculated with cells were taken out from the culture dish, and placed on the stage of the confocal laser microscope FV1200. The low-concentration NaCl solution was added throughout to the cover glasses, incubation was carried out statically for approximately 5 min, and then, stimulation and observation of cells were started. First, the low-concentration NaCl solution was perfused for 60 sec, to provide a ground state. Then, the high-concentration NaCl solution was perfused instead of the low-concentration NaCl solution for 60 sec, to stimulate the cells. Then, perfusion of the low-concentration NaCl solution was restarted. After the state of the cells virtually returned to the ground state, the ATP stimulation solution was perfused for 60 sec, to stimulate the cells.

Change of the intracellular calcium concentration was measured and analyzed with analysis software equipped with FV1200. An average YFP/CFP value of all the cell of which the YFP/CFP value was changed by stimulation with the ATP stimulation solution was calculated at each measurement. The perfusion was carried out in the longitudinal direction of each cover glass by adding a fresh solution at one end of the cover glass while removing a stale solution by suction from the other end of the cover glass.

Results are shown in FIG. 18. FIGS. 18A, B, and C represent change of the average YFP/CFP value obtained for the cells expressing the mouse/*Aotus nancymaae* chimeric TMC6 gene, the *Macaca mulatta* TMC6 gene, and the *Pongo abelii* TMC6 gene, respectively. FIG. 18D represents change of the average YFP/CFP value obtained for the control cells. The number of cells used for the analysis was 21 for the cells expressing the mouse/*Aotus nancymaae* chimeric TMC6 gene, 28 for the cells expressing *Macaca mulatta* TMC6 gene, 31 for the cells expressing the *Pongo abelii* TMC6 gene, and 34 for the control cells. In the TMC6-expressing cells for any of the TMC6 genes, there was observed an increase in the YFP/CFP value due to an increase in the intracellular calcium concentration resulting from activation of the cells by stimulation with the high-concentration NaCl solution (FIGS. 18A, B, and C). By contrast, in the control cells, there was not observed an increase in the YFP/CFP value by stimulation with the high-concentration NaCl solution (FIG. 18D).

These experimental results indicate that the CHO-K1 cells expressing the mouse/*Aotus nancymaae* chimeric TMC6 gene, the *Macaca mulatta* TMC6 gene, or the *Pongo abelii* TMC6 gene responded to stimulation with the high-concentration NaCl solution as with the CHO-K1 cells expressing the mouse or human TMC6 gene. Hence, it was revealed that TMC6 proteins of a wide variety of mammals and chimeric proteins thereof have an identical function.

Example 5: Functional Analysis of TMC6 Protein by Electrophysiological Method

In this Example, the TMC6 gene was expressed in insect cells, a membrane fraction containing the TMC6 protein was roughly purified from the cells to construct an artificial cell membrane, and the function of TMC6 protein was electrophysiologically analyzed by using the artificial cell membrane.

Gene expression in insect cells was carried out with reference to O'Reilly, D. et al. (1992) Baculovirus Expression Vectors: A Laboratory Manual. W. H. Freeman & Co., New York.; and King, L. et al. (1992) The Baculovirus Expression System: A Laboratory Guide. Chapman & Hall, New York. The detailed procedure was as follows.

(1) Construction of Plasmid

The CDS of the mouse TMC6 gene and a downstream DNA encoding 2×Gly and 6×His (i.e. Gly-Gly-His-His-His-His-His-His) were cloned into the multiple cloning site (MCS) of a baculovirus transfer vector pVL1392 (BD Biosciences), to construct a plasmid m-Tmc6 6×His in pVL1392. *Escherichia coli* OmniMAX (Thermo Fisher Scientific) was transformed with m-Tmc6 6×His in pVL1392, and cultured in a liquid medium in the presence of ampicillin. From cultured cells, m-Tmc6 6×His in pVL1392 (110.3 ng/μL) was purified. The nucleotide sequence of the CDS of the TMC6 gene cloned into m-Tmc6 6×His in pVL1392 was confirmed to be identical to the nucleotide sequence of mRNA transcript variant 1 of mouse (NM_145439) registered in NCBI by sequencing analysis. The nucleotide sequence of m-Tmc6 6×His in pVL1392 is shown as SEQ ID NO: 64. In SEQ ID NO: 64, the nucleotide sequence of positions 4161 to 6590 corresponds to the CDS of the mouse TMC6 gene, the nucleotide sequence of positions 6591 to 6596 corresponds to the DNA encoding 2×Gly, and the nucleotide sequence of positions 6597 to 6614 corresponds to the DNA encoding 6×His.

(2) Preparation of Baculovirus

The m-Tmc6 6×His cassette, which contains the CDS of the mouse TMC6 gene and the downstream DNA encoding 2×Gly and 6×His, was transferred from m-Tmc6 6×His in pVL1392 to virus DNA by homologous recombination to prepare a recombinant baculovirus for expression of the mouse TMC6 gene. The procedure was as follows.

Sf9 cells (Sf9 cells in Sf-900 III SFM, Thermo Fisher Scientific, Product No. 12659017) were co-transfected with m-Tmc6 6×His in pVL1392 and BacPAK 6 DNA (Bsu36 I digest) (Clontech, Product No. 631401, Kitts, P. A. & Possee, R. D. (1993) BioTechniques 14:810-817.) according to the supplier's protocol. After the co-transfection, the cells were cultured in the Sf-900 III SFM (Thermo Fisher Scientific, Product No. 12658019) at 27° C. for 72 hr, and 2 mL of a culture supernatant containing recombinant virus particles (culture supernatant A) was collected.

The recombinant virus was amplified in the following manner. Sf9 cells were statically cultured in Sf-900 III SFM contained in a culture flask (MS-21050, SUMILON) at 27° C. to obtain approximately 50-60% confluence. Then, 4 mL of the Sf9 cell culture was added with 1 mL of the culture supernatant A, and further cultured at 27° C. for approximately 96 hr. Then, a culture supernatant containing recombinant virus particles was collected by centrifugation (1,000×g, 5 min, 4° C.). This operation was repeated again, to obtain an additional set of the culture supernatant. Thus-obtained two sets of the culture supernatant were mixed mutually, and designated as "culture supernatant B".

A culture supernatant containing the recombinant virus for expression of the mouse TMC6 gene was obtained in the following manner. Sf9 cells were statically cultured in Sf-900 III SFM contained in a culture flask (MS-21250, SUMILON) at 27° C. to obtain approximately 50-60% confluence. Then, 15 mL of the Sf9 cell culture was added with 1 mL of the culture supernatant B, and further cultured at 27° C. for approximately 96 hr. Then, a culture supernatant containing virus particles (culture supernatant C) was collected by centrifugation (1,000×g, 5 min, 4° C.) for expression of the mouse TMC6 gene. The culture supernatant C was dispensed into cryotubes in 1 mL each, and stored at −80° C. until use.

Insertion of the m-Tmc6 6×His cassette in the recombinant virus DNA was confirmed in the following manner. First, Sf9 cells were statically cultured in Sf-900 III SFM contained in a culture flask (MS-21250, SUMILON) at 27° C. to obtain approximately 70-80% confluence. Then, 12 mL of the Sf9 cell culture was added with 100 μL of the culture supernatant C, and further cultured at 27° C. for approximately 96 hr. The recombinant virus was collected according to the method of K. Kamiya et al. Biomaterials, 32, 9899-9907 (2011). That is, a culture supernatant containing recombinant virus particles (culture supernatant D) was collected by centrifugation (1,000×g, 5 min, 4° C.) The culture supernatant D was centrifuged (100,000×g, 60 min, 15° C.), to precipitate the recombinant virus particles. The precipitated recombinant virus particles were suspended in PBS (1 mM $Na_2HPO_4$, 10.5 mM $KH_2PO_4$, 140 mM NaCl, 40 mM KCl, pH 6.2), and the suspension was subjected to a sucrose density-gradient centrifugation (40,000×g, 30 min, 15° C.), to collect a recombinant virus fraction. The recombinant virus fraction was centrifuged (100,000×g, 60 min, 15° C.), to precipitate the recombinant virus particles. The precipitated recombinant virus particles were suspended in PBS. DNA was purified from the recombinant virus particles by phenol/chloroform extraction and ethanol precipitation. PCR was performed by using the purified DNA as the template, and primers of SEQ ID NOS: 65 and 66, which primers were designed to interpose the MCS of pVL1392. The amplified product was subjected to sequencing analysis. As a result, it was confirmed that a gene encoding the mouse TMC6 protein added with 6×His at the C-terminus was inserted in the MCS.

(3) Expression of TMC6 Protein in Insect Cells

Sf9 cells were statically cultured in Sf-900 III SFM contained in a culture flask (MS-21250, SUMILON) at 27° C. to obtain approximately 70-80% confluence. Then, 12 mL of the Sf9 cell culture was added with 100 µL of the culture supernatant C, which contains the recombinant virus of which DNA was inserted with the m-Tmc6 6×His cassette by recombination, for infection of the virus to the cells, and further statically cultured, to obtain Sf9 cells having the TMC6 protein.

Localization of the TMC6 protein on the cell membranes of the Sf9 cells was confirmed by immunofluorescence assay in the following manner. The cell culture was centrifuged (1,000×g, 5 min, 15° C.), and the precipitated cells were suspended in PBS. A 1 µL aliquot of Alexa Fluor 488-conjugated monoclonal mouse anti-His (MBL, Product No. D291-A48) and a 1 µL aliquot of polyclonal chicken anti-m-Tmc6 (Scrum) were added to 500 µL of the cell suspension, and the resultant mixture was shaken at 25° C. for 1 hr. Then, the mixture was centrifuged (1,000×g, 5 min, 15° C.), and the precipitated cells were suspended in 500 µL of PBS. A 1 µL aliquot of Alexa Fluor 568-conjugated anti-chicken IgY (Invitrogen, Product No. A11041) was added thereto as the secondary antibody, and the resultant mixture was shaken at 25° C. for 1 hr. Then, the mixture was centrifuged (1,000×g, 5 min, 15° C.), and the precipitated cells were suspended in 500 µL of PBS. Observation of the cells was carried out with the confocal laser microscope FV1200.

Results are shown in FIG. 19. FIGS. 19A and B represent immunofluorescence images, in which the mouse TMC6 protein added with 6×His at the C-terminus was stained with the anti-His antibody (Alexa488) for FIG. 19A, or with anti-TMC6 antibody in combination with anti-chicken IgY antibody (Alexa568) for FIG. 19B. FIG. 19C represents a merged image of the immunofluorescence images of FIGS. 19A and B. FIG. 19D represents a differential interference contrast image of the bright field. From FIG. 19, it was revealed that the TMC6 protein was localized on the cell membranes of the Sf9 cells.

Next, a roughly purified fraction of cell membranes was prepared for Sf9 cells containing the TMC6 protein and for Sf9 cells not containing the TMC6 protein in the following manner. Sf9 cells were statically cultured in Sf-900 III SFM contained in a culture flask (MS-21250, SUMILON) at 27° C. to obtain approximately 70-80% confluence. Then, 12 mL of the Sf9 cell culture was added with 100 µL of the culture supernatant C, which contains the recombinant virus of which DNA was inserted with the m-Tmc6 6×His cassette by recombination, for infection of the virus to the cells, and further statically cultured, to obtain Sf9 cells having the TMC6 protein. Similarly, Sf9 cells not containing the TMC6 protein was prepared as a negative control by using the wild-type virus instead of the culture supernatant C. At approximately 96 hr after the infection, the cell culture was centrifuged (1,000×g, 5 min, 15° C.), and the precipitated cells were suspended in a sodium phosphate aqueous solution (pH7.0). The cell suspension was disrupted by ultrasonication, and centrifuged, to obtain a roughly purified fraction of cell membranes.

(4) Functional Analysis of TMC6 Protein by Electrophysiological Method

The function of TMC6 protein was electrophysiologically analyzed by using an ion channel recording device (Kawano R. et al., Automated Parallel Recordings of Topologically Identified Single Ion Channels, Scientific Reports, 3, No. 1995 (2013)). This device is equipped with a voltage-applied side well and a ground (earth) side well, the wells communicating each other through micropores, and an artificial lipid bilayer can be formed so as to fill the micropores. A 3.7 µL aliquot of 20 mg/mL phospholipid was added to each of the wells. Then, 21 µL of a solution (140 mM NaCl, 5 mM KCl, 2 mM $CaCl_2$, 2 mM $MgCl_2$, 10 mM HEPES, pH 7.4, containing the roughly purified membrane fraction) was added to the voltage-applied side well. In addition, 21 µL of a solution (140 mM CsCl, 5 mM EGTA, 2 mM ATP, 10 mM HEPES, pH 7.2) was added to the ground (earth) side well. Thereby, an artificial lipid bilayer was prepared between the wells. The cell membranes contained in the roughly purified membrane fraction were considered to be incorporated into the artificial lipid bilayer. A current generated between the wells derived from an ion channel was measured by using a multi-patch-clamp amplifier (JET-Bilayer, Tecella). Detailed measurement conditions were as follows: the applied voltage was set to 60 mV or −60 mV, the data acquisition frequency was set to 5,000 Hz, the low-pass filter was set to 1,000 Hz, and the measurement was carried out for approximately 2 hr.

Results are shown in FIGS. 20 and 21. When the roughly purified membrane fraction containing the TMC6 protein was used, signals indicating open and close of a single channel and flow of ions were observed at an amplitude of approximately 2 pA (FIGS. 20A, B, and C). By contrast, when the roughly purified membrane fraction not containing the TMC6 protein, which was obtained through infection of the wild-type virus, was used, the current exhibited a constant value (FIG. 21), and that is, such signals as observed in FIG. 20 indicating open and close of a single channel and flow of ions were not observed.

From these results, it was revealed that the roughly purified membrane fraction containing the TMC6 protein contained a protein that functions as an ion channel. Specifically, it was considered that sodium ions in the solution flow through the TMC6 protein in the roughly purified membrane fraction.

Explanation of Sequence Listing

SEQ ID NOS:

1-47: Amino acid sequences of TMC6 proteins of mammals
48-50: Target sequences for gene mutation
51: V5-epitope sequence
52: Nucleotide sequence of YC2.60-pcDNA
53-54: Primers
55: Nucleotide sequence of TMC6-pcDNA3.1
56-59: Primers
60: Nucleotide sequence of hTMC6-pcDNA3.1
61: Nucleotide sequence of *Macaca* mulatta TMC6-2A-YC260TM in pcDNA3.1(−)

62: Nucleotide sequence of *Pongo abelii* TMC6-2A-YC260TM in pcDNA3.1(−)
63: Nucleotide sequence of Mouse-*Aotus nancymaae* chimera TMC6 2A-YC260TM in pcDNA3.1(−)
64: Nucleotide sequence of m-Tmc6 6×His in pVL1392
65-66: Primers Numerous modifications and variations on the present invention are possible in light of the above teachings. It is, therefore, to be understood that within the scope of the accompanying claims, the invention may be practiced otherwise than as specifically described herein.

The invention claimed is:

1. A method for identifying a substance that affects salty taste, comprising:
   contacting a test substance with a transmembrane channel-like protein 6 (TMC6) protein;
   measuring an action of said test substance on the TMC6 protein upon contact;
   identifying said substance as a substance that affects salty taste on the basis of the action measured, wherein said action is binding of the test substance to the TMC6 protein, activation of the TMC6 protein by the test substance, or inactivation of the TMC6 protein by the test substance.

2. The method according to claim 1, wherein said action is binding of the test substance to the TMC6 protein.

3. The method according to claim 1, wherein the substance that acts on the TMC6 protein is a substance that activates or inactivates the TMC6 protein.

4. The method according to claim 1, wherein the substance that affects salty taste is a salty-taste alternative substance.

5. The method according to claim 1, wherein substance that affects salty taste is a salty-taste enhancing substance.

6. The method according to claim 1, wherein substance that affects salty taste is a salty-taste reducing substance.

7. The method according to claim 1, further comprising:
   following said measuring, determining an activation degree D1, the activation degree D1 being the degree of activation of the TMC6 protein upon the contact; and
   following said identifying, further identifying the test substance on the basis of the activation degree D1.

8. The method according to claim 7, further comprising:
   following said further identifying, classifying the test substance on the basis of a difference between the activation degree D1 and an activation degree D2, the activation degree D2 being the degree of activation of the TMC6 protein under a control condition.

9. The method according to claim 8, wherein the control condition comprises:
   a condition of not bringing the TMC6 protein and the test substance into contact with each other; or
   a condition of bringing the TMC6 protein and the test substance into contact with each other, where the concentration of the test substance is lower than that in said contacting a test substance with a TMC6 protein.

10. The method of claim 1, wherein the TMC6 protein is in a form isolated from its native host cell.

11. The method according to claim 1, wherein the TMC6 protein is carried by a cell or a cell membrane.

12. The method according to claim 11, wherein the activation or inactivation of the TMC6 protein is measured by using activation or inactivation of the cell as an index.

13. The method according to claim 11, wherein the activation or inactivation of the TMC6 protein is measured by using one or more parameters selected from the group consisting of: the membrane potential of the cell or of the cell membrane, the membrane current of the cell or of the cell membrane, and the cation concentration in the cell or in one of spaces separated by the cell membrane as an index or indices.

14. The method according to claim 13, wherein the cation is a sodium ion or a calcium ion.

15. The method according to claim 11, wherein the cell is a cell of an organism.

16. The method according to claim 11, wherein the cell is an animal cell.

17. The method according to claim 1, wherein said contacting is performed in the presence of a salty-taste substance.

18. The method according to claim 17, wherein if activation of the TMC6 protein by the test substance is observed, the test substance is identified as a salty-taste enhancing substance.

19. The method according to claim 17, wherein if inactivation of the TMC6 protein by the test substance is observed, the test substance is identified as a salty-taste reducing substance.

20. The method according to claim 15, wherein the salty-taste substance is a substance that provides a sodium ion in an aqueous medium.

21. The method according to claim 15, wherein the salty-taste substance is sodium chloride.

22. The method according to claim 1, wherein said contacting is carried out in the absence of a salty-taste substance.

23. The method according to claim 22, wherein if activation of the TMC6 protein by the test substance is observed, the test substance is identified as a salty-taste alternative substance.

24. The method according to claim 1, wherein the TMC6 protein is a protein defined in (A) or (B):
   (A) a mammalian TMC6 protein;
   (B) a chimeric TMC6 protein of two or more kinds of mammalian TMC6 proteins.

25. The method according to claim 1, wherein the TMC6 protein is a protein defined in (a), (b), or (c):
   (a) a protein comprising the amino acid sequence of any one of SEQ ID NOs: 1-47, or comprising a chimeric sequence of two or more kinds of amino acid sequences selected from the amino acid sequences of SEQ ID NOs: 1-47;
   (b) a protein comprising the amino acid sequence of any one of SEQ ID NOS: 1-47, or comprising a chimeric sequence of two or more kinds of amino acid sequences selected from the amino acid sequences of SEQ ID NOs: 1-47, but which includes substitution, deletion, insertion, and/or addition of 1 to 10 amino acid residues, and having a function of a salty-taste receptor;
   (c) a protein comprising an amino acid sequence showing an identity of 90% or higher to the amino acid sequence of any one of SEQ ID NOs: 1-47, or to a chimeric sequence of two or more kinds of amino acid sequences selected from the amino acid sequences of SEQ ID NOs: 1-47, and having a function of salty-taste receptor.

* * * * *